(12) United States Patent
Lee et al.

(10) Patent No.: US 9,975,883 B2
(45) Date of Patent: May 22, 2018

(54) 1,2-NAPHTHOQUINONE BASED DERIVATIVE AND METHOD OF PREPARING THE SAME

(71) Applicant: YUNGJIN PHARM. CO., LTD., Seoul (KR)

(72) Inventors: Whee Seong Lee, Suwon-si (KR); Mi Jung Lee, Yongin-si (KR); Bo Jung Kim, Yongin-si (KR); Tae Cheul Roh, Suwon-si (KR); Seung Hoon Lee, Suwon-si (KR); Kyu Dae Lee, Seoul (KR); You-Hui Lee, Seoul (KR); Tae Hwan Kwak, Yongin-si (KR)

(73) Assignee: YUNGJIN PHARM. CO., LTD., Seoul (KR)

( * ) Notice: Subject to any disclaimer, the term of this patent is extended or adjusted under 35 U.S.C. 154(b) by 0 days. days.

(21) Appl. No.: 15/102,968

(22) PCT Filed: Dec. 30, 2014

(86) PCT No.: PCT/KR2014/013040
§ 371 (c)(1),
(2) Date: Jun. 9, 2016

(87) PCT Pub. No.: WO2015/102371
PCT Pub. Date: Jul. 9, 2015

(65) Prior Publication Data
US 2016/0376258 A1 Dec. 29, 2016

(30) Foreign Application Priority Data
Dec. 30, 2013 (KR) .................. 10-2013-0166585

(51) Int. Cl.
| | | |
|---|---|---|
| C07D 405/04 | (2006.01) |
| A61K 31/4184 | (2006.01) |
| A61K 31/4439 | (2006.01) |
| A61K 31/498 | (2006.01) |
| A61K 31/5377 | (2006.01) |
| C07D 401/04 | (2006.01) |
| C07D 235/02 | (2006.01) |
| C07D 401/06 | (2006.01) |
| C07D 241/38 | (2006.01) |
| C07D 471/04 | (2006.01) |
| C07C 231/12 | (2006.01) |
| C07C 231/14 | (2006.01) |
| C07C 309/04 | (2006.01) |

(52) U.S. Cl.
CPC ........ *C07D 405/04* (2013.01); *A61K 31/4184* (2013.01); *A61K 31/4439* (2013.01); *A61K 31/498* (2013.01); *A61K 31/5377* (2013.01); *C07C 231/12* (2013.01); *C07C 231/14* (2013.01); *C07C 309/04* (2013.01); *C07D 235/02* (2013.01); *C07D 241/38* (2013.01); *C07D 401/04* (2013.01); *C07D 401/06* (2013.01); *C07D 471/04* (2013.01)

(58) Field of Classification Search
CPC ............................ C07D 235/02; A61K 31/415
IPC ............................ C07D 235/02; A61K 31/415
See application file for complete search history.

(56) References Cited

FOREIGN PATENT DOCUMENTS

| | | |
|---|---|---|
| JP | 2006-135144 | 5/2006 |
| WO | 2008066300 | 6/2008 |

OTHER PUBLICATIONS

Fouchard, D. et al., JOC vol. 69 pp. 2626-2629. Published 2004.*
Carroll, F.I. et al., J. Med. Chem. vol. 13, pp. 312-314. Published 1970.*
Carroll, F.I. et al., Journal of Heterocyclic Chemistry vol. 7 pp. 297-306. Published 1970.*
Fouchard, D.D.M. et al., Journal of Organic Chemistry. vol. 69, pp. 2626-2629. Published 2004.*
National Center for Biotechnology Information PubChem Compound Database, Dec. 5, 2007.
Ahmed Mustafa et al., "Photochemical Addition and Photochemical Dehydrogenation Reactions in Sunlight", Journal of American Chemical Society, Sep. 5, 1956, vol. 78(17) pp. 4306-4309.
F.I. Carroll et al, "Synthesis of 1,2-Disubstituted Naphth[1,2-d] imidazole-4,5-diones (1a, b)", The Chemistry and Life Sciences Laboratory, Research Triangle Institute, Apr. 1970, pp. 297-306.
NIST Mass Spectral Library Database Registry, Dec. 21, 2007, XP002770090.
European Patent Office, European Search Report of Application No. 14876975.5, dated May 30, 2017.

* cited by examiner

*Primary Examiner* — Timothy P Thomas
*Assistant Examiner* — George W Kosturko
(74) *Attorney, Agent, or Firm* — Lex IP Meister, PLLC

(57) ABSTRACT

Disclosed are a compound represented by Formula (1), or a pharmaceutically acceptable salt, hydrate, solvate, prodrug, tautomer, enantiomer, or pharmaceutically acceptable diastereomer thereof, a method of preparing the same, and a pharmaceutical composition, which have effects for treatment or prevention of metabolic syndromes, comprising the same:

wherein $R_1$ to $R_6$, $X_1$ to $X_4$, and n are the same as defined in Claim 1.

9 Claims, 16 Drawing Sheets

1,2-NAPHTHOQUINONE BASED DERIVATIVE AND METHOD OF PREPARING THE SAME

TECHNICAL FIELD

The present invention relates to a 1,2-naphthoquinone based derivative, a method of preparing the same, and a composition, which has treatment and prevention effects for metabolic syndromes, including the same.

BACKGROUND ART

Metabolic syndromes represent risk factors such as hypertriglyceridemia, hypertension, abnormal glucose metabolism, abnormal blood coagulation, and obesity and may cause diseases such as heart attack, ischemic heart diseases, type 2 diabetes, hypercholesterolemia, cancers, gallstones, arthritis, arthralgia, respiratory diseases, sleep apnea, benign prostatic hyperplasia, menstrual irregularity, and the like. Therefore, metabolic syndromes pose a great threat to modern people. According to a National Cholesterol Education Program (NCEP) standard published in America, 2001, a patient is judged to have a metabolic syndrome when the patient presents with at least one of ① a waist size of 40 inches (102 cm) or more in men, a waist size of 35 inches (88 cm) or more in women, ② triglycerides of 150 mg/dL or more, ③ HDL cholesterol of 40 mg/dL or less in men and 50 mg/dL or less in women, ④ a blood pressure of 130/85 mmHg or more, ⑤ fasting glucose of 110 mg/dL. In Asians, when men have a waist size of 90 cm or more and women have a waist size of 80 cm or more, they are judged to have abdominal obesity. When such standards were applied to Koreans, it was recently reported that approximately 25% Koreans have metabolic syndromes.

Chronic and long-term high-calorie intake is considered as a major risk factor of such metabolic syndromes. Metabolic efficiency is reduced due to excessive energy intake, lack of exercise, life extension, aging, and the like, thereby causing obesity, diabetes, and metabolic syndromes due to excessive caloric intake.

As treatment methods, diet therapies, exercise therapies, behavioral control therapies, drug treatments, and the like are carried out. However, since exact causes of metabolic syndromes are not known, treatment effects are presently insignificant and symptoms are merely alleviated or progression of diseases is delayed. A variety of therapeutic targets have been identified but an excellent treatment target has yet to be reported.

Meanwhile, since NADH and NADPH are used in a fat biosynthesis process when ratios of $NAD^+/NADH$ and $NADP^+/NADPH$ are reduced and, thus, NADH and NADPH remain in vivo or in vitro, and NADH and NADPH are used as major substrates causing reactive oxygen species (ROS) when present in excess, ROS causes diseases such as inflammatory diseases. For these reasons, if in vivo or in vitro environment may be changed such that a state, in which ratios of $NAD^+/NADH$ and $NADP^+/NADPH$ are increased, is stably maintained, fat oxidation due to $NAD^+$ and $NADP^+$ and a variety of energy consumption metabolism may be activated. As a result, if an action mechanism to continuously keep the low concentration of NAD(P)H can be activated, a variety of diseases including obesity may be treated by inducing consumption of excessive calories.

To increase the concentration and a ratio of $NAD(P)^+$ which is a signal messenger known as performing a variety of functions as described above, methods below are considered: first, a method of controlling a salvage synthesis process as an $NAD(P)^+$ biosynthesis process; second, a method of increasing the concentration of $NAD(P)^+$ in vivo by activating genes or proteins of enzymes using NAD(P)H as a substrate or a coenzyme; third, a method of increasing the concentration of $NAD(P)^+$ by supplying $NAD(P)^+$ or an analogue, derivative, precursor, or prodrug thereof from the outside; and the like.

NAD(P)H:quinone oxidoreductase (EC1.6.99.2) is called DT-diaphorase, quinone reductase, menadione reductase, vitamin K reductase, azo-dye reductase, or the like. Such NQO exists in two isoforms, namely, NQO1 and NQO2 (ROM. J. INTERN. MED. 2000-2001, vol. 38-39, 33-50). NQO is a flavoprotein and facilitates removal of quinone or quinone derivatives through detoxification reaction. NQO uses NADH and NADPH as electron donors. Activation of NQO prevents formation of highly reactive quinone metabolites removes benzo (d)pyrene or quinone, and lowers toxicity of chrome. Although activation of NQO occurs in all tissues, activation thereof depends on tissue types. Generally, it was confirmed that expression of NQO was increased in cancer cells and tissues such as the liver, stomach, kidney, and the like. Expression of the NQO gene is induced by xenobiotics, antioxidants, oxidants, heavy metals, ultraviolet light, radiation, and the like. NQO is a part of lots of cellular defense mechanisms induced by oxidative stress. Combined expression of genes related to defense mechanisms including NQO protects cells against oxidative stress, free radicals, and neoplasia. NQO has very broad substrate specificity and, as substrates thereof, quinone, quinone-imines, and nitro and azo compounds may be used.

Thereamong, NQO1 is mainly expressed in epithelial cells and endothelial cells. This means that NQO1 may function as a defense mechanism against compounds absorbed through air, the throat, or blood vessels. Recently, it was reported that expression of an NQO1 gene greatly increased in adipose tissues of humans having metabolic syndrome and expression of NQO1 in larger adipose cells was statistically significantly high. When weight loss was induced through diet treatments, expression of NQO1 proportionally decreased with weight loss. It was confirmed that the amount of NQO1 mRNA is proportional to GOT and GPT known as indicators of fatty liver syndrome. Therefore, it is judged that NQO1 may play a role in metabolic syndromes related to obesity, when it is considered that expression of NQO1 in adipose tissues relates to adiposity, glucose tolerance, and liver function index (Journal of Clinical Endocrinology & Metabolism 92 (6):2346. 2352).

DISCLOSURE

Technical Problem

Therefore, the present invention has been made to solve the above and other technical problems that have yet to be resolved.

In particular, the present invention aims to provide a 1,2-naphthoquinone based derivative having a novel structure.

In accordance with another aspect of the present invention, there is provided such a novel compound.

In accordance with another aspect of the present invention, there is provided a composition for treatment and prevention of metabolic syndromes, the composition including such a novel compound in a therapeutically effective amount, as an active ingredient.

In accordance with yet another aspect of the present invention, there is provided a method for treatment and prevention of metabolic syndromes using such a novel compound as an active ingredient.

Technical Solution

In accordance with an aspect of the present invention, the above and other objects can be accomplished by the provision of a compound represented by Formula (1) below, or a pharmaceutically acceptable salt, hydrate, solvate, prodrug, tautomer, enantiomer, or pharmaceutically acceptable diastereomer thereof:

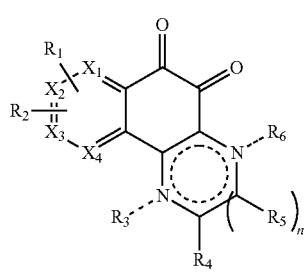

(1)

wherein $R_1$ and $R_2$ are each independently hydrogen, a halogen, substituted or unsubstituted C1-C20 alkoxy, substituted or unsubstituted C1-C6 alkyl, substituted or unsubstituted C4-C10 aryl, substituted or unsubstituted C4-C10 aryloxy, substituted or unsubstituted C2-C10 heteroaryl, —$NO_2$, —$NR'_1R'_2$, —$NR'_1$ (CO (O)$R'_2$), —$NR'_1$ (C (O)$NR'_1R'_2$), —CO (O)$R'_1$, —C(O)$NR'_1R'_2$, —CN, —SO (O)$R'_1$, —SO (O)$NR'_1R'_2$, —$NR'_1$ (SO (O)$R'_2$), —$CSNR'_1R'_2$, or $R_1$ and $R_2$ may form a ring structure of substituted or unsubstituted C4-C10 aryl through coupling or a ring structure of substituted or unsubstituted C2-C10 heteroaryl, where $R'_1$ and $R'_2$ are each independently hydrogen, substituted or unsubstituted C1-C6 alkyl, substituted or unsubstituted C3-C8 cycloalkyl, substituted or unsubstituted C4-C10 aryl, substituted or unsubstituted C4-C10 aryloxy, substituted or unsubstituted C1-C8 heteroaryl, substituted or unsubstituted —$(CR''_1R''_2)m'$-C4-C10 aryl or substituted or unsubstituted $NR''_1R''_2$;

where $R''_1$ and $R''_2$ may each independently be hydrogen or C1-C3 alkyl, or $R''_1$ and $R''_2$ may form a ring structure of substituted or unsubstituted C4-C10 aryl through coupling;

$R_3$, $R_4$, $R_5$, and $R_6$ are each independently hydrogen, a halogen, substituted or unsubstituted C1-C9 alkyl, substituted or unsubstituted C2-C20 alkene, substituted or unsubstituted C1-C20 alkoxy, substituted or unsubstituted C3-C8 cycloalkyl, substituted or unsubstituted C2-C8 heterocycloalkyl, substituted or unsubstituted C4-C10 aryl, substituted or unsubstituted C4-C10 aryloxy, substituted or unsubstituted C1-C10 heteroaryl, substituted or unsubstituted —$(CR'_5R'_6)_m$—C4-C10 aryl, substituted or unsubstituted —$(CR'_5R'_6)_m$—C4-C10 aryloxy, substituted or unsubstituted —$(CR'_5R'_6)_m$—C4-C10 heteroaryl, substituted or unsubstituted —$(CR'_5R'_6)_m$—C4-C10 heterocycloalkyl, substituted or unsubstituted —$(CR'_5R'_6)_m$—$NR'_3R'_4$, substituted or unsubstituted —$(CR'_5R'_6)_m$—$OR'_3$, —CO (O)$R'_3$, —$CONR'_3R'_4$, —$NR'_3R'_4$, —$NR'_3$ (C (O)$R'_4$), —SO (O)$R'_3$, —SO (O)$NR'_3R'_4$, —$NR'_3$ (SO (O)$R'_4$), —$CSNR'_3R'_4$, —$CH_2A$ when the compound of Formula (1) is "A", or -A when the compound of Formula (1) is "A";

where $R'_3$ and $R'_4$ are each independently hydrogen, substituted or unsubstituted C1-C6 alkyl, substituted or unsubstituted C3-C8 cycloalkyl, substituted or unsubstituted C4-C10 aryl, substituted or unsubstituted —$(CH_2)_m$—C4-C10 aryl, substituted or unsubstituted —$(CH_2)_m$—C4-C10 aryloxy, —CO (O)$R''_3$, or $R'_3$ and $R'_4$ may form a ring structure of substituted or unsubstituted C4-C10 heterocycloalkyl or substituted or unsubstituted C4-C10 heteroaryl through coupling;

$R'_5$ and $R'_6$ are each independently hydrogen or C1-C3 alkyl; and $R''_3$ may be C1-C6 alkyl;

wherein the substituted group is at least one selected from the group consisting of hydroxy, a halogen, C1-C10 alkyl, C2-C10 alkenyl, C2-C10 alkynyl, C1-C10 alkoxy, C1-C10 alkoxycarbonyl, C3-C8 cycloalkyl, C2-C8 heterocycloalkyl, C4-C10 aryl, and C2-C10 heteroaryl;

$R_3$ and $R_4$ are each independently not C4-C10 aryl, $R_4$ and $R_6$ are each independently not C4-C10 aryl, $R_4$ is not hydrogen, methyl, or

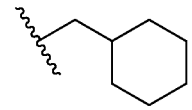 [SMILES: *CC1CCCCC1]

when $R_3$ is defined as above, and $R_5$ is not phenyl;

m and m' are each independently a natural number of 1 to 4;

the heteroatom is at least one selected from N, O, and S;

$X_1$, $X_2$, $X_3$ and $X_4$ are each independently CH or N; and n is 0 or 1 and, when n is 0, neighboring carbon atoms thereof form a ring structure through direct coupling.

In addition, in the formula, "∼∼∼∼" means that a single bond or a bond may not form and "◯" means that a ring structure including the same may be an aromatic structure or not.

Hereinafter, so long as not specified otherwise, the compound of Formula (1) as an active ingredient of a therapeutic agent includes any of a pharmaceutically acceptable salt, hydrate, solvate, prodrug, tautomer, enantiomer, or pharmaceutically acceptable diastereomer thereof and all thereof must be understood as being within the scope of the present invention. For convenience of description, they are simply called a compound of Formula (1).

The compound of Formula (1) according to the present invention has a novel structure which exhibits superior effects for treatment and prevention of metabolic diseases in vivo through exercise imitation effects as described in experimental examples below.

In particular, the compound of Formula (1) according to the present invention may increase a ratio of AMP/ATP by inducing that NAD(P)H:quinone oxidoreductase (NQO1) as an oxidation-reduction enzyme increases a ratio of NAD+/NADH in vivo. Increase of AMP in cells activates AMPK functioning as an energy gauge and, thus, lipometabolism is facilitated due to expression of PGC1a activating energy metabolism in mitochondria, thereby supplementing insufficient ATP energy. In addition, increased $NAD^+$ is used as a cofactor of glucose metabolism- and lipometabolism-related enzymes in vivo and, thus, facilitates metabolism. In addition, cADPR generated through decomposition of $NAD^+$ discharges $Ca^{2+}$ in the endoplasmic reticulum (ER) and, thus, synergistically activates mitochondria metabolism. Accordingly, exercise imitation effects may be induced in vivo.

Expressions used in the present invention will be simply described.

The expression "pharmaceutically acceptable salt" means a formulation of a compound that does not cause strong stimuli in an organism to which the compound is administered and does not destroy biological activity and properties thereof.

The expression "hydrate", "solvate", "prodrug", "tautomer", and "enantiomer or pharmaceutically acceptable diastereomer" has the same meaning as the above.

The pharmaceutical salt includes acids forming a nontoxic acid addition salt containing pharmaceutically acceptable anions, inorganic acids such as hydrochloric acid, sulfuric acid, nitric acid, phosphoric acid, hydrobromic acid, hydriodic acid, and the like, organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, and acid addition salts formed from sulfonic acids such as methanesulfonic acid, ethanesulfonic acid, benzenesulfonic acid, and p-toluenesulfonic acid, and the like. Examples of the pharmaceutically acceptable carboxylic acid salts include metal salts or alkaline earth metal salts formed from lithium, sodium, potassium, calcium, magnesium, and the like, amino acid salts such as lysine, arginine, guanidine, and the like, and organic salts such as dicyclohexylamine, N-methyl-D-glucamine, tris (hydroxymethyl)methylamine, diethanolamine, choline, triethylamine, and the like. The compound of Formula (1) according to the present invention may be transformed into salts thereof through a conventional method.

The expression "hydrate" means the compound according to the present invention including a stoichiometric or non-stoichiometric amount of water bound through non-covalent intermolecular forces or salts thereof.

The expression "solvate" means the compound according to the present invention including a stoichiometric or non-stoichiometric amount of solvent bound through non-covalent intermolecular forces or salts thereof. As preferable solvents therefor, there are volatile and/or non-toxic solvents which are suitable for administration to humans.

The expression "prodrug" means a drug modified into a parent drug in vivo. Since prodrugs may be more easily administered than parent drugs in some cases, they are often used. For example, a prodrug may be active upon oral administration while the corresponding parent drug is not. In addition, prodrugs may have better solubility than a parent drug in pharmaceutical compositions. For example, although water solubility of a prodrug negatively affects mobility thereof, the prodrug may be a compound, which is hydrolyzed into carboxylic acid as an activator, administered as an ester ("prodrug") which facilitates membrane transport. As another example of the prodrug, there is a short peptide (polyamino acid), which is bound to an acid radical, converted into an active form through metabolism.

The expression "tautomer" means a structural isomer type having an identical chemical or molecular formula but different coupling between constituent atoms. For example, a keto-eno structure is changed due to continuous movement between isomers.

The expression "enantiomer or pharmaceutically acceptable diastereomer" means each of two or more compounds with the same formula but a different arrangement of atoms in the molecule and different properties. The expression "enantiomer" means each of a pair of molecules that are mirror images of each other, like a right hand and a left hand. In addition, the expression "diastereomer" means a stereoisomer, which is not a mirror image, like a trans form or a cis form and is limited to a pharmaceutically acceptable diastereomer in the present invention. All isomers thereof and mixtures thereof are also within the scope of the present invention.

The expression "alkyl" means aliphatic hydrocarbon groups. In the present invention, "alkyl" includes "saturated alkyl", which does not include alkene or alkyne portions, and "unsaturated alkyl", which includes at least one alkene or alkyne portion. In particular, "alkyl" according to the present invention may be "saturated alkyl" which does not include alkene or alkyne portions. The alkyl may include branched, linear, and circular types. In addition, since "alkyl" includes structural isomers, for example, C3 alkyl may mean propyl and isopropyl.

The expression "alkene" means hydrocarbons including at least one carbon-carbon double bond and the expression "alkyne" means hydrocarbons including at least two carbon atoms are combined at least one carbon-carbon triple bond.

The expression "heterocycloalkyl" means a substituent in which cyclic carbon is substituted with oxygen, nitrogen, sulfur, or the like.

The expression "aryl" means an aromatic substituent including at least one ring having a covalent π electron system. "Aryl" includes monocyclic or fused-ring polycyclic (that is, rings sharing neighboring pairs of carbon atoms) groups. When substituted, a substituted group may be properly bound to ortho (o), meta (m), or para (p) positions.

The expression "heteroaryl" means an aromatic group including at least one heterocyclic ring.

Examples of "aryl" or "heteroaryl" include phenyl, furan, pyran, pyridyl, pyrimidyl, triazyl, and the like, but the present invention is not limited thereto.

The expression "halogen" means elements belonging to Group 17 of the periodic table and may be particularly fluorine, chlorine, bromine, or iodine.

The expression "aryloxy" means a group in which an oxygen atom is bound to one carbon of an aromatic ring. For example, when oxygen binds to a phenyl group, —O—$C_6H_5$ and —$C_6H_4$—O— are possible.

Other expressions may be interpreted as meanings generally understood in the art.

In a preferred embodiment according to the present invention, the compound of Formula (1) may be a compound of Formula (2) below:

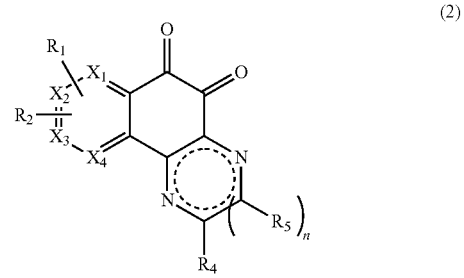

(2)

wherein $R_1$, $R_2$, $R_4$, $R_5$, $X_1$, $X_2$, $X_3$ and $X_4$ are the same as defined in Formula (1).

The compound of Formula (2) may be a compound of Formula (2-1) below but the present invention is not limited to Formula (2-1) below.

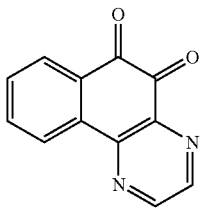

(2-1)

In another embodiment according to the present invention, the compound of Formula (1) may be a compound of Formula (3) below and/or a compound of Formula (4):

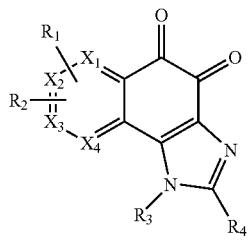

(3)

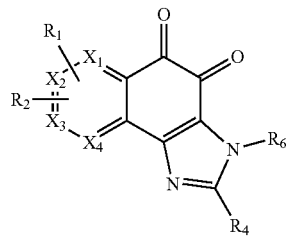

(4)

wherein $R_1$ to $R_4$, $R_6$, $X_1$, $X_2$, $X_3$ and $X_4$ are the same as defined in Formula (1).

In particular, in the compound of Formula (3) and the compound of Formula (4), $R_1$ and $R_2$ may each independently be hydrogen, a halogen, substituted or unsubstituted C1-C20 alkoxy, substituted or unsubstituted C1-C6 alkyl, substituted or unsubstituted C4-C10 aryl, substituted or unsubstituted C2-C10 heteroaryl, $-NO_2$, $-NR'_1R'_2$, $-NR'_1(C(O)R'_2)$, $-NR'_1(SO_2R'_2)$, $-NR'_1(CO_2R'_2)$, $-NR'_1(C(O)NR'_1R'_2)$, $-COOR'_1$, $-C(O)NR'_1R'_2$, $-CN$, or $R_1$ and $R_2$ may form a ring structure of substituted or unsubstituted C4-C10 aryl through coupling or a ring structure of substituted or unsubstituted C2-C10 heteroaryl, where $R'_1$ and $R'_2$ may each independently be hydrogen, substituted or unsubstituted C1-C6 alkyl, substituted or unsubstituted C3-C8 cycloalkyl, substituted or unsubstituted C4-C10 aryl, or substituted or unsubstituted $-(CH_2)_m-$C4-C10 aryl, wherein the substituted group may be at least one selected from the group consisting of hydroxy, a halogen, C1-C10 alkyl, C2-C10 alkenyl, C2-C10 alkynyl, C1-C10 alkoxy, C1-C10 alkoxycarbonyl, C3-C8 cycloalkyl, C2-C8 heterocycloalkyl, C4-C10 aryl, and C2-C10 heteroaryl.

More particularly, $R_1$ and $R_2$ may each independently be H, F, Cl, $-NO_2$, $NH_2$, $-N(CH_3)_2$, $-NHCOCH_3$, $-NHCOC_3H_5$ or $-NHCH_2C_6H_5F$, and $X_2$ and $X_3$ each may be CH.

More particularly, in the compound of Formula (3) and the compound of Formula (4), $R_1$ and $R_2$ may each independently be H, F, Cl, $-NO_2$, $NH_2$, $-N(CH_3)_2$, $-NHCOCH_3$, $-NHCOC_3H_5$ or $-NHCH_2C_6H_5F$;

$X_2$ and $X_3$ each may be CH;

$R_3$ and $R_6$ may each independently be H, a halogen, substituted or unsubstituted C1-C9 alkyl, substituted or unsubstituted C3-C8 cycloalkyl, substituted or unsubstituted $-(CR'_5R'_6)_m-$C4-C10 aryl, substituted or unsubstituted $-(CR'_5R'_6)_m-$C4-C10 aryloxy, substituted or unsubstituted $-(CR'_5R'_6)_m-$C4-C10 heteroaryl, substituted or unsubstituted $-(CR'_5R'_6)_m-$C4-C10 heterocycloalkyl, substituted or unsubstituted $-(CHR'_5)_m-$NR'$_3$R'$_4$, $-CO(O)R'_3$, $-CONR'_3R'_4$, $-NR'_3R'_4$, $-NR'_3(C(O)R'_4)$, or $-CH_2A$ when the compound of Formula (1) is "A";

$R_4$ may be a halogen, substituted or unsubstituted C2-C9 alkyl, substituted or unsubstituted C1-C10 alkoxy, substituted or unsubstituted C3-C8 cycloalkyl, substituted or unsubstituted C2-C8 heterocycloalkyl, substituted or unsubstituted C4-C10 aryl, substituted or unsubstituted C4-C10 aryloxy, substituted or unsubstituted C1-C10 heteroaryl, substituted or unsubstituted $-(CR'_5R'_6)_m-$C4-C10 aryl, substituted or unsubstituted $-(CR'_5R'_6)_m-$C4-C10 aryloxy, substituted or unsubstituted $-(CR'_5R'_6)_m-$C4-C10 heteroaryl, substituted or unsubstituted $-(CHR'_5)_m-$NR'$_3$—C4-C10 aryl, substituted or unsubstituted $-(CR'_5R'_6)_m-$C4-C10 heterocycloalkyl, substituted or unsubstituted $-(CR'_5R'_6)_m-$NR'$_3$R'$_4$, substituted or unsubstituted $-(CR'_5R'_6)_m-$OR'$_3$, $-NR'_3R'_4$, or -A when the compound of Formula (1) is "A", f where R'$_3$ and R'$_4$ may each independently be hydrogen, substituted or unsubstituted C1-C6 alkyl, substituted or unsubstituted C3-C8 cycloalkyl, substituted or unsubstituted $-(CH_2)_m-$C4-C10 aryl, substituted or unsubstituted $-(CH_2)_m-$C4-C10 aryloxy, $-CO(O)R''_3$, or R'$_3$ and R'$_4$ may form a ring structure of substituted or unsubstituted C4-C10 heterocycloalkyl through coupling, or a ring structure of substituted or unsubstituted C4-C10 heteroaryl;

R'$_5$, and R'$_6$ may each independently be hydrogen or C1-C3 alkyl; R''$_3$ is C1-C6 alkyl, wherein the substituted group may be at least one selected from the group consisting of hydroxy, a halogen, C1-C10 alkyl, C2-C10 alkenyl, C2-C10 alkynyl, C1-C10 alkoxy, C1-C10 alkoxycarbonyl, C3-C8 cycloalkyl, C2-C8 heterocycloalkyl, C4-C10 aryl, and C2-C10 heteroaryl;

m may be a natural number of 1 to 4; and the heteroatom may be at least one selected from N, O, and S.

More particularly, $R_1$ and $R_2$ may each independently be H, F, Cl, $-NO_2$, $NH_2$, $-N(CH_3)_2$, $-NHCOCH_3$, $-NHCOC_3H_5$ or $-NHCH_2C_6H_5F$;

$X_2$ and $X_3$ each may be CH;

$R_3$ and $R_6$ may each independently be H, a halogen, substituted or unsubstituted C1-C9 alkyl, substituted or unsubstituted $-(CH_2)_m-$C4-C10 aryl, substituted or unsubstituted $-(CH_2)_m-$C4-C10 aryloxy, substituted or unsubstituted $-(CHR'_5)_m-$C4-C10 heteroaryl, substituted or unsubstituted $-(CHR'_5)_m-$C4-C10 heterocycloalkyl, substituted or unsubstituted $-(CHR'_5)_m-$NR'$_3$R'$_4$, $-CO(O)R'_3$, $-CONR'_3R'_4$, $-NR'_3R'_4$, $-NR'_3(C(O)R'_4)$, or $-CH_2A$ when the compound of Formula (1) is "A";

$R_4$ may be a halogen, substituted or unsubstituted C2-C9 alkyl, substituted or unsubstituted C1-C10 alkoxy, substituted or unsubstituted C3-C8 cycloalkyl, substituted or unsubstituted C2-C8 heterocycloalkyl, substituted or unsubstituted C4-C10 aryl, substituted or unsubstituted C4-C10 aryloxy, substituted or unsubstituted C1-C10 heteroaryl, substituted or unsubstituted —(CH$_2$)$_m$—C4-C10 aryl, substituted or unsubstituted —(CH$_2$)$_m$—C4-C10 aryloxy, substituted or unsubstituted —(CHR'$_5$)$_m$—C4-C10 heteroaryl, substituted or unsubstituted —(CHR'$_5$)$_m$—NR'$_3$—C4-C10 aryl, substituted or unsubstituted —(CHR'$_5$)$_m$—C4-C10 heterocycloalkyl, substituted or unsubstituted —(CHR'$_5$)$_m$—NR'$_3$R'$_4$, —NR'$_3$R'$_4$, or -A when the compound of Formula (1) "A", where R'$_3$ and R'$_4$ are each independently hydrogen, substituted or unsubstituted C1-C6 alkyl, substituted or unsubstituted C3-C8 cycloalkyl, substituted or unsubstituted —(CH$_2$)$_m$—C4-C10 aryl, substituted or unsubstituted —(CH$_2$)$_m$—C4-C10 aryloxy, —COOC (CH$_3$)$_3$, or R'$_3$ and R'$_4$ may form a ring structure of substituted or unsubstituted C4-C10 heterocycloalkyl or substituted or unsubstituted C4-C10 heteroaryl through coupling;

R'$_5$ may be hydrogen or C1-C3 alkyl;

wherein a substituted group may be at least one selected from the group consisting of hydroxy, a halogen, C1-C10 alkyl, C2-C10 alkenyl, C2-C10 alkynyl, C1-C10 alkoxy, C1-C10 alkoxycarbonyl, C3-C8 cycloalkyl, C2-C8 heterocycloalkyl, C4-C10 aryl, and C2-C10 heteroaryl;

m may be a natural number of 1 to 4; and the heteroatom may be at least one selected from N, O, and S.

More particularly,

R$_3$ and R$_6$ may each independently be H, substituted or unsubstituted C1-C3 alkyl, substituted or unsubstituted —(CH$_2$)$_m$—C5-C6 aryl, substituted or unsubstituted —(CH$_2$)$_m$—C5-C6 aryloxy, substituted or unsubstituted —(CHR'$_5$)$_m$—C4-C6 heteroaryl, substituted or unsubstituted —(CHR'$_5$)$_m$—C4-C6 heterocycloalkyl, substituted or unsubstituted —(CHR'$_5$)$_m$—NR'$_3$R'$_4$, —CO (O)R'$_3$, or —CH$_2$A when the compound of Formula (1) is "A", where R'$_3$ and R'$_4$ may each independently be hydrogen, C1-C5 alkyl, or C3-C5 cyclo alkyl, or R'$_3$ and R'$_4$ may form a ring structure of substituted or unsubstituted C4-C10 heterocycloalkyl through coupling; R'$_5$ may be H;

the substituted group is methyl, a halogen, or hydroxy; and

M may be 1 to 3.

More particularly, the halogen may be fluorine or chlorine and the aryl may be C6 aryl.

More particularly,

R$_4$ may be a halogen, substituted or unsubstituted C2-C5 alkyl, substituted or unsubstituted C1-C3 alkoxy, substituted or unsubstituted C3-C6 cycloalkyl, substituted or unsubstituted C4-C6 aryl, substituted or unsubstituted —(CH$_2$)$_m$—C5-C6 aryl, substituted or unsubstituted C4-C10 aryloxy, substituted or unsubstituted —(CH$_2$)$_m$—C5-C6 aryloxy, substituted or unsubstituted C5-C6 heteroaryl, substituted or unsubstituted —(CHR'$_5$)$_m$—C5-C6 heteroaryl, substituted or unsubstituted C4-C6 heterocycloalkyl, substituted or unsubstituted —(CHR'$_5$)$_m$—C3-C6 heterocycloalkyl, —NR'$_3$R'$_4$, substituted or unsubstituted —(CHR'$_5$)$_m$—NR'$_3$—C5-C6 aryl, substituted or unsubstituted —(CHR'$_5$)$_m$—NR'$_3$R'$_4$, or -A when the compound of Formula (1) is "A";

R'$_3$ and R'$_4$ may each independently be hydrogen, methyl, ethyl, or —COOC (CH$_3$)$_3$, or R'$_3$ and R'$_4$ may form a ring structure of substituted or unsubstituted C4-C6 heterocycloalkyl through coupling; R'$_5$ may be H, methyl, ethyl, propyl, or butyl;

a substituted group may be methyl, a halogen, hydroxy; and

M may be 1 or 2.

More particularly, the halogen may be fluorine and aryl may be C6 aryl.

The compound of Formula (3) and the compound of Formula (4) may be exemplified by one of compounds below, but the present invention is not limited to compounds below.

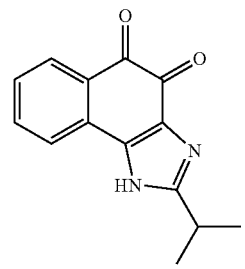

1

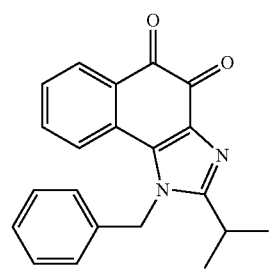

2

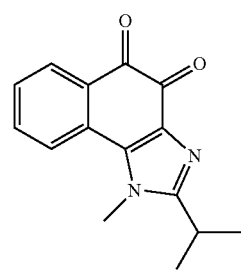 [SMILES: Cn1c(C(C)(C)C)nc2c1-c1cccnc1C(=O)C2=O]

3

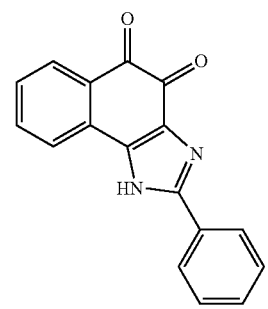

4

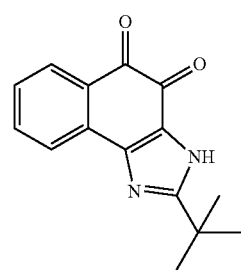

5

6
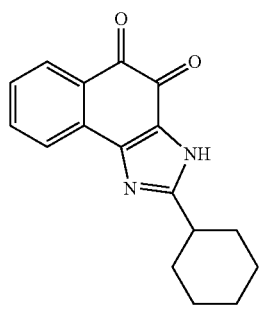
7
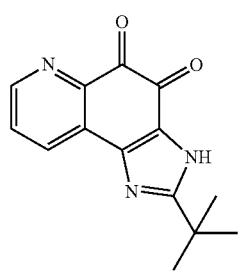
8
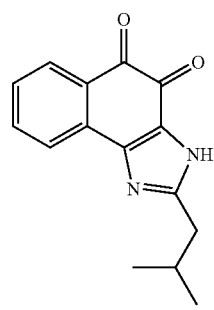
14
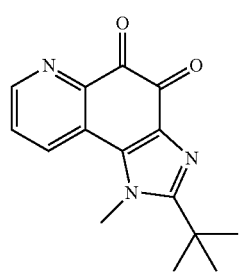
9
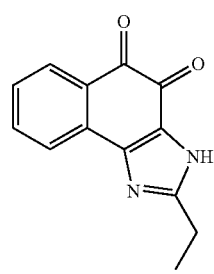
10
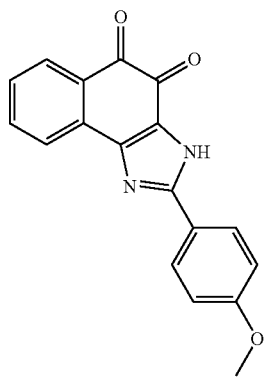
11
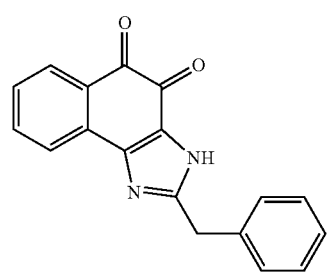
12
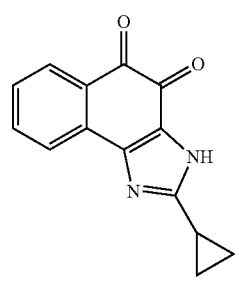
15
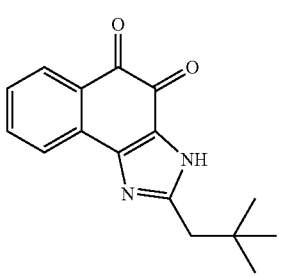
16
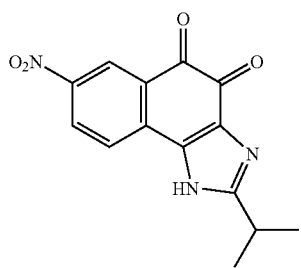

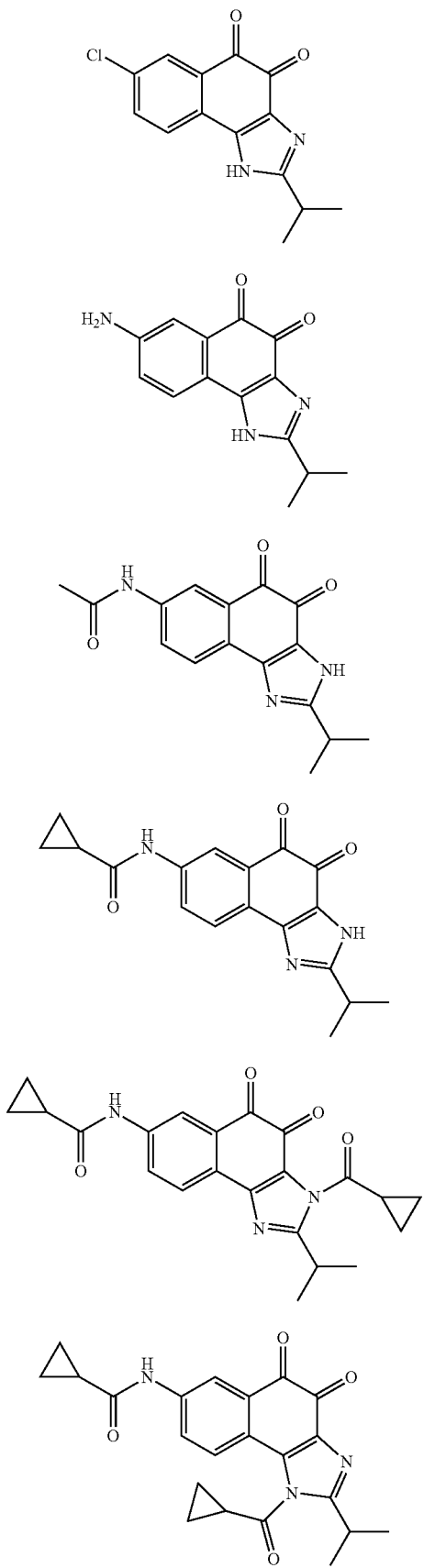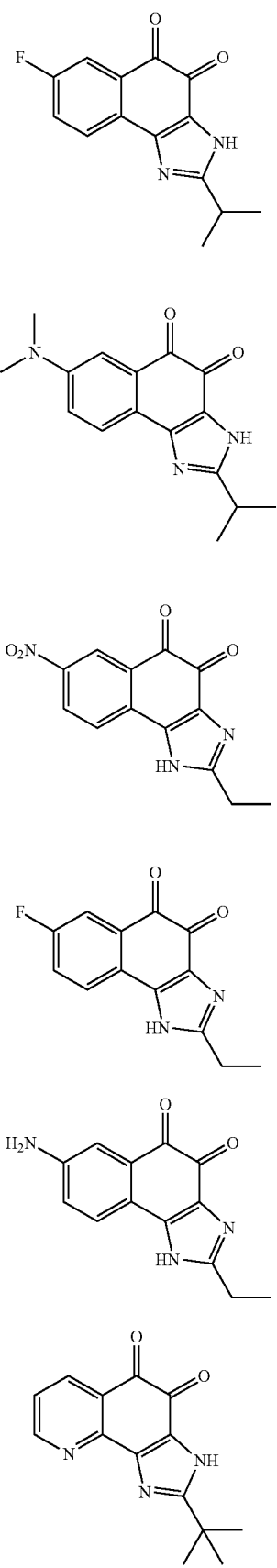

28
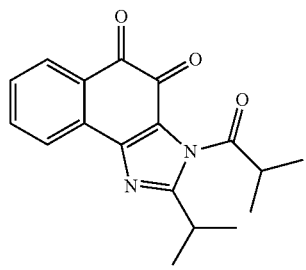
29
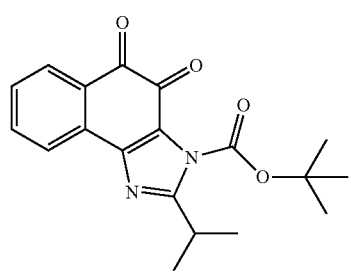
30
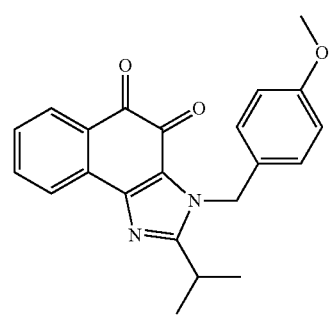
31
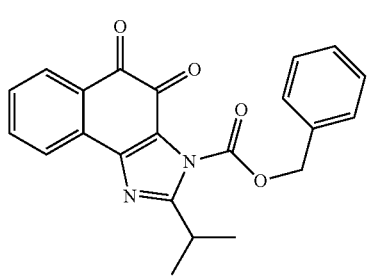
32
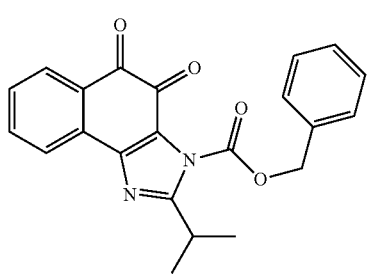
33
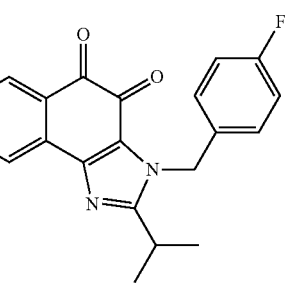
34
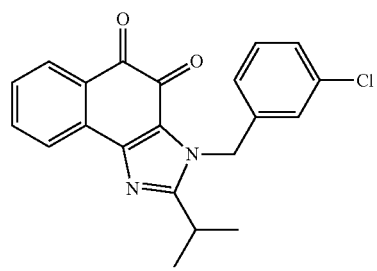
35
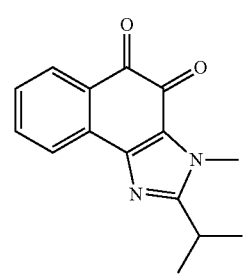
36
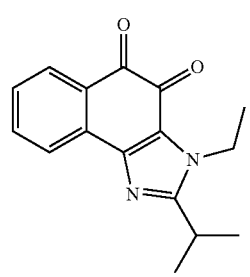
37
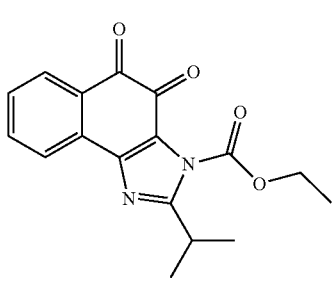
38
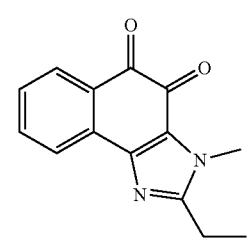

-continued
39
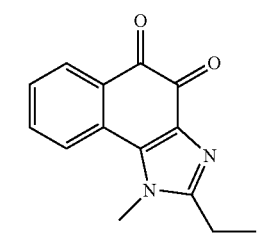
40
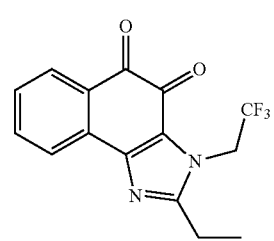
41
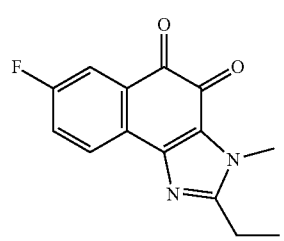
42
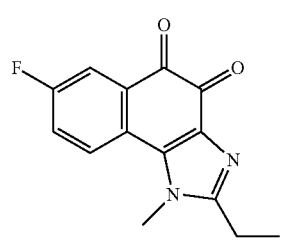
43
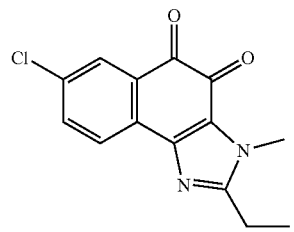
44
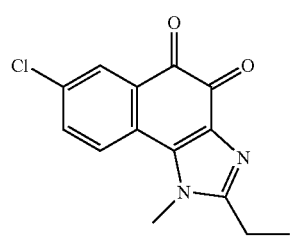
-continued
45
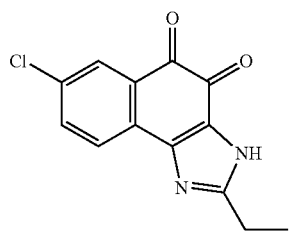
46
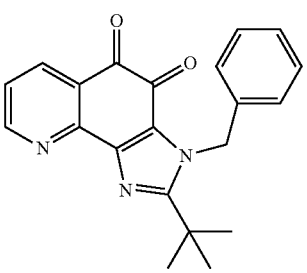
47
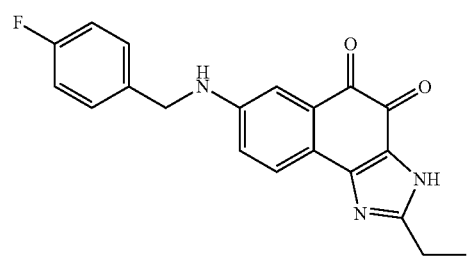
48
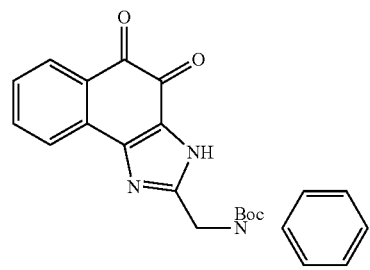
49
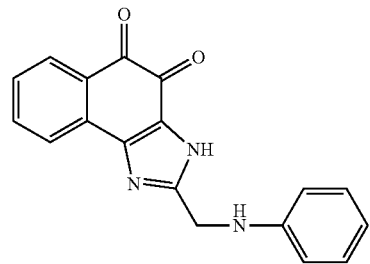
50
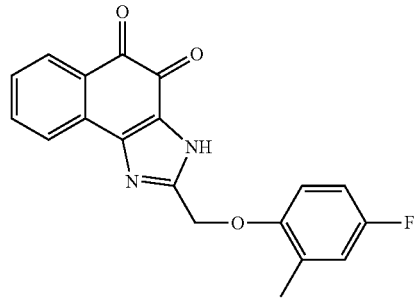

51
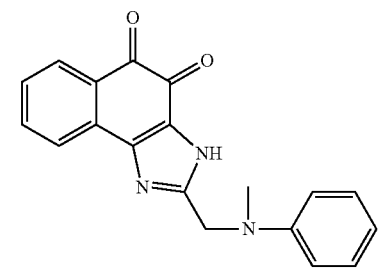
52
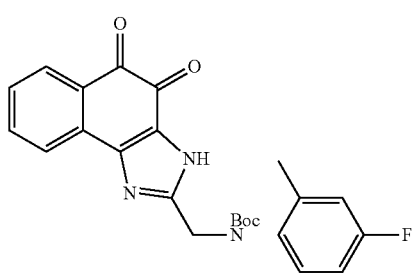
53
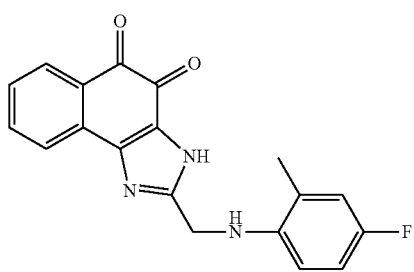
54
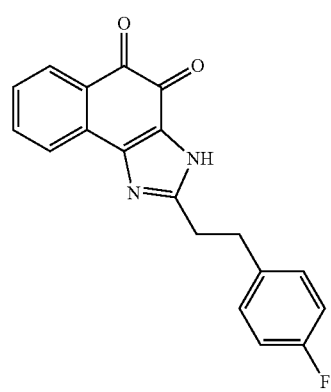
55
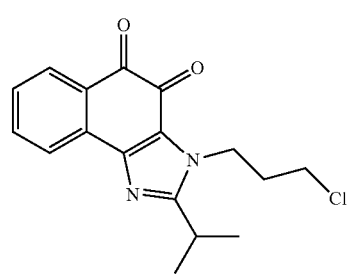
56
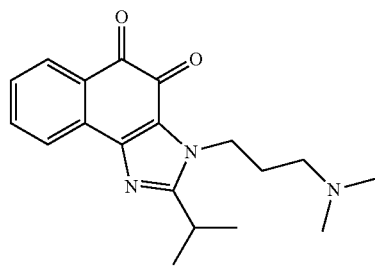
57
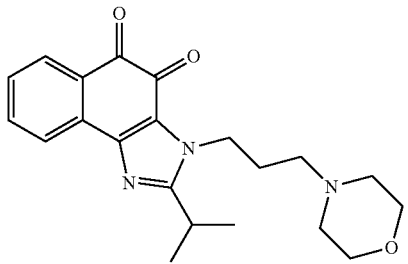
58
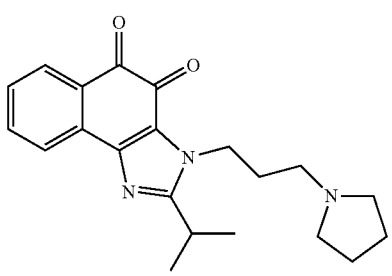
59
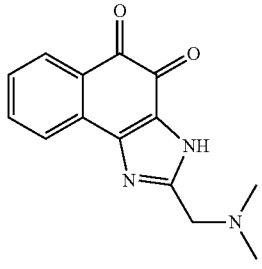
60
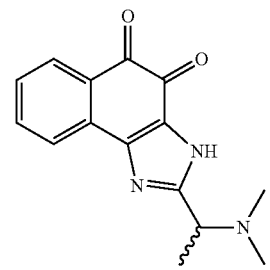
61
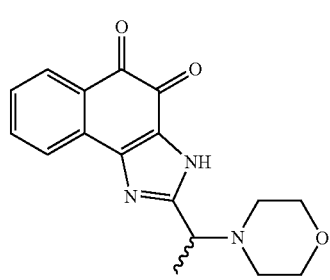

62
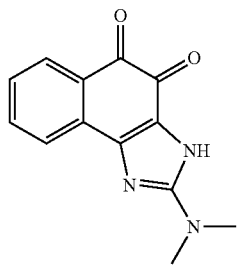
63
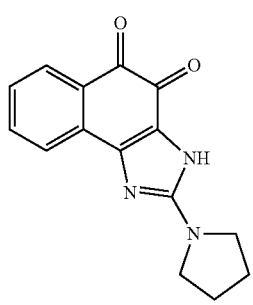
64
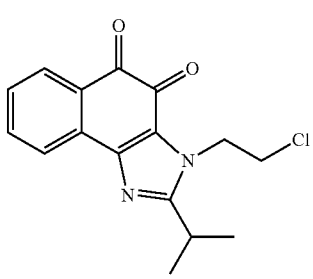
65
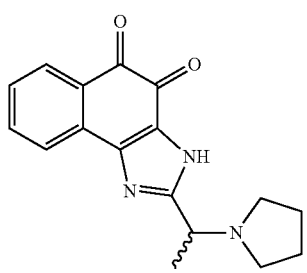
66
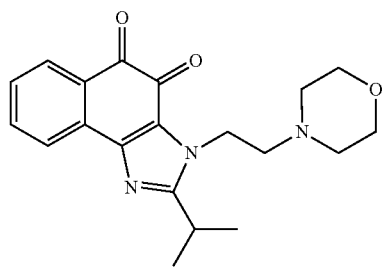
67
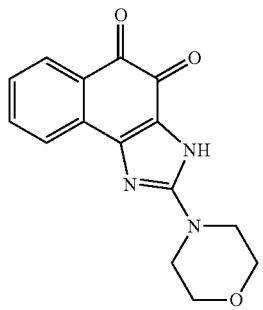
68
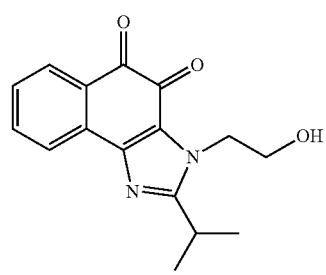
69
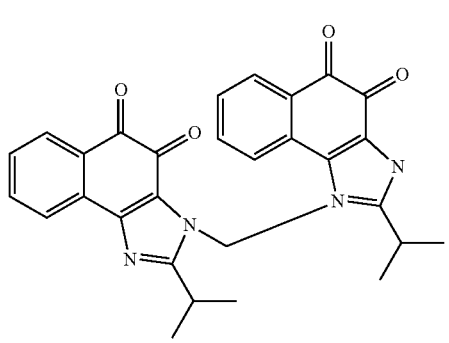
70
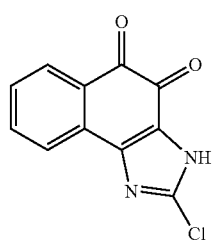
71
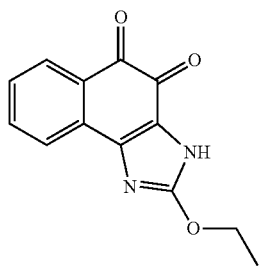

-continued
72
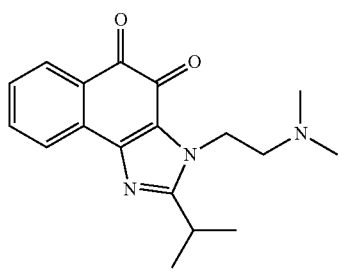
73
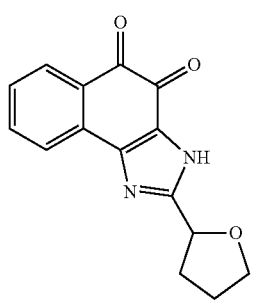
74
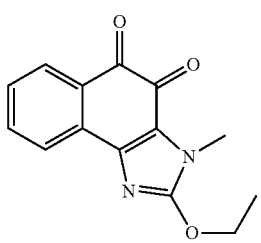
75
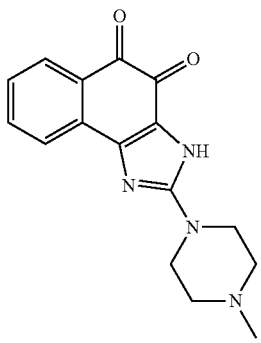
76
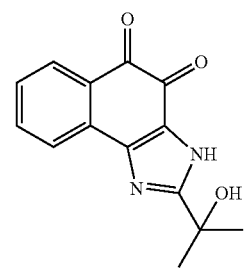
-continued
77
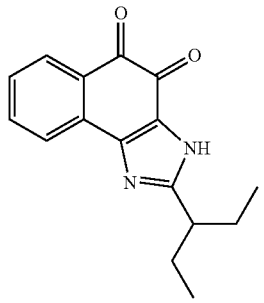
78
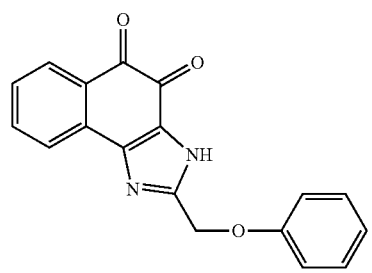
79
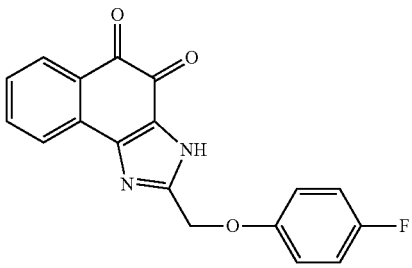
80
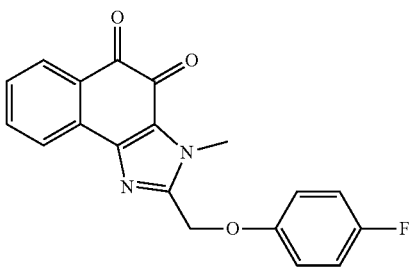
81
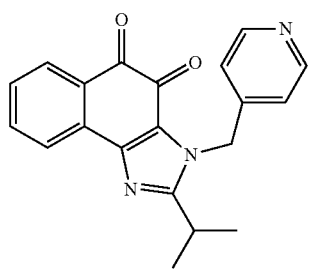

-continued
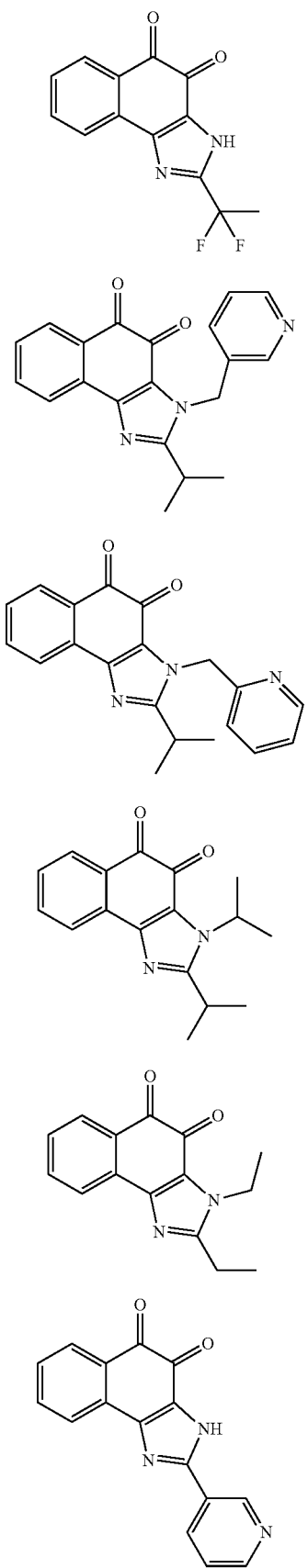
82
83
84
85
86
87
-continued
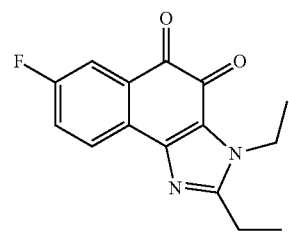
88
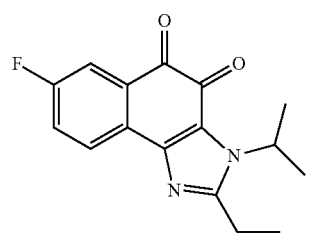
89
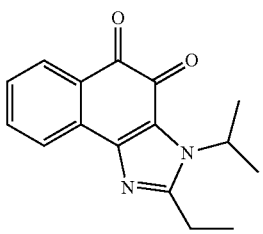
90
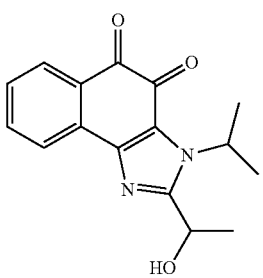
91
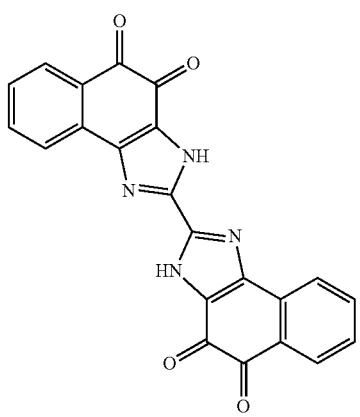
92

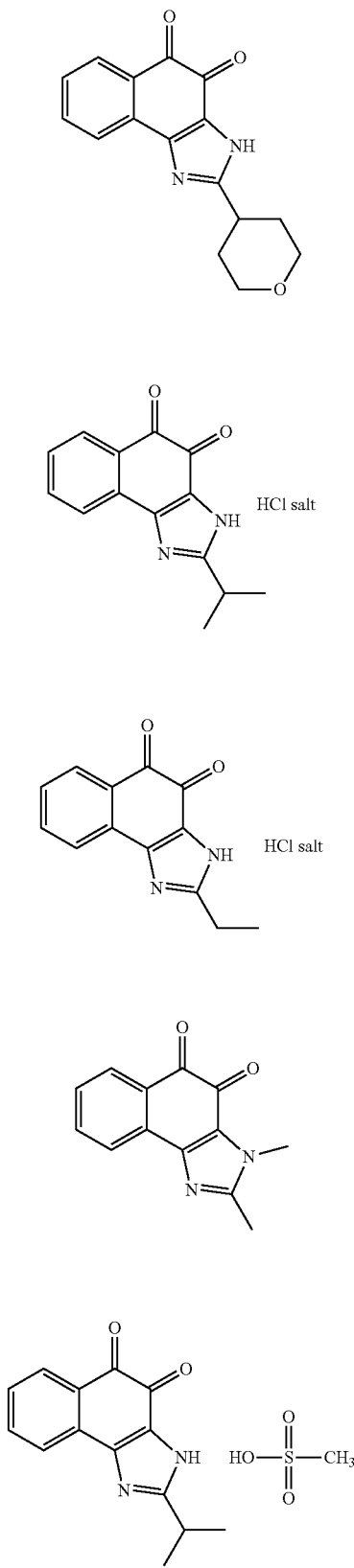
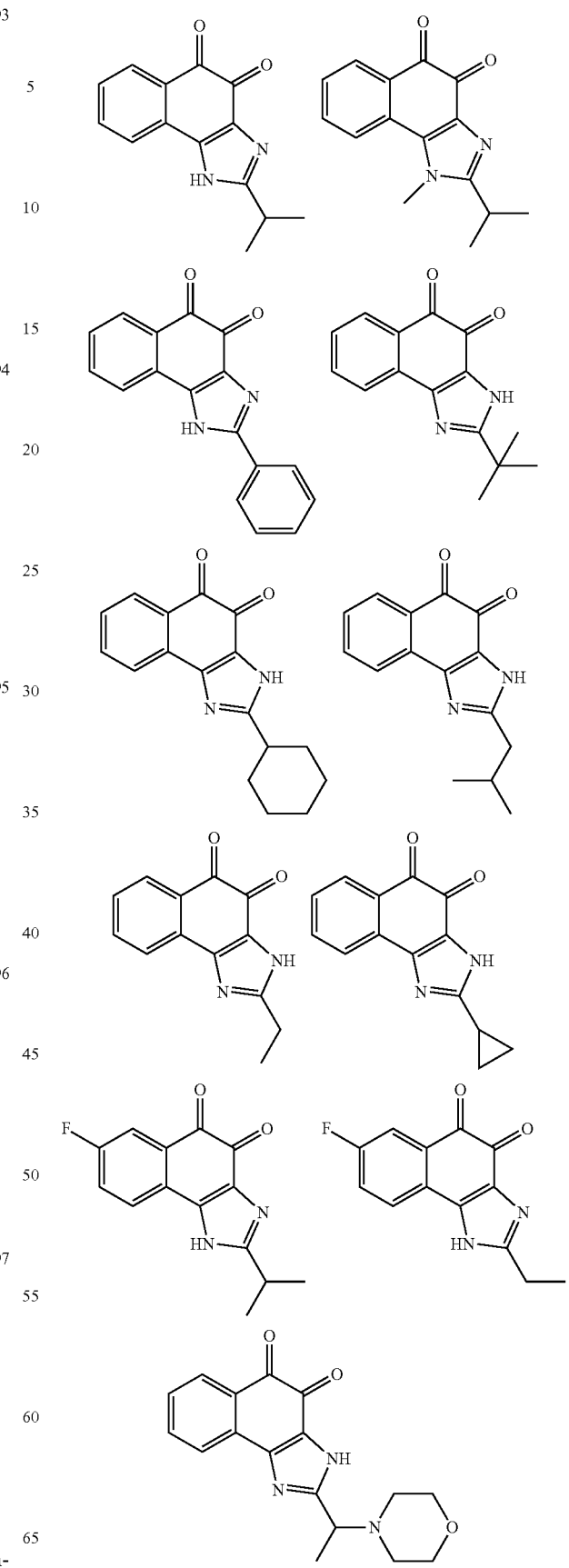
More preferably, the compound of Formula and the compound of Formula (4) may be one of compounds below.

-continued

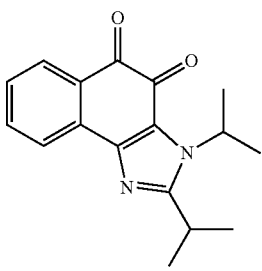

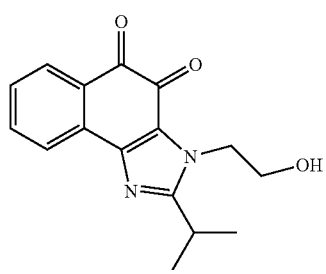

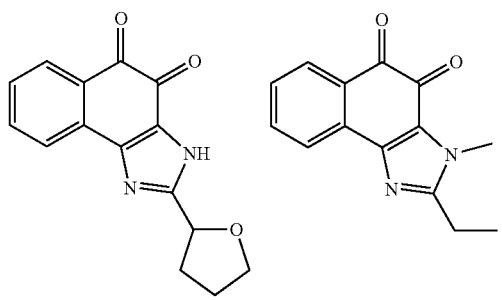

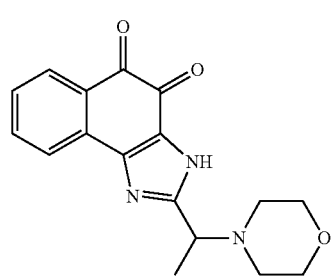

More particularly, the compound of Formula and the compound of Formula (4) may be one of compounds below.

-continued

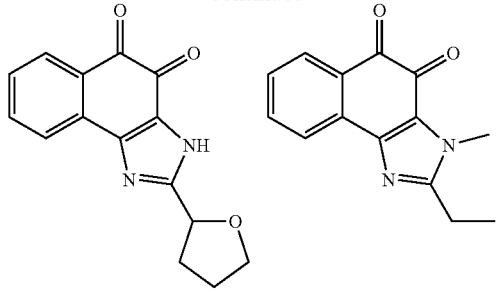

In addition, the present invention provides a method of preparing the compound of Formula (1).

Those skilled in the art ("a person skilled in the art") can prepare compounds based on the structure of Formula (1) according to a variety of methods. Thus, the present invention is intended to cover such methods. That is, the compound of Formula (1) may be prepared by randomly combining a variety of synthesis methods used in the prior art of the present invention. Therefore, the scope of the present invention is not limited thereto.

In one embodiment, a method of preparing the compound of Formula (1) may include, depending on a structure thereof:

A) synthesizing a compound of Formula (7) below by reacting a compound of Formula (5) below and a compound of Formula (6) below under basic conditions;

B) reacting the compound generated in the synthesizing (A) and $HNO_3$ under acidic conditions to introduce —$NO_2$ into a compound of Formula (7) below;

C) reducing —$NO_2$ to —$NH_2$ through reduction of the compound generated in the introducing (B);

D) cyclizing the compound generated in the reducing (C) under acidic conditions; and E) generating a final product through selectively oxidation after selectively reacting the compound generated in the cyclizing (D) under basic conditions.

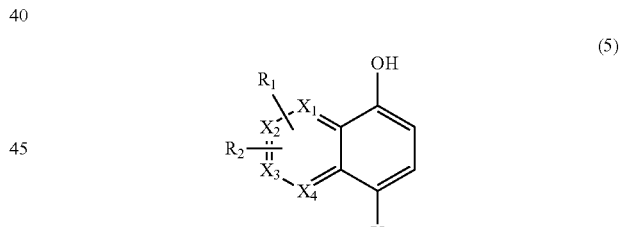

(5)

(6)

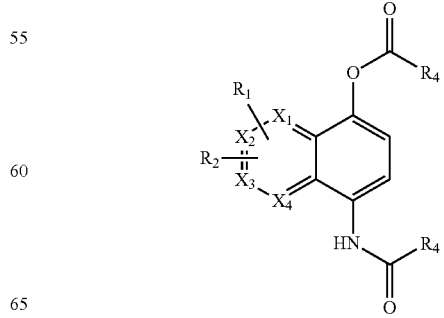

(7)

wherein $X_1$, $X_2$, $X_3$, $X_4$, $R_1$, $R_2$, and $R_4$ are the same as defined in Formula (1);

Z' is a halogen or R'COO—, where R' is substituted or unsubstituted C1-C9 alkyl, substituted or unsubstituted —(CH$_2$)$_m$—C4-C10 aryl, substituted or unsubstituted —(CH$_2$)$_m$—C4-C10 aryloxy, or substituted or unsubstituted C4-C10 aryl, wherein the substituted group is at least one selected from the group consisting of hydroxy, a halogen, C1-C10 alkyl, C2-C10 alkenyl, C2-C10 alkynyl, C1-C10 alkoxy, C1-C10 alkoxycarbonyl, C3-C8 cycloalkyl, C3-C8 heterocycloalkyl, C4-C10 aryl, and C5-C10 heteroaryl; and Y is —NH$_2$, —NH$_3$Z or —NO$_2$, where Z is a halogen.

In —NH$_3$Z defined above, —NH$_2$ and HZ may have a coordinate covalent bond.

The basic conditions of the present invention may be formed using triethyl amine, diisopropylethylamine, or pyridine, but the present invention is not limited thereto.

The acidic conditions of the present invention may be formed using nitric acid, sulfuric acid, acetic acid, or acetic acid anhydride, but the present invention is not limited thereto.

The reduction in the present invention may be, for example, hydrogenation. Hydrogenation is a process in which hydrogen is reacted with a metal catalyst such as Pd/C or the like, which is widely known in the art. Therefore, detailed description thereof will be omitted.

In the present invention, the expression "cyclizing" means that a ring is formed in the reaction product.

In the present invention, the expression "selectively" means that a corresponding reaction may be included or may not be included in some cases.

In particular, in Formula (5), $X_1$ and $X_4$ may each independently be CH or N $X_2$ and $X_3$ may be CH.

In the present invention, between the introducing and the reducing, processes below may be further included:

B-1) ester hydrolyzing the compound generated in the introducing (B); and

B-2) reacting the compound generated in the ester hydrolyzing (B-1) with R$_3$Z or R$_6$Z, where R$_3$ and R$_6$ are the same as defined Formula (1) and Z is a halogen.

The ester hydrolysis is widely known in the art. Thus, detailed description thereof will be omitted.

The method may further include at least one process sequentially selected from the group consisting of:

F) reacting the compound generated in the generating (E) with HNO$_3$ under acidic conditions;

G) reducing NO$_2$ to —NH$_2$ through reduction of the compound generated in the reacting (F); and H) reacting the compound generated in the reducing (G) with MZ", where M is hydrogen or a bivalent metal and Z" is a halogen, under acidic conditions to generate a final product.

The expression "at least one process sequentially selected from" means that the process (F), or (F) and (G), or (F), (G), and (H) may be selected.

In addition, the present invention may include:

F) reacting the compound generated in the generating (E) with HNO$_3$ under acidic conditions;

G) reducing —NO$_2$ to —NH$_2$ through reduction of the compound generated in the reacting (F); and I) reacting the compound generated in the reducing (G) with R$_1$Z" or R$_2$Z", where R$_1$ and R$_2$ each are the same as defined in claim 1 and Z" is a halogen, to generate a final product.

In another embodiment, a process below may be further included:

F') reacting the compound generated in the generating (E) with (R$_6$)$_2$O, R$_3$Z" or R$_6$Z", where R$_3$ and R$_6$ each are the same as defined Formula (1) and Z" is a halogen, to generate a final product.

In addition, a process below may be further included:

G') reacting the compound generated in the reacting (F') with R$_8$R$_9$NH to generate a final product.

R$_8$ and R$_9$ may each independently be hydrogen or C1-C5 alkyl, R$_8$ and R$_9$ may form a ring structure of C4-C10 heterocycloalkyl or a ring structure of C4-C10 heteroaryl through coupling, wherein a heteroatom may be at least one selected from the group consisting of N, O, and S.

In another embodiment, a process below may be further included:

F") introducing —NO$_2$ by reacting the compound generated in the generating (E) with HNO$_3$ under acidic conditions to generate a final product.

In addition, a process below may be further included:

G") reducing —NO$_2$ to —NH$_2$ through hydrogenation of the compound generated in the introducing (F") to generate a final product.

In addition, a process below may be further included:

H") reacting the compound generated in the reducing (G") with any one selected from the group consisting of (i) to (iv) below to generate a final product, i) MZ" under acidic conditions, where M is hydrogen or a bivalent metal and Z" is a halogen, ii) R'$_2$COCl or (R'$_2$)$_2$O, where R'$_2$ is the same as defined in claim 1, under basic conditions, iii) paraformaldehyde (paraformaldehyde) or R$_7$COH (R$_7$ is C1-C4 alkyl) in the presence of NaBH$_3$CH or NaBH$_4$, and iv) R$_3$Z$_2$" or R$_6$Z$_2$", where R$_3$ and R$_6$ each are the same as defined in claim 1 and Z$_2$" is a halogen, after reacting with MZ1" under acidic conditions, where M is hydrogen or bivalent metal and, Z$_1$" is a halogen).

In this regard, a process below may be further included:

I") reacting the compound generated in the reacting (H") with R$_3$Z" or R$_6$Z", where R$_3$ and R$_6$ each are the same as defined in claim 1 and Z" is a halogen, to generate a final product.

In another embodiment of the present invention, the method of preparing the compound of Formula (1) may include:

A$_1$) reacting the compound of Formula (5) with a base and then with Z'Z, where Z' is C$_6$H$_5$CH$_2$—, CH$_3$OC$_6$H$_4$CH$_2$— or —CH$_3$— and Z is a halogen;

B$_1$) reacting the compound generated in the reacting (A$_1$) with the compound of Formula (6) and then reacting HNO$_3$ under acidic conditions to introduce —NO$_2$;

C$_1$) reducing —NO$_2$ to —NH$_2$ through reduction the compound generated in the reacting (B$_1$);

D$_1$) cyclizing the compound generated in the reducing (C$_1$) under acidic conditions; and E$_1$) generating a final product through oxidation after hydrolyzing the compound generated in the cyclizing (D$_1$), wherein the compounds of Formulas (5) and (6) are the same as defined in claim 1.

The base may be any base widely used in the art, for example, a strong base, more particularly K$^+$ (CH$_3$)$_3$CO$^-$ or K$_2$CO$_3$.

In addition, the present invention may include a process below:

F$_1$) reacting the compound generated in the generating (E$_1$) with R$_3$Z" or R$_6$Z", where R$_3$ and R$_6$ each are the same as defined in claim 1 and Z" is a halogen, to generate a final product.

In another embodiment of the present invention, the method of preparing the compound of Formula (1) may include:

$A_2$) reacting the compound of Formula (5) with Z'Z, where Z' is $C_6H_5CH_2$—, $CH_3OC_6H_4CH_2$— or —$CH_3$— and Z is a halogen;

$B_2$) reducing —$NO_2$ to —$NH_2$ through reduction of the compound generated in the reacting ($A_2$);

$C_2$) reacting the compound generated in the reducing ($B_2$) with the compound of Formula (6) under a base condition and then reacting with $HNO_3$ under acidic conditions to introduce —$NO_2$;

$D_2$) reducing —$NO_2$ to —$NH_2$ through reduction of the compound generated in the reacting ($C_2$);

$E_2$) cyclizing the compound generated in the reducing ($D_2$) under acidic conditions; and $F_2$) generating a final product through oxidation after hydrogenating the compound generated in the cyclizing ($E_2$), wherein the compounds of Formulas (5) and (6) are the same as defined in claim 10.

In this regard, in the compound of Formula (5), $X_1$ may be N, $X_2$, $X_3$, and $X_4$ may be CH, and Y may be $NO_2$.

Isolation of a mixture after finishing the reaction according to the present invention may be carried out through conventional post-processing methods, for example, column chromatography, recrystallization, HPLC, or the like.

The preparation method may further include, between the reducing ($D_2$) and the cyclizing ($E_2$), a process below:

$D_2$-1) reacting the compound generated in the reducing ($D_2$) with $R_3Z$ or $R_6Z$, where $R_3$ and $R_6$ are the same as defined Formula (1) and Z is a halogen.

In another embodiment of the present invention, the method of preparing the compound of Formula (1) may include:

$A_3$) reacting the compound of Formula (5) with Z'Z, where Z' is $C_6H_5CH_2$—, $CH_3OC_6H_4CH_2$— or —$CH_3$— and Z is a halogen;

$B_3$) reducing —$NO_2$ to —$NH_2$ through reduction of the compound generated in the reacting ($A_3$);

$C_3$) introducing —$NO_2$ by reacting the compound generated in the reducing ($B_3$) with $HNO_3$ under acidic conditions and then reducing —$NO_2$ to —$NH_2$;

$D_3$) reacting the compound generated in the introducing ($C_3$) with $R_4COOH$, $(R_4)_2O$, carbonyldiimidazole (CDI), $(CH_2)_{n'}(COOH)_2$ or $(R_4)_4C$, where $R_4$ is the same as defined in claim 1 and n' is an integer of 0 or more;

$E_3$) cyclizing the compound generated in the reacting ($D_3$) selectively under acidic conditions and selectively reacting with $R_{10}R_{11}NH$, and then reducing; and $F_3$) generating a final product through oxidation of the compound generated in the cyclizing ($E_3$).

The compound of Formula (5) is the same as defined in claim 10, and $R_{10}$ and $R_{11}$ may each independently be hydrogen, a halogen, substituted or unsubstituted C1-C5 alkyl, or $R_8$ and $R_9$ may form a ring structure of substituted or unsubstituted C4-C10 heterocycloalkyl through coupling, or a ring structure of substituted or unsubstituted C4-C10 heteroaryl, where the heteroatom may be at least one selected from the group consisting of N, O, and S, and a substituted group may be methyl, ethyl or propyl.

The reduction may be, for example, hydrogenation.

The expression "selectively" means that performance or not of a corresponding reaction depends on a synthesized compound type.

For example, the present invention may further include a process below:

$G_3$) reacting the compound generated in generating ($F_3$) with $CF_3COOH$ (Trifluoroacetic acid; TFA) or a C1-C4 alkyl to generate a final product.

In addition, the present invention may include processes below:

$C_3'$) reacting the compound generated in the reducing ($B_3$) with $HNO_3$ under acidic conditions to introduce —$NO_2$;

$D_3'$) reacting the compound generated in the reacting ($C_3'$) with $R_4COOZ_1$, $(R_4)_2O$, or $(R_4)_4C$, where $R_4$ is the same as defined in claim 1 and $Z_1$ is hydrogen or a halogen;

$E_3'$) reducing the compound generated in the reacting ($D_3'$) and then cyclizing under acidic conditions; and $F_3'$) generating a final product through oxidation of the compound generated in the reducing ($E_3'$).

In addition, the present invention may further include a process below:

$G_3'$) reacting the compound generated in the generating ($F_3$) or ($F_3'$) with $R_3Z_2$ or $R_6Z_2$, where $R_3$ and $R_6$ are the same as defined Formula (1) and $Z_2$ is a halogen, to generate a final product.

Meanwhile, the method of preparing the compound of Formula (1) according to the present invention comprises:

a) reacting the compound of Formula (8) below and $H_2NCH_2CH_2NH_2$ in a protic solvent to cyclize the same; and b) generating a final product through oxidation of the compound generated in the reacting (a).

In particular, in the reacting (a), $H_2NCH_2CH_2NH_2$ may be reacted in a protic solvent and the protic solvent may be, for example, ethanol or acetic acid.

The present invention will be described in more detail through examples and experimental examples below.

In addition, the present invention provides a pharmaceutical composition for treatment and prevention of metabolic syndromes including (a) a therapeutically effective amount of the compound of Formula (1) according to claim 1 and/or a pharmaceutically acceptable salt, hydrate, solvate, tautomer, enantiomer, and/or pharmaceutically acceptable diastereomer thereof, and (b) a pharmaceutically acceptable carrier, diluent, or vehicle, or a combination thereof.

The expression "pharmaceutical composition" means a mixture of the compound according to the present invention and chemical ingredients such as a diluent, a carrier, and the like. A pharmaceutical composition aids in administration of a compound to organisms. As methods to administer a compound, there are oral, injection, aerosol, parenteral, and local administration, but the present invention is not limited thereto. A pharmaceutical composition may be obtained by reacting with acidic compounds such as hydrochloric acid, bromic acid, sulfuric acid, nitric acid, phosphoric acid, methanesulfonic acid, p-toluenesulfonic acid, salicylic acid, or the like.

The expression "therapeutically effective amount" means a therapeutically effective amount of active ingredient in a compound administered to alleviate or reduce one symptom or more of a target disorder or to delay initiation of clinical markers or symptoms of diseases requiring prevention. Therefore, "therapeutically effective amount" means an amount having (1) effects of slowing progression of a disease, (2) effects of partly stopping progression of a disease, and/or (3) effects of partly alleviating (preferably, eliminating) one symptom or more related to a disease. A therapeutically effective amount may be empirically determined by testing a compound in vivo and in vitro model systems publicly known for a disease requiring treatment.

The expression "carrier" is defined as a compound aiding in application of a compound to cells or tissues. For example, dimethyl sulfoxide (DMSO) is a conventional carrier facilitating addition of a variety of organic compounds to cells or tissues of organisms.

The expression "diluent" is defined as a compound stabilizing biological activity of a subject compound and diluted in water including the compound. In the art, a buffer solution including a dissolved salt is used as a diluent. As a conventionally used buffer solution, there is a phosphate buffered solution imitating a salt concentration of the human body. Since a buffer salt may control pH of a solution at low concentration, a buffer diluent has little effect on biological activity of a compound.

The compounds used in the present invention may be administered alone or as a pharmaceutical composition including other active ingredients, or proper carriers or vehicles. In this regard, technologies related to formulations and administration methods of compounds may be found in "Remington's Pharmaceutical Sciences," Mack Publishing Co., Easton, Pa., 18th edition, 1990.

The pharmaceutical composition according to the present invention may be prepared by publicly known methods using conventional mixing, dissolution, granulation, conservation, pulverization, emulsification, encapsulation, trapping, freeze-drying, or the like.

Therefore, the pharmaceutical composition according to the present invention may be prepared by a conventional method using at least one therapeutically acceptable carrier including vehicles or additives helping to prepare an active compound into a pharmaceutically acceptable formulation. A suitable formulation is determined according to a selected administration manner. Publicly known technology and any carriers and vehicles may be suitably used according to methods known in the art, for example, methods described in Remington's Pharmaceutical Sciences. The compound of Formula (1) according to the present invention may be formulated into an injectable formulation, an oral formulation, or the like.

For injectable formulation, the ingredients according to the present invention may be formulated into a liquid, preferably a therapeutically proper buffer such as Hank's solution, Ringer's solution, or a saline solution. For mucosal penetration administration, a non-penetrative agent suitable for a penetrated barrier is used in a formulation. Such non-penetrative agents are publicly known in the art.

For oral administration, compounds may be easily formulated by combining therapeutically acceptable carriers publicly known in the art with active compounds. Such carriers help the compounds according to the present invention to be formulated into tablets, drugs, powders, granules, confectioneries, capsules, liquids, gels, syrups, slurries, suspensions, and the like, preferably capsules, tablets, pills, powders, and granules, more particularly capsules. Tablets and pills are preferably prepared in enteric coating. Drug preparation for oral administration may be performed by mixing one compound or more according to the present invention with one vehicle or more. In some cases, tablets or confection cores may be obtained by pulverizing a reaction product mixture and treating a granule mixture after selectively adding a proper additive. As proper vehicles, there are fillers such as lactose, sucrose, mannitol, or sorbitol, corn starch, wheat starch, rice starch, potato starch, gelatin, gum tragacanth, methylcellulose, hydroxypropyl methylcellulose, sodium carboxymethylcellulose, and/or a cellulose based material such as polyvinylpyrrolidone (PVP). As needed, a disintegrating agent such as crosslinked polyvinyl pyrrolidone, agar, or alginic acid or salts thereof such as alginic acid sodium, a lubricant such as magnesium stearate, or a carrier such as a binder may be added thereto.

Examples of pharmaceutical preparations used for oral administration include a smooth sealed capsule prepared from gelatin and a plasticizer such as glycol or sorbitol, and a hard-shelled capsule prepared from gelatin. The hard-shelled capsule is prepared from a mixture of a filler such as lactose, a binder such as starch, and/or a lubricant such as talc or magnesium stearate and may include active ingredients. In a soft capsule, active compounds may be dissolved or dispersed in proper solutions such as fatty acids, liquid paraffin, or liquid polyethylene glycol. In addition, a stabilizer may be included therein. All preparations for oral administration must have a content suitable for such administration.

The compounds may be formulated for parenteral administration by injection, e.g., by bolus injection or continuous infusion. A formulation for injection may be provided in a unit amount type using, for example, an ampoule including a preservative or a multi-dose container. A composition may be an oil or liquid vehicle-type suspension, a solution, or an emulsion and may include ingredients such as a suspension, a stabilizer and/or a dispersant for a formulation.

In addition, active ingredients may be powders for application of a proper vehicle such as water as a sterilized non-pyrogenic material such as water before application.

The compounds, for example, may be formulated into compositions for rectal administration such as suppositories or retention enema agents including conventional suppository substrates such as cocoa butter or other glycerides.

A pharmaceutical composition suitable for the present invention includes a composition containing active ingredients in effective amounts to accomplish an intended object thereof. More particularly, the expression "therapeutically effective amount" means an amount effective for preservation of a treated subject or prevention, reduction, or alleviation of disease symptoms. The therapeutically effective amount may be determined by a person skilled in the art.

When formulated in a unit amount, the compound of Formula (1) as an active ingredient is preferably included in a unit amount of approximately 0.1 to 1,000 mg. An administration amount of the compound of Formula (1) is determined according to prescription by a physician considering the weight and age of a patient, and characteristics and severity of a disease. However, a general administration amount required for adult treatment is approximately 1 to 1000 mg per day depending on a frequency and intensity of administration. In adults, a total administration amount intramuscularly or intravenously administered per day is approximately 1 to 500 mg and some patients are preferably administered a higher amount.

The metabolic diseases according to the present invention may be obesity, fatty liver syndrome, arteriosclerosis, stroke, myocardial infarction, cardiovascular disorders, ischemic heart diseases, diabetes, hyperlipidemia, hypertension, retinitis or renal failure, Huntington's disease, or inflammation, particularly fatty liver syndrome, diabetes, or Huntington's disease, but the present invention is not limited thereto.

In addition, the present invention provides a method of treating or preventing metabolic syndromes using a therapeutically effective amount of the compound of Formula (1) according to claim 1 or a pharmaceutically acceptable salt, hydrate, solvate, tautomer, enantiomer, or pharmaceutically acceptable diastereomer thereof. The expression "treating" means that progression of a disease is stopped or delayed when applied to a subject having disease symptoms and the expression "preventing" means that onset of a disease is stopped or delayed by applying to a subject having high disease onset risk although disease symptoms are not yet exhibited.

Advantageous Effects

As described above, a novel 1,2-naphthoquinone derivative according to the present invention causes system improvement through mitochondrial biosynthesis due to mitochondrial activation and change in motor muscle fiber related to endurance by inducing genetic changes typical of long-term calorie restriction and exercise such as activation of AMPK as an energy consumption mechanism according to energy environment change in cells, expression of PGC1a activating energy metabolism of mitochondria, and the like through increase in a ratio of NAD(P)+/NAD(P)H through NQO1 activity in vivo so as to exhibit exercise imitation effects. Therefore, a drug using the novel 1,2-naphthoquinone derivative as an effective ingredient may be usefully used to treat or prevent metabolic syndromes.

BRIEF DESCRIPTION OF THE DRAWINGS

The above and other objects, features and other advantages of the present invention will be more clearly understood from the following detailed description taken in conjunction with the accompanying drawing, in which.

MODE FOR INVENTION

Figure 1:
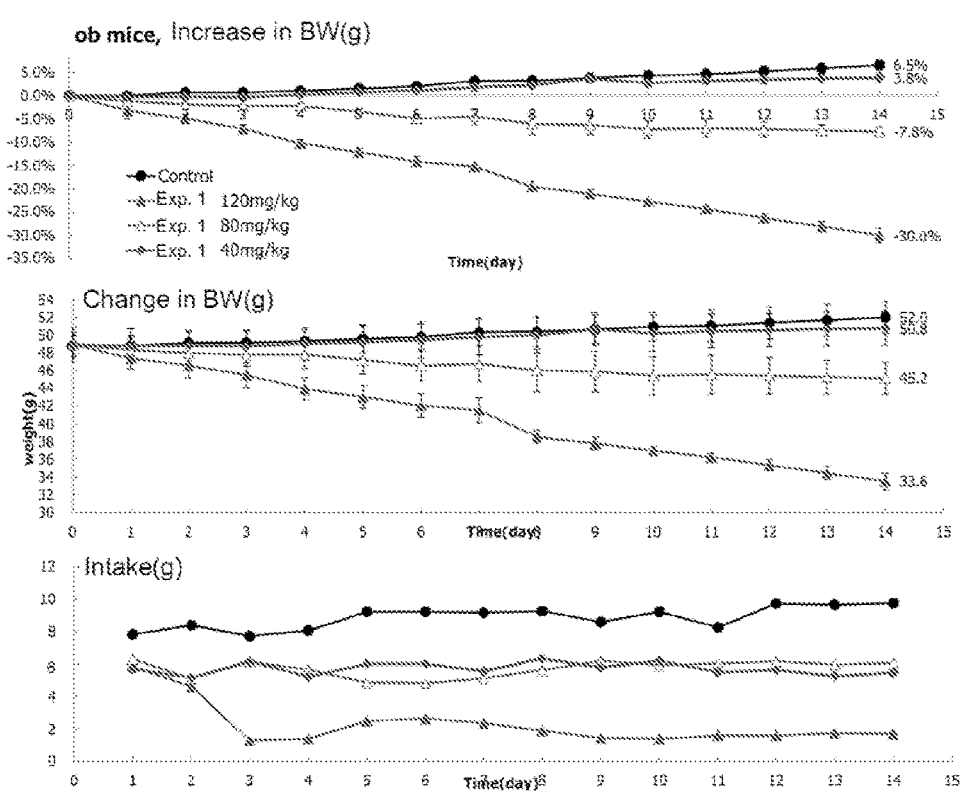
FIG. 1 illustrates graphs representing weight increase ratios, weight changes, and intake amounts in obese mice (ob/ob) administered a compound according to Example 1 and a control in Experimental Example 3-1.

Now, the present invention will be described in more detail with reference to the following examples. These examples are provided only for illustration of the present invention and should not be construed as limiting the scope and spirit of the present invention. In examples below, methods of preparing intermediates to prepare final compounds and methods of preparing final compounds using the intermediates will be described.

Herein, all temperature are in Celsius, unless mentioned otherwise.

EXAMPLE 1

Synthesis of Compound 1

2-isopropyl-1H-naphtho[2,1-d]imidazole-4,5-dione

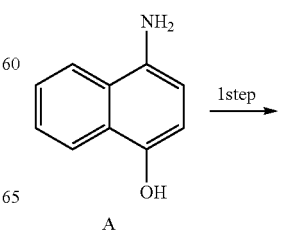

A

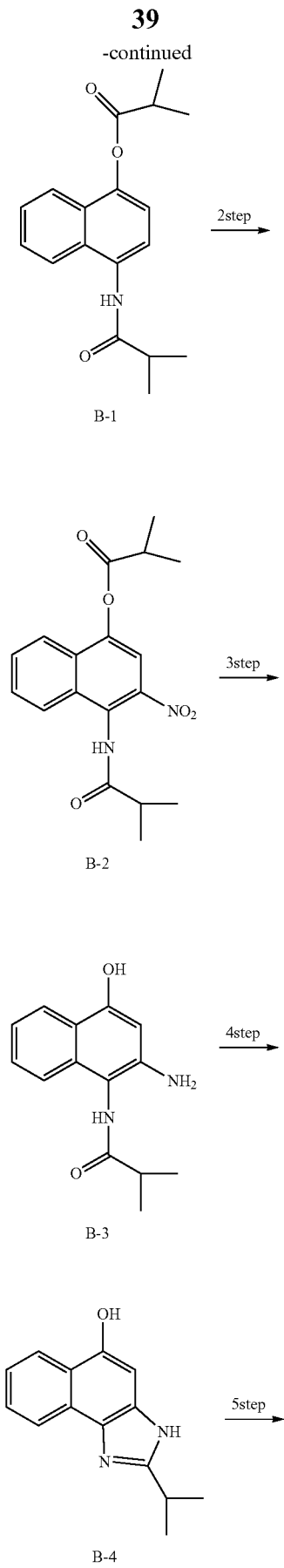

B-1

B-2

B-3

B-4

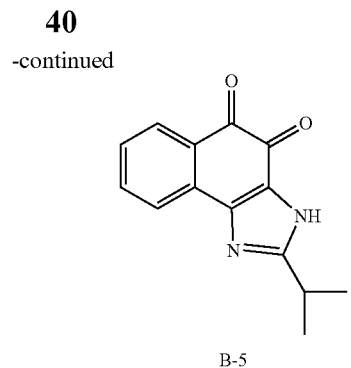

B-5

1) Step 1

Pyridine (5 ml) was added to compound A (4-amino-1-naphthol hydrochloride, 500 mg, 2.55 mmol) and then cooled in an ice bath. Subsequently, isobutyric anhydride (1.7 ml, 10.2 mmol) was added dropwise thereto. The reaction product was stirred for 2.5 hours at the same temperature. The reaction product was quenched using methanol and then vacuum evaporated to remove some pyridine. pH was adjusted to approximately pH 6.5 using a 1 N aqueous HCl solution after adding EA and distilled water thereto and then an organic layer was washed several times to remove a pyridine remainder. The organic layer was dried and filtered using $Na_2SO_4$ and then vacuum evaporated. A concentrated reaction product was purified through silica gel column chromatography, thereby obtaining Compound B-1 (686 mg, 90%).

2) Step 2

Compound B-1 (300 mg, 1.00 mmol) was added to acetic anhydride (3 ml) and then fuming nitric acid (0.20 ml, 2.00 mmol) was added dropwise thereto at 0° C. The reaction product was stirred for 1 hour and then filtered. In this regard, a filtered solid was Compound B-2 and the compound was washed several times with hexane, thereby obtaining Compound B-2 (217 mg, 63%).

$^1$H NMR (300 MHz, Acetone-$d_6$) δ 9.55 (s, 1H), 8.33 (d, J=6.6 Hz, 1H), 8.06 (d, J=6.2 Hz, 1H), 7.86 (s, 1H), 7.81-7.73 (m, 2H), 3.16-3.07 (m, 1H), 2.96-2.87 (m, 1H), 1.41 (d, J=7.0 Hz, 6H), 1.25 (d, J=7.0 Hz, 6H)

3) Step 3

Compound B-2 (500 mg, 1.45 mmol) was dissolved in ethanol (5 ml) and then Pd/C (50 mg) and hydrazine (0.29 ml, 5.81 mmol) were sequentially added thereto. The reaction product reacted for 1 hour at 70° C. The reaction product was cooled and filtered over Celite at room temperature to remove Pd/C. The filtrate was vacuum evaporated and purified via silica gel column chromatography, thereby obtaining Compound B-3 (232 mg, 51%).

$^1$H NMR (300 MHz, $CD_3OD$) δ 8.02 (d, J=8.4 Hz, 1H), 7.50 (d, J=8.0 Hz, 1H), 7.35 (t, J=8.0 Hz, 1H), 7.13 (t, J=8.1 Hz, 1H), 6.47 (s, 1H), 2.85-2.83 (m, 1H), 1.31 (d, J=7.0 Hz, 6H)

LC-MS m/z 245.1 (M+1)

4) Step 4

Acetic acid (15 ml) was added to Compound B-3 (700 mg, 2.86 mmol), followed by refluxing with stirring for three hours. Acetic acid was removed through vacuum evaporation and purified using silica gel column chromatography, thereby obtaining Compound B-4 (575 mg, 89%).

$^1$H NMR (300 MHz, $CD_3OD$) δ 8.30 (d, J=8.4 Hz, 2H), 7.60 (t, J=8.0 Hz, 1H), 7.47 (t, J=8.1 Hz, 1H), 6.99 (s, 1H), 3.35-3.28 (m, 1H), 1.46 (d, J=7.0 Hz, 6H)

LC-MS m/z 227.0 (M+1)

5) Step 5

Compound B-4 (50 mg, 0.22 mmol) was dissolved in DMF (2.5 ml) and then IBX (159 mg, 0.26 mmol) was added thereto. The reaction product was reacted for 1 hour at room temperature. After adding EA thereto, an organic layer was washed with saturated aqueous $NaHCO_3$. The separated organic layer was dried over $MgSO_4$ and then filtered. The filtrate was vacuum evaporated and then purified using column chromatography, thereby obtaining Compound B-5 (47 mg, 89%).

$^1H$ NMR (300 MHz, $CDCl_3$) δ 9.96 (N—H, s, 1H), 8.06 (d, J=7.7 Hz, 1H), 7.99 (d, J=7.7 Hz, 1H), 7.65 (t, J=7.7 Hz, 1H), 7.44 (t, J=7.7 Hz, 1H), 3.26-3.17 (m, 1H), 1.45 (d, J=7.0 Hz, 6H)

EXAMPLE 2

Synthesis of Compound 2

1-benzyl-2-isopropyl-1H-naphtho[2,1-d]imidazole-4,5-dione

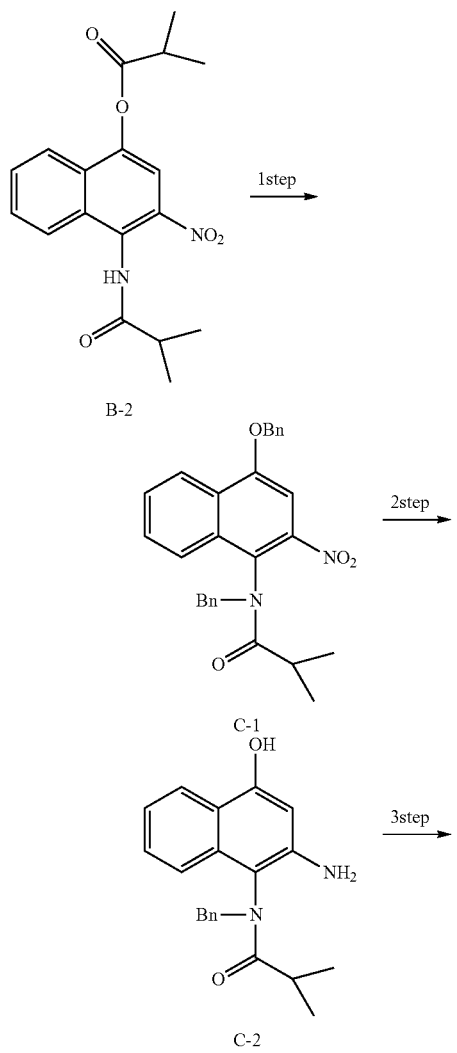

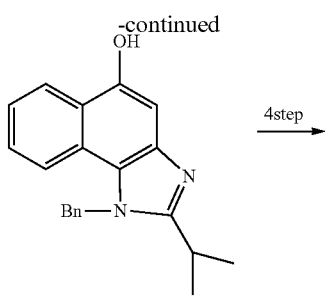

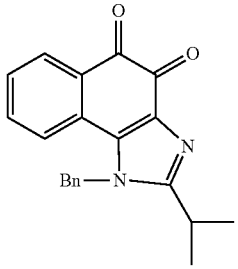

1) Step 1

Acetone (8 ml) was added to B-2 (429 mg, 1.56 mmol), and then $K_2CO_3$ (538 mg, 3.9 mmol) was added thereto, followed by stirring at room temperature. After 10 minutes, BnCl (0.45 ml, 3.9 mmol) was added dropwise thereto and reacted for 18 hours at room temperature EA and distilled water were added to the reaction product for extraction and then an organic layer was dried over $Na_2SO_4$, filtered, and vacuum evaporated. A crude product was recrystallized using ether/hexane and then filtered, thereby obtaining Compound C-1 (332 mg, 47%).

$^1H$ NMR (300 MHz, $CDCl_3$) δ 8.41 (d, J=7.7 Hz, 1H), 7.75 (d, J=8.4 Hz, 1H), 7.67-7.44 (m, 7H), 7.28 (s, 1H), 7.20-7.00 (m, 5H), 5.33-5.23 (m, 3H), 4.64 (d, J=13.6 Hz, 1H), 2.27-2.21 (m, 1H), 1.04 (d, J=6.6 Hz, 6H)

2) Step 2

C-1 (200 mg, 0.44 mmol) was dissolved in EtOH (3 ml), and then Pd/C (20 mg) and hydrazine (0.12 ml, 2.2 mmol) were sequentially added thereto, followed by refluxing with stirring for one hour at 70° C. The reaction product was cooled and filtered over Celite at room temperature to remove Pd/C. The filtrate was vacuum evaporated and purified via silica gel column chromatography, thereby obtaining Compound C-2 (122 mg, 83%).

3) Step 3

Acetic acid (15 ml) was added to Compound C-2 (500 mg, 1.49 mmol), followed by refluxing with stirring for 3.5 hours. Acetic acid was removed through vacuum evaporation and purified via silica gel column chromatography, thereby obtaining Compound C-3 (298 mg, 63%).

4) Step 4

Compound C-3 (50 mg, 0.16 mmol) was dissolved in DMF (2.5 ml), and then IBX (113 mg, 0.19 mmol) was added thereto. The reaction product was reacted for 1 hour at room temperature. After adding EA thereto, an organic layer was washed with saturated aqueous $NaHCO_3$. The separated organic layer was dried over $MgSO_4$ and then filtered. The filtrate was vacuum evaporated and then purified using column chromatography, thereby obtaining Compound C-4 (41 mg, 81%).

$^1$H NMR (300 MHz, CDCl$_3$) δ 8.08 (d, J=8.0 Hz, 1H), 7.44-7.32 (m, 5H), 7.29 (d, J=8.0 Hz, 1H), 7.11 (d, J=7.0 Hz, 2H), 5.58 (s, 2H), 3.04-2.96 (m, 1H), 1.38 (d, J=8.0 Hz, 6H)

EXAMPLE 3

Synthesis of Compound 3

2-isopropyl-1-methyl-1H-naphtho[2,1-d]imidazole-4,5-dione

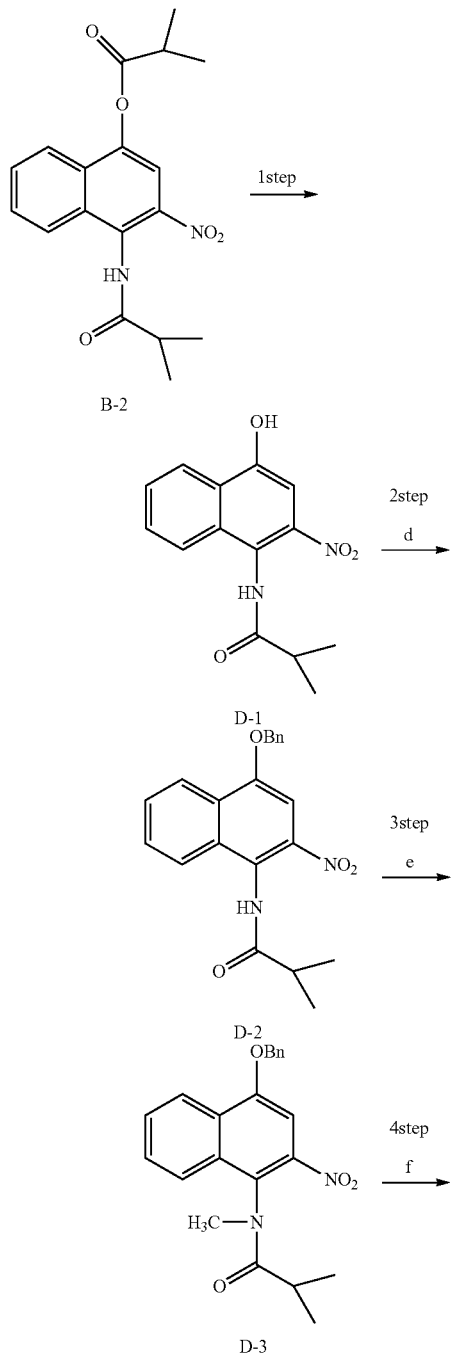

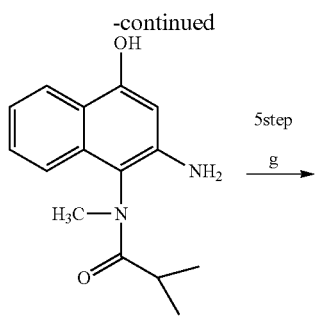

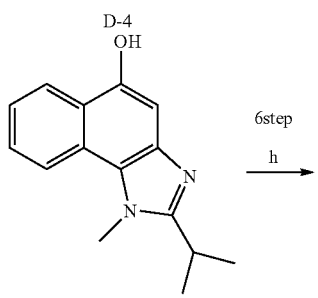

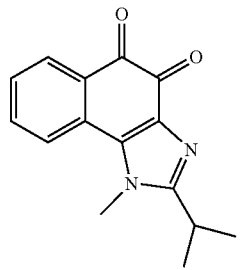

Step 1

B-2 (600 mg, 1.74 mmol) was dissolved in Methanol (8 ml) and then NaOMe (94 mg, 1.74 mmol) was added thereto, followed by stirring for one hour at room temperature. The reaction product was neutralized using a 1 M HCl aqueous solution and then extracted using EA. The organic layer was dried, filtered, and vacuum evaporated using Na$_2$SO$_4$, and then purified suing silica gel column chromatography, thereby obtaining Compound D-1 (429 mg, 90%).

2) Step 2

Acetone (8 ml) was added to D-1 (429 mg, 1.56 mmol), and then K$_2$CO$_3$ (538 mg, 3.9 mmol) was added thereto, followed by stirring at room temperature. After 10 minutes, BnCl (0.18 ml, 1.56 mmol) was added dropwise thereto and reacted for 12 hours at room temperature. EA and distilled water were added to the reaction product for extraction and then an organic layer was dried over Na$_2$SO$_4$, filtered, and vacuum evaporated. A crude product was recrystallized using ether/hexane and then filtered, thereby obtaining Compound D-2 (380 mg, 67%).

$^1$H NMR (300 MHz, DMSO) δ 10.14 (s, N—H, 1H), 8.31 (d, J=9.5 Hz, 1H), 8.13 (d, J=8.8 Hz, 1H), 7.78-7.74 (m, 2H), 7.59-7.37 (m, 6H), 5.41 (s, 2H), 2.79-2.75 (m, 1H), 1.16 (d, J=6.6 Hz, 6H));

3) Step 3

D-2 (380 mg, 1.04 mmol) was dissolved in DMF (5 ml) and then NaH (63 mg, 1.56 mmol) was added thereto at 0° C. CH$_3$I (0.10 ml, 1.56 mmol) was added dropwise thereto, followed by stirring for two hours. EA and distilled water were added thereto for extraction and then the organic layer was dried over Na$_2$SO$_4$, filtered, and vacuum evaporated. A crude product was purified via silica gel column chromatography, thereby obtaining Compound D-3 (334 mg, 85%).

$^1$H NMR (300 MHz, CDCl$_3$) 8.47-8.44 (m, 1H), 7.92-7.89 (m, 1H), 7.75-7.71 (m, 2H), 7.57-7.42 (m, 6H), 5.34 (s, 2H), 3.32 (s, 3H), 2.16-2.12 (m, 1H), 0.94 (d, J=6.6 Hz, 6H),

4) Step 4

D-3 (500 mg, 1.45 mmol) was dissolved in EtOH (5 ml), and then Pd/C (50 mg) and hydrazine (0.29 ml, 5.81 mmol) were sequentially added thereto at 70° C., followed by $^1$H NMR (300 MHz, CD$_3$OD) δ 8.03 (d, J=8.0 Hz, 1H), 7.98 (d, J=8.0 Hz, 1H), 7.69 (t, J=7.7 Hz, 1H), 7.45 (t, J=7.7 Hz, 1H), 4.01 (s, 3H), 3.31-3.27 (m, 1H), 1.36 (d, J=7.0 Hz, 6H);

EXAMPLE 4

Synthesis of Compound 4

2-phenyl-3H-naphtho[2,1-d]imidazole-4,5-dione

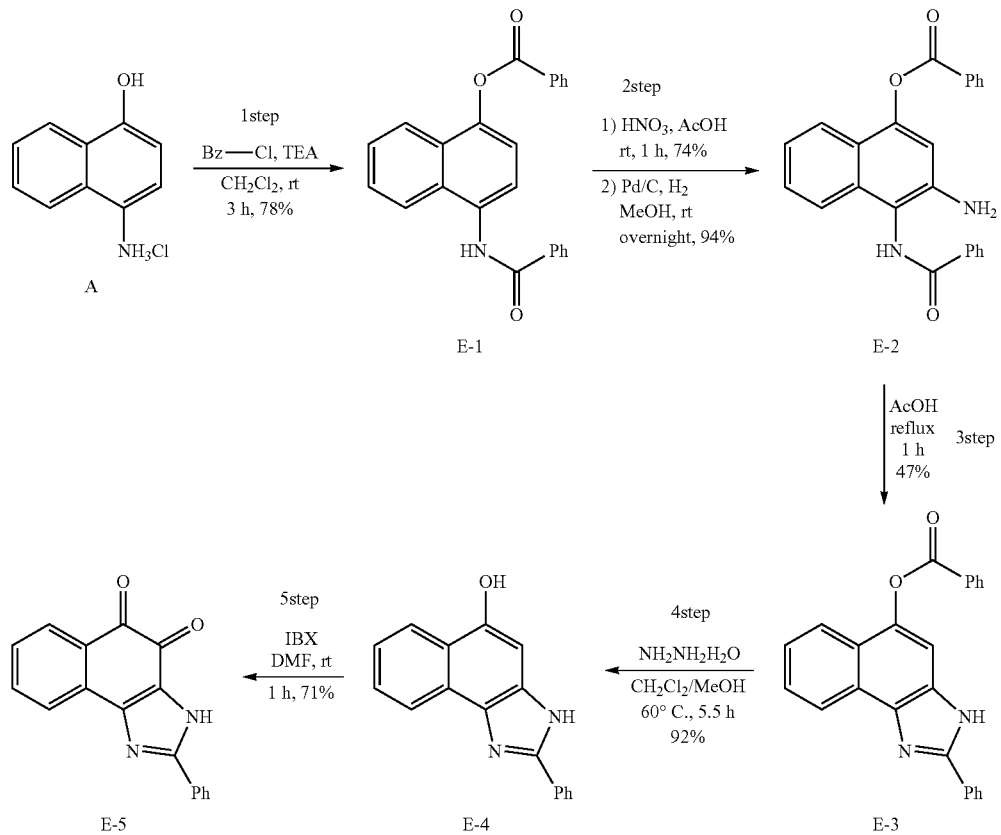

refluxing with stirring for one hour. The reaction product was cooled and filtered over Celite at room temperature to remove Pd/C. The filtrate was vacuum evaporated and purified via silica gel column chromatography, thereby obtaining Compound D-4 (232 mg, 51%).

5) Step 5

Acetic acid (15 ml) was added to Compound D-4 (700 mg, 2.86 mmol), followed by refluxing with stirring for three hours. Acetic acid was removed through vacuum evaporation and purified via silica gel column chromatography, thereby obtaining Compound D-5 (575 mg, 89%).

6) Step 6

DMF (2.5 ml) was added to Compound D-5 (50 mg, 0.22 mmol) and dissolved, and then IBX (159 mg, 0.26 mmol) was added thereto. The reaction product was reacted for 1 hour at room temperature. After adding EA thereto, an organic layer was washed with saturated aqueous NaHCO$_3$. The separated organic layer was dried over MgSO$_4$ and then filtered. The filtrate was vacuum evaporated and then purified using column chromatography, thereby obtaining Compound D-6 (47 mg, 89%).

Step 1

A (4-amino-1-naphthol hydrochloride, 2.0 g, 10.22 mmol) was dissolved in MC (40 ml) and then placed in an ice bath. To the solution, triethylamine (7.2 ml, 51.11 mmol) and benzoyl chloride (1.8 ml, 15.33 mmol) were added, followed by stirring at room temperature. After one hour, benzoyl chloride (0.8 ml, 7.16 mmol) was additionally added thereto, followed by stirring for two additional hours. After adding MC and distilled water thereto, an organic layer was washed with saturated aqueous NaHCO$_3$. The separated organic layer was dried over Na$_2$SO$_4$ and then filtered. The filtrate was vacuum evaporated and then recrystallized.

E-1: yield 78%

1H NMR (300 MHz, CDCl$_3$): 8.35-8.33 (m, 2H), 8.21 (brs, 1H), 8.04-7.93 (m, 5H), 7.73-7.68 (m, 1H), 7.64-7.51 (m, 7H), 7.42 (d, J=8.4 Hz, 1H)

2) Step 2

E-1 (3.86 g, 10.51 mmol) was added to acetic acid (21 ml), and then 90% nitric acid (1 ml, 15.76 mmol) was added thereto, followed by stirring for one hour at room temperature. Distilled water was added to the reaction solution, followed by stirring in an ice bath for a while. A crystalline product was filtered and then washed with distilled water. A filtrate was extracted using MC and dried over Na$_2$SO$_4$, and then filtered. The filtrate was vacuum evaporated and then recrystallized. A reaction product was dried with the solids previously filtered.

Yield 74%

1H NMR (300 MHz, CDCl$_3$): 9.83 (s, 1H), 8.35-8.32 (m, 2H), 8.17-8.04 (m, 4H), 7.77-7.56 (m, 9H)

A reaction product nitro compound (3.1 g, 7.52 mmol) was dissolved in methanol (75 ml), and then Pd/C (1.6 g, 0.75 mmol) was added thereto, followed by attachment of a hydrogen-filled balloon. Stirring was performed for one hour at room temperature and then filtration was performed through Celite. The filtrate was vacuum evaporated and then recrystallized.

E-2: yield 94%

1H NMR (300 MHz, CDCl$_3$): 8.31-8.26 (m, 2H), 8.00-7.96 (m, 2H), 7.86-7.76 (m, 2H), 7.72-7.62 (m, 2H), 7.59-7.46 (m, 6H), 7.44-7.39 (m, 2H)

3) Step 3

E-2 (2.67 g, 6.98 mmol) was added to acetic acid (90 ml) and then refluxed. After one hour, the reaction product was cooled to room temperature and then MC and saturated aqueous NaHCO$_3$ were added thereto to adjust pH to 4 to 5. After extracting using MC and then drying over Na$_2$SO$_4$, the reaction product was filtered. The filtrate was vacuum evaporated and then purified through column chromatography and recrystallization.

E-3: yield 47%

1H NMR (300 MHz, CDCl$_3$): 8.45-8.42 (m, 2H), 7.84 (brs, 2H), 7.76 (t, J=7.3 Hz, 2H), 7.63 (t, J=7.3 Hz, 2H), 7.48 (brs, 2H), 7.35 (brs, 5H)

4) Step 4

E-3 (0.97 g, 2.66 mmol) was dissolved in MC (27 ml) and methanol (26 ml), and then hydrazine hydrate (50~60%, 0.65 ml, 10.38 mmol) was added thereto, followed by stirring at room temperature. After one hour, the reaction product was heated to 60° C. After approximately three hours, additional hydrazine hydrate (0.4 ml, 6.65 mmol) was added thereto, followed by stirring. After two hours, the reaction product was cooled to room temperature and then THF and DOWEX MAC-3 were added thereto. After filtering a resultant solution, a filtrate was vacuum evaporated. Distilled water was added to a remaining solid and filtered. A filtered solid was washed with distilled water and then dried.

E-4: yield 92%

1H NMR (300 MHz, MeOH-d$^4$): 8.45 (d, J=8.0 Hz, 1H), 8.29 (d, J=8.4 Hz, 1H), 8.12-8.09 (m, 2H), 7.61-7.42 (m, 5H), 7.07 (s, 1H)

5) Step 5

E-4 (640 mg, 2.46 mmol) was dissolved in DMF (24.8 ml) and then IBX (1.84 g, 2.95 mmol) was added thereto in an ice bath. Stirring was performed for one hour at room temperature. MC and distilled water were added thereto and then an organic layer was washed with saturated aqueous NaHCO$_3$. The separated organic layer was dried over MgSO$_4$ and then filtered. The filtrate was vacuum evaporated and then purified through column chromatography and recrystallization.

E-5: yield 71%

1H NMR (300 MHz, acetone-d$^6$): 8.30-8.27 (m, 2H), 8.08 (d, J=7.0 Hz, 1H), 7.98 (d, J=7.7 Hz, 1H), 7.75 (t, J=7.7 Hz, 1H), 7.58-7.56 (m, 3H), 7.51 (t, J=7.3 Hz, 1H)

EXAMPLE 5

Synthesis of Compound 5

2-tert-butyl-3H-naphtho[2,1-d]imidazole-4,5-dione

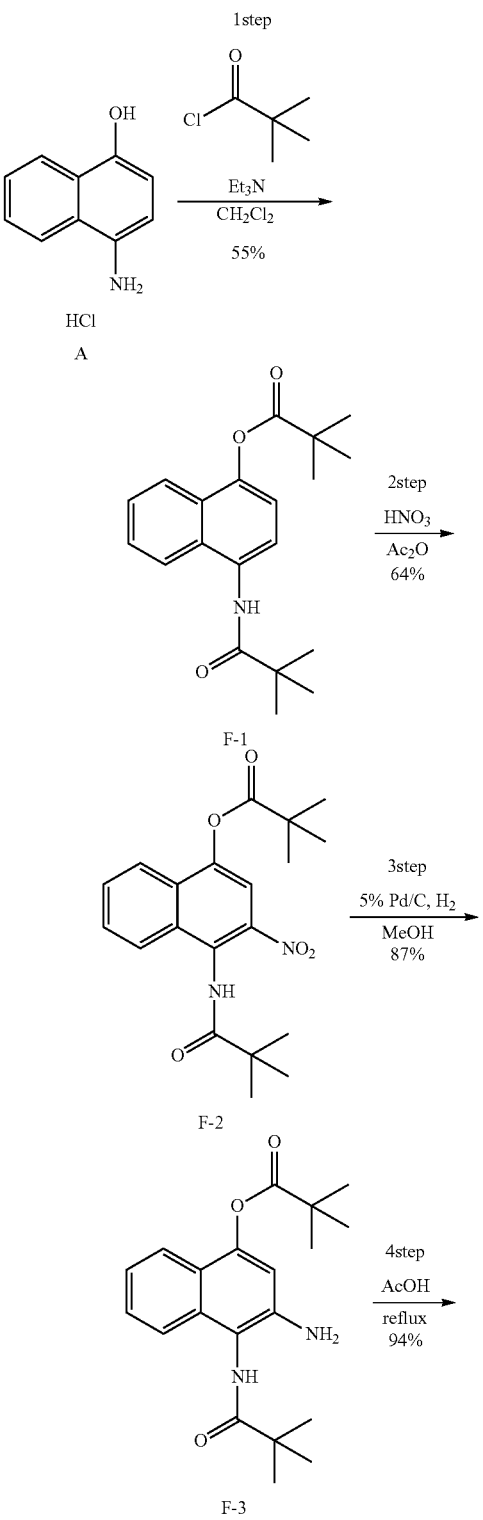

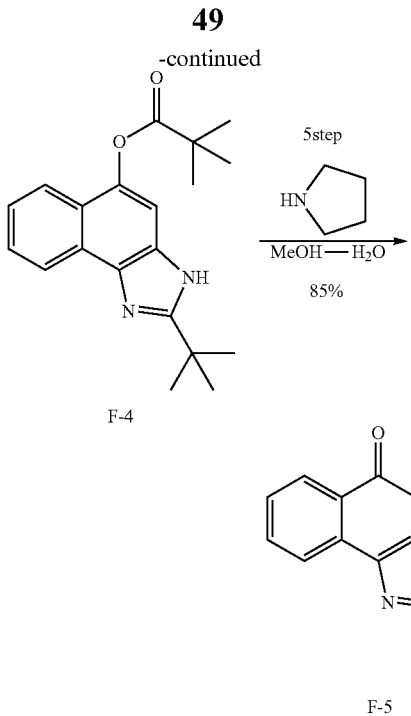

F-4

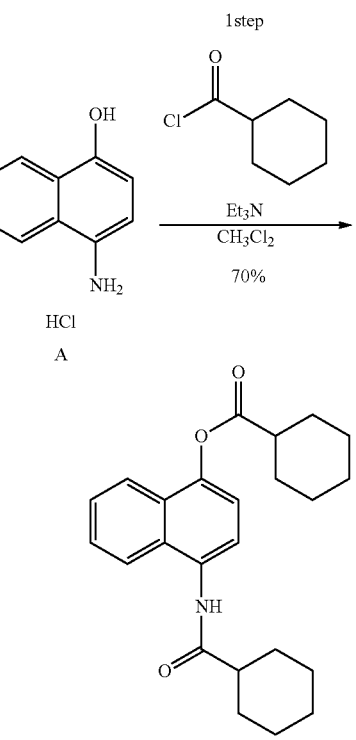

F-5

1) Step 1

A (4-amino-1-naphthol hydrochloride, 3 g, 15.33 mmol) was dissolved in MC (60 ml) and then placed in an ice bath. Triethylamine (11 ml, 76.65 mmol) and pivaloyl chloride (4 ml, 33.73 mmol) were added to a reaction product solution, followed by stirring for 1.5 hours at room temperature. After adding EA and distilled water thereto, an organic layer was washed with saturated aqueous $NaHCO_3$. The separated organic layer was dried over $MgSO_4$ and then filtered. The filtrate was vacuum evaporated and then recrystallized (HX:EA).

F-1: light pink solid_3.2 g (65%)

2) Step 2

F-1 (3.2 g, 9.8 mmol) was added to acetic anhydride (33 ml), followed by stirring in an ice bath. 90% nitric acid was added thereto, followed by stirring for 30 minutes at room temperature. Distilled water and MC were added to a reaction solution and then an organic layer was washed with saturated aqueous $NaHCO_3$. The separated organic layer was dried over $MgSO_4$ and then filtered. The filtrate was vacuum evaporated and then recrystallized (HX:EA).

F-2: light yellow solid_2.3 g (64%)

3) Step 3

F-2 (3.2 g, 8.6 mmol) was dissolved in methanol (86 ml), followed by addition of Pd/C, followed by attachment of a hydrogen-filled balloon. Stirring was performed for one hour at room temperature and then filtration was performed through Celite. The filtrate was vacuum evaporated and then recrystallized (HX:EA)

F-3: Ivory solid_2.57 g (87%)

4) Step 4

F-3 (1.6 g, 4.85 mmol) was added to acetic acid (97 ml) and then refluxed. After one hour, the reaction product was cooled to room temperature and then EA and saturated aqueous $NaHCO_3$ were added thereto to adjust pH to 4 to 5. The reaction product was extracted using EA and dried over $MgSO_4$, and then filtered. The filtrate was vacuum evaporated and then recrystallized (HX:EA).

F-4: Ivory solid_1.48 g (94%)

5) Step 5

24 ml of methanol, 12 ml of distilled water, and 0.5 ml of pyrrolidine (3.08 mmol) were sequentially added to F-4 (0.2 g, 0.62 mmol), followed by stirring for 2.5 hours at 55° C. When the reaction was completed, after adding distilled water thereto and then adding 1 N HCl thereto to adjust pH to approximately 2 to 3, the reaction product was extracted using MC. The separated organic layer was dried over $MgSO_4$ and then filtered. The filtrate was vacuum evaporated and then recrystallized (HX:ether).

F-5: Orange solid_0.1 g (65%)

$^1$H NMR (300 MHz, $CDCl_3$) δ 10.37 (brs, 1H), 8.04-7.99 (m, 2H), 7.64-7.59 (m, 1H), 7.42-7.37 (m, 1H), 1.49 (s, 9H)

EXAMPLE 6

Synthesis of Compound 6

2-cyclohexyl-3H-naphtho[2,1-d]imidazole-4,5-dione

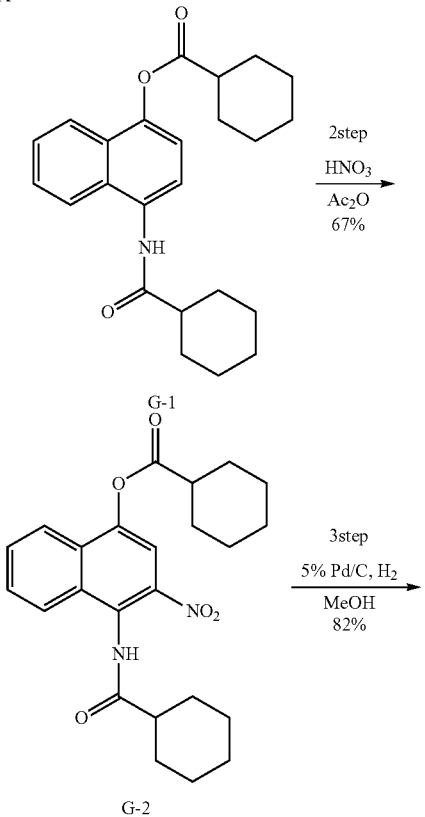

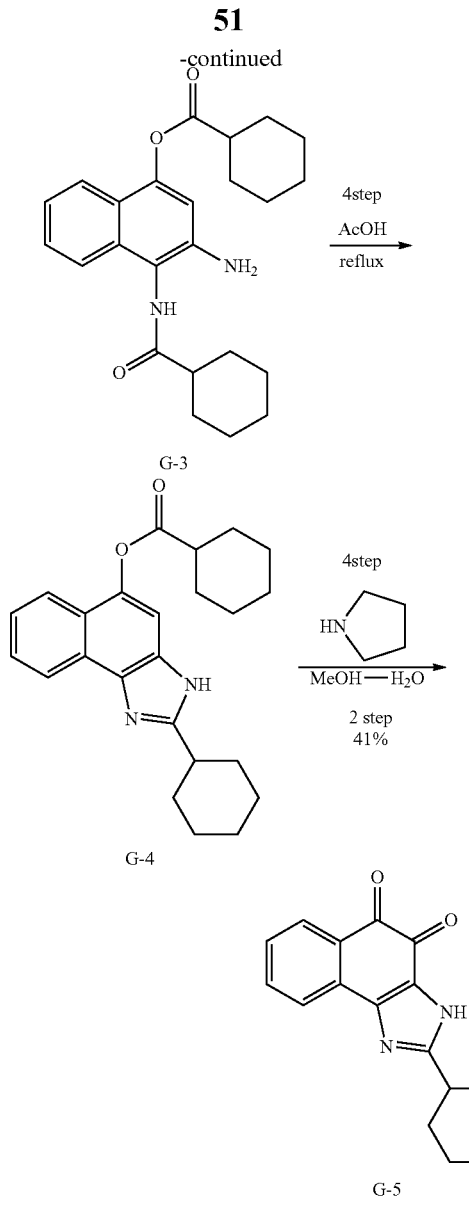

G-3

G-4

G-5

1) Step 1

A (4-amino-1-naphthol hydrochloride, g, 46 mmol) was dissolved in MC (20 ml) and then placed in an ice bath. Triethylamine (3.6 ml, 25.6 mmol) and cyclohexanecarbonyl chloride (2.1 ml, 15.33 mmol) were added to the reaction product solution and were stirred for 1.5 hours at room temperature. After adding EA and distilled water thereto, an organic layer was washed with saturated aqueous NaHCO$_3$. The separated organic layer was dried over MgSO$_4$ and then filtered. The filtrate was vacuum evaporated and then recrystallized (HX:EA).

G-1: 1.2 g (70%)

2) Step 2

G-1 (1.1 g, 2.9 mmol) was added to acetic anhydride (15 ml), followed by stirring in an ice bath. 90% nitric acid (0.17 ml, 3.5 mmol) was added thereto, followed by stirring for 40 minutes at room temperature. Distilled water and MC were added to a reaction solution and then an organic layer was washed with saturated aqueous NaHCO$_3$. The separated organic layer was dried over MgSO$_4$ and then filtered. The filtrate was vacuum evaporated and then recrystallized (HX:EA).

G-2: 0.82 g (67%)

3) Step 3

G-2 (1.27 g, 2.99 mmol) was dissolved in methanol (30 ml), and then 0.64 g of 5% Pd/C (10 mol %) was added thereto, followed by attachment of a hydrogen-filled balloon. Stirring was performed for one hour at room temperature and then filtration was performed through Celite. The filtrate was vacuum evaporated and then recrystallized (HX:EA).

G-3: 0.97 g (82%)

4) Step 4

G-3 (0.56 g, 1.42 mmol) was added to acetic acid (28 ml) and then refluxed.

After one hour, the reaction product was cooled to room temperature and then MC and saturated aqueous NaHCO$_3$ were added thereto for neutralization. The reaction product was extracted using MC and dried over MgSO$_4$, and then vacuum evaporated. The crude reaction product (G-4) was used in the next reaction.

57 ml of methanol, 28 ml of distilled water, and 0.6 ml of pyrrolidine (7.1 mmol) were sequentially added to crude G-4, followed by stirring for 1.5 hours at 55° C. When the reaction was completed, after adding distilled water and then 1 N HCl to adjust pH to approximately 2 to 3, the reaction product was extracted using MC. The separated organic layer was dried over MgSO$_4$ and then filtered. The filtrate was vacuum evaporated and then recrystallized (HX:ether).

G-5: 0.16 g (41%)

$^1$H NMR (300 MHz, CDCl$_3$) δ 10.91 (brs, 1H), 8.03-7.96 (m, 2H), 7.63-7.59 (m, 1H), 7.42-7.37 (m, 1H), 2.96-2.88 (m, 1H), 2.15-1.32 (m, 10H)

EXAMPLE 7

Synthesis of Compound 7

2-tert-butyl-3H-imidazo[4,5-f]quinoline-4,5-dione

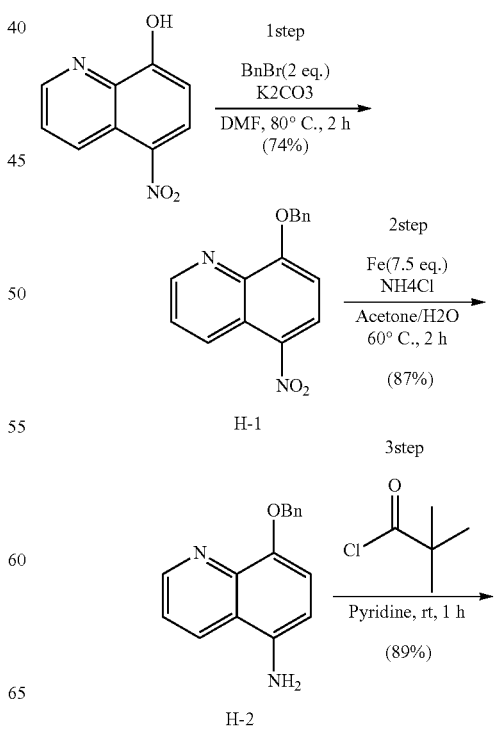

H-1

H-2

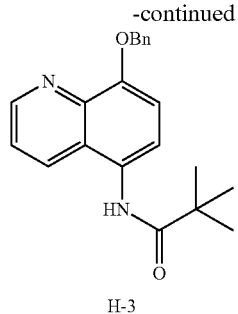

H-3

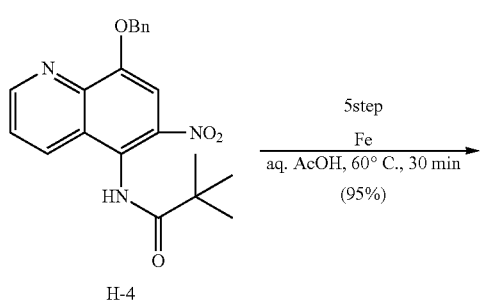

H-4

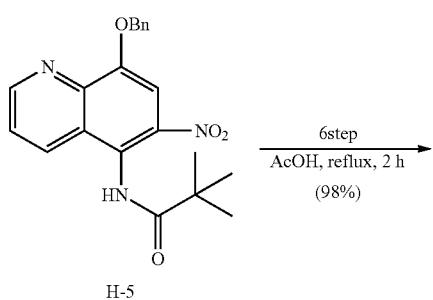

H-5

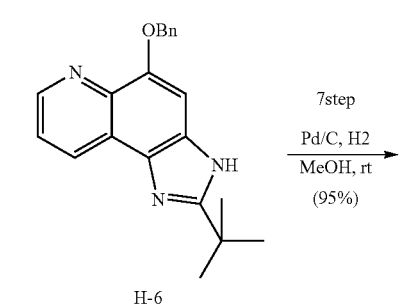

H-6

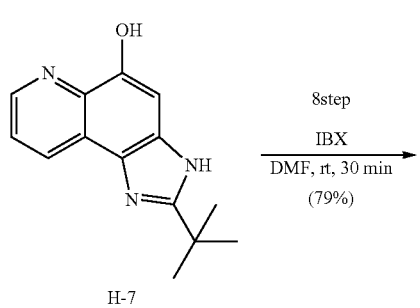

H-7

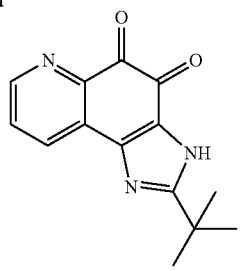

H-8

1) Step 1

10 g of 5-nitroquinolin-8-ol was dissolved in 202 ml of DMF (0.26 M), and then 21.8 g of K₂CO₃ (3 eq.) was added thereto, followed by stirring for 40 minutes at 70° C. A dilute solution was changed into an orange colored slush. 12.5 ml of benzyl bromide (2 eq.) was added thereto at the same temperature and reacted for 5 hours at 80° C. When the reaction was completed, the reaction product was diluted with 800 ml of EA and then washed with 700 ml of H₂O approximately three times. An EA layer was treated with MgSO₄, filtered, and vacuum evaporated and then short-column chromatography was performed. (Hex:MC=2:1).

H-1: Light yellow solid: 10.93 g (74%)

2) Step 2

496 ml of acetone (0.12M) and H₂O (0.5M) were added to 17.4 g of H-1 to prepare a dilute solution. NH₄Cl 20 g (6 eq.) was added thereto and an inner temperature was adjusted to 60° C., and then 16.8 g of Fe (5 eq.) was added thereto, followed by stirring for 1.5 hours. A reaction state may be confirmed by directly spotting on TLC without workup. If reaction was not completed, approximately two equivalents of Fe was further added thereto and reacted until a starting material disappeared. When the reaction was completed, the reaction product was filtered through Celite and washed with EA. A filtrate was neutralized using aq. NaHCO₃, and then an organic layer was collected and an aqueous layer was washed once with MC. An EA layer and an MC layer were mixed, and then treated with MgSO₄, filtered, and vacuum evaporated. Subsequently, the reaction product was purified through recrystallization using MC:Ether.

H-2: Light yellow solid: 13.588 g (87%)

$^1$H NMR (300 MHz, CDCl$_3$) δ 8.98 (dd, J=4.5 Hz, 1.8 Hz, 1H), 8.19 (dd, J=9.0 Hz, 1.8 Hz, 1H), 7.52-7.45 (m, 2H), 7.42 (dd, J=8.4 Hz, 3.9 Hz, 1H), 7.39-7.22 (m, 3H), 6.87 (d, J=8.4 Hz, 1H), 6.67 (d, J=8.4 Hz, 1H), 5.38 (s, 2H), 3.85 (brs, 2H)

3) Step 3

18 ml of Pyridine was added to H-2 2.3 g (0.5M) and 1.25 ml of pivaloyl chloride (1.1 eq.) was added thereto dropwise at 0° C., and then stirring was performed for 1.5 hours at room temperature. When the reaction was completed, EA was added thereto and the reaction product was washed several times to remove pyridine. An EA layer was vacuum evaporated and then was purified through recrystallization in ether:hexane.

H-3: Light gray solid: 3.1 g (89%)

$^1$H NMR (300 MHz, CDCl$_3$) δ 8.98 (dd, J=3.9 Hz, 1.5 Hz, 1H), 8.04 (dd, J=8.4 Hz, 1.5 Hz, 1H), 7.51-7.43 (m, 5H), 7.39-7.29 (m, 3H), 6.98 (d, J=8.4 Hz, 1H), 5.43 (s, 2H), 1.39 (s, 9H)

4) Step 4

82 ml of AcOH (0.1 M) was added to 3.1 g of H-3 and 0.48 ml of HNO$_3$ (90% w) was added thereto in an ice bath, followed by stirring. 20 ml of AcOH including 4 ml of H$_2$SO$_4$ was slowly added dropwise thereto and then stirring was performed for 2.5 hours at room temperature. The reaction product was neutralized using aq. NaHCO$_3$ and then extracted using EA. An EA layer was treated with MgSO$_4$, filtered, and vacuum evaporated, and then filtered by recrystallization in ether:hexane.

H-4: Ivory solid: 1.83 g (52%)

$^1$H NMR (300 MHz, CDCl$_3$) δ 9.10 (dd, J=3.9 Hz, 1.5 Hz, 1H), 9.02 (s, 1H), 8.17 (dd, J=9.0 Hz, 1.8 Hz, 1H), 7.64 (s, 1H), 7.60-7.52 (m, 3H), 7.42-7.33 (m, 3H), 5.48 (s, 2H), 1.42 (s, 9H)

5) Step 5

90 ml of Acetone (0.05M), 45 ml of H$_2$O (0.1 M), and 9 ml of AcOH (0.5M) were added to H-4 1.71 g and external temperature was adjusted to ° C. Subsequently, 1.2 g of Fe (5 eq.) was added portionwise, temperature was elevated to 60° C., and stirring was performed for 30 minutes. The reaction product was filtered over Celite using EA and then neutralized using aq. NaHCO$_3$. An EA layer was separated, treated with MgSO$_4$, filtered, and vacuum evaporated, and then purified through recrystallization in ether:hexane.

H-5: Gray Solid: 1.5 g (95%)

6) Step 6

54 ml of AcOH was added to H-5 1.5 g, followed by reflux stirring for two hours. When the reaction was completed, some AcOH was removed through vacuum evaporation, and then extracted using EA after neutralizing using aq. NaHCO$_3$. An EA layer was treated with MgSO$_4$, filtered, and vacuum evaporated. The crude reaction product was used in the next process.

H-6: Crude solid: 1.37 g (96%)

7) Step 7

1.37 g of H-6 was dissolved in 41 ml of MeOH (0.1 M) and then Pd/C 274 mg was added thereto. After degassing, H$_2$ was filled, followed by stirring for 5 hours at room temperature. When the reaction was completed, a solid present in the reaction product was completely dissolved by adding MC thereto and then filtered through silica gel. The filtrate was vacuum evaporated. The crude reaction product was used in the next process.

H-7: Crude solid: 1.37 g (95%)

8) Step 8

950 mg of H-7 was dissolved in DMF 25 ml (0.16 M) and then 2.58 g of 47% IBX was added thereto portionwise. After stirring for one hour at room temperature and basify using aq. NaHCO$_3$, the reaction product was washed with EA several times. An EA layer was treated with MgSO$_4$ and then filtered through silica gel. The filtrate was vacuum evaporated and then filtered after recrystallizing using ether/hexane.

H-8: Light orange solid: 790 mg (79%)

$^1$H NMR (300 MHz, CDCl$_3$) δ 11.25 (s, 1H), 8.68 (d, J=3.6 Hz, 1H), 8.35 (d, J=6.9 Hz, 1H), 7.52 (dd, J=7.5 Hz, 4.5 Hz, 1H), 1.47 (s, 9H)

EXAMPLE 8

Synthesis of Compound 8

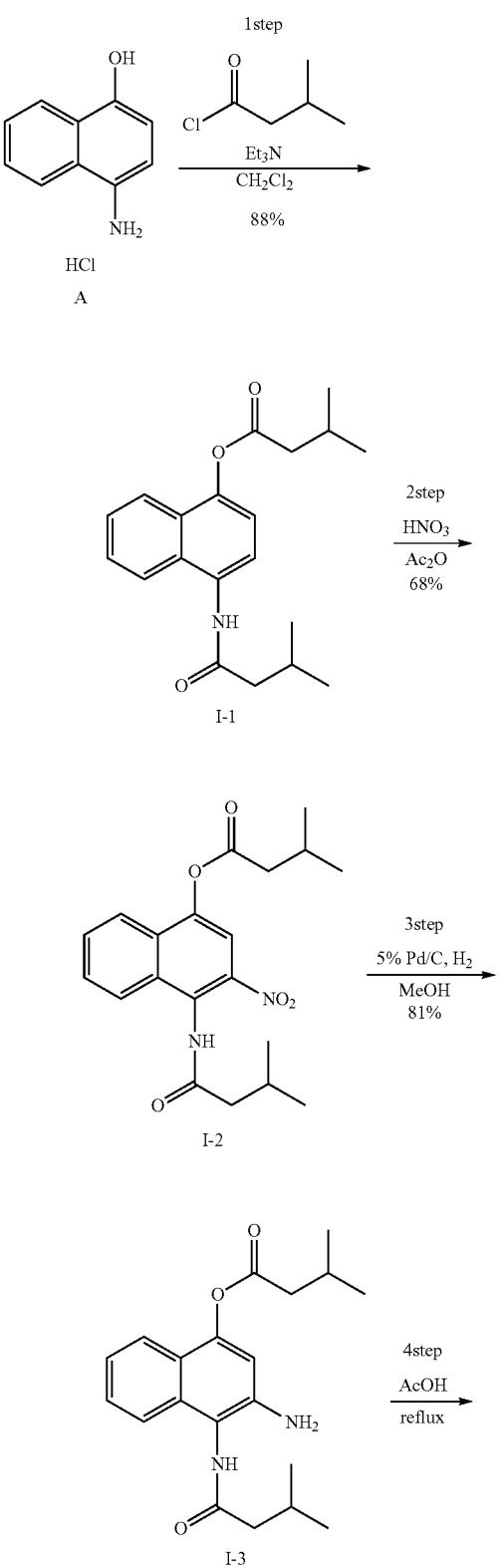

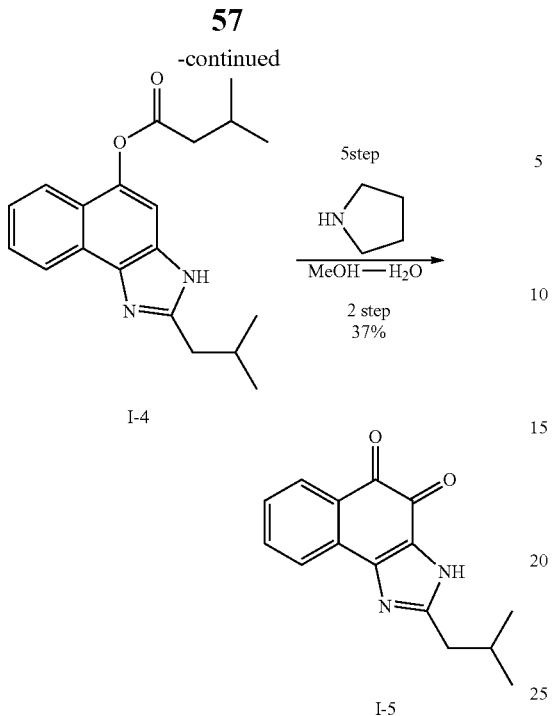

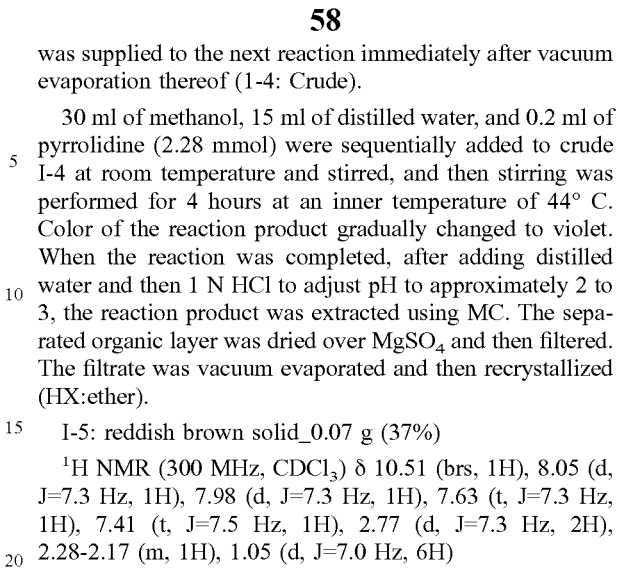

was supplied to the next reaction immediately after vacuum evaporation thereof (1-4: Crude).

30 ml of methanol, 15 ml of distilled water, and 0.2 ml of pyrrolidine (2.28 mmol) were sequentially added to crude I-4 at room temperature and stirred, and then stirring was performed for 4 hours at an inner temperature of 44° C. Color of the reaction product gradually changed to violet. When the reaction was completed, after adding distilled water and then 1 N HCl to adjust pH to approximately 2 to 3, the reaction product was extracted using MC. The separated organic layer was dried over MgSO₄ and then filtered. The filtrate was vacuum evaporated and then recrystallized (HX:ether).

I-5: reddish brown solid_0.07 g (37%)

$^1$H NMR (300 MHz, CDCl$_3$) δ 10.51 (brs, 1H), 8.05 (d, J=7.3 Hz, 1H), 7.98 (d, J=7.3 Hz, 1H), 7.63 (t, J=7.3 Hz, 1H), 7.41 (t, J=7.5 Hz, 1H), 2.77 (d, J=7.3 Hz, 2H), 2.28-2.17 (m, 1H), 1.05 (d, J=7.0 Hz, 6H)

EXAMPLE 9

Synthesis of Compound 9

1) Step 1

A (4-amino-1-naphthol hydrochloride, 3.5 g, 17.9 mmol) was dissolved in MC (36 ml) and then placed in an ice bath. Triethylamine (12.6 ml, 89.5 mmol) and isovaleryl chloride 6.5 ml (53.7 mmol) were added to a reaction product solution, followed by stirring for 3.5 hours at room temperature. After adding EA and distilled water thereto, an organic layer was washed with saturated aqueous NaHCO₃. The separated organic layer was dried over MgSO₄ and then filtered. The filtrate was vacuum evaporated and then recrystallized (HX:EA).

I-1: Pinkish ivory solid_3.6 g (68%)

2) Step 2

I-1 (0.5 g, 1.53 mmol) was added to acetic anhydride (8 ml), followed by stirring in an ice bath. 0.09 ml of 90% nitric acid (1.83 mmol) was added thereto, followed by stirring for 30 minutes at room temperature. When the reaction was completed, distilled water and MC were added to a reaction solution and then an organic layer was washed with saturated aqueous NaHCO₃. The separated organic layer was dried over MgSO₄ and then filtered. The filtrate was vacuum evaporated and then recrystallized (HX:EA).

I-2: solid_0.39 g (68%)

3) Step 3

I-2 (0.37 g, 0.99 mmol) was dissolved in methanol (10 ml) and MC (10 ml), and then 5% Pd/C 0.2 g (10 mol %) was added, followed by attachment of a hydrogen-filled balloon. Stirring was performed for two hours at room temperature and then filtration was performed through Celite. The filtrate was vacuum evaporated and then recrystallized (HX:EA)

I-3: Ivory solid_0.27 g (81%)

4) Step 4

I-3 (0.26 g, 0.76 mmol) was added to acetic acid (15 ml, 0.05M) and then refluxed. After 30 minutes, the reaction product was cooled to room temperature and then vacuum evaporated to maximally remove acetic acid. EA and saturated aqueous NaHCO₃ were added thereto to adjust pH to 4 to 5. The reaction product was extracted using EA, and then was dried over MgSO₄ and then filtered. The filtrate

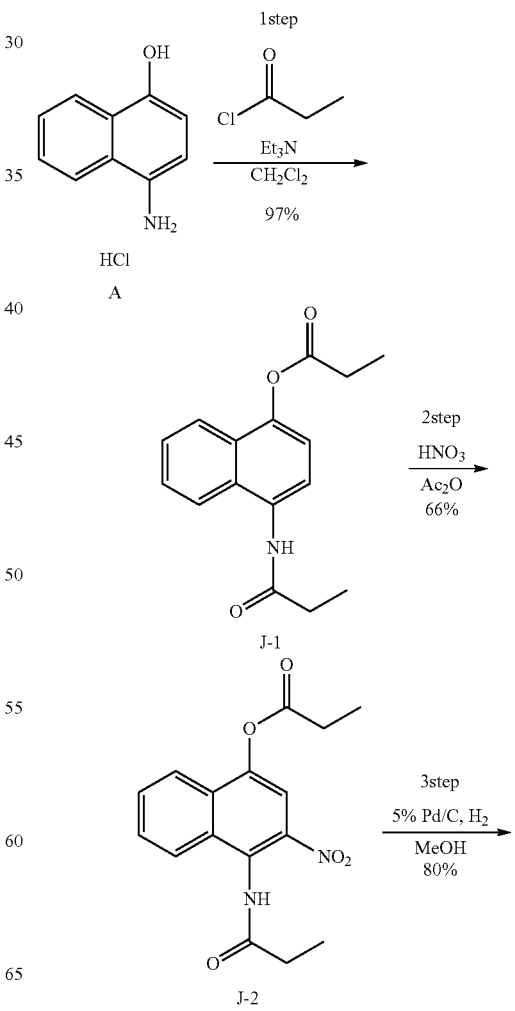

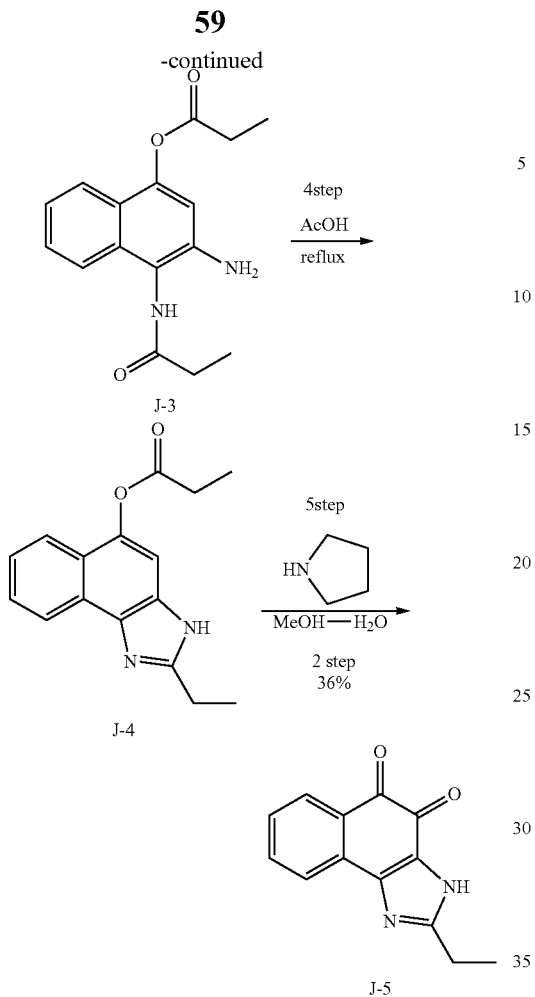

4) Step 4

J-3 (2.15 g, 7.51 mmol) was added to acetic acid (150 ml, 0.05M) and then refluxed. After 1.5 hours, the reaction product was cooled to room temperature and then vacuum evaporated to maximally remove acetic acid. EA and saturated aqueous NaHCO₃ were added thereto to adjust pH to 4 to 5. The reaction product was extracted using EA, dried over MgSO₄, and then filtered. The filtrate was supplied to the next reaction immediately after vacuum drying thereof (J-4: Crude).

Methanol (300 ml, 0.025M), distilled water (150 ml, 0.05M), and pyrrolidine (5.6 ml, 67.6 mmol) were sequentially added to crude J-4, followed by stirring at room temperature. Subsequently, additional stirring was performed for 18 hours at an inner temperature of 44° C. When the reaction was completed, after adding distilled water and then 1 N HCl to adjust pH to approximately 2 to 3, the reaction product was extracted using MC. The separated organic layer was dried over MgSO₄ and then filtered. The filtrate was vacuum evaporated and then recrystallized (HX: ether).

J-5: Deep orange solid_0.61 g (36%)

¹H NMR (300 MHz, CDCl₃) δ 8.03 (d, J=7.7 Hz, 1H), 7.97 (d, J=6.6 Hz, 1H), 7.62 (t, J=7.3 Hz, 1H), 7.41 (t, J=7.0 Hz, 1H), 2.96 (q, J=7.3 Hz, 2H), 1.45 (t, J=7.3 Hz, 3H)

EXAMPLE 10

Synthesis of Compound 10

1) Step 1

A (4-amino-1-naphthol hydrochloride, 2 g, 10.22 mmol) was dissolved in MC (51 ml, 0.2M) and then placed in an ice bath. Triethylamine (7 ml, 51.1 mmol) was added to the reaction product solution and propionyl chloride (2 ml, 22.5 mmol) was added thereto, followed by stirring for 1 hour at room temperature. After adding EA and distilled water thereto, an organic layer was washed with saturated aqueous NaHCO₃. The separated organic layer was dried over MgSO₄ and then filtered. The filtrate was vacuum evaporated and then recrystallized (HX:EA).

J-1: Light pink solid_2.42 g (97%)

2) Step 2

J-1 (2.4 g, 8.85 mmol) was added to acetic anhydride (44 ml, 0.2M), followed by stirring in an ice bath. 0.5 ml of 90% nitric acid (10.62 mmol) was added thereto, followed by stirring for 25 minutes at room temperature. When the reaction was completed, distilled water and MC were added to a reaction solution and then an organic layer was washed with saturated aqueous NaHCO₃. The separated organic layer was dried over MgSO₄ and then filtered. The filtrate was vacuum evaporated and then recrystallized (HX:EA).

J-2: solid_1.85 g (66%)

3) Step 3

J-2 (3 g, 9.48 mmol) was dissolved in methanol (95 ml, 0.1 M) and MC (95 ml, 0.1 M), and then 2 g of 5% Pd/C (10 mol %) was added thereto, followed by attachment of a hydrogen balloon. Stirring was performed for 16.5 hours at room temperature and then filtration was performed through Celite. The filtrate was vacuum evaporated and then recrystallized (HX:EA)

J-3: Ivory solid_2.2 g (80%)

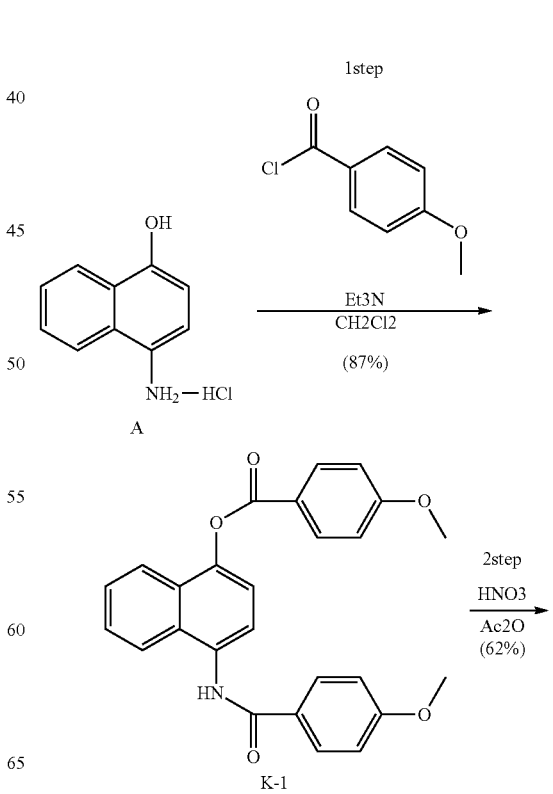

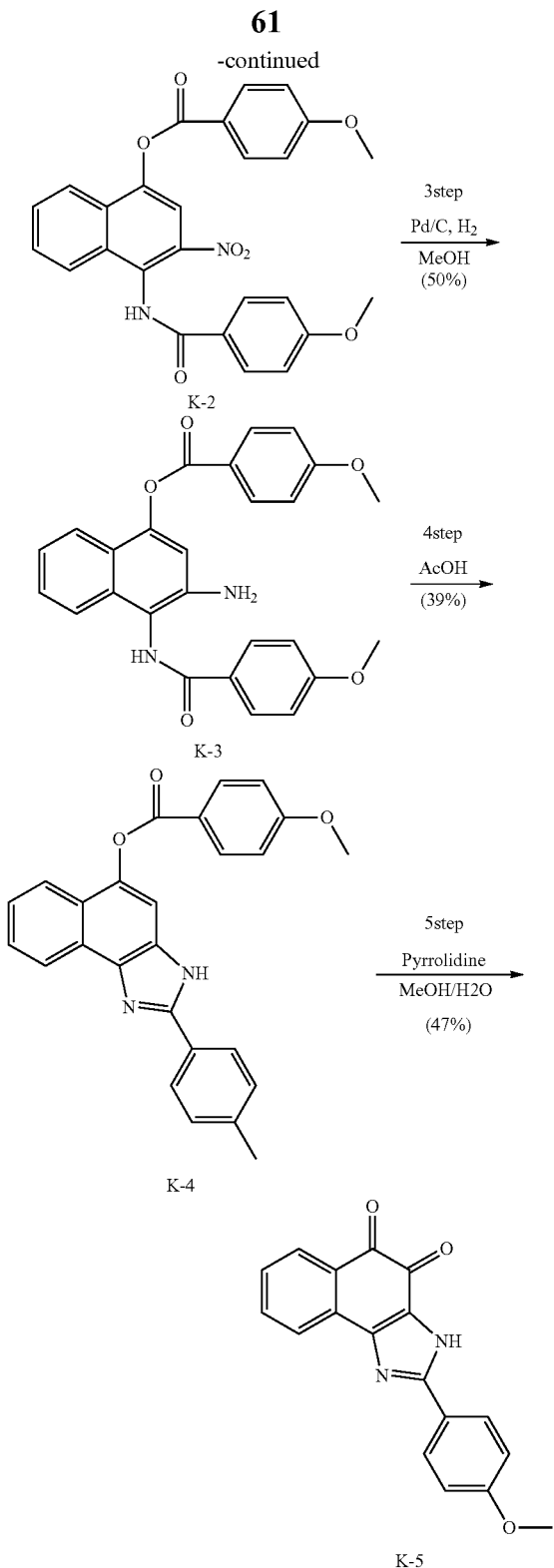

1) Step 1

A (4-amino-1-naphthol hydrochloride, 2.5 g, 12.778 mmol) was dissolved in MC (26 ml, 0.5M) and then placed in an ice bath. Triethylamine (9.0 ml, 63.89 mmol) was added to the reaction product solution and then 4-methoxybenzoyl chloride (3.8 ml, 28.111 mmol) was added thereto, followed by stirring for 1 hour at room temperature. After adding EA and distilled water thereto, an organic layer was washed with saturated aqueous NaHCO$_3$. The separated organic layer was dried over MgSO$_4$ and then filtered. The filtrate was vacuum evaporated and then recrystallized (HX:EA).

K-1: solid_4.757 g (87%)

$^1$H NMR (300 MHz, CDCl$_3$) δ 8.28 (d, J=9.0 Hz, 2H), 8.17 (s, 1H), 7.98-7.92 (m, 5H), 7.57-7.48 (m, 2H), 7.38 (d, J=8.1 Hz, 1H), 7.06-6.99 (m, 4H), 3.93 (s, 3H), 3.90 (s, 3H)

2) Step 2

K-1 (4.7 g, 10.995 mmol) was added to acetic anhydride (75 ml), followed by stirring in an ice bath. 90% nitric acid (0.62 ml, 13.914 mmol) was added thereto, followed by stirring for 4 hours at room temperature. When the reaction was completed, hexane/ether was added to a reaction solution, stirred, and then filtered.

K-2: light yellow solid_3.21 g (62%)

$^1$H NMR (300 MHz, CDCl$_3$) δ 9.81 (s, 1H), 8.28 (d, J=8.4 Hz, 2H), 8.15-8.10 (m, 1H), 8.07-8.02 (m, 4H), 7.70-7.63 (m, 2H), 7.08-7.04 (m, 4H), 3.94 (s, 3H), 3.92 (s, 3H)'

3) Step 3

K-2 (4.09 g, 8.657 mmol) was dissolved in methanol (86 ml), MC (170 ml), and THF (86 ml), and then Pd/C 800 mg was added thereto, followed by attachment of a hydrogen balloon. After stirring for two hours at room temperature and then completely dissolving a product by adding DMF, filtration was performed through Celite. The filtrate was vacuum evaporated and then recrystallized (HX:EA)

K-3: Ivory solid_1.9 g (50%)

4) Step 4

K-3 (1.9 g, 4.29 mmol) was added to acetic acid (54 ml, 0.08M) and then refluxed. After one hour, the reaction product was cooled to room temperature and then filtered to remove insoluble solids. The filtrate was vacuum evaporated. EA and saturated aqueous NaHCO$_3$ were added to the filtrate and extraction was performed. An EA layer was separated and was dried over MgSO$_4$, and then filtered. The filtrate was vacuum evaporated and then subjected to column chromatography. (HX:MC:EA=2:1:1)

K-4: solid_0.7 g (39%)

$^1$H NMR (300 MHz, CDCl$_3$) δ 8.38 (d, J=9.0 Hz, 2H), 7.81-7.74 (m, 3H), 7.43 (s, 1H), 7.35-7.20 (m, 3H), 7.09 (d, J=9.0 Hz, 2H), 6.82 (d, J=9.0 Hz, 2H), 3.96 (s, 3H), 3.82 (s, 3H)

5) Step 5

56 ml of methanol, 28 ml of distilled water, and 0.68 ml of pyrrolidine (8.245 mmol) were sequentially added to K-4 (0.7 g, 1.649 mmol) at room temperature and stirred, and then were stirred for 6 hours at an inner temperature of 50° C. When the reaction was completed, after adding distilled water and then 1 N HCl to adjust pH to approximately 2 to 3, the reaction product was extracted using MC. The separated organic layer was dried over MgSO$_4$ and then filtered. The filtrate was vacuum evaporated and then recrystallized (HX:ether).

K-5: Reddish brown solid_0.237 g (47%)

1H NMR (300 MHz, CDCl$_3$) δ 8.16 (d, J=8.7 Hz, 2H), 7.95 (d, J=7.8 Hz, 1H), 7.89 (d, J=7.8 Hz, 1H), 7.71 (t, J=7.8 Hz, 1H), 7.46 (t, J=7.8 Hz, 1H), 7.10 (d, J=8.7 Hz, 2H), 3.84 (s, 3H)

EXAMPLE 11

Synthesis of Compound 11

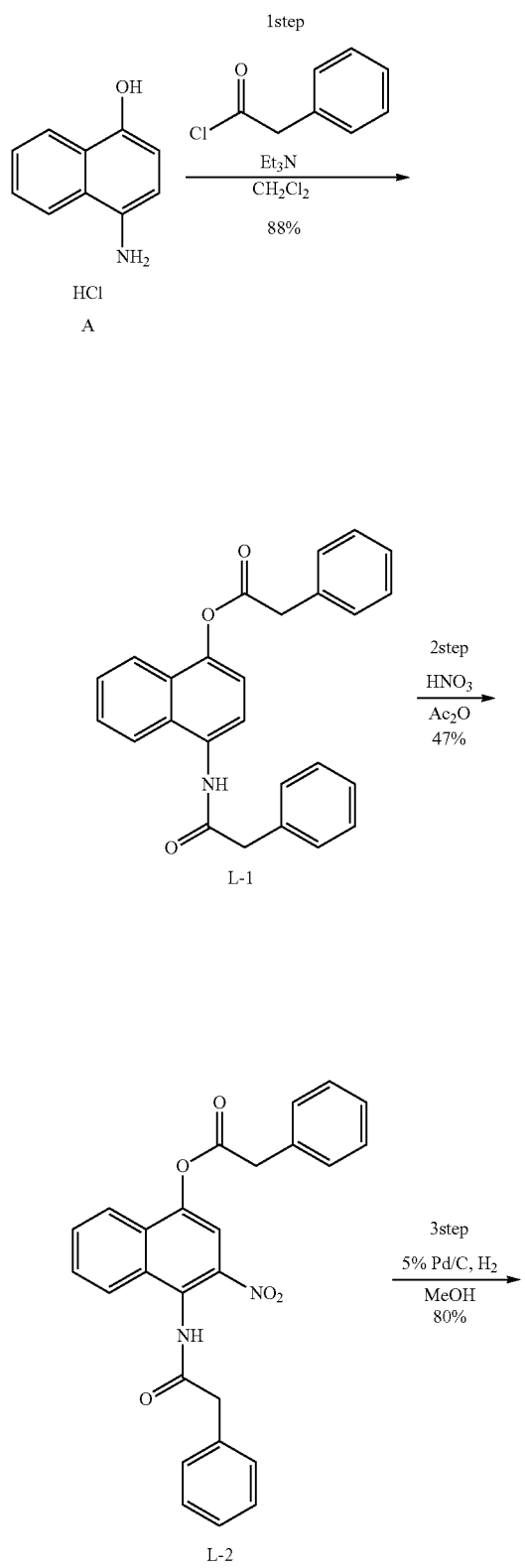

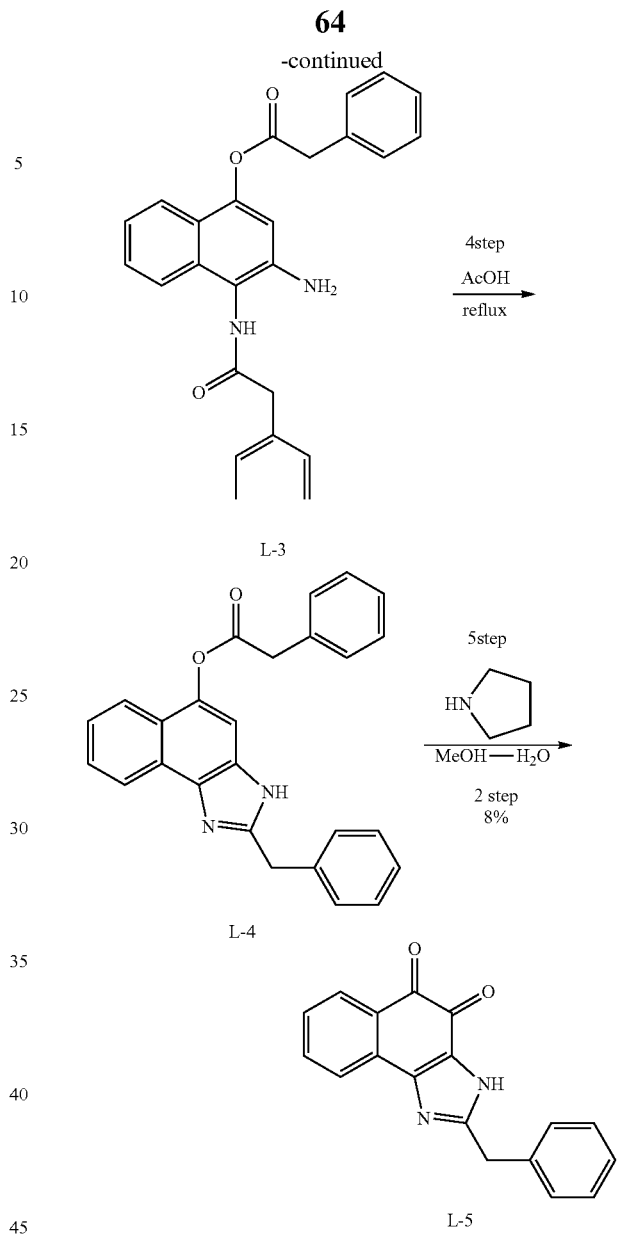

1) Step 1

A (4-amino-1-naphthol hydrochloride, 3 g, 15.33 mmol) was dissolved in MC (77 ml, 0.2M) and then placed in an ice bath. Triethylamine (11 ml, 76.67 mmol) and phenylacetyl chloride (4.5 ml, 33.73 mmol) were added to a solution, followed by stirring for 3.5 hours at room temperature. After adding EA and distilled water thereto, an organic layer was washed with saturated aqueous $NaHCO_3$. The separated organic layer was dried over $MgSO_4$ and then filtered. The filtrate was vacuum evaporated and then recrystallized (HX: EA).

L-1: Ivory solid_4.8 g (88%)

2) Step 2

L-1 (1.37 g, 3.46 mmol) was added to acetic anhydride (17 ml, 0.2M), followed by stirring in an ice bath. 0.2 ml of 90% nitric acid (4.16 mmol) was added thereto, followed by stirring for 2 hours at room temperature. When the reaction was completed, distilled water and MC were added to a reaction solution and then an organic layer was washed with saturated aqueous $NaHCO_3$. The separated organic layer was dried over MgSO₄ and then filtered. The filtrate was vacuum evaporated and then recrystallized (HX:EA).

L-2: Light yellow solid_0.72 g (47%)

3) Step 3

L-2 (0.7 g, 1.59 mmol) was dissolved in methanol (16 ml, 0.1 M) and MC (16 ml, 0.1 M), and then 0.34 g of 5% Pd/C (10 mol %) was added thereto, followed by attachment of a hydrogen-filled balloon. Stirring was performed for 1.5 hours at room temperature and then filtration was performed through Celite. The filtrate was vacuum evaporated and then recrystallized (HX:EA).

L-3: brown solid_0.39 g (60%)

4) Step 4

L-3 (0.37 g, 0.9 mmol) was added to acetic acid (18 ml, 0.05 M) and then refluxed. After one hour, the reaction product was cooled to room temperature and then vacuum evaporated to maximally remove acetic acid. EA and saturated aqueous NaHCO₃ were added thereto to adjust pH to 4 to 5. The reaction product was extracted using EA, and dried over MgSO₄, and then filtered. The filtrate was supplied to the next reaction immediately after vacuum drying thereof (L-4: Crude).

Methanol (36 ml, 0.025M), distilled water (18 ml, 0.05M), and pyrrolidine (1.4 ml, 16.2 mmol) were sequentially added to crude L-4 at room temperature, followed by stirring. Subsequently, additional stirring was performed for 2 hours at an inner temperature of 44° C. When the reaction was completed, after adding distilled water and then 1 N HCl to adjust pH to approximately 2 to 3, the reaction product was extracted using MC. The separated organic layer was dried over MgSO₄ and then filtered. The filtrate was vacuum evaporated and then separated using Prep TLC.

L-5: Reddish brown solid_0.02 g (8%)

¹H NMR (300 MHz, DMSO) δ 13.56 (brs, 1H), 7.85 (d, J=7.7 Hz, 1H), 7.79 (d, J=7.7 Hz, 1H), 7.65 (t, J=7.7 Hz, 1H), 7.41 (t, J=7.7 Hz, 2H), 7.33-7.20 (m, 4H), 4.08 (s, 2H)

EXAMPLE 12

Synthesis of Compound 12

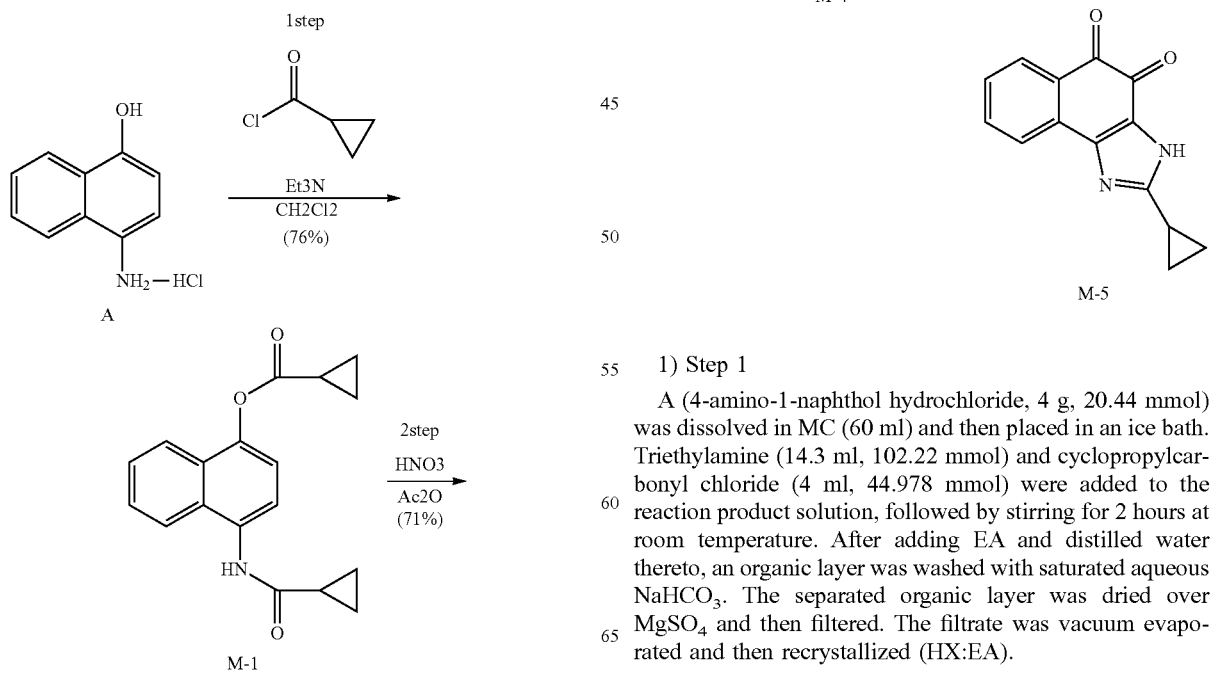

1) Step 1

A (4-amino-1-naphthol hydrochloride, 4 g, 20.44 mmol) was dissolved in MC (60 ml) and then placed in an ice bath. Triethylamine (14.3 ml, 102.22 mmol) and cyclopropylcarbonyl chloride (4 ml, 44.978 mmol) were added to the reaction product solution, followed by stirring for 2 hours at room temperature. After adding EA and distilled water thereto, an organic layer was washed with saturated aqueous NaHCO₃. The separated organic layer was dried over MgSO₄ and then filtered. The filtrate was vacuum evaporated and then recrystallized (HX:EA).

M-1: Light pink solid_4.6 g (76%)

2) Step 2

M-1 (4 g, 13.54 mmol) was added to acetic anhydride (68 ml) and then stirred in an ice bath. 90% nitric acid (0.7 ml, 14.9 mmol) was added thereto, followed by stirring for 30 minutes at room temperature. When the reaction was completed, hexane/ether was added to a reaction solution and stirred, followed by filtration.

M-2: Ivory solid_3.26 g (71%)

3) Step 3

M-2 (3.2 g, 9.4 mmol) was dissolved in methanol (94 ml) and MC (94 ml), and then Pd/C 640 mg was added thereto, followed by attachment of a hydrogen-filled balloon. Stirring was performed for two hours at room temperature and then filtration was performed for two hours using silica gel. The filtrate was vacuum evaporated and then recrystallized (Ether)

M-3: Ivory solid_2.7 g (93%)

4) Step 4

M-3 (2.7 g, 8.695 mmol) was added to acetic acid (108 ml) and then refluxed.

After 1.5 hours, the reaction product was cooled to room temperature and then vacuum evaporated to maximally remove acetic acid. For neutralization, after adding saturated aqueous $NaHCO_3$ thereto, the reaction product was extracted using EA, dried over $MgSO_4$, and then filtered. The filtrate was vacuum evaporated and then recrystallized (hexane/ether M-4: solid_1.8 g (71%)

5) Step 5

246 ml of methanol, 123 ml of distilled water, and 2.5 ml of pyrrolidine (30.787 mmol) were sequentially added to M-4 (1.7 g, 5.815 mmol) at room temperature, followed by stirring. Subsequently, additional stirring was performed for 4 hours at an inner temperature of 45° C. After adding distilled water and then 1 N HCl to adjust pH to approximately 2 to 3, the reaction product was extracted using MC. The separated organic layer was dried over $MgSO_4$ and then filtered. The filtrate was vacuum evaporated and then recrystallized (HX:ether).

M-5: Orange solid_0.39 g (28%)

1H NMR (300 MHz, DMSO) δ 13.35 (brs, 1H), 7.84 (d, J=7.5 Hz, 1H), 7.75 (d, J=7.5 Hz, 1H), 7.64 (t, J=7.5 Hz, 1H), 7.41 (t, J=7.5 Hz, 1H), 2.10-2.00 (m, 1H), 1.15-0.90 (m, 4H)

EXAMPLE 13

Synthesis of Compound 13

1) Step 1

19 ml of ethanol was added to 2-hydroxy 1,4-naphthoquinone (0.1 g, 0.57 mmol) and stirred at room temperature. 0.12 ml of ethylenediamine (1.72 mmol) was added thereto at room temperature, followed by stirring for 18 hours. After adding EA and distilled water thereto, an EA layer was washed using $NaHCO_3$ (aq). An EA layer was treated with $MgSO_4$, filtered, and vacuum evaporated, and then purified through column chromatography (HX:EA=4:1).

Orange solid 48%

1H NMR (300 MHz, $CD_3OD$) δ 9.16-9.13 (m, 1H), 8.74-8.71 (m, 2H), 8.40-8.37 (m, 1H), 7.83-7.77 (m, 2H), 7.13 (s, 1H)

2) Step 2

50 ml of DMF was added to benzo[f]quinoxalin-6-ol 0.5 g (2.55 mmol) and then IBX was added thereto. After stirring at room temperature for 4.5 hours, EA and aq. $NaHCO_3$ were added thereto, thereby generating a salt. The salt was removed through filtration and then a filtrate was extracted using EA. An EA layer was treated with $MgSO_4$ and filtered through silica gel, and then purified through recrystallization (Hex/EA).

Opaque yellow solid 34%

1H NMR (300 MHz, $CDCl_3$) δ 8.88 (d, J=2.2 Hz, 1H), 8.81 (d, J=2.2 Hz, 1H), 8.68 (d, J=7.9 Hz 1H), 8.28 (d, J=7.9 Hz 1H), 7.90-7.84 (m, 1H), 7.70-7.65 (m, 1H)

EXAMPLE 14

Synthesis of Compound 14

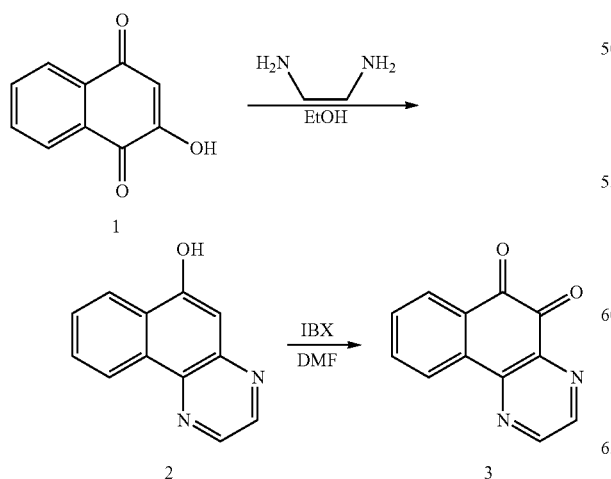

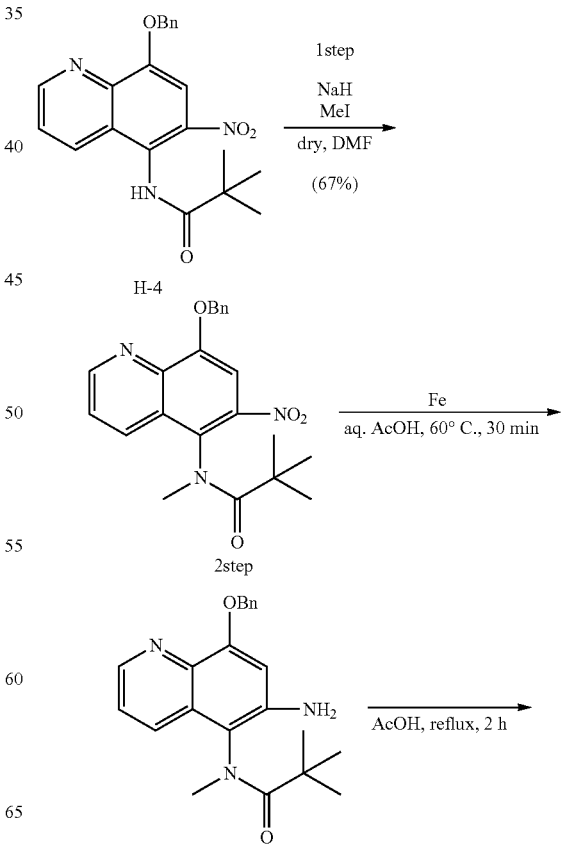

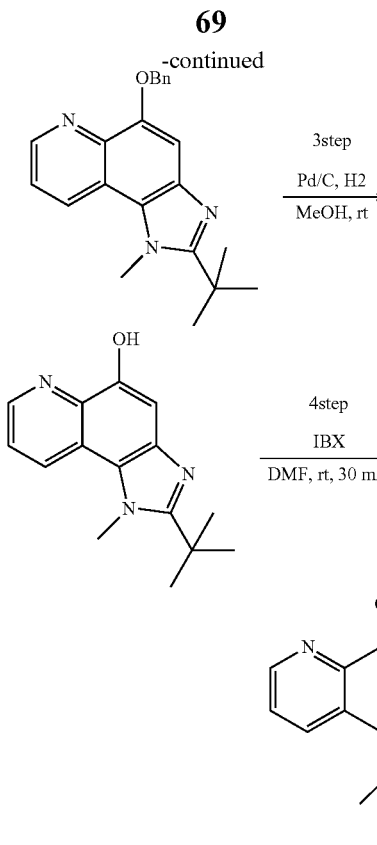

Step 1

26 ml of dried DMF was added to N-(8-benzyloxy)-6-nitroquinolin-5-yl)pivalamide (H-4) 1 g (2.236 mmol). NaH was added thereto in an ice bath and then stirred for 30 minutes at 0° C. 0.2 ml of MeI (3.43 mmol) was added dropwise thereto d and then stirred for 2.5 hours at room temperature. EA was added thereto and the reaction product was washed with water several times. An EA layer was treated with MgSO₄, filtered, and vacuum concentrated, and then purified using column chromatography.

697 mg (67%)

2) Step 2

Acetone (7.5 ml), AcOH (0.75 ml), and H₂O (3.7 ml) were added to N-(8-(benzyloxy)-6-nitroquinolin-5-yl)-N-methyl pivalamide (148 mg, 0.376 mmol) and temperature was elevated to 40 to 50° C. Fe was added thereto, followed by stirring for 1.5 hours at 60° C. room to 70° C. Celite filtration was performed to remove Fe and a filtrate was extracted by adding EA and aq. NaHCO₃. An EA layer was treated with MgSO₄, filtered, and vacuum concentrated, and then a crude reaction product was used in the next reaction.

The reaction product was dissolved in AcOH (4.7 ml) and then reflux stirred for one hour. After cooling, vacuum evaporation was performed, followed by purification using column chromatography.

3) Step 3

5-(benzyloxy)-2-tert-butyl-1-methyl-1H-imidazo[4,5-f]quinoline (0.1 g, 0.289 mmol) was dissolved in methanol (5.7 ml), and then 20 mg of Pd/C was added thereto, followed by attachment of a hydrogen-filled balloon. Stirring was performed for 18 hours at room temperature and then filtration was performed through Celite. The filtrate was vacuum evaporated and then purified using column chromatography.

4) Step 4

2-tert-butyl-1-methyl-1H-imidazo[4,5-f]quinolin-5-ol (40 mg, 0.157 mmol) was dissolved in DMF (1.6 ml) and then IBX (103 mg, 0.172 mmol) was added thereto. Stirring was performed for one hour at room temperature. MC and distilled water were added thereto and then an organic layer was washed with saturated aqueous NaHCO₃. The separated organic layer was dried over MgSO₄ and then filtered. The filtrate was vacuum evaporated and then purified through prep. TLC and recrystallization.

1H NMR (300 MHz, CDCl₃) δ 8.75 (d, J=4.8 Hz, 1H), 8.23 (d, J=8.4 Hz, 1H), 7.54 (dd, J=8.1 Hz, 4.8 Hz, 1H), 3.77 (s, 3H), 1.75 (s, 9H)

EXAMPLE 15

Synthesis of Compound 15

2-neopentyl-1H-naphtho[2,1-d]imidazole-4,5-dione

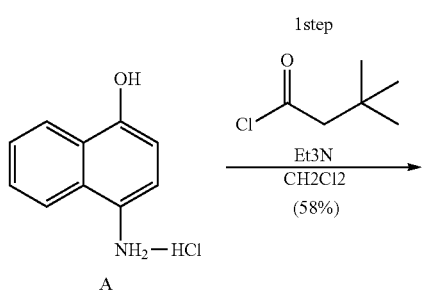

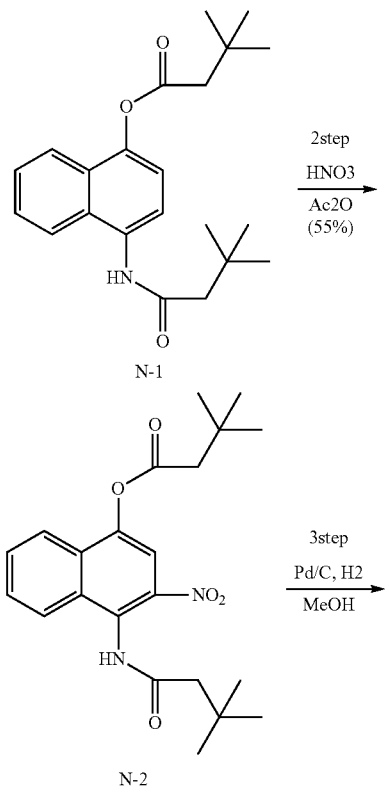

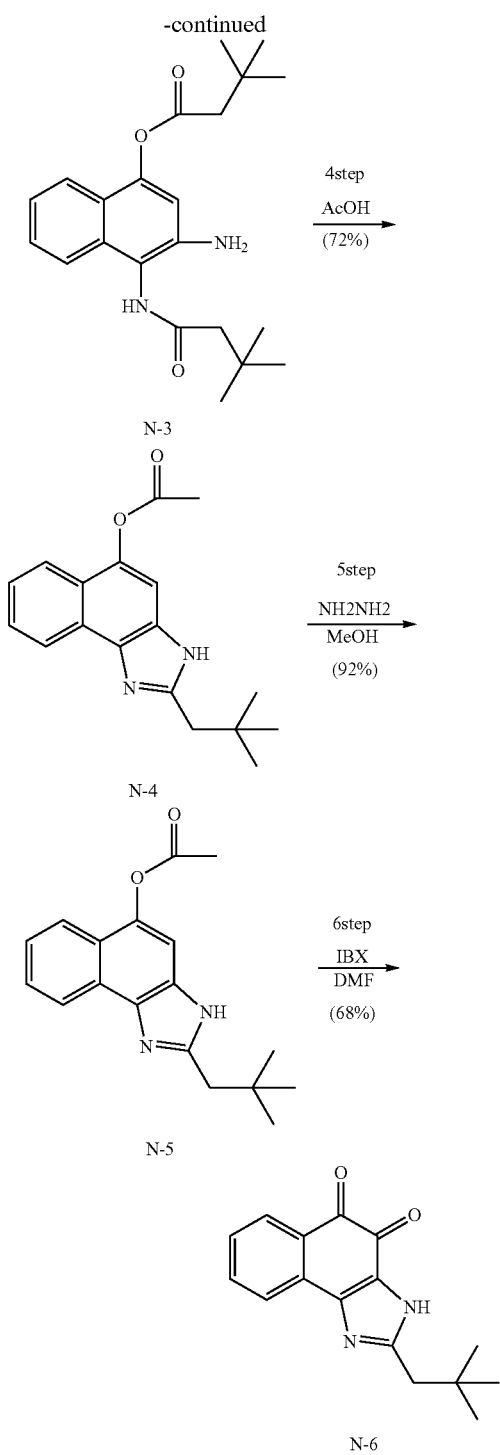

fied using silica gel column chromatography, thereby obtaining N-1.

N-1: 5.26 g (58%)

$^1$H NMR (300 MHz, CDCl$_3$) 7.89 (t, J=7.3 Hz, 2H), 7.82 (d, J=4.4 Hz, 1H), 7.53 (t, J=3.8 Hz, 2H), 7.37 (s, 1H), 7.21 (s, 1H), 2.62 (s, 2H), 2.37 (s, 2H), 1.20 (s, 9H), 1.18 (s, 9H)

2) Step 2

N-1 (3 g, 8.44 mmol) was added to acetic anhydride (30 ml) and then stirred in an ice bath. 90% nitric acid (1.15 ml, 16.88 mmol) was added thereto, followed by stirring for 1 hour at 0° C. When the reaction was completed, hexane/ether was added to a reaction solution and stirred, and then filtration was performed.

N-2: 1.84 g (55%)

$^1$H NMR (300 MHz, CDCl$_3$) 9.54 (s, 1H), 8.26 (dd, J=7.1 Hz, 2.4 Hz, 1H), 8.02 (dd, J=6.9 Hz, 2.2 Hz, 1H), 7.80 (s, 1H), 7.72-7.67 (m, 2H), 2.74 (s, 2H), 2.47 (s, 2H), 1.19 (s, 9H), 1.12 (s, 9H)

3) Step 3

N-2 (1.7 g, 4.25 mmol) was dissolved in methanol (50 ml), and then 170 mg of Pd/C was added thereto, followed by attachment of a hydrogen-filled balloon. Stirring was performed for 23 hours at room temperature and then filtration was performed through silica gel. The filtrate was vacuum evaporated and then recrystallized. (Ether)_crude N-3.

$^1$H NMR (300 MHz, CD$_3$OD) 7.71 (t, J=7.1 Hz, 2H), 7.42 (t, J=7.7 Hz, 1H), 7.23 (t, J=7.7 Hz, 1H), 6.91 (s, 1H), 2.63 (s, 2H), 2.45 (s, 2H), 1.19 (s, 18H)

4) Step 4

Crude N-3 (1.78 g, 4.80 mmol) was added to acetic acid (100 ml) and then refluxed while stirring for 24 hours. The reaction product was cooled to room temperature and then vacuum evaporated to maximally remove acetic acid. A saturated aqueous NaHCO$_3$ solution was added to the reaction product for neutralization and then the reaction product was extracted using EA, dried over MgSO$_4$, and then filtered. The filtrate was vacuum evaporated and then purified through silica gel column chromatography, thereby obtaining N-4.

N-4: solid_1.23 g (72%)

$^1$H NMR (300 MHz, CD$_3$OD) 8.41 (d, J=8.0 Hz, 1H), 7.92 (d, J=8.4 Hz, 1H), 7.62 (t, J=7.1 Hz, 1H), 7.49 (t, J=7.1 Hz, 1H), 7.41 (s, 1H), 2.83 (s, 2H), 2.67 (s, 2H), 1.20 (s, 9H), 1.06 (s, 9H)

5) Step 5

N-4 (1.92 g, 5.45 mmol) was dissolved in methanol (16 ml), and then hydrazine hydrate (50~60%, 0.40 ml, 10.9 mmol) was added thereto, followed by stirring for 13 hours at 40° C. The reaction product was cooled to room temperature and then vacuum evaporated. Crude N-5 was purified through silica gel column chromatography.

N-5: 1.27 g (92%)

$^1$H NMR (300 MHz, CD$_3$OD) 8.26 (t, J=9.0 Hz, 2H), 7.53 (t, J=7.2 Hz, 1H), 7.39 (t, J=7.7 Hz, 1H), 6.99 (s, 1H), 2.78 (s, 2H), 1.05 (s, 9H)

6) Step 6

N-5 (1.27 g, 4.99 mmol) was dissolved in DMF (50 ml) and then IBX (1.84 g, 2.95 mmol) was added thereto. Stirring was performed for one hour at room temperature. MC and distilled water were added thereto and then an organic layer was washed with saturated aqueous NaHCO$_3$. The separated organic layer was dried over MgSO$_4$ and then filtered. The filtrate was vacuum evaporated and then purified through column chromatography and recrystallization.

N-6: 915 mg (68%)

$^1$H NMR (300 MHz, CD$_3$OD) 8.00 (d, J=7.7 Hz, 1H), 7.91 (d, J=8.1 Hz, 1H), 7.67 (t, J=7.5 Hz, 1H), 7.44 (t, J=7.7 Hz, 1H), 2.69 (s, 2H), 1.05 (s, 9H)

1) Step 1

A (4-amino-1-naphthol hydrochloride, 5 g, 25.56 mmol) was added to pyridine (50 ml) and then stirred at room temperature for 30 minutes. In an ice bath, t-butyl acetyl chloride (10.65 ml, 76.6 8 mmol) was added dropwise thereto and then stirred for 2 hours at 0° C. EA was added thereto and pH was adjusted to approximately 6.5 using a 1 M aqueous HCl solution, followed by washing several times. The separated organic layer was dried over MgO$_4$ and then filtered for vacuum evaporation. Crude N-1 was puri

EXAMPLE 16

Synthesis of Compound 16

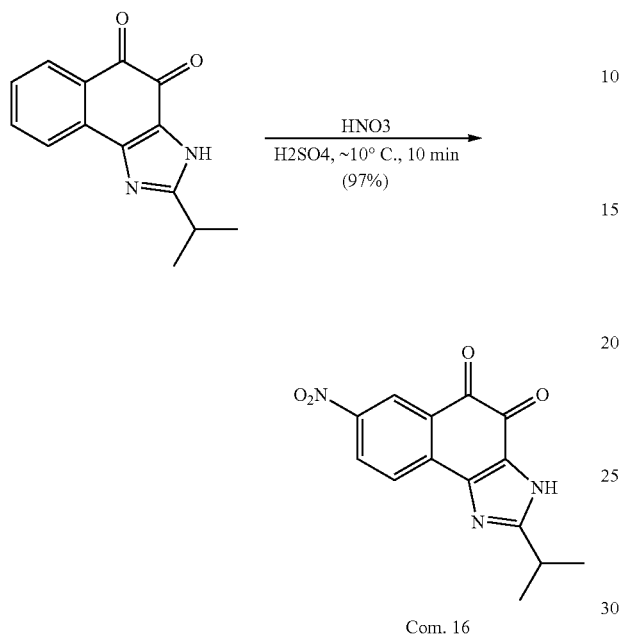

Com. 16

After putting a flask in an ice bath, H$_2$SO$_4$ (0.5 M, 4.16 ml) was added to the flask. 2-isopropyl-3H-naphtho[2,1-d]imidazole-4,5-dione (500 mg, 2.081 mmol) was added thereto portionwise and stirred for uniform mixing. 90% nitric acid was added thereto, followed by stirring for 10 minutes. The reaction product was poured onto ice water and then neutralized using NaHCO$_3$, thereby generating an orange solid. A filtered solid was washed with water several times.

Orange solid: 577 mg (97%)

1H NMR (300 MHz, small amount of CDCl$_3$+DMSO) δ 13.43 (brs, 1H), 8.82 (d, J=2.2 Hz, 1H), 8.45 (dd, J=8.4 Hz, 2.2 Hz, 1H), 8.17 (d, J=8.4 Hz, 1H), 3.23-3.14 (m, 1H), 1.42 (d, J=7.0 Hz, 6H)

EXAMPLE 17

Synthesis of Compound 17

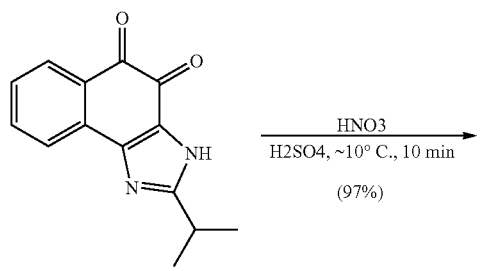

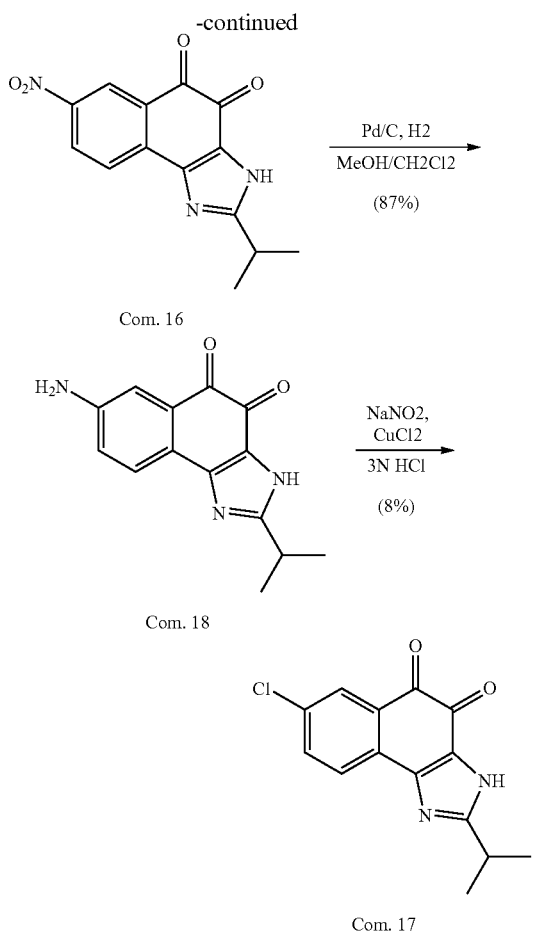

Com. 16

Com. 18

Com. 17

Compound 18 (70 mg, 0.275 mmol) was added to 3 N HCl (2.7 ml) and stirred for 3 minutes at room temperature. NaNO$_2$ (27 mg, 0.385 mmol) was dissolved in 0.5 ml of water, and then slowly added dropwise thereto in an ice bath. After further stirring for 3 minutes, CuCl$_2$ was added thereto and then stirred for 18 hours at room temperature. Aq. NaHCO$_3$ was added thereto for neutralization and then extracted using EA. An EA layer was treated with MgSO$_4$, filtered, and vacuum concentrated, and then separated using prep TLC.

Deep red: 6 mg (8%)

1H NMR (300 MHz, DMSO) δ 7.83-7.71 (m, 3H), 3.11-3.02 (m, 1H), 2.96 (d, J=7.0 Hz, 6H)

EXAMPLE 18

Synthesis of Compound 18

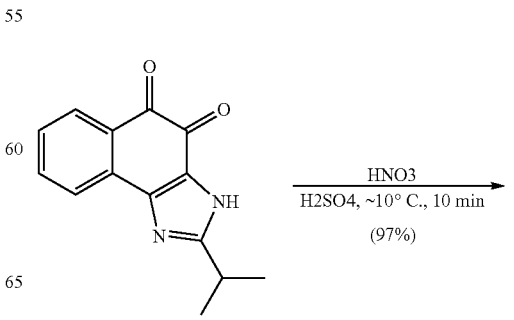

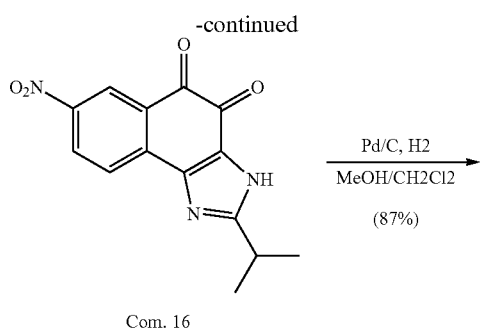

Com. 16

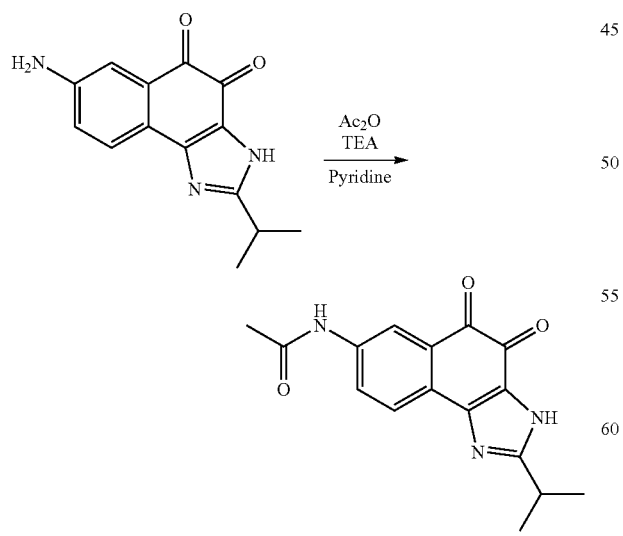

Com. 18

Compound 16 (570 mg, 2.0 mmol) was dissolved in methanol (20 ml), MC (10 ml), and then 114 mg of Pd/C was added thereto, followed by attachment of a hydrogen-filled balloon. Stirring was performed for two hours at room temperature and then filtration was performed through silica gel. The filtrate was vacuum evaporated and then recrystallized (Ether/EA/Hex)

Indigo solid: 444 mg (87%)

1H NMR (300 MHz, DMSO) δ 12.99 (brs, 1H), 7.46 (d, J=8.0 Hz, 1H), 7.10 (s, 1H), 6.73 (d, J=8.4 Hz, 1H), 5.78 (s, 2H), 3.02-2.96 (m, 1H), 1.27 (d, J=7.0 Hz, 6H)

EXAMPLE 19

Synthesis of Compound 19

Dry CH$_2$Cl$_2$ (2.75 ml) was added to Compound 18 (70 mg, 0.275 mmol) and then Et$_3$N (0.12 ml, 0.825 mmol) and pyridine (2.75 ml) were added thereto. Ac$_2$O (0.031 ml, 0.33 mmol) was added thereto in an ice bath and reacted for 18 hours at room temperature. The reaction product was vacuum evaporated and then extracted by adding MC and distilled water. An MC layer was treated with MgSO$_4$ and then filtered through silica gel. The filtrate was vacuum evaporated and then recrystallized using EA/Hex, thereby obtaining Compound 19.

(40 mg, 49%)

1H NMR (300 MHz, DMSO) δ 10.24 (s, 1H), 8.10 (s, 1H), 7.86 (d, J=8.4 Hz, 1H), 7.73 (d, J=8.1 hz, 1H), 3.10-3.00 (m, 1H), 2.07 (s, 3H), 1.29 (d, J=7.0 Hz, 6H)

EXAMPLE 20

Synthesis of Compound 20, and

EXAMPLE 21

Synthesis of Compound 21

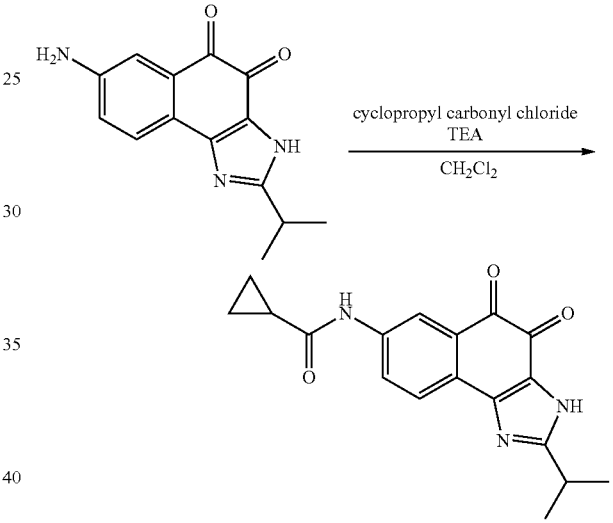

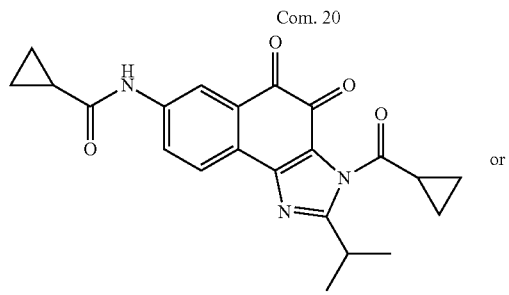

Com. 21

Dry CH$_2$Cl$_2$ (2.75 ml) was added to Compound 18 (70 mg, 0.275 mmol) and then Et$_3$N (0.12 ml, 0.825 mmol) was added thereto. Cyclopropyl carbonyl chloride (0.031 ml, 0.33 mmol) was added thereto and reacted for 2 hours in an ice bath. MC and distilled water were added to the reaction product and extraction was performed. An MC layer was treated with MgSO$_4$ and then vacuum evaporated. Purification was performed using column chromatography. Compound 20: 10 mg (11%), Compound 21: 20 mg (19%)

Compound 20: 1H NMR (300 MHz, small amount of CDCl$_3$+DMSO-d6) δ 13.06 (brs, 1H), 10.05 (s, 1H), 8.25-8.20 (m, 1H), 8.07 (s, 1H), 7.75-7.85 (m, 1H), 3.18-3.11 (m, 1H), 1.80-1.74 (m, 1H), 1.38 (d, J=7.0 Hz, 6H), 1.08-0.98 (m, 2H), 0.86-0.80 (m, 2H)

Compound 21: 1H NMR (300 MHz, CDCl$_3$) δ 8.23 (d, J=8.4 Hz, 1H), 8.02 (d, J=8.4 Hz, 1H), 7.96 (d, J=2.2 Hz, 1H), 7.87 (brs, 1H), 3.35-3.26 (m, 1H), 2.14-2.06 (m, 1H), 1.67-1.59 (m, 1H), 1.49-1.45 (m, 2H), 1.40 (d, J=7.0 Hz, 6H), 1.33-1.24 (m, 2H), 1.16-1.11 (m, 2H), 0.95-0.89 (m, 2H)

EXAMPLE 22

Synthesis of Compound 22

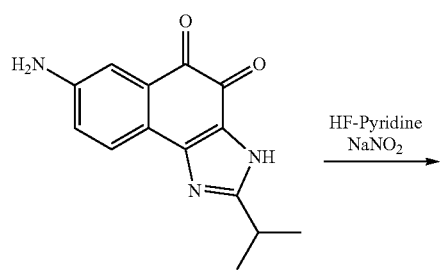

HF-Pyridine (2 ml) was added to a conical tube and Compound 18 (100 mg, 0.392 mmol) was added thereto at 0° C., followed by stirring for 15 minutes at room temperature. NaNO$_2$ (38 mg, 0.549 mmol) was added thereto, followed by stirring for 15 minutes at room temperature. After stirring for 2 hours at 110° C., the reaction product was cooled. Water and MC were added thereto for extraction and an MC layer was treated with MgSO$_4$ and filtered through silica gel, followed by vacuum evaporation. Recrystallization was performed using EA/Hex.

59 mg (58%)

1H NMR (300 MHz, DMSO-d6) δ 7.87-7.82 (m, 1H), 7.60-7.49 (m, 2H), 3.11-3.01 (m, 1H), 1.29 (d, J=7.0 Hz, 6H)

EXAMPLE 23

Synthesis of Compound 23

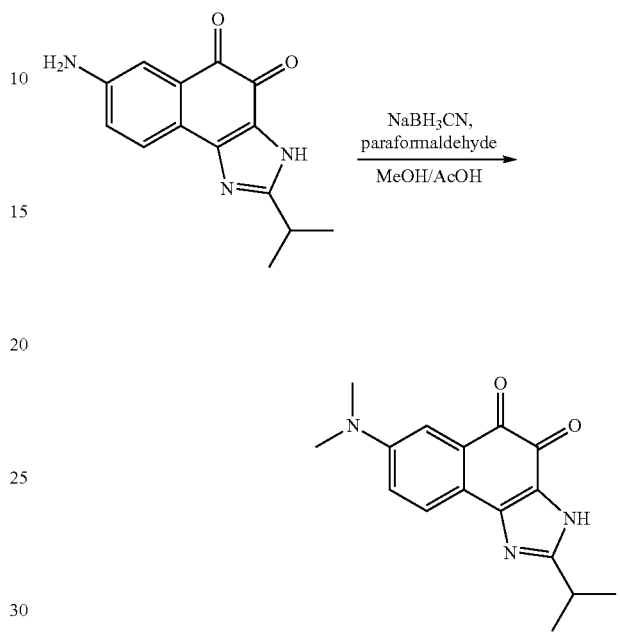

Compound 18 (100 mg, 0.392 mmol) and paraformaldehyde (26 mg, 0.86 mmol) were dissolved in MeOH and then stirred for 15 minutes at room temperature. NaBH$_3$CN (54 mg, 0.86 mmol) was added thereto and then AcOH (0.5 ml) was added thereto, followed by stirring for 18 hours at room temperature. Water and MC were added thereto for extraction and an MC layer was treated with MgSO$_4$, filtered through silica gel, and then vacuum evaporated. For recrystallization, EA/Hex was used.

30 mg (27%)

1H NMR (300 MHz, small amount of CDCl$_3$+DMSO-d6) δ 12.82 (brs, 1H), 7.72 (d, J=8.0 Hz, 1H), 7.32 (d, J=2.6 Hz, 1H), 6.81 (d, J=8.8 Hz, 1H), 3.15-3.06 (m, 7H), 1.38 (d, J=7.0 Hz, 6H)

EXAMPLES 24, 25, AND 26

Synthesis of Compounds 24, 25, and 26

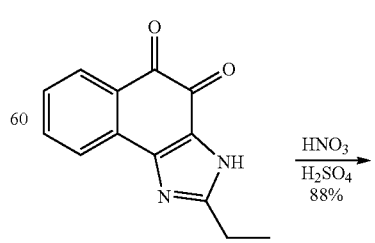

-continued

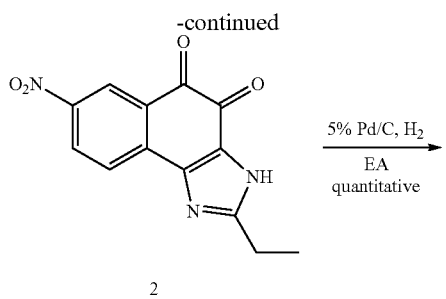

Examples 24, 25, and 26

H$_2$SO$_4$ was cooled in an ice bath and then Compound 1 (1.76 g, 7.8 mmol) was added thereto. HNO$_3$ (90%) (0.44 ml, 9.33 mmol) was slowly added thereto and then further stirred for 30 minutes. The reaction solution was poured onto ice and a solid was filtered out. The solid was washed with distilled water and EA.

Orange solid 1.8 g (85%)

Example 24: $^1$H NMR (300 MHz, DMSO) δ 13.62 (br, s, 1H), 8.45-8.44 (m, 2H), 8.00 (d, J=9.1 Hz, 1H), 2.76 (q, J=7.7 Hz, 2H), 1.28 (t, J=7.7 Hz, 3H)

Compound 2 was dissolved in EA (63 ml), and then 5% Pd/C (0.34 g, 10 mol %) was added thereto, followed by stirring for one hour under a hydrogen atmosphere. After Celite filtration, purification was performed through recrystallization.

Indigo solid (quantitative yield)

Example 25: $^1$H NMR (300 MHz, DMSO) δ 7.44 (d, J=8.1 Hz, 1H), 7.10 (s, 1H), 6.73 (d, J=8.1 Hz, 1H), 5.81 (br, s, 2H), 2.67 (q, J=7.3 Hz, 2H), 1.26-1.21 (m, 3H)

HF-Pyridine (2 ml) was added to a conical tube and Compound 18 (100 mg, 0.392 mmol) was added thereto at 0° C., and then stirring was performed for 15 minutes. NaNO$_2$ (38 mg, 0.549 mmol) was added thereto, followed by stirring for 15 minutes at room temperature. After stirring for 2 hours at 110° C., the reaction product was cooled. Water and MC were added thereto for extraction, and an MC layer was treated with MgSO$_4$ and filtered through silica gel, followed by vacuum evaporation. For recrystallization, EA/Hex was used.

59 mg (58%)

Example 26: $^1$H NMR (300 MHz, CDCl$_3$+DMSOd6) δ 13.28 (brs, 1H), 7.95-7.91 (m, 1H), 7.66 (dd, J=8.1 Hz, 2.7 Hz, 1H), 7.31 (td, J=7.8 Hz, 2.7 Hz, 1H), 2.83 (q, J=7.8 Hz, 2H), 1.39 (t, J=7.2 Hz, 3H)

Example 27

Synthesis of Compound 27

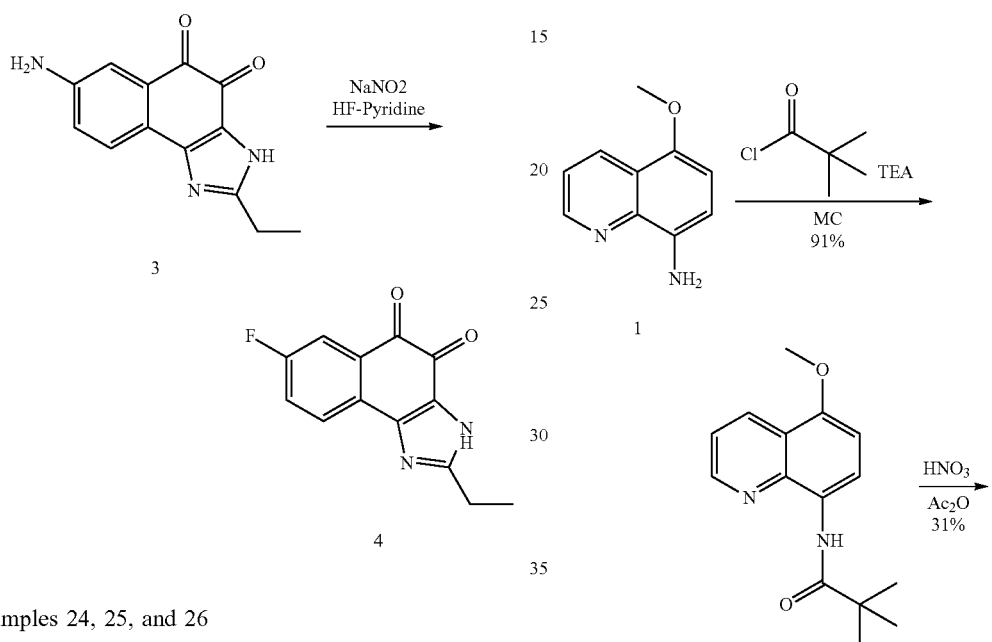

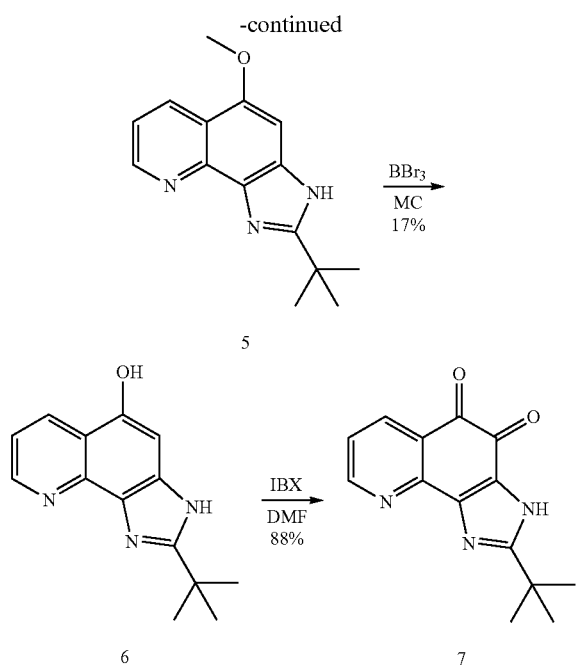

1->2

Compound 1 (5-methoxyquinolin-8-amine, 4.5 g, 25.83 mmol) dissolved in methylene chloride (125 ml), and then triethylamine (2.16 ml, 77.50 mmol) was added thereto, followed by stirring for 10 minutes. Pivaloyl chloride (2.9 ml, 31.00 mmol) was slowly added to the reaction product and then stirred for 10 minutes. The reaction product was quenched with an aqueous NaHCO₃ solution and then an organic layer was wished with a NaHCO₃ aqueous solution three times. An organic layer was dried over Na₂SO₄ and filtered, and then vacuum evaporated. A solid extracted by recrystallization using EA and hexane was filtered and then dried, thereby obtaining Compound 2 (6.05 g, 91%).

¹H NMR (300 MHz, CDCl₃) δ 10.04 (br s, N—H, 1H), 8.83-8.82 (dd, J=4.2, 1.8 Hz, 1H), 8.74-8.71 (d, J=9.0 Hz, 1H), 8.59-8.56 (dd, J=8.4, 1.8 Hz, 1H), 7.46-7.42 (dd, J=8.4, 4.2 Hz, 1H), 6.85-6.82 (d, J=9.0 Hz, 1H), 3.99 (s, 3H), 1.42 (s, 9H)

2->3

Compound 2 (3.0 g, 11.61 mmol) was dissolved in Ac₂O (240 ml) and then stirred for 20 minutes in an ice bath. HNO₃ (0.58 ml, 12.19 mmol) was slowly added to the reaction product. After quenching with methanol, vacuum evaporation was performed. A concentrated reaction product was dissolved in EA and then washed with an aqueous NaHCO₃ solution several times. An EA layer was dried over Na₂SO₄ and filtered, and then vacuum evaporated. A concentrated reaction product was maximally dissolved, and then filtered through short silica column chromatography and washed with MC to remove Rf=0.3 spot. The filtrate was vacuum evaporated and a solid extracted by recrystallization using MC and hexane was filtered and dried. As a result, Compound 3 (1.2 g, 34%) was obtained.

¹H NMR (300 MHz, CDCl₃) δ 9.61 (br s, N—H, 1H), 8.94-8.91 (dd, J=4.2, 1.5 Hz, 1H), 8.58-8.54 (dd, J=8.4, 1.5 Hz, 1H), 7.60-7.55 (dd, J=8.4, 4.2 Hz, 1H), 7.25 (s, 1H), 4.03 (s, 3H), 1.42 (s, 9H)

3->4

Compound 3 (1.0 g, 3.30 mmol) was dissolved in MeOH/MC (33 ml/33 ml) and then 5% Pd/C (0.35 g, 0.165 mmol) was added thereto. The reaction product was degassed, and then 1 atmosphere of H₂ was supplied thereto, followed by stirring for 18 hours at room temperature. Pd/C was removed through Celite filtration and then short silica column chromatography was performed to remove impurities. Subsequently, vacuum evaporation was performed, thereby obtaining Compound 4 (0.9 g, yield 99%).

¹H NMR (300 MHz, CDCl₃) δ 9.26 (br s, N—H, 1H), 8.71-8.69 (dd, J=4.2, 1.5 Hz, 1H), 8.37-8.33 (dd, J=8.4, 1.5 Hz, 1H), 7.18-7.13 (dd, J=8.4, 4.2 Hz, 1H), 6.33 (s, 1H), 4.98 (br s, 2H), 3.93 (s, 3H), 1.45 (s, 9H)

4->5->6

Compound 4 (950 mg, 3.476 mmol) was dissolved in AcOH (70 ml) and then refluxed for 12 hours. AcOH was maximally removed through vacuum evaporation (crude Compound 5). A concentrated reaction product was dissolved in 48% aq HBr (35 ml) and then refluxed for 12 hours. Temperature of the reaction product was lowered using an ice bath and then pH thereof was adjusted to 7 using an aqueous 2N NaOH solution. Extracted solids were filtered and washed with water several times. An obtained solid was dried, thereby obtaining Compound 5 (710 mg, 84%, Step 2 yield).

Compound 5 ¹H NMR (300 MHz, CDCl₃) δ 10.29 (br s, N—H, 1H), 8.83 (d, J=4.5 Hz, 1H), 8.67 (d, J=8.4 Hz, 1H), 7.41-7.36 (dd, J=8.4, 4.5 Hz, 1H), 7.29 (s, 1H), 4.02 (s, 3H), 1.55 (s, 9H)

Compound 6 ¹H NMR (300 MHz, CDCl₃) δ 8.87-8.86 (dd, J=4.5, 1.5 Hz, 1H), 8.69-8.66 (dd, J=8.4, 1.5 Hz, 1H), 7.58 (s, 1H), 7.44-7.40 (dd, J=8.4, 4.5 Hz, 1H), 1.57 (s, 9H)

6->7

Compound 6 (700 mg, 2.9 mmol) was dissolved in DMF (60 ml), and then temperature of a reaction product solution was lowered using an ice bath and stirring was performed for 30 minutes. 47% IBX (4.15 g, 10.4 mmol) was added to the reaction product and stirred for 10 minutes. The reaction product was diluted with EA and then washed with an aqueous NaHCO₃ solution several times. An EA layer was dried over Na₂SO₄ and filtered, and then vacuum evaporated. A concentrated reaction product was recrystallized using EA and hexane, thereby obtaining Compound 7 (500 mg, 68%).

¹H NMR (300 MHz, CDCl₃) δ 8.85-8.83 (dd, J=4.8, 1.5 Hz, 1H), 8.28-8.25 (dd, J=7.8, 1.5 Hz, 1H), 7.37-7.33 (dd, J=7.8, 4.8 Hz, 1H), 1.54 (s, 9H)

EXAMPLE 28

Synthesis of Compound 28

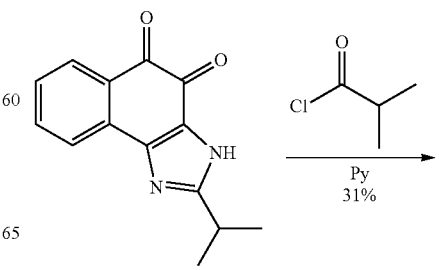

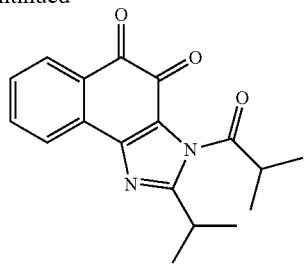

In an ice bath, Compound 1 (0.1 g, 0.42 mmol) was dissolved in pyridine (0.84 ml, 0.5 M). Isobutyryl chloride (53 ul, 0.5 mmol) was slowly added thereto and then stirred for one hour under a nitrogen atmosphere. After adding MC and distilled water thereto a reaction solution, extraction was performed several times. The separated organic layer was dried over MgSO$_4$ and then filtered. The filtered solution was vacuum evaporated and then purified through recrystallization.

Orange solid 41 mg (31%)

$^1$H NMR (300 MHz, CDCl$_3$) δ 8.10-8.06 (m, 2H), 7.67 (t, J=7.5 Hz, 7.7 Hz, 1H) 7.46 (t, J=7.7 Hz, 7.7 Hz, 1H), 3.43-3.36 (m, 1H), 3.18-3.11 (m, 1H), 1.42 (d, J=6.6 Hz, 6H), 1.27 (d, J=6.6 Hz, 6H)

EXAMPLE 29

Synthesis of Compound 29

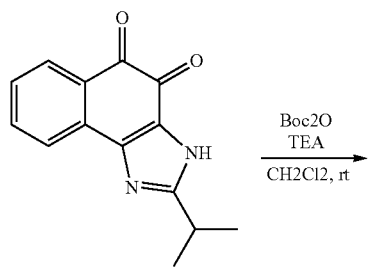

SM (500 mg, 2.081 mmol) was dissolved in THF (0.2 M, 10 ml), and then TEA (0.44 ml, 3.121 mmol), di-tert-butyldicarbonate (0.52 ml, 2.289 mmol), and DMAP (50 mg) were sequentially added thereto, followed by stirring for 15 hours at room temperature. After vacuum distillation, 594 mg of a light-orange solid (84%) was obtained through short-column chromatography. (Hex:EA=5:1).

EXAMPLE 30

Synthesis of Compound 30

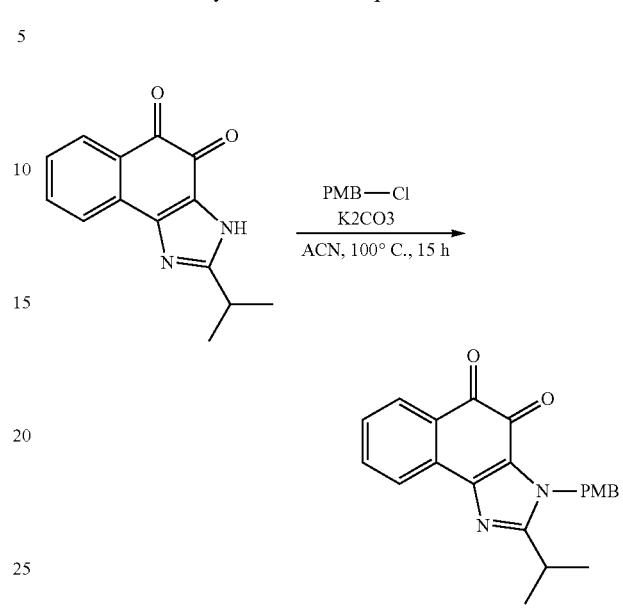

Example 1

CAN (6.2 ml, 0.2 M) and K$_2$CO$_3$ (518 mg, 3.747 mmol) were added to SM (300 mg, 1.249 mmol) and stirred for 15 minutes at room temperature. Subsequently, PMB-Cl was added thereto and refluxed while stirring for 15 hours. Water was added to the reaction product and then the reaction product was extracted using EA. The separated organic layer was dried over MgSO$_4$ and then a filtrate was vacuum evaporated. For recrystallization, Hex/EA was used, thereby obtaining 400 mg of an orange solid (89%).

EXAMPLE 31

Synthesis of Compound 31

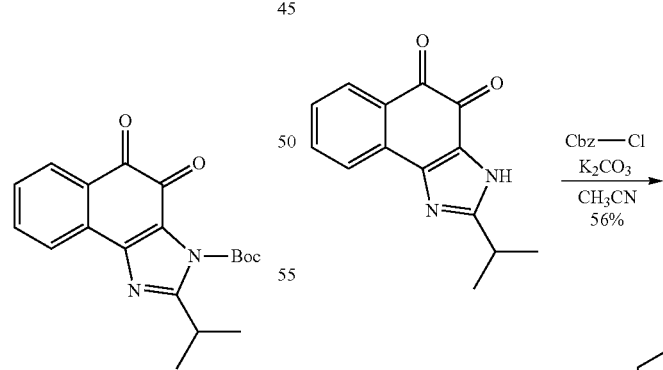

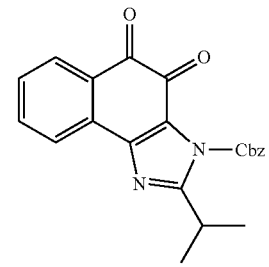

Example 1

In an ice bath, Compound 1 (0.5 g, 2.08 mmol) was dissolved in CH₃CN (10 ml). K₂CO₃ (0.9 g, 6.24 mmol) was added thereto and then was stirred for 10 minutes at room temperature. Benzyl chloroformate (0.36 ml, 1.2 mmol) was added thereto and then reflux for 21 hours. EA and distilled water were added thereto and then washed several times. The separated organic layer was dried over MgSO₄ and then filtered. The filtered solution was vacuum evaporated and then purified via silica gel column chromatography.

Red solid 0.44 g (56%)

$^1$H NMR (300 MHz, CDCl$_3$) δ 8.04-8.01 (m, 2H), 7.61 (t, J=7.7 Hz, 8.2 Hz, 1H), 7.41-7.15 (m, 6H), 5.59 (s, 2H), 3.08-3.04 (m, 1H), 1.31 (d, J=6.8 Hz, 6H)

Example 32

Synthesis of Compound 32

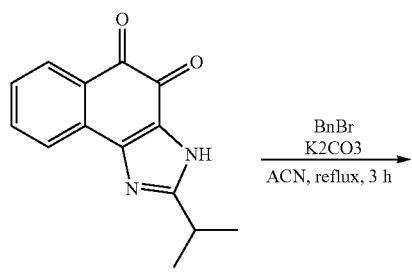

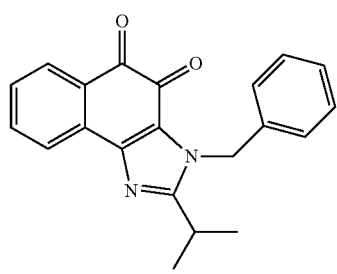

Example 1

CAN (2 ml, 0.2 M) was added to SM (100 mg, 0.413 mmol). K$_2$CO$_3$ (172 mg, 1.248 mmol) and benzyl bromide (59 ul, 0.499 mmol) were sequentially added thereto and refluxed while stirring for 3 hours. After neutralizing with EA and water, an separated organic layer was dried over MgSO$_4$, filtered, and vacuum distilled, and then filtered through silica gel. A filtrate was purified through recrystallization in ether. Yield 110 mg (80%)

$^1$H NMR (300 MHz, CDCl$_3$) δ 8.02 (d, J=7.8 Hz, 2H), 7.61 (t, J=7.2 Hz, 1H), 7.41-7.26 (m, 4H), 7.16 (d, J=7.8 Hz, 2H), 5.59 (s, 2H), 3.08-3.03 (m, 1H), 1.30 (d, J=6.9 Hz, 6H)

EXAMPLE 33

Synthesis of Compound 33

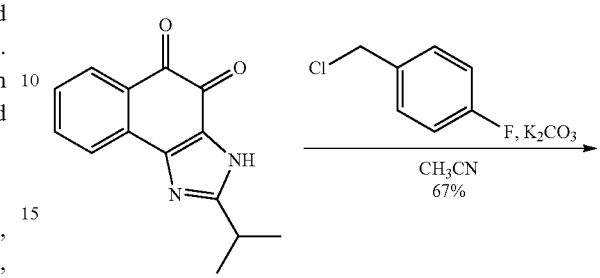

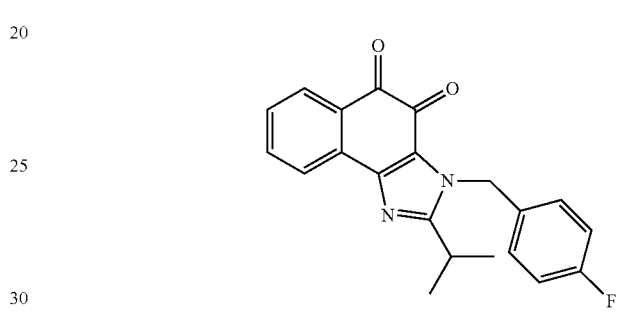

Example 1

Compound 1 (0.2 g, 0.83 mmol) was dissolved in CH$_3$CN (8.5 ml). K$_2$CO$_3$ (0.35 g, 2.5 mmol) was added thereto, followed by stirring for 10 minutes at room temperature. 4-fluorobenzyl chloride (0.12 ml, 1.0 mmol) was added thereto and then refluxed for 4 hours. EA and distilled water were added thereto and then washed several times. The separated organic layer was dried over MgSO$_4$ and then filtered. The filtered solution was vacuum evaporated and then purified via silica gel column chromatography Bright-orange solid 0.19 g (67%)

$^1$H NMR (300 MHz, CDCl$_3$) δ 8.03-8.00 (m, 2H), 7.61-7.07 (m, 6H), 5.54 (s, 2H), 3.08-3.04 (m, 1H), 1.32 (d, J=6.8 Hz, 6H)

EXAMPLE 34

Synthesis of Compound 34

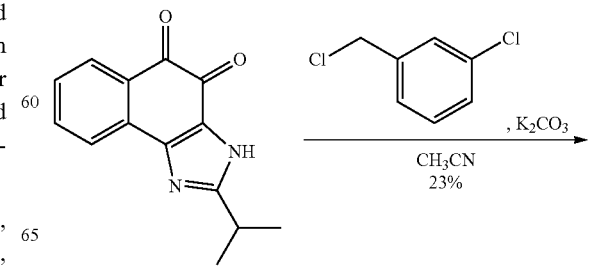

-continued

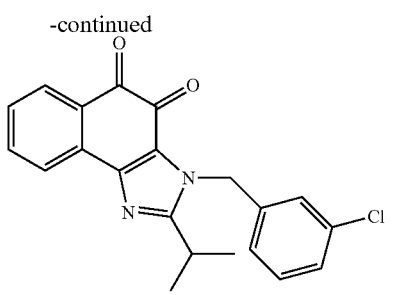

Example 1

Compound 1 (0.2 g, 0.83 mmol) was dissolved in CH₃CN (8.5 ml). K₂CO₃ (0.35 g, 2.5 mmol) was added thereto, followed by stirring for 10 minutes at room temperature. 3-chlorobenzyl chloride (0.13 ml, 1.0 mmol) was added thereto and then refluxed for 4 hours. EA and distilled water were added thereto and then washed several times. The separated organic layer was dried over MgSO₄ and then filtered. The filtered solution was vacuum evaporated and then purified via silica gel column chromatography.

Red solid 69 mg (23%)

$^1$H NMR (300 MHz, CDCl₃) δ 8.04-8.01 (m, 2H), 7.63-7.04 (m, 6H), 5.56 (s, 2H), 3.06-3.00 (m, 1H), 1.33 (d, J=6.8 Hz, 6H)

EXAMPLE 35

Synthesis of Compound 35

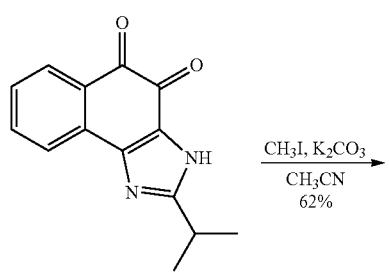

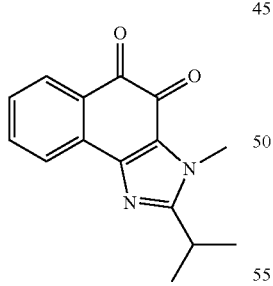

Compound 1 (0.2 g, 0.83 mmol) was dissolved in CH₃CN (8.5 ml). K₂CO₃ (0.35 g, 2.5 mmol) was added thereto, followed by stirring for 10 minutes at room temperature. Iodomethane (65 ul, 1.0 mmol) was added thereto and then stirred for 2 hours at 80° C. EA and distilled water were added thereto and washed several times. The separated organic layer was dried over MgSO₄ and then filtered. The filtered solution was vacuum evaporated and then purified via silica gel column chromatography.

Red solid 0.13 g (62%)

$^1$H NMR (300 MHz, CDCl₃) δ 8.00-7.94 (m, 2H), 7.58 (t, J=7.5 Hz, 1H), 7.36 (t, J=7.5 Hz, 1H), 3.94 (s, 3H), 3.11-3.06 (m, 1H), 1.42 (d, J=6.8 Hz, 6H)

EXAMPLE 36

Synthesis of Compound 36

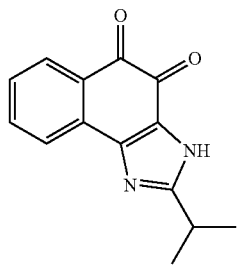

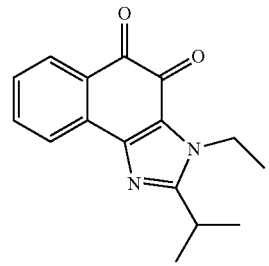

Compound 1 (0.2 g, 0.83 mmol) was dissolved in CH₃CN (8.5 ml). K₂CO₃ (0.35 g, 2.5 mmol) was added thereto, followed by stirring for 10 minutes at 80° C. A reaction solution was cooled to 40° C., and then ethyl bromide (75 ul, 1.0 mmol) was added thereto and further stirred at 80° C. for 19 hours. EA and distilled water were added thereto and then washed several times. The separated organic layer was dried over MgSO₄ and then filtered. The filtered solution was vacuum evaporated and then purified via silica gel column chromatography.

Red solid 64 mg (29%)

$^1$H NMR (300 MHz, CDCl₃) δ 8.02-7.98 (m, 2H), 7.60 (t, J=7.5 Hz, 7.7 Hz, 1H), 7.36 (t, J=7.7 Hz, 6.9 Hz, 1H), 4.33 (q, J=7.1 Hz, 2H), 3.10-3.06 (m, 1H), 1.44-1.42 (m, 9H)

EXAMPLE 37

Synthesis of Compound 37

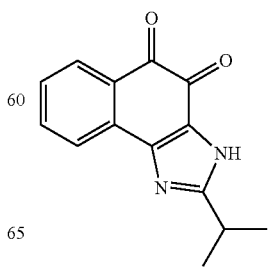

-continued

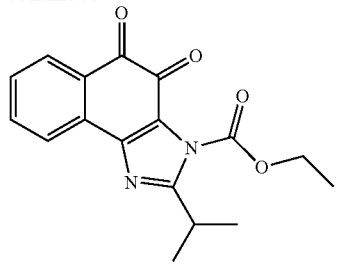

Compound 1 (0.2 g, 0.83 mmol) was dissolved in CH₃CN (8.5 ml). K₂CO₃ (0.35 g, 2.5 mmol) was added thereto, followed by stirring for 10 minutes at room temperature. Ethyl chloroformate (0.11 ml, 1.16 mmol) was added thereto followed by refluxing for 30 minutes. Subsequently, washing was performed with EA and distilled water several times. The separated organic layer was dried over MgSO₄ and then filtered. The filtered solution was vacuum evaporated and then purified via silica gel column chromatography.

Red solid 67 mg (26%)

$^1$H NMR (300 MHz, CDCl₃) δ 8.09-8.05 (m, 2H), 7.66 (t, J=7.5 Hz, 1H), 7.45 (t, J=7.5 Hz, 1H), 3.52-3.47 (m, 1H), 1.48 (t, J=7.1 Hz, 3H), 1.43 (d, J=6.8 Hz, 6H)

EXAMPLES 38 AND 39

Synthesis of Compounds 38 and 39

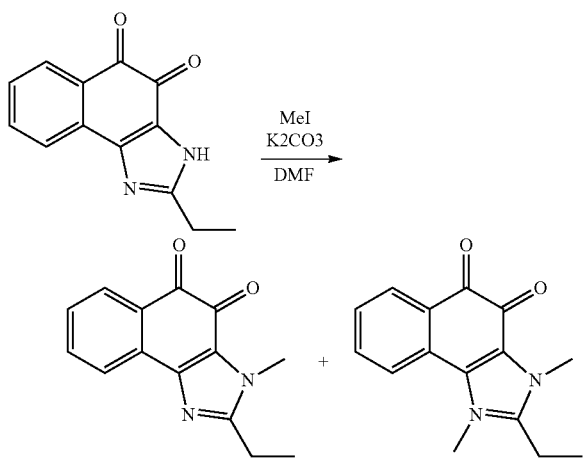

Examples 38 and 39

Example 38: 2-ethyl-3-methyl-3H-naphtho[2,1-d]imidazole-4,5-dione

Example 39: 2-ethyl-1-methyl-1H-naphtho[2,1-d]imidazole-4,5-dione 2-ethyl-3H-naphtho[2,1-d]imidazole-4,5-dione (700 mg, 3.097 mmol) was dissolved in CAN. K₂CO₃ (1.28 g, 9.29 mmol) was added thereto, followed by stirring for 30 minutes at room temperature, and then MeI (0.27 ml, 4.33 mmol) was added thereto and reflux stirred for one hour. EA/H₂O was added to the reaction product for extraction, and then an organic layer was dried over MgSO₄, filtered, and vacuum distilled. Finally, short-column chromatography was performed, thereby obtaining compounds as follows.

Example 38: 620 mg (83%), Example 39: 3 mg (4%)

Example 38: $^1$H NMR (300 MHz, CDCl₃) δ 8.02 (d, J=8.1 Hz, 1H), 7.95 (d, J=7.8 Hz, 1H), 7.60 (t, J=7.5 Hz, 1H), 7.38 (t, J=7.5 Hz, 1H), 3.93 (s, 3H), 2.81 (q, J=7.8 Hz, 1H), 1.42 (t, J=7.8 Hz, 1H)

Example 39: $^1$H NMR (300 MHz, CDCl₃) δ 8.18 (d, J=8.1 Hz, 1H), 7.71 (d, J=7.8 Hz, 1H), 7.62 (t, J=7.5 Hz, 1H), 7.42 (t, J=7.5 Hz, 1H), 3.96 (s, 3H), 2.83 (q, J=7.5 Hz, 2H), 1.42 (t, J=7.5 Hz, 3H)

EXAMPLE 40

Synthesis of Compound 40

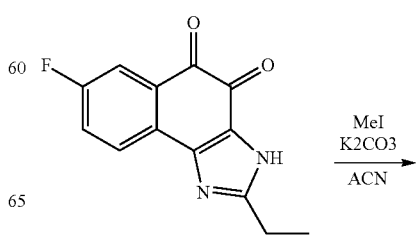

Example 40: 2-ethyl-3-(2,2,2-trifluoroethyl)-3H-naphtho[2,1-d]imidazole-4,5-dione 2-ethyl-3H-naphtho[2,1-d]imidazole-4,5-dione (80 mg, 0.354 mmol) was dissolved in DMF (1.75 ml, 0.2 M), and then K₂CO₃ (98 mg, 0.708 mmol) was added thereto, followed by stirring for 30 minutes. ICH₂CF₃ (0.35 ml, 1 M) was added thereto and reacted for 16 hours at 120° C. EA/H₂O was added to the reaction product for extraction and then an organic layer was dried over MgSO₄, filtered, and vacuum distilled. Finally, after short-column chromatography, separation was performed using prep TLC. Obtained amount: 2 mg (2%).

Example 40: $^1$H NMR (300 MHz, CDCl₃) δ 10.00 (brs, 1H), 7.73 (d, J=8.1 Hz, 1H), 7.32-7.30 (m, 2H), 6.83 (d, J=8.1 Hz, 1H), 3.99 (s, 2H), 3.17 (q, J=6.9 hz, 2H), 1.42 (t, J=6.9 Hz, 3H)

EXAMPLES 41 AND 42

Synthesis of Compounds 41 and 42

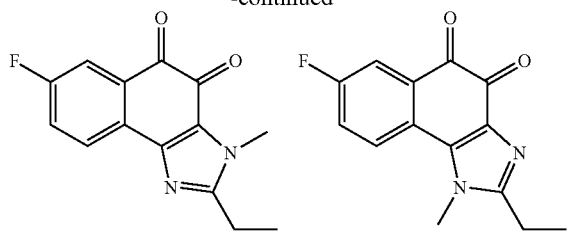

Example 41            Example 42

Example 41: 2-ethyl-7-fluoro-3-methyl-3H-naphtho[2,1-d]imidazole-4,5-dione

Example 42: 2-ethyl-7-fluoro-1-methyl-1H-naphtho[2,1-d]imidazole-4,5-dione

CAN was added to Compound 26 (620 mg, 2.541 mmol) and K$_2$CO$_3$ (1.05 g, 7.623 mmol) and stirred for 30 minutes at room temperature. MeI (0.2 ml, 3.557 mmol) was added thereto, and then stirred for 3 hours 40 minutes and refluxed. Aq. NaHCO$_3$ was added thereto and then EA was added thereto for extraction. The organic layer was dried over MgSO$_4$, and then filtered and vacuum distilled. A concentrated solution was separated through column chromatography. Example 41: 2-ethyl-7-fluoro-3-methyl-3H-naphtho[2,1-d]imidazole-4,5-dione: 580 mg (88%), Example 42: 2-ethyl-7-fluoro-1-methyl-1H-naphtho[2,1-d]imidazole-4,5-dione: 10 mg (2%)

Example 41: $^1$H NMR (300 MHz, CDCl$_3$) δ 7.97-7.92 (m, 1H), 7.71-7.67 (m, 1H), 7.32-7.26 (m, 1H), 3.91 (s, 3H), 2.80 (q, J=7.5 Hz, 2H), 1.41 (t, J=7.5 Hz, 3H)

Example 42: $^1$H NMR (300 MHz, CDCl$_3$) δ 7.86-7.82 (m, 1H), 7.74-7.70 (m, 1H), 7.34-7.26 (m, 1H), 3.94 (s, 3H), 2.82 (q, J=7.5 Hz, 2H), 1.42 (t, J=7.5 Hz, 3H)

EXAMPLES 43, 44, AND 45

Synthesis of Compounds 43, 44, and 45

Step 1: 7-chloro-2-ethyl-3H-naphtho[2,1-d]imidazole-4,5-dione (Compound 45)

1N HCl (68 ml, 0.1 M) was added to 7-amino-2-ethyl-3H-naphtho[2,1-d]imidazole-4,5-dione (1.65 g, 6.846 mmol). In an ice bath, N$_2$ was used for substitution. NaNO$_2$ (661 mg, 9.585 mmol) including 6.8 ml of distilled water was added to the solution and then stirred for 10 minutes. 3.4 ml of distilled water was added to CuCl2 (5.8 g, 34.23 mmol) and dissolved, and then a reaction product solution was added to the solution. The reaction product was reacted for 2 hours at 60° C. An organic layer extracted using EA was dried over MgSO$_4$, and then filtered through silica gel and vacuum distilled. A concentrated solution was crystallized using EA/Hex and then filtered to obtain a target compound. 600 mg (34%)

Step 2

Compound 43: 7-chloro-2-ethyl-3-methyl-3H-naphtho[2,1-d]imidazole-4,5-dione,

Compound 44: 7-chloro-2-ethyl-1-methyl-1H-naphtho[2,1-d]imidazole-4,5-dione

ACN was added to Compound 45 (100 mg, 0.383 mmol) and K$_2$CO$_3$ (159 mg, 1.149 mmol) and stirred for 3 minutes at room temperature. MeI (33 ul, 0.536 mmol) was added thereto, and then stirred for 2 hours and refluxed. Aq. NaHCO$_3$ was added thereto and then EA was added thereto for extraction. The organic layer was dried over MgSO$_4$, and then filtered and vacuum distilled. A concentrated solution was separated using a column. Compound 43: 80 mg (76%), Compound 44: 4 mg (4%)

Compound 43: $^1$H NMR (300 MHz, CDCl$_3$) δ 7.98 (s, 1H), 7.91 (d, J=7.2 Hz, 1H), 7.57 (dd, J=8.4 Hz, 2.1 Hz, 1H), 3.92 (s, 3H), 2.80 (q, J=7.5 Hz, 2H), 1.42 (t, J=7.5 Hz, 3H)

Compound 44: $^1$H NMR (300 MHz, CDCl$_3$) δ 8.09 (d, J=2.4 Hz, 1H), 7.66 (d, J=8.4 Hz, 1H), 7.57 (dd, J=8.4, 2.4 Hz, 1H), 3.94 (s, 3H), 2.83 (q, J=7.5 Hz, 2H), 1.42 (t, J=7.5 Hz, 3H)

Compound 45: $^1$H NMR (300 MHz, small amount of CDCl$_3$+DMSO) δ 13.23 (brs, 1H), 7.96 (s, 1H), 7.89 (d, J=8.4 Hz, 1H), 7.57 (d, J=8.4 Hz, 1H), 2.84 (q, J=7.8 Hz, 2H), 1.39 (t, J=7.8 Hz, 3H)

EXAMPLE 46

Synthesis of Compound 46

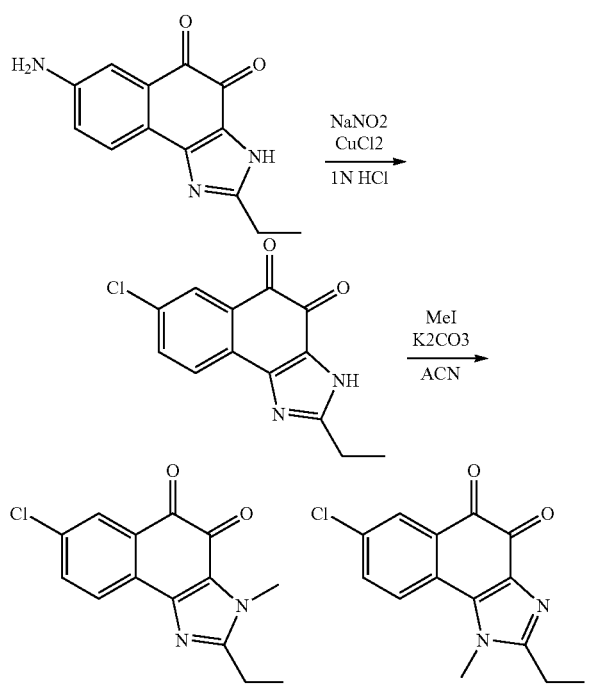

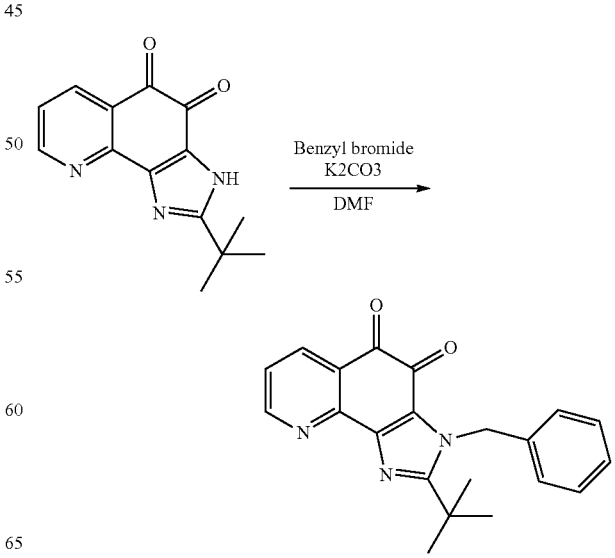

93

Compound 46: 3-benzyl-2-tert-butyl-3H-imidazo[4,5-h]quinoline-4,5-dione

DMF (3.9 ml, 0.1 M) was added to 2-tert-butyl-3H-imidazo[4,5-h]quinoline-4,5-dione (100 mg, 0.392 mmol) and K₂CO₃ (163 mg, 1.176 mmol) and stirred for 30 minutes at room temperature. Benzyl bromide (56 μl, 0.47 mmol) was added thereto and then reacted for 2 hours at 90° C. Aq. NaHCO₃ was added thereto and then EA was added thereto for extraction. The organic layer was dried over MgSO₄, and then filtered and vacuum distilled. A concentrated solution was separated using a column. 7 mg (5%)

Compound 46: ¹H NMR (300 MHz, DMSO) δ 8.77 (dd, J=5.1 Hz, 2.4 Hz, 1H), 8.17 (dd, J=7.8 Hz, 1.8 Hz, 1H), 7.47 (dd, J=7.8 Hz, 5.1 Hz, 1H), 7.31-7.23 (m, 3H), 7.08 (d, J=7.2 Hz, 1H), 5.80 (s, 2H), 1.34 (s, 9H)

EXAMPLE 47

Synthesis of Compound 47

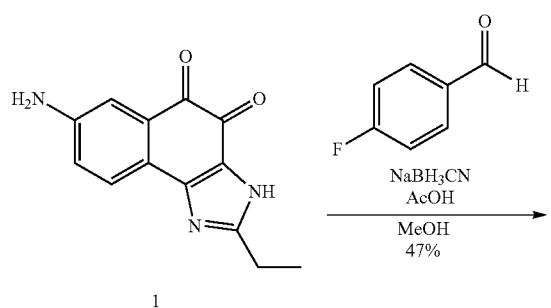

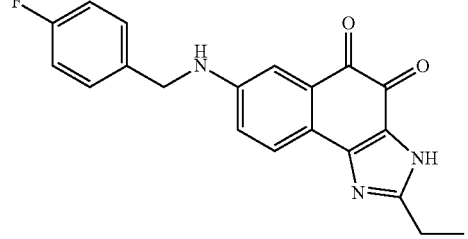

Compound 25

Compound 25 (0.2 g, 0.83 mmol) and 4-fluorobenzaldehyde (89 ul, 0.83 mmol) were dissolved in MeOH (8.5 ml) and then stirred for 30 minutes at room temperature. NaBH₃CN (62.5 mg, 0.995 mmol) was added thereto and further stirred for 5 minutes, and then AcOH (1.3 ml, 0.65 M) was added thereto. The reaction solution was further stirred for 5 minutes at the same temperature. The reaction solution was poured onto ice and saturated aqueous NaHCO₃ and EA were added thereto for extraction. The separated organic layer was dried over MgSO₄ and filtered. The filtered solution was vacuum evaporated and then purified through recrystallization.

Indigo solid 0.135 g (47%)

¹H NMR (300 MHz, DMSO) δ 12.98 (br, s, 1H), 7.47 (d, J=8.2 Hz, 1H), 7.40-7.35 (m, 2H), 7.18-7.11 (m, 3H), 6.97 (br, s, 1H), 6.75 (d, J=8.4 Hz, 1H), 4.33 (d, J=6.0 Hz, 2H), 2.66 (q, J=7.5 Hz, 2H), 1.23 (t, J=7.5 Hz, 3H)

EXAMPLES 48 AND 49

Synthesis of Compounds 48 and 49

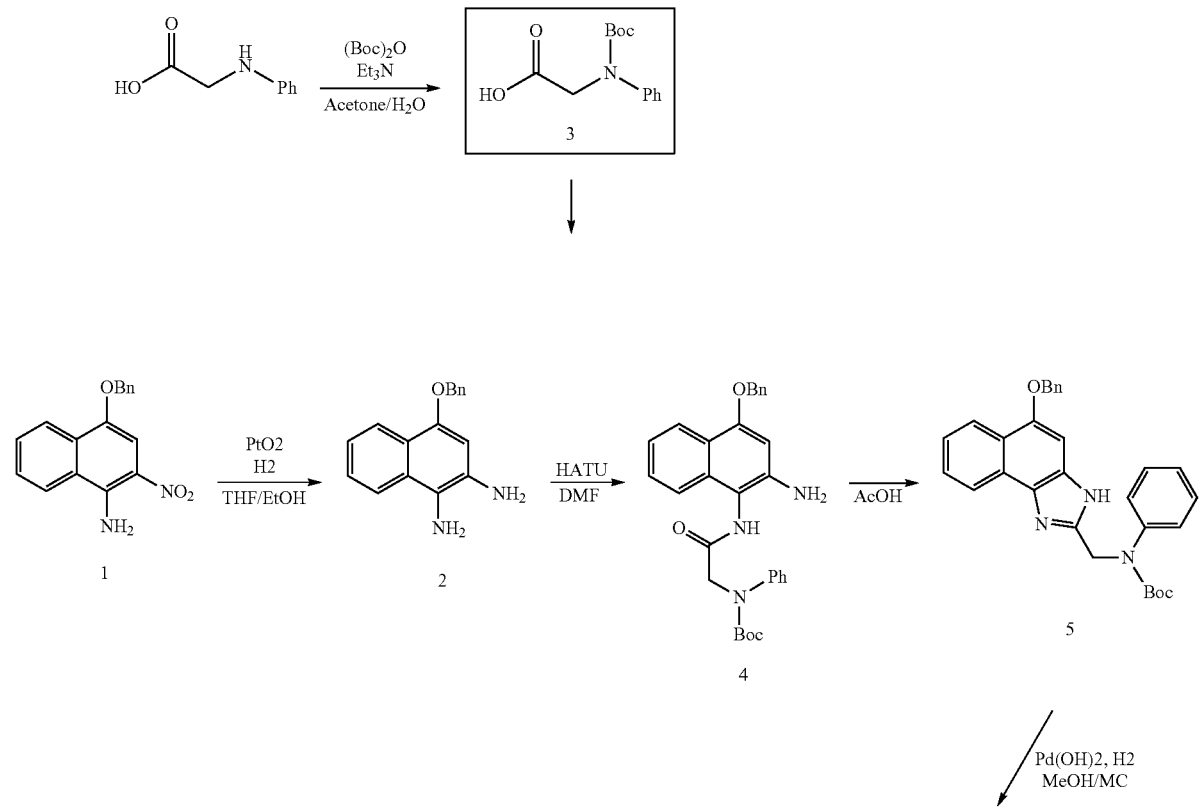

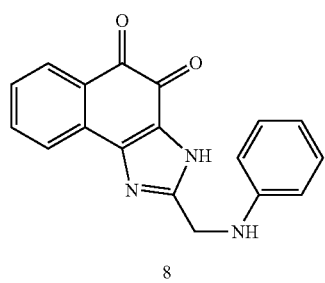 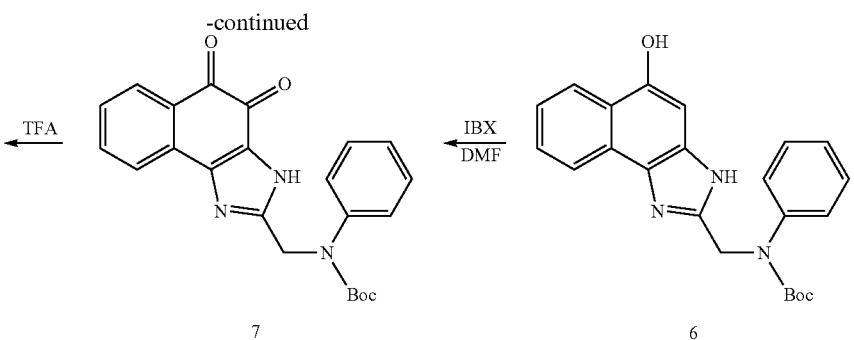 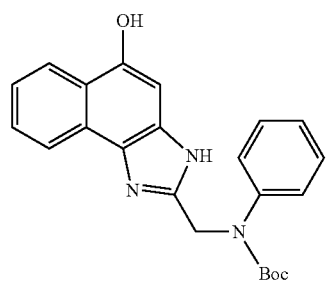

Example 49 Example 48
Compound 3

11 ml of a mixture of acetone and water in a ratio of 1:1 was added to 2-(phenylamino)acetic acid (2 g, 13.23 mmol). $Et_3N$ (5.76 ml, 41.01 mmol) and $(Boc)_2O$ (8.7 g, 39.69 mmol) were added thereto while stirring. The reaction product was reacted for 19 hours at room temperature. EA was added thereto, and then an EA layer was separated and discarded. 1N HCl was added to an aqueous layer and then EA was added thereto for extraction. An EA layer was dried over $MgSO_4$ and then filtered through silica gel. Finally, washing was performed using MC/MeOH, 10:1, thereby obtaining a target compound. 2.48 g (75%)

Compound 4

EtOH (6.7 ml, 0.2 M) and THF (6.7 ml, 0.2 M) were added to 4-(benzyloxy)-2-nitronaphthalen-1-amine (400 mg, 1.359 mmol), and then $PtO_2$ was added thereto, degassing was performed, followed by substituting with $H_2$. Stirring was performed for 3 hours at room temperature and then filtration was performed. 2-(tert-butoxycarbonyl (phenyl)amino)acetic acid (three times, 444 mg, 1.767 mmol), DMF (2 ml), and HATU (723 mg, 1.903 mmol) was added to the filtrate in one direction, followed by stirring for 10 minutes at room temperature. Stirred acid moiety was added to a filtered filtrate and stirred for 2 hours at room temperature. Aq. $NaHCO_3$ was added to the reaction product and then EA was added thereto for extraction. EA layer was dehydrated by adding $MgSO_4$ thereto, and filtered. After vacuum distillation, column chromatography was used to obtain a target compound. 253 mg (37%)

Compound 5

AcOH (6.4 ml, 0.08 M) was added to tert-butyl 2-(2-amino-4-(benzyloxy)naphthalen-1-ylamino)-2-oxoethyl (phenyl)carbamate (253 mg, 0.509 mmol) and then reacted for 1 hour at 80° C. After terminating reaction, AcOH was removed therefrom through vacuum distillation and then aq. $NaHCO_3$ was added thereto for neutralization. MC was added thereto for extraction, and then $MgSO_4$ was added to an MC layer, dehydrated, and then filtered. Subsequently, vacuum distillation was performed. Recrystallization was performed using Hex/EA, thereby obtaining 150 mg of a target compound (62%).

Compound 6

EtOH (2 ml) and MC (2 ml) were added to tert-butyl (5-(benzyloxy)-3H-naphtho[2,1-d]imidazol-2-yl)methyl (phenyl)carbamate (50 mg, 0.132 mmol) and then 10 mg of Pd $(OH)_2$ was added thereto. After degassing, substitution was performed using $H_2$, followed by stirring for 24 hours at room temperature. After filtering through Celite, the filtrate was vacuum distilled and purified by column chromatography, thereby obtaining a compound. 42 mg (82%)

EXAMPLE 48

DMF (1 ml, 0.1 M) was added to tert-butyl (5-hydroxy-3H-naphtho[2,1-d]imidazol-2-yl)methyl (phenyl)carbamate (40 mg, 0.103 mmol) and then IBX (67 mg, 0.113 mmol) was added thereto, followed by stirring for 30 minutes at room temperature. Aq. $NaHCO_3$ was added to EA for extraction. An EA layer was dried over $MgSO_4$, filtered, vacuum distilled, and separated using prep TLC, thereby obtaining 11 mg of a target compound (27%).

Example 48: $^1H$ NMR (300 MHz, $CDCl_3$) δ 8.43 (d, J=7.8 Hz, 1H), 7.92 (d, J=7.5 Hz, 1H), 7.61 (t, J=7.5 Hz, 1H), 7.42-7.31 (m, 3H), 7.26-7.20 (m, 3H), 4.91 (s, 2H), 1.44 (s, 9H)

EXAMPLE 49

TFA (2 ml, 0.09 M) was added to Example 48 (70 mg, 0.174 mmol) and then was reacted for 20 minutes at 50° C. Aq. $NaHCO_3$ was added thereto for neutralization and then extracted using MC. An MC layer was dried over $MgSO_4$, filtered, vacuum distilled, and then filtered through silica, thereby obtaining a target compound. 14 mg (27%)

Example 49: $^1H$ NMR (300 MHz, DMSO) δ 7.84 (t, J=7.5 Hz, 2H), 7.66 (t, J=7.2 Hz, 1H), 7.41 (t, J=7.5 Hz, 1H), 7.07 (t, J=7.8 Hz, 2H), 7.64 (d, J=8.1 Hz, 2H), 6.56 (t, J=7.5 Hz, 1H), 6.18 (t, J=6.3 Hz, 1H), 4.36 (d, J=6.0 Hz, 2H)

EXAMPLE 50

Synthesis of Compound 50

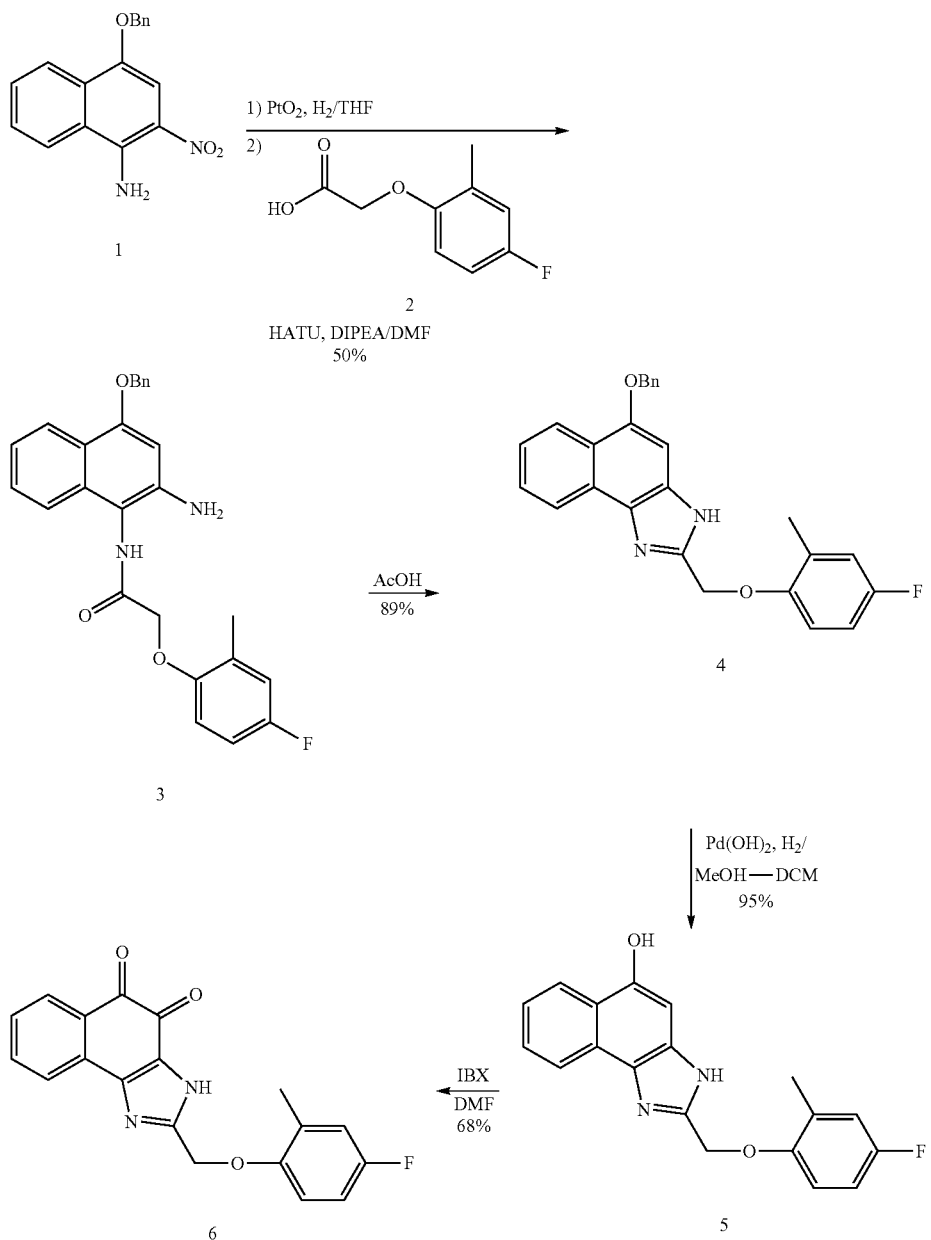

Compound 1 (0.4 g, 1.36 mmol) and PtO$_2$ (26 mg) were dissolved in THF (3 ml) and then stirred for one hour under a hydrogen atmosphere. Compound 2 (0.2 g, 1.09 mmol) and HATU (0.41 g, 1.09 mmol) were dissolved in DMF (5.5 ml) and then stirred for 5 minutes, and then Compound 1 was filtered through Celite (MC 20 ml) in the reaction solution. DIPEA (0.17 ml, 2.72 mmol) was added to the reaction solution and stirred for 1.5 hours under a nitrogen atmosphere. A saturated aqueous NaHCO$_3$ solution and a saturated aqueous NaCl solution were added thereto and extraction was performed using EA. Subsequently, a separated organic layer was dried over MgSO$_4$ and then filtered. The filtered solution was vacuum evaporated and then purified through recrystallization.

Ivory solid 0.29 g (50%)

Compound 3 (0.29 g, 0.67 mmol) was dissolved in AcOH (9.6 ml) and then refluxed for 30 minutes. Ice was poured into a reaction solution and neutralization was performed using saturated aqueous NaHCO$_3$, and then extraction was performed using EA several times. The separated organic layer was dried over MgSO$_4$ and then filtered. The filtered solution was vacuum evaporated and then purified through recrystallization.

Ivory solid 0.25 g (89%)

Compound 4 (0.24 g, 0.58 mmol) was dissolved in MeOH (6 ml) and MC (3 ml) and then Pd (OH)$_2$ (20 wt %) (24 mg, 10 wt %) was added thereto. A reaction solution was stirred for 2 hours under a hydrogen atmosphere and then filtered through Celite. The filtered solution was vacuum evaporated and then purified through recrystallization.

Ivory solid 0.18 g (95%)

In an ice bath, Compound 5 (0.16 g, 0.5 mmol) was dissolved in DMF (10 ml) and then IBX (0.35 g, 0.6 mmol) was added thereto. Reaction was performed for one hour at room temperature and then extraction was performed using saturated aqueous NaHCO₃ and EA several times. The separated organic layer was dried over MgSO₄ and then filtered. The filtered solution was vacuum evaporated and then purified through recrystallization.

Orange solid 0.11 g (68%)

¹H NMR (300 MHz, DMSO) δ 13.88 (br, s, 1H), 7.90-7.84 (m, 2H), 7.69 (t, J=7.5 Hz, 1H), 7.45 (t, J=7.5 Hz, 1H), 5.18 (s, 2H), 2.20 (s, 3H)

EXAMPLE 51

Synthesis of Compound 51 and MeI (1.36 ml, 21.831 mmol) were sequentially added thereto. The reaction product was stirred for 3 hours at 60° C. Distilled water was added thereto and extraction was performed using EA. An EA layer was dried over MgSO₄, filtered, and vacuum distilled. A target compound was obtained through column separation. 1.5 g (84%)

2-(methyl (phenyl)amino)acetic acid

H₂O (10 ml, 0.8 M) was added to NaOH (1 g, 25.11 mmol) and stirred. Methyl 2-(methyl (phenyl)amino)acetate (1.5 g, 8.37 mmol) was added to a reaction product solution and then stirred for 1 hour at room temperature. Distilled water and EA were added thereto to remove EA and 3N HCl was added to an aqueous layer to adjust pH to 2. EA was repeatedly added thereto for extraction and then an EA layer

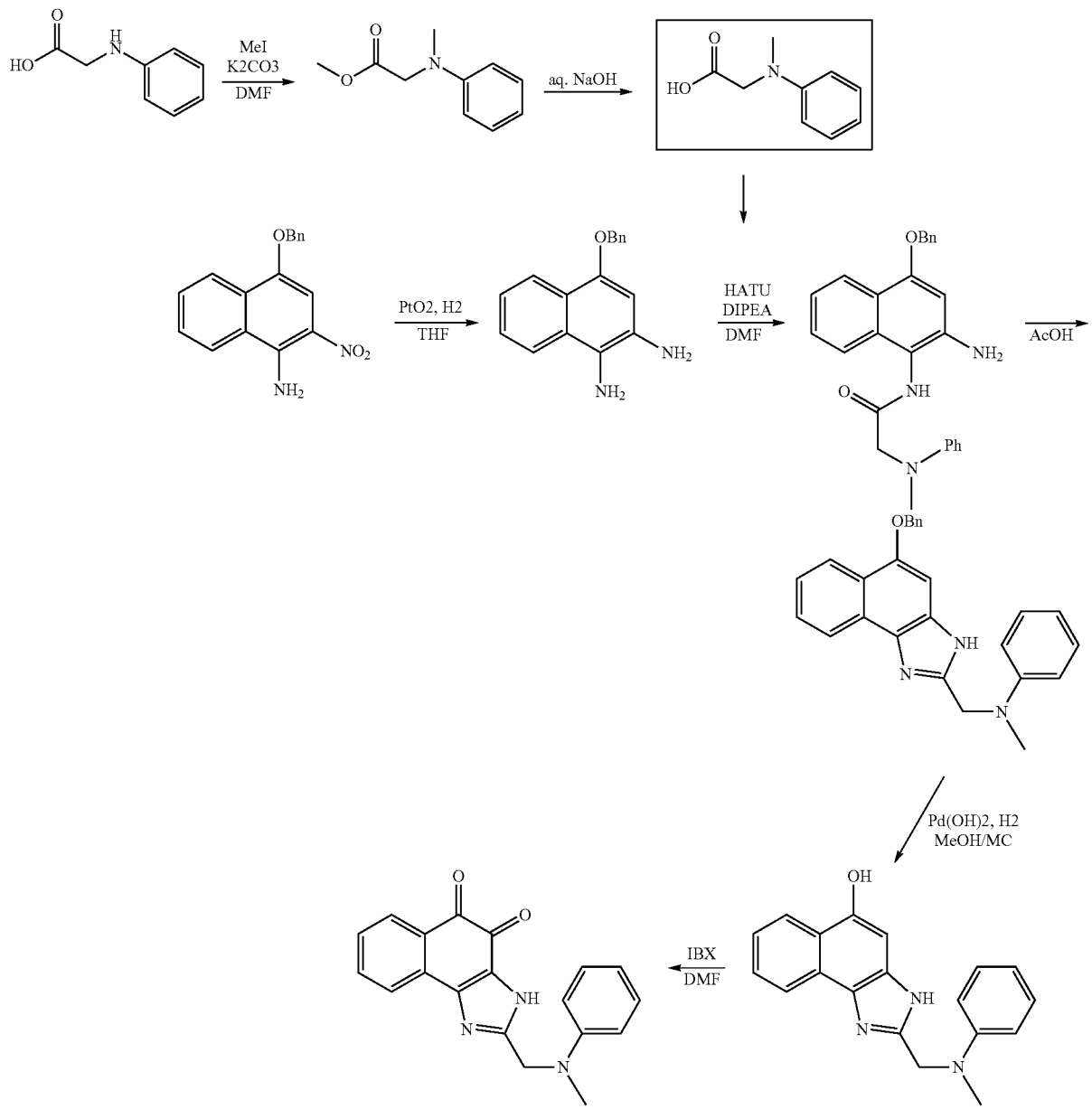

Methyl 2-(methyl (phenyl)amino)acetate

DMF (50 ml, 0.2 M) was added to 2-(phenylamino)acetic acid (1.5 g, 9.923 mmol) and K₂CO₃ (4.1 g, 29.769 mmol)

was extracted using MgSO₄, filtered, and vacuum distillated, and then short-column chromatography was performed, thereby obtaining a target compound. 740 mg (54%)

N-(2-amino-4-(benzyloxy)naphthalen-1-yl)-2-(methyl (phenyl)amino)acetamide

THF (3 ml, 0.5 M) was added to 4-(benzyloxy)-2-nitronaphthalen-1-amine (400 mg, 1.359 mmol) and then PtO$_2$ (26 mg) was added thereto for degassing. Subsequently, substitution was performed using H$_2$. A reaction product was at room temperature was stirred for 3 hours and then filtered. 2-(methyl (phenyl)amino)acetic acid (187 mg, 1.133 mmol), DMF (6 ml), and HATU (430 mg, 1.133 mmol) were added to the filtrate in one direction, followed by stirring for 10 minutes at room temperature. Stirred acid moiety was added to a filtrate and DIPEA (0.39 ml, 2.266 mmol) was added thereto, and then stirring was performed for 1 hour at room temperature. Aq. NaHCO$_3$ was added to the reaction product and then EA was added thereto for extraction. MgSO$_4$ was added to an EA layer for dehydration, filtered, vacuum distilled, and then recrystallization was performed using EA/Hex, thereby obtaining a target compound. 257 mg (55%)

2-((methyl (phenyl)amino)methyl)-3H-naphtho[2,1-d]imidazol-5-ol

AcOH (10 ml) was added to N-(2-amino-4-(benzyloxy)naphthalen-1-yl)-2-(methyl (phenyl)amino)acetamide (240 mg, 0.583 mmol) and stirred for 1 hour at 90° C. The reaction product was vacuum distilled, and then aq. NaHCO$_3$ was added thereto for neutralization and EA was poured thereonto for extraction. An EA layer was dried over MgSO$_4$, filtered, and vacuum distilled. MeOH (2 ml) and MC (1 ml) was poured onto the concentrated solution and Pd (OH)$_2$ was added thereto. After degassing, substitution was performed using H$_2$ and then stirred for 2.5 hours at room temperature. After filtering through Celite, recrystallization was performed using EA/Hex, thereby obtaining a target compound. 180 mg (95%)

Compound 51: 2-((methyl (phenyl)amino)methyl)-3H-naphtho[2,1-d]imidazole-4,5-dione DMF (5.9 ml, 0.1 M) was added to 2-((methyl (phenyl) amino)methyl)-3H-naphtho[2,1-d]imidazol-5-ol (180 mg, 0.593 mmol), and then IBX (354 mg, 0.652 mmol) was added thereto, followed by stirring for 16 hours at room temperature. Aq. NaHCO$_3$ was added to EA for extraction. An EA layer was dried over MgSO$_4$, filtered, and vacuum distilled, and then recrystallization was performed using Hex/EA, thereby obtaining a target compound. 60 mg (32%)

Compound 51: $^1$H NMR (300 MHz, CDCl$_3$) δ 7.83 (t, J=8.1 Hz, 2H), 7.66 (t, J=7.5 Hz, 1H), 7.42 (t, J=7.5 Hz, 1H), 7.16 (t, J=9.0 Hz, 2H), 6.78 (d, J=8.1 Hz, 2H), 6.64 (t, J=7.2 Hz, 1H), 4.63 (s, 2H), 3.09 (s, 3H)

EXAMPLES 52 AND 53

Synthesis of Compounds 52 and 53

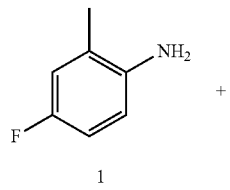

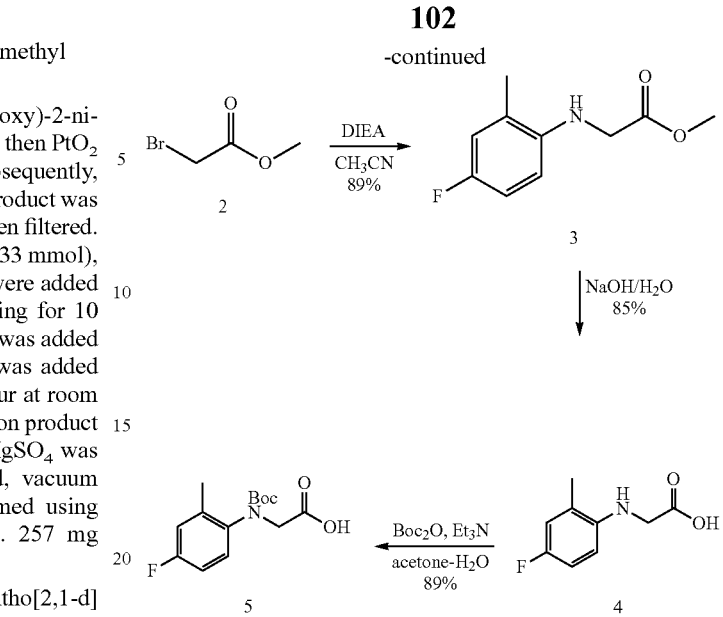

CH$_3$CN (8 ml) was dissolved in Compound 1 (4-fluoro-2-methylaniline, 1 g, 7.99 mmol) and then DIPEA (2.85 ml, 16.38 mmol) was added thereto. The reaction product was heated to 60° C. and then Compound 2 (Methylbromoacetate, 0.76 ml, 7.99 mmol) was added thereto. After stirring for 4 hours and vacuum filtrating at the same temperature, distilled water and EA were added thereto and extraction was performed several times. The separated organic layer was dried over MgSO$_4$ and then filtered. The filtered solution was vacuum evaporated and then purification was performed through silica gel column chromatography.

Orange liquid 1.41 g (89%)

An aqueous 10 wt % NaOH (0.4 g/4 ml) solution was added to Compound 2 (1.3 g, 6.59 mmol). The reaction solution was heated to 70° C. and then further stirred for two hours at the same temperature. The reaction solution was poured onto ice and pH thereof was adjusted to approximately 2 using a 1 M aqueous HCl solution. Extraction was performed using EA several times, and then the separated organic layer was dried over MgSO$_4$ and then filtered. The filtered solution was vacuum evaporated and then purified through recrystallization.

White solid 1.03 g (85%)

In an ice bath, Compound 4 (0.9 g, 4.91 mmol) was dissolved in acetone-H$_2$O (8.2 ml, 1:1) and then Et$_3$N (2.2 ml, 15.23 mmol) was added thereto. Boc$_2$O (3.4 ml, 14.74 mmol) was added thereto at the same temperature and then stirred for 22.5 hours at room temperature. Distilled water and EA were added to a reaction solution and an aqueous layer was washed several times. An aqueous 1 M HCl solution was added to an aqueous layer to adjust pH thereof to approximately 2. Extraction was performed using EA several times, and then the separated organic layer was dried over MgSO$_4$ and then filtered. The filtered solution was vacuum evaporated and then intactly collected.

White solid 1.24 g (89%)

$^1$H NMR (300 MHz, CDCl$_3$) δ 9.84 (br, s, 1H), 7.31-7.27 (m, 1H), 6.93-6.85 (m, 2H), 4.58 (d, J=17.6 Hz, 1H), 3.85 (d, J=17.6 Hz, 1H), 2.25 (d, J=5.5 Hz, 1H), 1.49 (s, 3H), 1.36 (s, 6H)

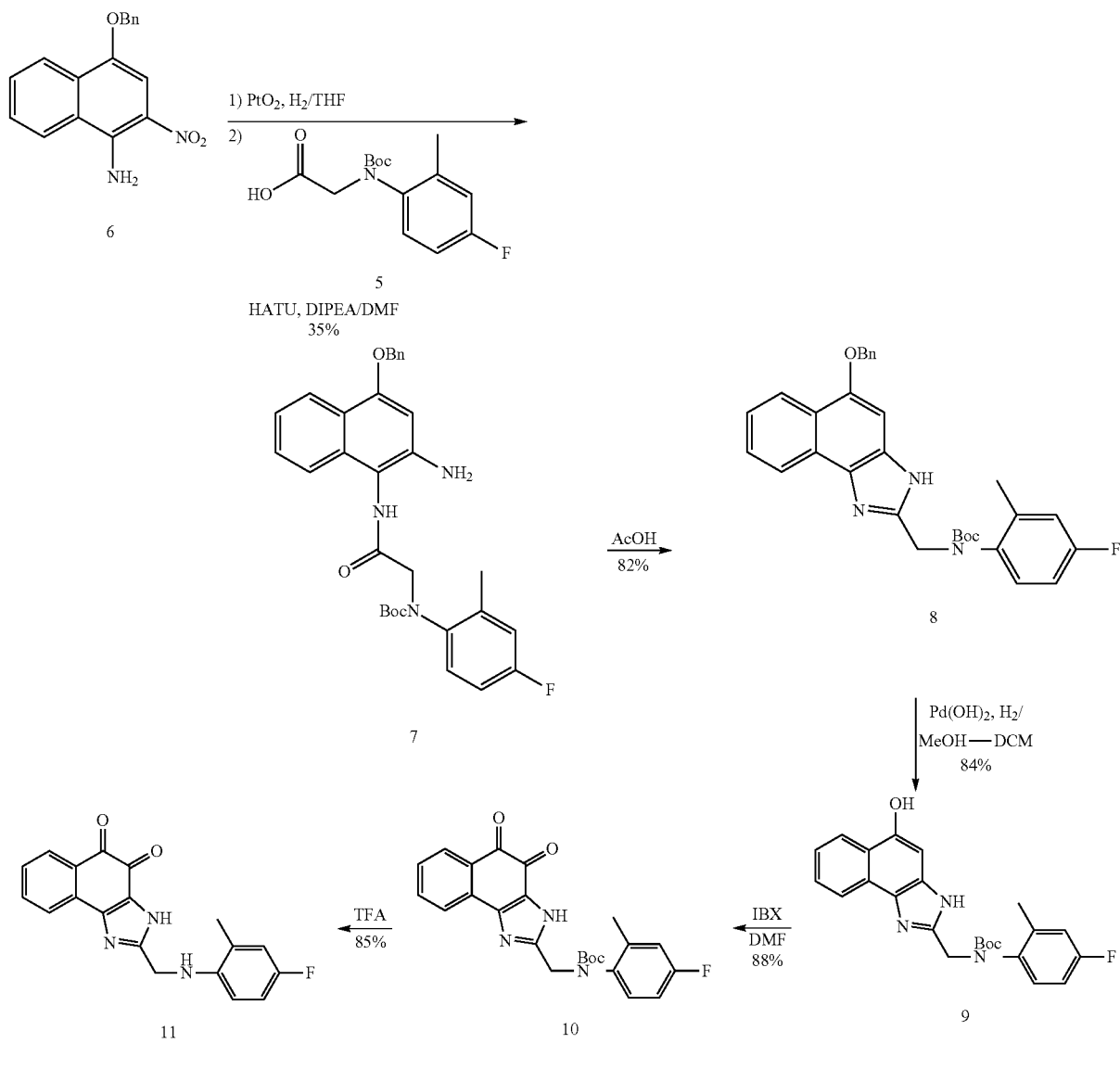

Example 53 Example 52

Compound 6 (0.3 g, 1.02 mmol) and PtO$_2$ (20 mg) were dissolved in THF (2 ml) and then stirred for 2.5 hours under a hydrogen atmosphere. Compound 5 (0.375 g, 1.325 mmol) and HATU (0.504 g, 1.325 mmol) were dissolved in DMF (6 ml) and stirred for 5 minutes, and then a solution of Compound 6 was filtered through Celite in the reaction solution. DIPEA (0.36 ml, 2.04 mmol) was added to a reaction solution and stirred for 30 minutes under a nitrogen atmosphere. A saturated aqueous NaHCO$_3$ solution and a saturated aqueous NaCl solution were added thereto and extraction was performed using EA. Subsequently, a separated organic layer was dried over MgSO$_4$ and then filtered. The filtered solution was vacuum evaporated, and then purified via silica gel column chromatography.

White solid 0.19 g (35%)

Compound 7 (0.24 g, 0.453 mmol) was dissolved in AcOH (6.5 ml) and then stirred for 30 minutes at 80° C. The reaction solution was poured onto ice and was neutralized using saturated aqueous NaHCO$_3$, and then extraction was performed using EA several times. The separated organic layer was dried over MgSO$_4$ and then filtered. The filtered solution was vacuum evaporated and then purified through recrystallization.

Ivory solid 0.19 g (82%)

Compound 8 (0.19 g, 0.0.37 mmol) was dissolved in MeOH (3.7 ml) and MC (3.7 ml) and then Pd (OH)$_2$ (20 wt %) (19 mg) was added thereto. A reaction solution was stirred for 2 hours under a hydrogen atmosphere and then filtered through Celite. The filtered solution was vacuum evaporated and then purified through recrystallization.

Ivory solid 0.146 g (94%)

In an ice bath, Compound 9 (0.14 g, 0.335 mmol) was dissolved in DMF (6.7 ml) and then IBX (0.24 g, 0.402 mmol) was added thereto. Reaction was performed for 1.5 hours at room temperature and then extraction was performed using saturated aqueous NaHCO$_3$ and EA several times. The separated organic layer was dried over MgSO$_4$ and then filtered. The filtered solution was vacuum evaporated and then purified through recrystallization.

Orange solid 95.4 mg (65%)

$^1$H NMR (300 MHz, CDCl$_3$) δ 13.59 (br, s, 1H), 7.88-7.81 (m, 1H), 7.69 (br, s, 1H), 7.56-7.41 (m, 2H), 7.12-7.01 (m, 2H), 4.89 (d, J=16.0 Hz, 1H), 4.62 (d, J=16.0 Hz, 1H), 2.22 (s, 3H), 1.28 (s, 9H)

Compound 10 (62.9 mg, 0.144 mmol) was dissolved in TFA (2 ml) and then stirred for 10 minutes. The reaction solution was poured onto ice and neutralized using saturated aqueous NaHCO$_3$. Subsequently, extraction was performed using EA several times. The separated organic layer was dried over MgSO$_4$ and then filtered. The filtered solution was vacuum evaporated and then purified through recrystallization.

Red-brown solid 41.1 mg (85%)

$^1$H NMR (300 MHz, CDCl$_3$) δ 13.47 (br, s, 1H), 7.87-7.83 (m, 1H), 7.67 (t, J=7.5 Hz, 1H), 7.43 (t, J=7.5 Hz, 1H), 6.91-6.87 (m, 1H), 6.43-6.39 (m, 1H), 5.50-5.46 (m, 1H), 4.44 (d, J=6.1 Hz, 2H), 2.18 (s, 3H)

EXAMPLE 54

Synthesis of Compound 54

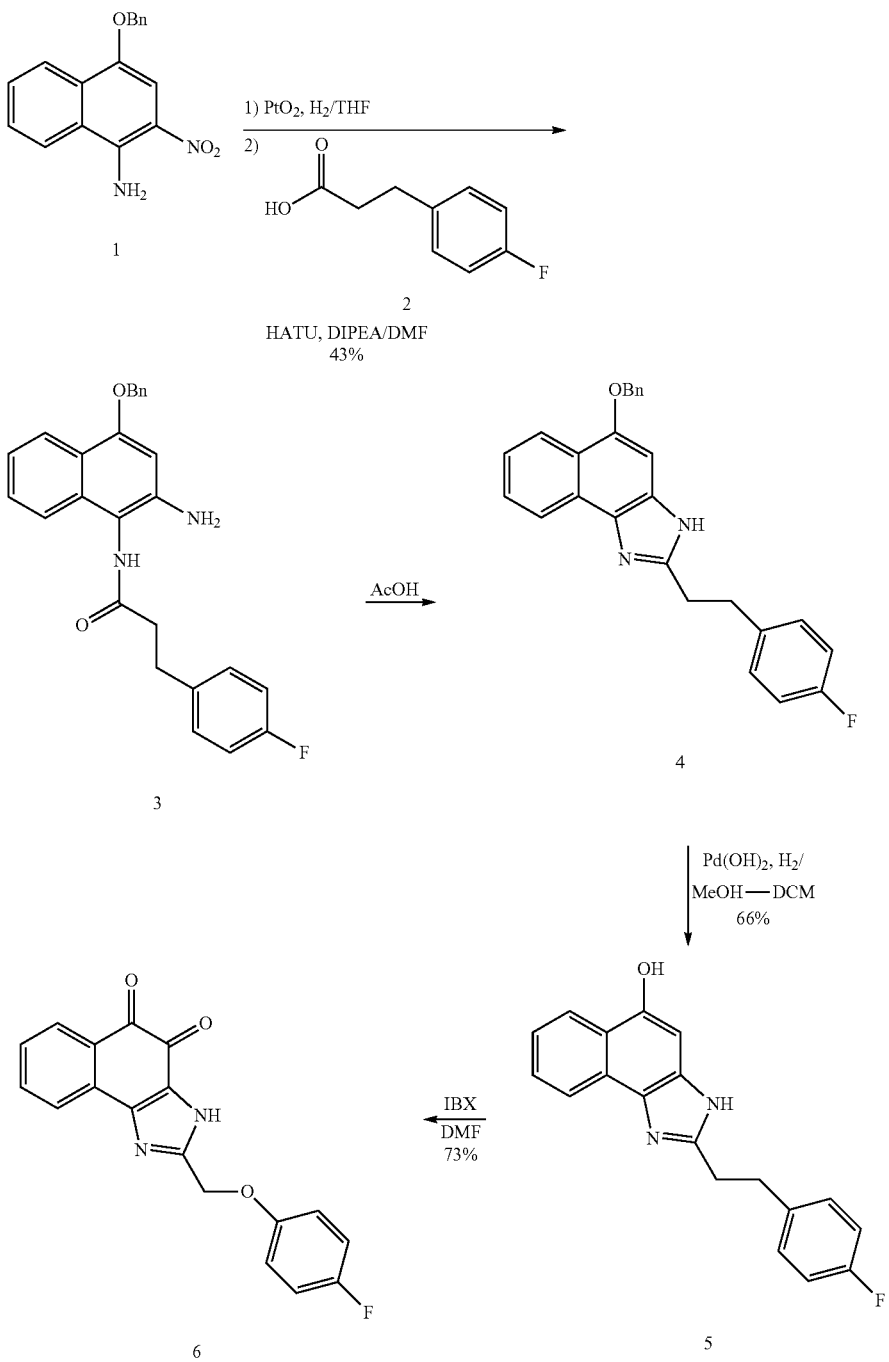

Compound 1 (0.4 g, 1.36 mmol) and PtO$_2$ (26 mg) were dissolved in THF (3 ml) and then stirred for 2 hours under a hydrogen atmosphere. Compound 2 (0.18 g, 1.09 mmol), and HATU (0.41 g, 1.09 mmol) were dissolved in DMF (6 ml) and stirred for 5 minutes, and then a solution of Compound 1 was filtered through Celite in the reaction solution. DIPEA (0.17 ml, 2.72 mmol) was added to the reaction solution and stirred for 30 minutes under a nitrogen atmosphere. A saturated aqueous NaCl solution was added thereto and extraction was performed using EA. Next, the separated organic layer was dried over MgSO$_4$ and then filtered. The filtered solution was vacuum evaporated and then separated through silica gel column chromatography. Subsequently, recrystallization was performed for purification.

Ivory solid 0.24 g (43%)

Compound 3 (0.23 g, 0.55 mmol) was dissolved in AcOH (11 ml) and then stirred for one hour at 80° C. The reaction solution was poured onto ice and neutralization was performed using saturated aqueous NaHCO$_3$. Next, extraction was performed using EA several times. The separated organic layer was dried over MgSO$_4$ and then filtered. The filtered solution was vacuum evaporated and then dissolved in MeOH (5.5 ml) and MC (5.5 ml, 0.1 M). Pd (OH)$_2$ (20 wt %) (39 mg, 10 mol %) was added to a reaction solution under a hydrogen atmosphere for one hour and then filtered through Celite. The filtered solution was vacuum evaporated and then purified through recrystallization.

Ivory solid 0.11 g (66%)

In an ice bath, Compound 5 (0.105 g, 0.344 mmol) was dissolved in DMF (7 ml) and then IBX (0.25 g, 0.412 mmol) was added thereto. Reaction was performed for 2.5 hours at room temperature and then The reaction solution was poured onto ice. A saturated aqueous NaHCO$_3$ solution and EA were added thereto and extraction was performed several times. The separated organic layer was dried over MgSO$_4$ and then filtered. The filtered solution was vacuum evaporated and then purified through recrystallization.

Brown solid 80.1 mg (73%)

$^1$H NMR (300 MHz, DMSO) δ 7.85 (d, J=7.7 Hz, 1H), 7.80 (d, J=7.5 Hz, 1H), 7.66 (t, J=7.5 Hz, 1H), 7.42 (t, J=7.5 Hz, 1H), 7.30-7.25 (m, 2H), 7.12-7.07 (m, 2H), 3.08-2.99 (m, 4H)

EXAMPLES 55, 56, 57, AND 58

Synthesis of Compounds 55, 56, 57, and 58

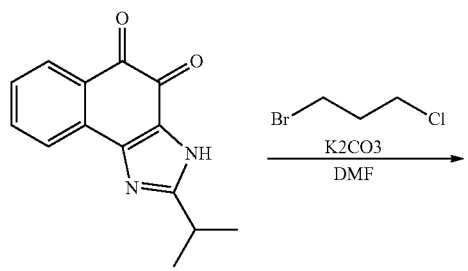

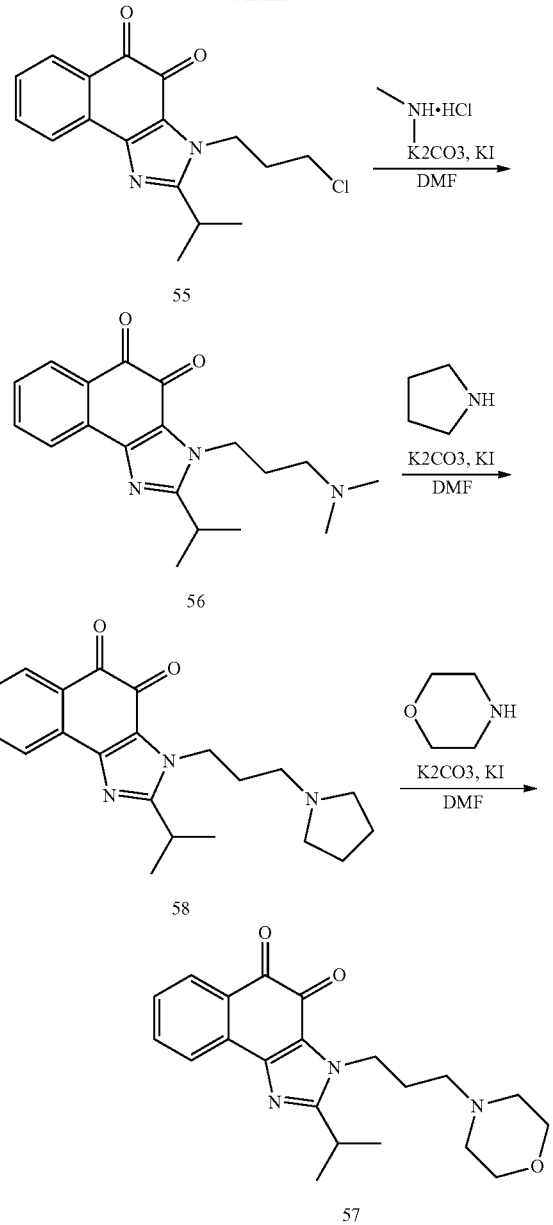

Compound 55: 3-(3-chloropropyl)-2-isopropyl-3H-naphtho[2,1-d]imidazole-4,5-dione DMF (21 ml, 0.1 M) was added to Compound 1 (500 mg, 2.08 mmol) and K$_2$CO$_3$ (431 mg, 3.12 mmol) and 1-bromo-3-chloropropane (226 ul, 2.289 mmol) were sequentially added thereto. The reaction product was stirred for 20 hours at room temperature. Extraction was performed using distilled water and EA and then an EA layer was dried over MgSO$_4$, filtered, and vacuum distilled. Next, recrystallization was performed using Hex/EA, thereby obtaining a target compound. 377 mg (57%)

Compound 55: $^1$H NMR (300 MHz, CDCl$_3$) δ 8.02 (d, J=6.3 Hz, 2H), 7.61 (t, J=7.5 Hz, 1H), 7.39 (t, J=7.5 Hz, 1H), 4.43 (t, J=7.2 Hz, 2H), 3.62 (t, J=6.0 Hz, 2H), 3.19-3.15 (m, 1H), 2.31-2.26 (m, 2H), 1.43 (d, J=6.6 Hz, 6H)

Compound 56: 3-(3-(dimethylamino)propyl)-2-isopropyl-3H-naphtho[2,1-d]imidazole-4,5-dione DMF (1.3 ml) was added to 3-(3-chloropropyl)-2-isopropyl-3H-naphtho[2,1-d]imidazole-4,5-dione (90 mg, 0.284 mmol), and then KI (46 mg, 0.28 mmol) was added thereto, followed by stirring for 20 minutes at room temperature. Dimethylamine hydrochloride (28 mg, 0.34 mmol) and K₂CO₃ (118 mg, 0.852 mmol) were sequentially added thereto, followed by stirring for 15 hours at 50° C. Aq. NaHCO₃ was added thereto and extraction was performed by adding EA, and then an EA layer was dried over MgSO₄, filtered, and vacuum distilled, and then short-column chromatography was performed, thereby obtaining a target compound. 16 mg (17%)

Compound 56: ¹H NMR (300 MHz, DMSO-d6) δ 7.87 (d, J=7.5 Hz, 2H), 7.68 (t, J=7.5 Hz, 1H), 7.45 (t, J=7.5 Hz, 1H), 4.27 (t, J=7.2 Hz, 2H), 3.50-3.25 (m, 7H), 2.47-2.35 (m, 2H), 1.92 (t, J=7.2 Hz, 2H), 1.31 (d, J=6.9 Hz, 6H)

Compound 57: 2-isopropyl-3-(3-(pyrrolidin-1-yl)propyl)-3H-naphtho[2,1-d]imidazole-4,5-dione DMF (1.3 ml) was added to 3-(3-chloropropyl)-2-isopropyl-3H-naphtho[2,1-d]imidazole-4,5-dione (90 mg, 0.284 mmol), and then KI (46 mg, 0.28 mmol) was added thereto, followed by stirring for 20 minutes at room temperature. Pyrrolidine (28 μl, 0.34 mmol) and K₂CO₃ (77 mg, 0.5 6 mmol) were sequentially added thereto, followed by stirring for 15 hours at 50° C. Aq. NaHCO₃ was added thereto and extraction was performed by using EA. Next, an EA layer was dried over MgSO₄, filtered, vacuum distilled, and then short-column chromatography was performed, thereby obtaining a target compound. 26 mg (26%)

Compound 57: ¹H NMR (300 MHz, DMSO-d6) δ 7.86 (dd, J=7.2 Hz, 2.4 Hz, 2H), 7.67 (t, J=7.5 Hz, 1H), 7.43 (t, J=7.8 Hz, 1H), 4.25 (t, J=6.9 Hz, 2H), 3.57-3.54 (m, 4H), 3.36-3.31 (m, 1H), 2.32-2.28 (m, 6H), 1.89-1.84 (m, 2H), 1.30 (d, J=6.3 Hz, 6H)

Compound 58: 2-isopropyl-3-(3-morpholinopropyl)-3H-naphtho[2,1-d]imidazole-4,5-dione DMF (1 ml) was added to 3-(3-chloropropyl)-2-isopropyl-3H-naphtho[2,1-d]imidazole-4,5-dione (80 mg, 0.253 mmol), and then KI (42 mg, 0.253 mmol) was added thereto, followed by stirring for 20 minutes at room temperature. Morpholine (27 ul, 0.304 mmol) and K₂CO₃ (70 mg, 0.506 mmol) were sequentially added thereto, followed by stirring for 15 hours at 50° C. Aq. NaHCO₃ was added thereto and extraction was performed using EA, and then an EA layer was dried over MgSO₄, filtered, and vacuum distilled, and then short-column chromatography was performed, thereby obtaining a target compound. 26 mg (28%)

Compound 58: ¹H NMR (300 MHz, DMSO-d6) δ 7.87 (d, J=8.1 Hz, 2H), 7.69 (t, J=7.8 Hz, 1H), 7.45 (t, J=7.8 Hz, 1H), 4.28 (t, J=6.6 Hz, 1H), 3.34-3.26 (m, 5H), 2.47-2.45 (m, 2H), 1.92-1.87 (m, 2H), 1.80-1.69 (m, 4H), 1.31 (d, J=6.9 Hz, 6H)

EXAMPLE 59

Synthesis of Compound 59

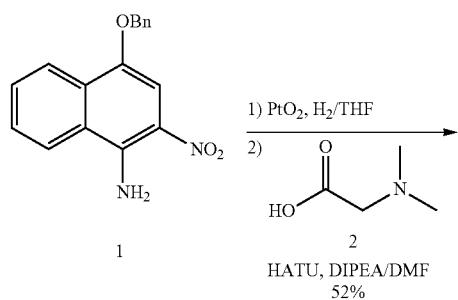

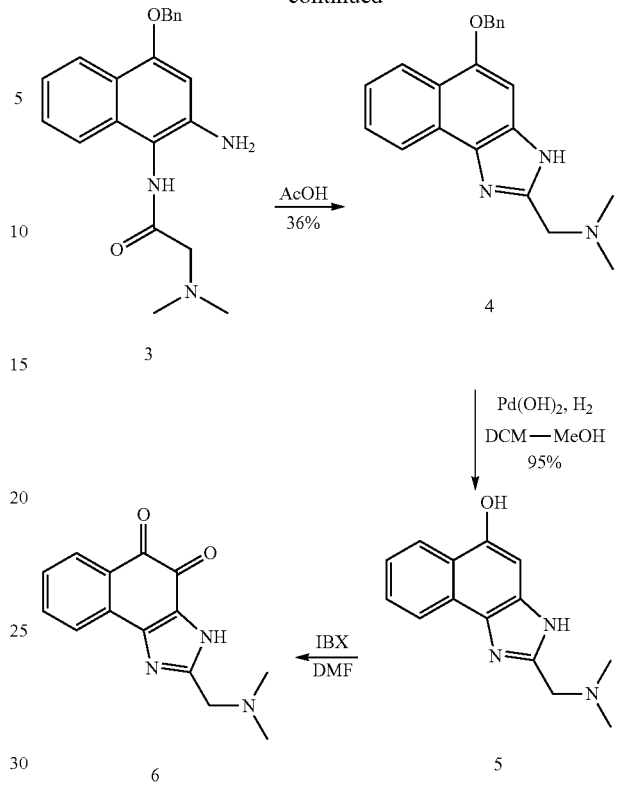

Compound 1 (0.4 g, 1.36 mmol) and PtO₂ (26 mg) were dissolved in THF (3 ml) and then stirred for 2 hours under a hydrogen atmosphere. Compound 2 (0.11 g, 1.09 mmol) and HATU (0.41 g, 1.09 mmol) were dissolved in DMF (6 ml) and stirred for 5 minutes, and then a reaction solution of Compound 1 was filtered through Celite. DIPEA (0.17 ml, 2.72 mmol) was added to a reaction solution and further stirred for 5 minutes under a nitrogen atmosphere. The reaction solution was poured onto ice and distilled water and EA were added thereto for extraction. The separated organic layer was dried over MgSO₄ and then filtered. The filtered solution was vacuum evaporated and then purified through recrystallization.

Ivory solid 0.24 g (52%)

Compound 3 (0.23 g, 0.645 mmol) was dissolved in AcOH (13 ml) and then stirred for 2 hours at 80° C. The reaction solution was poured onto ice, neutralization was performed using saturated aqueous NaHCO₃, and then extraction was performed using EA several times. The separated organic layer was dried over MgSO₄ and then filtered. The filtered solution was vacuum evaporated and then separation was performed through silica gel column chromatography. Subsequently, purification was performed through recrystallization.

White solid 76.1 mg (36%)

Compound 4 (71.4 mg, 0.215 mmol) was dissolved in a mixture of MeOH (2 ml) and MC (2 ml), and then Pd (OH)₂ (20 wt %) (15 mg, 10 mol %) was added thereto and stirring was performed for one hour under a hydrogen atmosphere. Subsequently, filtration was performed through Celite (EA). The filtered solution was vacuum evaporated and then purified through recrystallization.

White solid 49.2 mg (95%)

In an ice bath, Compound 5 (45 mg, 0.19 mmol) was dissolved in DMF (2 ml), and then IBX (0.14 g, 0.22 mmol)

was added thereto and reacted for 2 hours at room temperature. Subsequently, The reaction solution was poured onto ice. Distilled water EA was added thereto and pH thereof was adjusted to 2 using 1 M HCl, and then an aqueous layer was washed several times. A separated aqueous layer was vacuum filtered and then washed with EA. Filtration was performed through silica, thereby obtaining Compound 6 (red-brown solid).

$^1$H NMR (300 MHz, DMSO) δ 7.87 (d, J=7.7 Hz, 2H), 7.67 (t, J=7.5 Hz, 7.7 Hz, 1H), 7.43 (t, J=7.5 Hz, 7.7 Hz, 1H) 3.48 (s, 2H), 2.26 (s, 6H)

EXAMPLE 60

Synthesis of Compound 60

Compound 1 (Ethyl 2-bromopropionate, 1.5 g, 8.29 mmol) was dissolved in MeCN (22 ml). K$_2$CO$_3$ (3.5 g, 24.86 mmol) was added thereto, followed by stirring under a nitrogen atmosphere. Dimethylamine solution (40 wt % in H$_2$O) (3 ml, 24.86 mmol) was added thereto, followed by stirring for 17.5 hours at room temperature. An aqueous 1 N NaOH solution (22 ml) was added thereto and further stirred for 10 minutes. Distilled water and EA were added to a reaction solution, extracted several times, dried over MgSO$_4$ and then filtered. The filtered solution was vacuum evaporated and then intactly collected.

Colorless oil 0.397 g (33%)

An aqueous 10 wt % NaOH (0.15 g/1.5 ml) solution was added to Compound 2 (0.375 g, 2.58 mmol) and stirred for 4.5 hours at room temperature. The reaction solution was poured onto ice and pH thereof was adjusted to approximately 2 using a 1 M aqueous HCl solution. After adding EA thereto, an aqueous layer was washed several times and then a separated aqueous layer was vacuum evaporated. A concentrated solution was dissolved in MC and MeOH and then undissolved solids were removed by filtration. The filtered solution was vacuum evaporated and then intactly collected.

White solid (quantitative)

$^1$H NMR (300 MHz, DMSO) δ 4.06 (q, J=7.1 Hz, 1H) 2.74 (s, 6H), 1.44 (d, J=7.1 Hz, 3H)

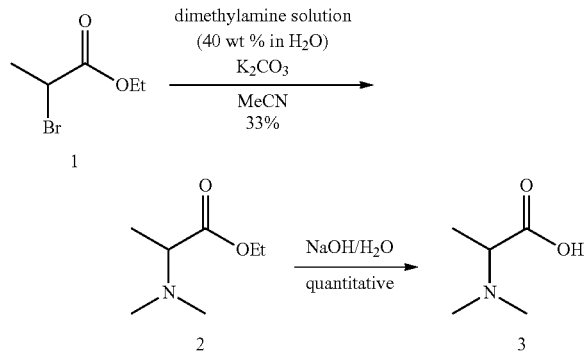

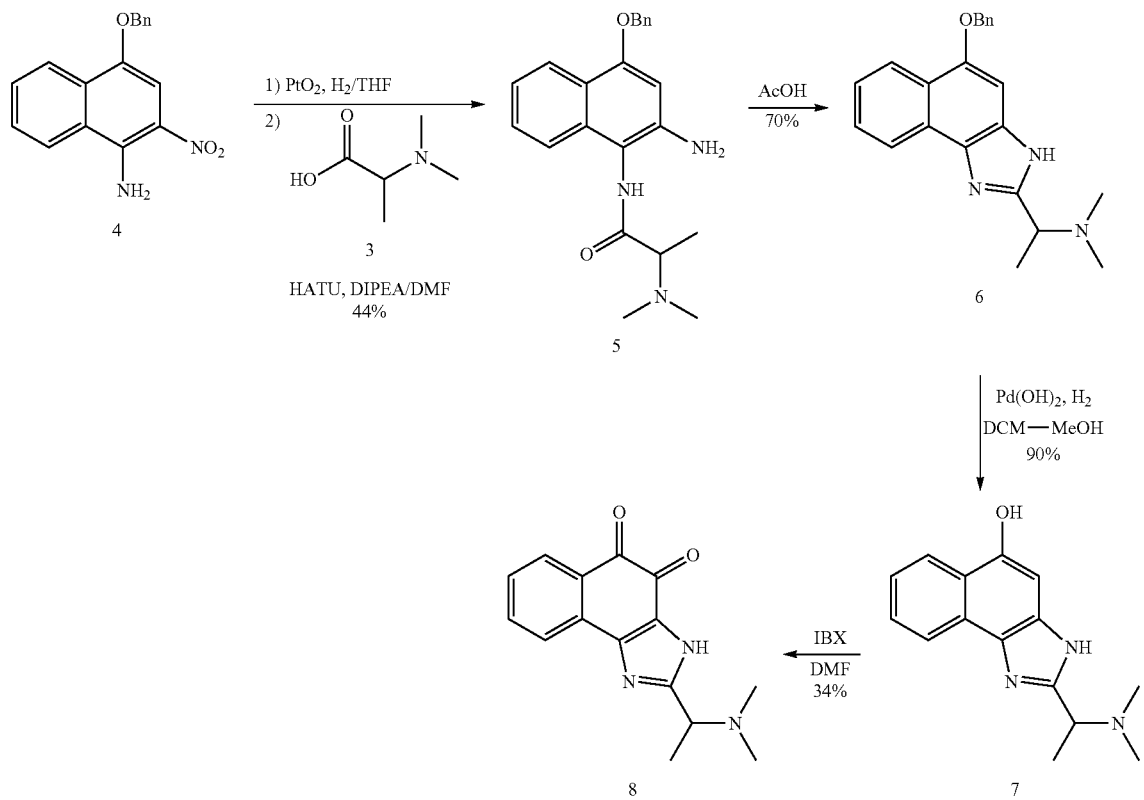

Compound 4 (0.5 g, 1.7 mmol) and PtO$_2$ (48 mg, 10 mol %) were dissolved in THF (17 ml) and then stirred for 2 hours under a hydrogen atmosphere. Compound 3 (0.21 g, 1.7 mmol) and HATU (0.52 g, 1.36 mmol) were dissolved in DMF (8.5 ml, 0.2 M) and stirred for 5 minutes, and then a solution of Compound 4 was filtered through Celite in the reaction solution (MC 20 ml). DIPEA (0.9 ml, 5.1 mmol) as a reaction solution was added thereto, followed by stirring for 30 minutes under a nitrogen atmosphere. The reaction solution was poured onto ice and distilled water and EA were added thereto, and then extraction was performed several times. The separated organic layer was dried over MgSO$_4$ and then filtered. The filtered solution was vacuum evaporated and then separated through silica gel column chromatography.

Brown crystal 0.27 g (44%)

Compound 5 (0.26 g, 0.72 mmol) was dissolved in AcOH (14 ml) and then stirred for one hour at 70° C. The reaction solution was poured onto ice, neutralization was performed using saturated aqueous NaHCO$_3$, and then extraction was performed using EA several times. The separated organic layer was dried over MgSO$_4$ and then filtered. The filtered solution was vacuum evaporated and then separated through silica gel column chromatography.

White solid 0.17 g (70%)

Compound 6 (0.17 g, 0.484 mmol) was dissolved in MeOH (2.4 ml) and MC (2.4 ml) and then 5% Pd/C (0.1 g, 10 mol %) was added thereto. A reaction solution was stirred for 2 hours under a hydrogen atmosphere and then filtered through Celite (EA). The filtered solution was vacuum evaporated and then purified through recrystallization.

White solid 0.11 g (90%)

In an ice bath, Compound 7 (0.1 g, 0.397 mmol) was dissolved in DMF (8 ml), and then IBX (0.28 g, 0.476 mmol) was added thereto and reacted for one hour at room temperature. Subsequently, saturated aqueous NaHCO$_3$ and MC were added thereto and extraction was performed several times. A separated organic layer was dried over MgSO$_4$ and then filtered. The filtered solution was vacuum evaporated and then purified through recrystallization.

Orange solid 36.6 mg (34%)

$^1$H NMR (300 MHz, DMSO) δ 8.05 (d, J=7.7 Hz, 1H), 7.96 (d, J=7.7 Hz, 1H), 7.62 (t, J=7.7 Hz, 7.5 Hz, 1H), 7.40 (t, J=7.7 Hz, 7.5 Hz, 1H), 3.84 (q, J=6.8 Hz, 1H) 2.33 (s, 6H), 1.49 (d, J=6.8 Hz, 6H)

LC-MS m/z 270.0 (M+1)

EXAMPLE 61

Synthesis of Compound 61

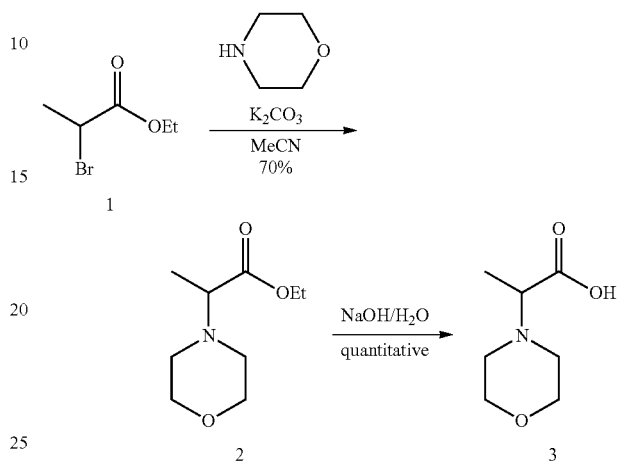

Compound 1 (Ethyl 2-bromopropionate, 1.5 g, 8.29 mmol) was dissolved in MeCN (22 ml). K$_2$CO$_3$ (3.5 g, 24.86 mmol) was added thereto, followed by stirring under a nitrogen atmosphere. Morpholine (2.2 ml, 24.86 mmol) was added thereto, followed by stirring for 18 hours at room temperature. An aqueous 1 N NaOH solution (22 ml) was added thereto and further stirred for 10 minutes. Distilled water and EA were added to a reaction solution and extraction was performed several times. Subsequently, drying was performed using MgSO$_4$ and then filtration was performed. The filtered solution was vacuum evaporated and then intactly collected.

Colorless oil 1.09 g (70%)

In an ice bath, an aqueous 10 wt % NaOH (0.34 g/3.4 ml) solution was added to Compound 2 (1.062 g, 5.67 mmol) and stirred for 3 hours at room temperature. The reaction solution was poured onto ice and pH thereof was adjusted to approximately 2 using a 4 M HCl solution. EA was added thereto and an aqueous layer was washed several times. Subsequently, a separated aqueous layer was vacuum evaporated. A concentrated solution was dissolved in MC and MeOH again and undissolved solids were filtered out. The filtered solution was vacuum evaporated and then intactly collected.

Ivory solid (quantitative)

$^1$H NMR (300 MHz, DMSO) δ 4.13 (q, J=7.2 Hz, 1H) 3.96-3.87 (m, 4H), 3.38-3.26 (m, 4H), 1.53 (d, J=7.2 Hz, 3H)

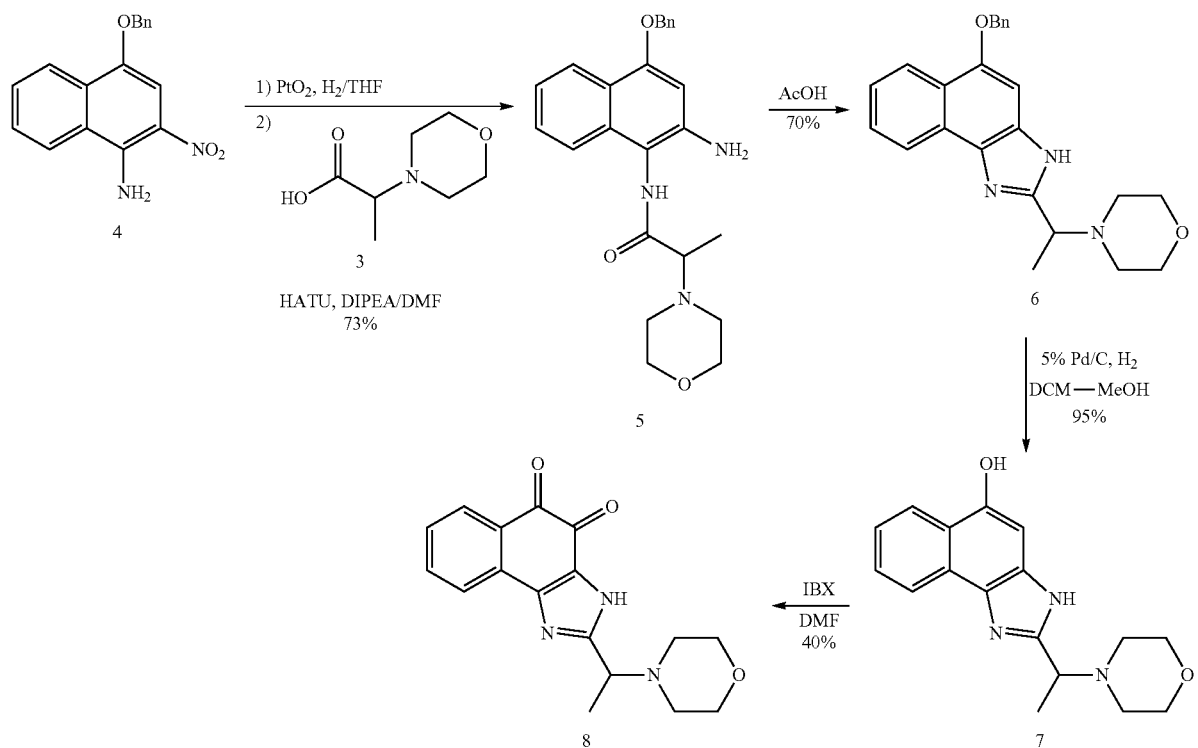

Compound 4 (0.5 g, 1.7 mmol) and PtO$_2$ (48 mg, 10 mol %) were dissolved in THF (17 ml) and then stirred for 1.5 hours under a hydrogen atmosphere. Compound 3 (0.27 g, 1.7 mmol) and HATU (0.52 g, 1.36 mmol) were dissolved in DMF (8.5 ml) and stirred for 5 minutes, and then a solution of Compound 4 was filtered through Celite in the reaction solution (MC 20 ml). DIPEA (0.9 ml, 5.1 mmol) was added thereto, followed by stirring for 30 minutes under a nitrogen atmosphere. The reaction solution was poured onto ice and distilled water and EA were added thereto, and then extraction was performed several times. The separated organic layer was dried over MgSO$_4$ and then filtered. The filtered solution was vacuum evaporated and then separated through silica gel column chromatography.

Ivory crystal 0.502 g (73%)

Compound 5 (0.49 g, 1.21 mmol) was dissolved in AcOH (24 ml) and then stirred for one hour at 70° C. The reaction solution was poured onto ice and neutralization was performed using saturated aqueous NaHCO$_3$, and then extraction was performed using EA several times. The separated organic layer was dried over MgSO$_4$ and then filtered. The filtered solution was vacuum evaporated and then recrystallized.

White solid 0.33 g (70%)

Compound 6 (0.32 g, 0.83 mmol) was dissolved in a mixture of MeOH (4 ml) and MC (4 ml) and then 5% Pd/C (0.18 g, 10 mol %) was added thereto. A reaction solution was stirred for 3 hours under a hydrogen atmosphere and then filtered through Celite. The filtered solution was vacuum evaporated and then purified through recrystallization.

White solid 0.23 g (95%)

In an ice bath, Compound 7 (0.11 g, 0.37 mmol) was dissolved in DMF (7.5 ml) and then IBX (0.26 g, 0.44 mmol) was added thereto. Reaction was performed for 30 minutes at room temperature and then extraction was performed using saturated aqueous NaHCO$_3$ and MC several times. The separated organic layer was dried over MgSO$_4$ and then filtered. The filtered solution was vacuum evaporated and then purified through recrystallization.

Red solid 46 mg (40%)

$^1$H NMR (300 MHz, DMSO) δ 7.87 (d, J=7.9 Hz, 2H), 7.68 (t, J=7.5 Hz, 1H), 7.43 (t, J=7.5 Hz, 1H), 3.80 (q, J=7.0 Hz, 1H), 3.58-3.55 (m, 4H), 2.50-2.39 (m, 4H), 1.42 (d, J=7.0 Hz, 3H)

LC-MS m/z 312.0 (M+1)

EXAMPLE 62

Synthesis of Compound 62

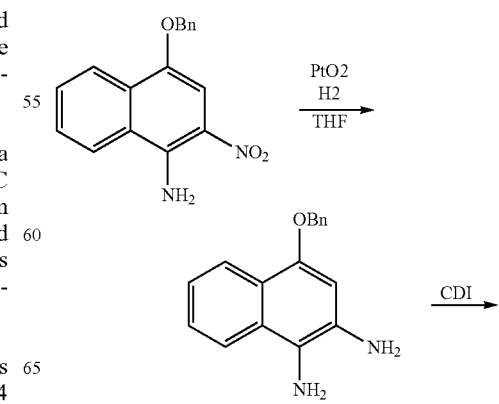

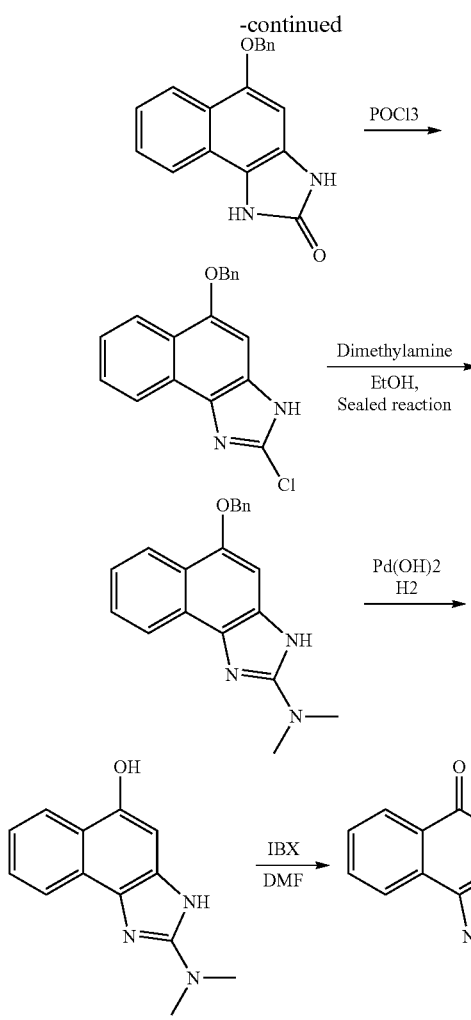

5-(benzyloxy)-1H-naphtho[2,1-d]imidazol-2 (3H)-one

THF (14 ml, 0.3M) was added to 4-(benzyloxy)-2-nitronaphthalen-1-amine (1.2 g, 4.078 mmol) and then PtO2 (84 mg) was added thereto. After degassing, substitution was performed using H$_2$. Stirring was performed for 4 hours at room temperature and then filtration was performed. CDI (528 mg, 3.26 mmol) was added to a filtrate and stirred for 15 hours at room temperature. Aq. NaHCO$_3$ was added to the reaction product and then extraction was performed by adding EA. After adding MgSO$_4$ to an EA layer, dehydration, filtration, and vacuum distillation were performed. Subsequently, recrystallization was performed using EA/Hex, thereby obtaining a target compound. 613 mg (52%)

5-(benzyloxy)-2-chloro-3H-naphtho[2,1-d]imidazole

POCl$_3$ (9 ml, 0.25M) was added to 5-(benzyloxy)-1H-naphtho[2,1-d]imidazol-2 (3H)-one (677 mg, 2.33 mmol) and then stirred at 140° C. for 18 hours. POCl$_3$ was removed through vacuum distillation, and then aq. NaHCO$_3$ was added thereto and EA was added thereto for extraction. An EA layer was dehydrated using Na$_2$SO$_4$, filtered using silica, and vacuum distilled, and then recrystallization was performed using Hex/EA, thereby obtaining a target compound. 618 mg (86%)

5-(benzyloxy)-N,N-dimethyl-3H-naphtho[2,1-d]imidazol-2-amine 5-(benzyloxy)-2-chloro-3H-naphtho[2,1-d]imidazole (100 mg, 0.324 mmol), dimethylamine (in H$_2$O) (1.5 ml), and EtOH (1.5 ml) were added to a sealed tube and then reacted for 41 hours at 130° C. Extraction was performed by pouring distilled water and EA thereinto and then an EA layer was vacuum distilled and separated through short-column chromatography. Subsequently, recrystallization was performed using Hex/EA, thereby obtaining a target compound. 55 mg (53%)

2-(dimethylamino)-3H-naphtho[2,1-d]imidazol-5-ol

MeOH (2 ml) and MC (1 ml) were poured into 5-(benzyloxy)-N,N-dimethyl-3H-naphtho[2,1-d]imidazol-2-amine (55 mg, 0.173 mmol) and Pd (OH)$_2$ (10 mg) was added thereto. After degassing, substitution was performed using H$_2$ and then stirring was performed for 4 hours at room temperature. Filtration was performed using filter paper and then vacuum distillation was performed. Subsequently, filtration was performed through silica gel again, thereby obtaining a target compound. 22 mg (56%)

Compound 62: 2-(dimethylamino)-3H-naphtho[2,1-d]imidazole-4,5-dione

DMF (1 ml, 0.1 M) was added to 2-(dimethylamino)-3H-naphtho[2,1-d]imidazol-5-ol (22 mg, 0.097 mmol), and then IBX (63 mg, 0.106 mmol) was added thereto, followed by stirring for 1 hour at room temperature. Aq. NaHCO$_3$ was added thereto and extraction was performed by adding EA thereto. An EA layer was dried over MgSO$_4$, filtered, vacuum distilled, and separated using prep TLC, thereby obtaining a target compound. 12 mg (51%)

Compound 62: $^1$H NMR (300 MHz, DMSO-d6) δ 8.10-8.07 (m, 1H), 7.95-7.92 (m, 1H), 7.76-7.73 (m, 2H), 3.53 (s, 3H), 3.24 (s, 3H)

EXAMPLE 63

Synthesis of Compound 63

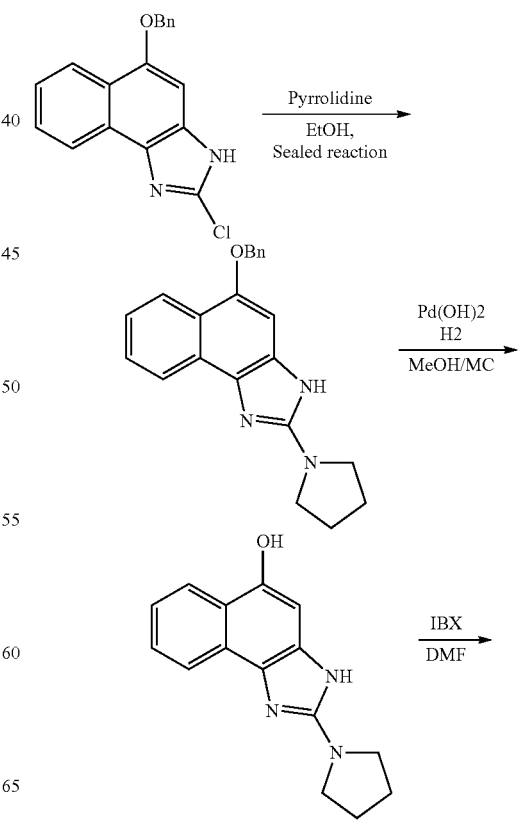

-continued

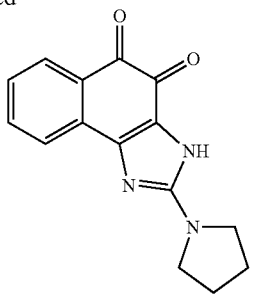

5-(benzyloxy)-2-(pyrrolidin-1-yl)-3H-naphtho[2,1-d]imidazole 5-(benzyloxy)-2-chloro-3H-naphtho[2,1-d]imidazole (100 mg, 0.324 mmol), pyrrolidine (1 ml), and EtOH (2 ml) were added to a sealed tube and then reacted for 41 hours at 130° C. Extraction was performed by adding distilled water and EA thereto and then an EA layer was vacuum distilled and separated through short-column chromatography. Subsequently, recrystallization was performed using Hex/EA, thereby obtaining a target compound. 88 mg (79%)

2-(pyrrolidin-1-yl)-3H-naphtho[2,1-d]imidazol-5-ol

MeOH (2 ml) and MC (1 ml) were poured into 5-(benzyloxy)-2-(pyrrolidin-1-yl)-3H-naphtho[2,1-d]imidazole (80 mg, 0.233 mmol) and Pd (OH)2 (10 mg) was added thereto. After degassing, substitution was performed using $H_2$ and then stirred for 4 hours at room temperature. Filtration was performed using a filter and then vacuum distillation was performed. Subsequently, filtration was performed through silica gel, thereby obtaining a target compound. 55 mg (93%)

Compound 63: 2-(pyrrolidin-1-yl)-3H-naphtho[2,1-d]imidazole-4,5-dione

DMF (2 ml, 0.1 M) was added to 2-(pyrrolidin-1-yl)-3H-naphtho[2,1-d]imidazol-5-ol (47 mg, 0.186 mmol), and then IBX (66 mg, 0.1 mmol) was added thereto, followed by stirring for 1 hour at room temperature. Aq. $NaHCO_3$ was added thereto and extraction was performed by adding EA thereto. An EA layer was dried over $MgSO_4$, filtered, and vacuum distilled, and then separation was performed using a column, thereby obtaining a target compound. 23.1 mg (46%)

Compound 63: $^1$H NMR (300 MHz, DMSO-d6) δ 8.08-8.05 (m, 1H), 7.94-7.91 (m, 1H), 7.76-7.72 (m, 2H), 4.05-3.98 (m, 2H), 3.62-3.56 (m, 2H), 2.03-1.91 (m, 4H)

EXAMPLES 64, 66, AND 72

Synthesis of Compound 64, 66, and 72

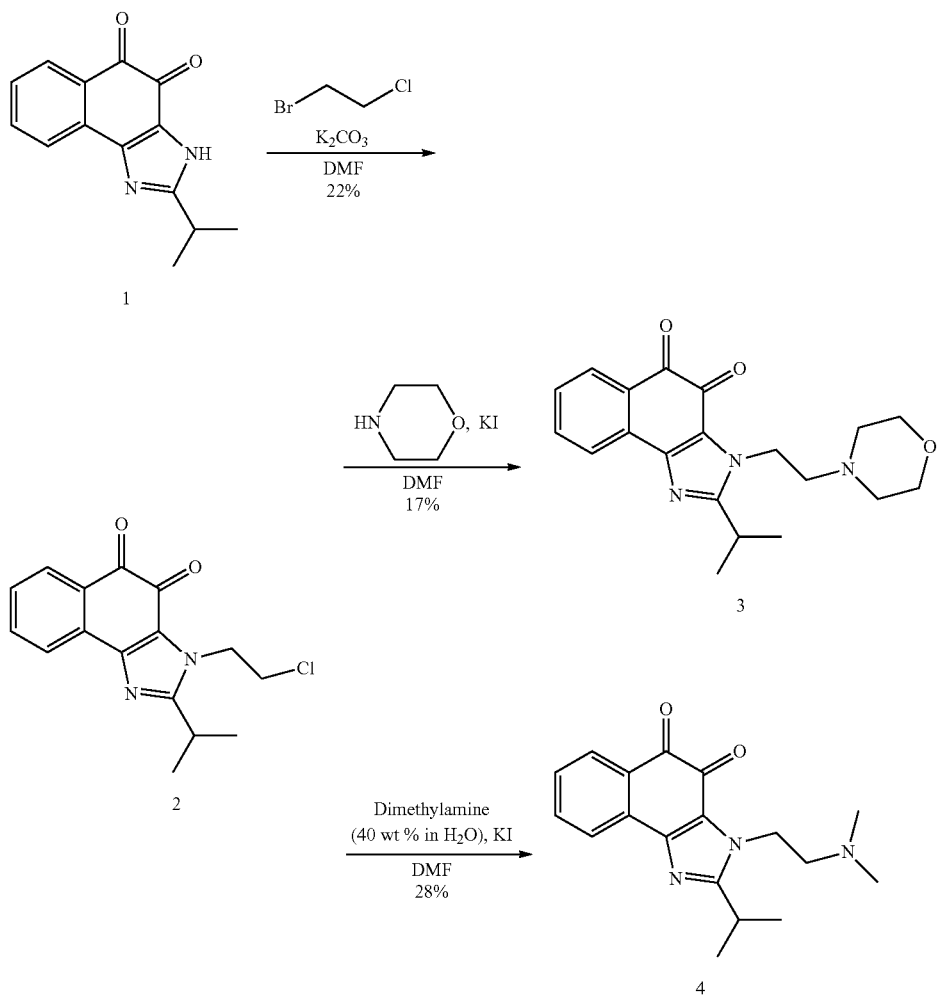

Compound 2: Example 64

Compound 3: Example 66

Compound 4: Example 72

Compound 1 (Compound 1, 2 g, 8.32 mmol) was dissolved in DMF (83 ml), and then K$_2$CO$_3$ (1.73 g, 12.49 mmol) was added thereto, followed by stirring under a nitrogen atmosphere. 1-bromo-2-chloroethane (0.76 ml, 9.16 mmol) was added thereto and further stirred for 29 hours at the same temperature. Extraction was performed using saturated aqueous NaHCO$_3$ and EA several times. The separated organic layer was dried over MgSO$_4$ and then filtered. The filtered solution was vacuum evaporated and then separated through silica gel column chromatography.

Red solid 0.55 g (22%)

Compound 64: $^1$H NMR (300 MHz, DMSO) δ 7.89-7.86 (m, 2H), 7.68 (t, J=7.5 Hz, 1H), 7.45 (t, J=7.5 Hz, 1H), 4.60 (t, J=5.7 Hz, 2H), 3.96 (t, J=5.7 Hz, 2H), 3.33-3.26 (m, 1H), 1.31 (d, J=6.8 Hz, 6H)

Compound 2 (0.1 g, 0.33 mmol) was dissolved in DMF (3.3 ml). K$_2$CO$_3$ (91 mg, 0.66 mmol), KI (8 mg), and morpholine (0.142 ml, 3.3 mmol) were added thereto and heated to 80° C. Stirring was performed for 24 hours at the same temperature. Extraction was performed using distilled water and EA several times, and then drying was performed using MgSO$_4$ and filtration was performed. The filtered solution was vacuum evaporated and then separated using PLC.

Orange solid 10 mg (17%)

Compound 66: $^1$H NMR (300 MHz, CDCl$_3$) δ 8.04-7.99 (m, 2H), 7.61 (t, J=7.7 Hz, 7.5 Hz, 1H), 7.38 (t, J=7.5 Hz, 7.7 Hz, 1H), 4.37 (t, J=6.6 Hz, 6.8 Hz, 2H), 3.69-3.66 (m, 4H), 3.11-3.07 (m, 1H), 2.71 (t, J=6.8 Hz, 6.6 Hz, 2H), 2.57-2.54 (m, 4H), 1.43 (d, J=6.8 Hz, 6H)

Compound 2 (80 mg, 0.264 mmol) and KI (4.5 mg, 0.026 mmol) were dissolved in DMF (2.5 ml) and then stirred for 10 minutes. A dimethylamine solution (40 wt % in H$_2$O) (0.14 ml, 2.64 mmol) was added thereto and heated to 80° C. for 20 hours. Extraction was performed using distilled water and EA several times. Subsequently, drying was performed using MgSO$_4$ and then filtration was performed. The filtered solution was vacuum evaporated and then separated using PLC.

Orange solid 22.8 mg (28%)

Compound 72: $^1$H NMR (300 MHz, CDCl$_3$) δ 8.03-8.01 (m, 2H), 7.60 (t, J=7.5 Hz, 7.8 Hz, 1H), 7.37 (t, J=7.8 Hz, 7.5 Hz, 1H), 4.36 (t, J=6.9 Hz, 7.2 Hz, 2H), 3.11-3.07 (m, 1H), 2.65 (t, J=7.2 Hz, 6.9 Hz, 2H), 2.32 (s, 6H), 1.42 (d, J=6.9 Hz, 6H)

EXAMPLE 65

Synthesis of Compound 65

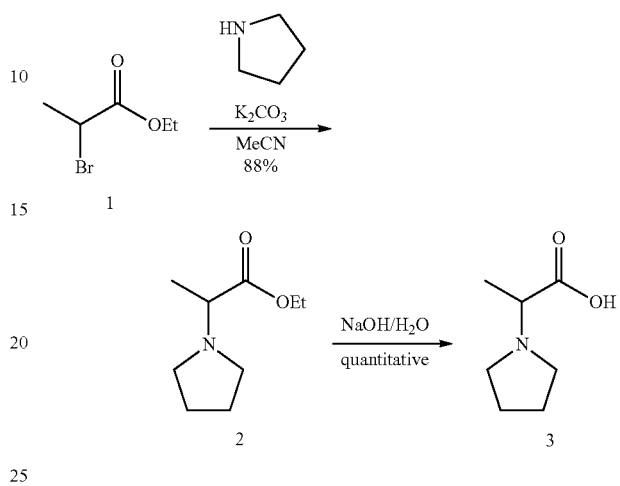

Compound 1 (Ethyl 2-bromopropionate, 2 g, 11.05 mmol) was dissolved in MeCN (30 ml). K$_2$CO$_3$ (4.6 g, 33.14 mmol) was added thereto, and then pyrrolidine (2.8 ml, 33.14 mmol) was added thereto while stirring under a nitrogen atmosphere. Stirring was performed for 22 hours at room temperature, and then an aqueous 1 N NaOH solution (30 ml) was added thereto and further stirred for 10 minutes. Distilled water and EA were added to a reaction solution and extracted several times. Subsequently, drying was performed using MgSO$_4$ and then filtration was performed. The filtered solution was vacuum evaporated and then intactly collected.

Colorless oil 1.67 g (88%)

In an ice bath, an aqueous 10 wt % NaOH (0.52 g/5.2 ml) solution was added to Compound 2 (1.5 g, 8.76 mmol). A reaction solution was stirred for 3 hours at room temperature. The reaction solution was poured onto ice and pH was adjusted to approximately 2 using an aqueous 4 M HCl solution. EA was added thereto and an aqueous layer was washed several times, and then a separated aqueous layer was vacuum evaporated. A concentrated solution was dissolved in MC and MeOH again and undissolved solids were filtered out. The filtered solution was vacuum evaporated and then intactly collected.

Ivory solid (quantitative)

$^1$H NMR (300 MHz, DMSO) δ 10.99 (br, s, 1H), 4.18 (q, J=6.6 Hz, 1H) 3.74-3.13 (m, 4H), 1.91 (s, 4H), 1.50 (d, J=7.1 Hz, 3H)

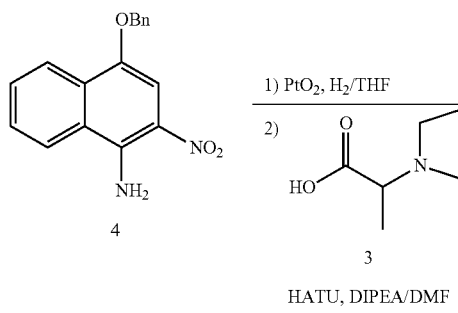
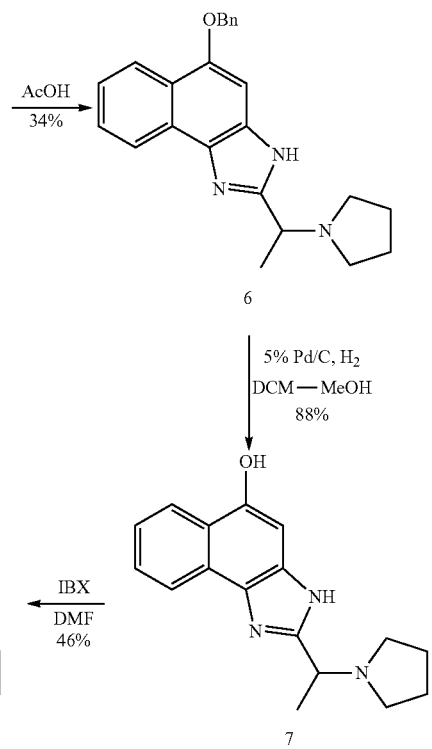

Compound 4 (0.5 g, 1.7 mmol) and PtO$_2$ (48 mg, 10 mol %) were dissolved in THF (8.5 ml) and then stirred for 4 hours under a hydrogen atmosphere. Compound 3 (0.19 g, 1.36 mmol) and HATU (0.52 g, 1.36 mmol) were dissolved in DMF (8.5 ml) and stirred for 5 minutes, and then a solution of Compound 4 was filtered through Celite in the reaction solution (MC 20 ml). DIPEA (0.9 ml, 5.1 mmol) was added to the reaction solution and stirred for 12 hours under a nitrogen atmosphere. The reaction solution was poured onto ice and distilled water and EA were added thereto, and then extraction was performed several times. The separated organic layer was dried over MgSO$_4$ and then filtered. The filtered solution was vacuum evaporated and then separated using silica gel column chromatography, followed by vacuum evaporation. A concentrated solution was dissolved in AcOH (34 ml) and then stirred for 1.5 hours at 70° C. The reaction solution was poured onto ice and neutralization was performed using saturated aqueous NaHCO$_3$, and then extraction was performed using EA several times. The separated organic layer was dried over MgSO$_4$ and then filtered. The filtered solution was vacuum evaporated and then purified through recrystallization.

White solid 0.21 g (34%)

Compound 6 (0.21 g, 0.56 mmol) was dissolved in a mixture of MeOH (3 ml) and MC (3 ml) and then 5% Pd/C (0.12 g, 10 mol %) was added thereto. A reaction solution was stirred for 2.5 hours under a hydrogen atmosphere and then filtered through Celite. The filtered solution was vacuum evaporated and then purified through recrystallization.

White solid 0.14 g (88%)

In an ice bath, Compound 7 (0.126 g, 0.45 mmol) was dissolved in DMF (9 ml) and then IBX (0.32 g, 0.54 mmol) was added thereto. Reaction was performed for 1.5 hours at room temperature and then extraction was performed using saturated aqueous NaHCO$_3$ and MC several times. The separated organic layer was dried over MgSO$_4$ and then filtered. The filtered solution was vacuum evaporated and then separated using PLC.

Red-brown solid 61.6 mg (46%)

$^1$H NMR (300 MHz, CDCl$_3$) δ 8.04 (d, J=7.1 Hz, 1H), 7.94 (d, J=7.1 Hz, 1H), 7.62 (t, J=7.5 Hz, 7.7 Hz, 1H), 7.59 (t, J=7.5, 7.7 Hz, 1H), 3.90 (q, J=6.8 Hz, 1H), 2.77-2.75 (m, 2H), 2.66-2.63 (m, 2H), 1.85 (s, 4H), 1.55 (d, J=6.8 Hz, 3H)

EXAMPLE 67

Synthesis of Compound 67

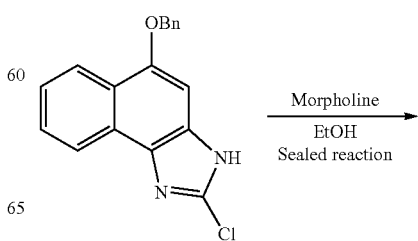

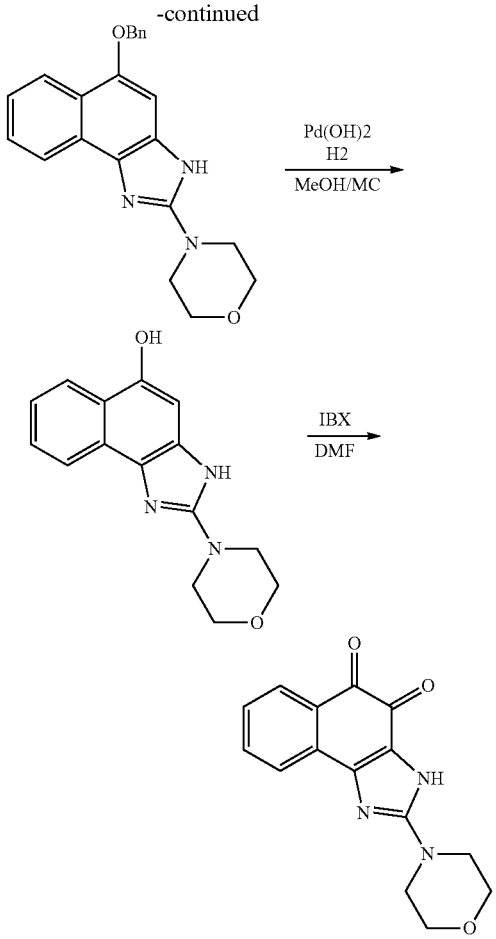

4-(5-(benzyloxy)-3H-naphtho[2,1-d]imidazol-2-yl)morpholine 5-(benzyloxy)-2-chloro-3H-naphtho[2,1-d]imidazole (100 mg, 0.324 mmol), pyrrolidine (1 ml), and EtOH (2 ml) were added to a sealed tube and then reacted for 72 hours at 130° C. Extraction was performed by pouring distilled water and EA thereinto and then an EA layer was vacuum distilled and separated through short-column chromatography. Subsequently, recrystallization was performed using Hex/EA, thereby obtaining a target compound. 96 mg (82%)

2-morpholino-3H-naphtho[2,1-d]-imidazole-4,5-dione

MeOH (2.5 m) was poured onto 4-(5-(benzyloxy)-3H-naphtho[2,1-d]imidazol-2-yl)morpholine (90 mg, 0.25 mmol) and Pd (OH)$_2$ (18 mg) was added thereto. After degassing, substitution was performed using H$_2$ and then stirring was performed for 4 hours at room temperature. Filtration was performed using filter paper, and then vacuum distillation was performed and DMF (2.5 ml, 0.1 M) was added thereto. Subsequently, IBX (74 mg, 0.1 mmol) was added thereto and stirring was performed for 1 hour at room temperature. Aq. NaHCO$_3$ was added thereto and extraction was performed by adding EA thereto. An EA layer was dried over MgSO$_4$, filtered, vacuum distilled, and separated through a column, thereby obtaining a target compound. 18 mg (25%)

Compound 67: $^1$H NMR (300 MHz, DMSO-d6) δ 7.79 (d, J=6.9 Hz, 1H), 7.71 (d, J=7.2 Hz, 1H), 7.60 (t, J=7.2 Hz, 1H), 7.39 (t, J=6.9 Hz, 1H), 3.72-3.65 (m, 4H), 3.62-3.57 (m, 4H)

EXAMPLE 68

Synthesis of Compound 68

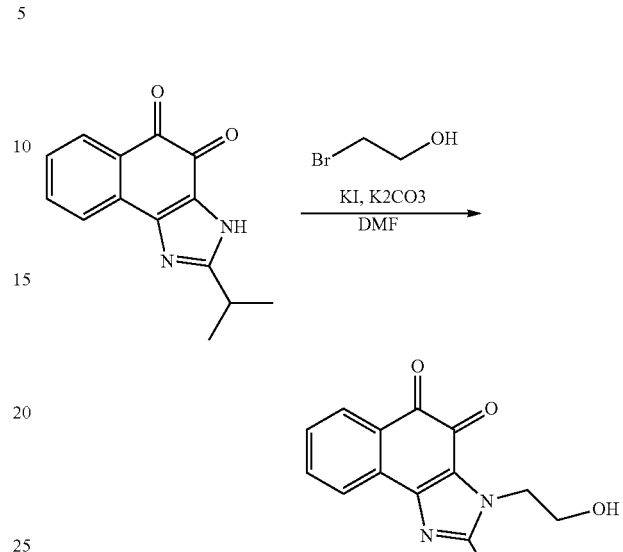

Compound 68: 3-(2-hydroxyethyl)-2-isopropyl-3H-naphtho[2,1-d]imidazole-4,5-dione DMF (62 ml, 0.2M) was added to Compound 1 (3 g, 12.486 mmol), and then K$_2$CO$_3$ (3.45 g, 24.973 mmol), KI (2.07 g, 12.486 mmol), and bromoethanol (1.8 ml, 24.97 mmol) were sequentially added thereto, followed by stirring for 2 days at 90° C.

Extraction was performed by pouring distilled water and EA thereinto, and then an EA layer was vacuum distilled and separated through column chromatography. Subsequently, recrystallization was performed using Hex/EA, thereby obtaining a target compound. 841 mg (24%)

Compound 68: $^1$H NMR (300 MHz, DMSO-d6) δ 7.94 (d, J=7.8 Hz, 1H), 7.88 (d, J=7.5 Hz, 1H), 7.55 (t, J=7.5 Hz, 1H), 7.36 (t, J=7.5 Hz, 1H), 4.42 (t, J=5.1 Hz, 2H), 4.02-3.97 (m, 2H), 3.23-3.19 (m, 1H), 2.48-2.45 (m, 1H), 1.42 (d, J=6.9 Hz, 6H)

EXAMPLE 69

Synthesis of Compound 69

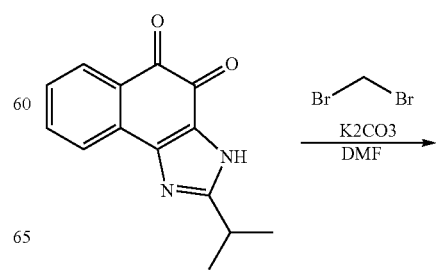

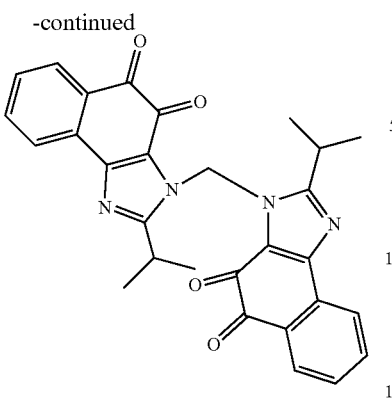

Compound 1 (500 mg, 2.08 mmol) was added to DMF (20 ml, 0.1 M), and then K₂CO₃ (575 mg, 4.16 mmol) and dibromomethane (173 µl, 2.479 mmol) were added thereto and reacted for 5 hours at 50° C. Extraction was performed by pouring aq. NaHCO₃ and EA thereinto, dehydration was performed using MgSO₄ and then filtration and vacuum distillation were performed. Subsequently, separation was performed using a column, thereby obtaining a target compound. 100 mg (20%)

Compound 69: ¹H NMR (300 MHz, CDCl₃) δ 8.06 (t, J=8.1 Hz, 4H), 7.66 (t, J=7.5 Hz, 2H), 7.45 (t, J=7.5 Hz, 2H), 7.21 (s, 2H), 3.06-2.97 (m, 2H), 1.17 (d, J=6.6 Hz, 12H)

EXAMPLE 70

Synthesis of Compound 70

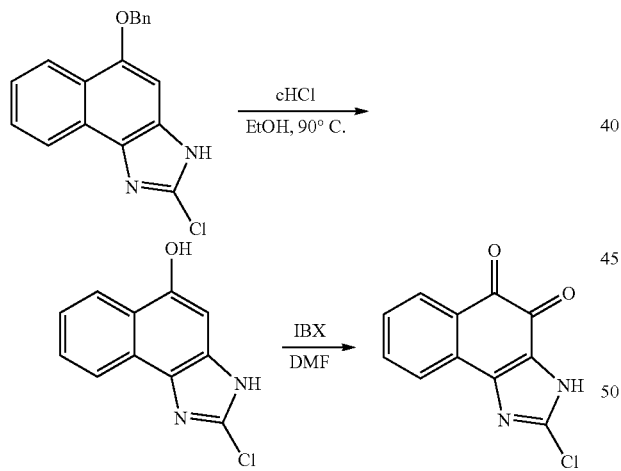

2-chloro-3H-naphtho[2,1-d]imidazol-5-ol

EtOH (1 ml) was added to 5-(benzyloxy)-2-chloro-3H-naphtho[2,1-d]imidazole (80 mg, 0.259 mmol) and cHCl (1 ml) was added thereto. Refluxing was performed for 2.5 hours while stirring. Neutralization was performed using aq. NaHCO₃ and then extraction was performed using EA. An EA layer was dried over MgSO₄, filtered, and then vacuum distilled. Subsequently, recrystallization was performed using Hex/EA, thereby obtaining a target compound. 35 mg (62%)

2-chloro-3H-naphtho[2,1-d]imidazole-4,5-dione

DMF (1.6 ml, 0.1 M) was added to 2-chloro-3H-naphtho[2,1-d]imidazol-5-ol (35 mg, 0.16 mmol), and then IBX (105 mg, 0.177 mmol) was added thereto, followed by stirring for 2 hours. Extraction was performed by pouring aq. NaHCO₃ and EA thereinto, and then dehydration was performed using Na₂SO₄ and filtration was performed. After vacuum distillation, recrystallization was performed using Hex/EA, thereby obtaining a target compound. 13 mg (35%)

Compound 70: ¹H NMR (300 MHz, DMSO-d6) δ 7.88 (d, J=7.8 Hz, 1H), 7.76 (d, J=7.5 Hz, 1H), 7.68 (t, J=6.0 Hz, 1H), 7.45 (t, J=6.6 Hz, 1H)

EXAMPLES 71 AND 74

Synthesis of Compounds 71 and 74

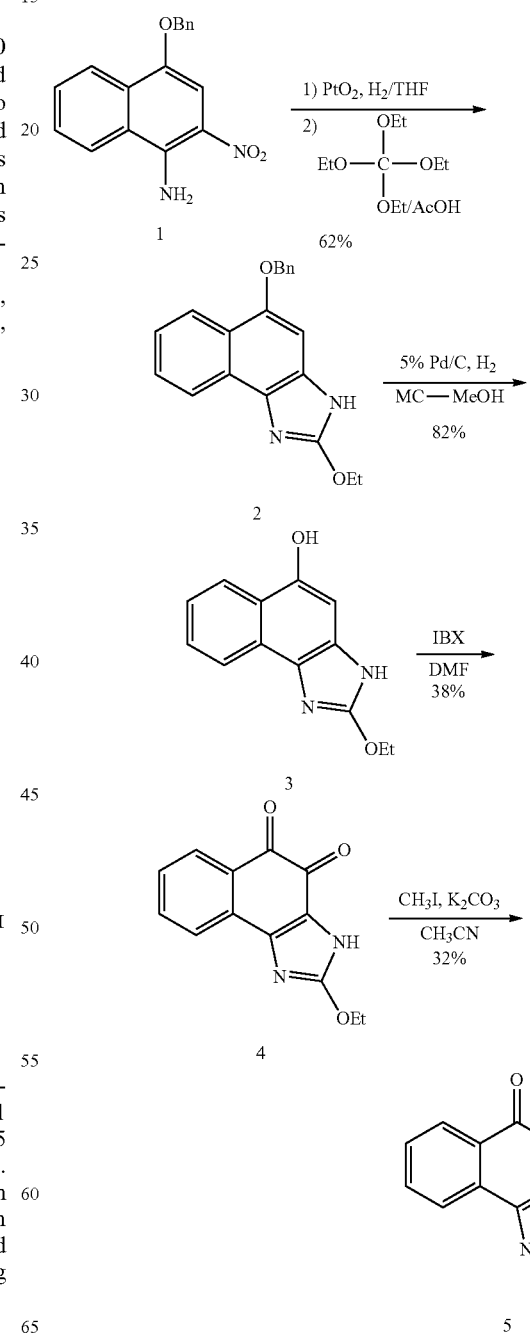

Example 71 Example 74

Compound 1 (1 g, 6.4 mmol) and PtO$_2$ (0.1 g, 10 mol %) were dissolved in THF (34 ml, 0.1 M) and then stirred for 2.5 hours under a hydrogen atmosphere. After filtering through Celite (MC 50 ml), vacuum evaporation was performed. In an ice bath, the reaction product was dissolved in AcOH (17 ml) again and tetraethoxymethane (0.9 ml, 4.08 mmol) was added thereto. Stirring was performed for 30 minutes at room temperature, and then the reaction solution was poured onto ice and undissolved solids were filtered out.

Khaki solid 0.67 g (62%)

Compound 2 (0.67 g, 0.2.1 mmol) was dissolved in a mixture of MeOH (10 ml) and DCM (10 ml). 5% Pd/C (0.44 g, 10 mol %) was added thereto, followed by stirring for 4 hours under a hydrogen atmosphere. Filtration was performed through Celite and then vacuum evaporation was performed. Subsequently, purification was performed through recrystallization.

Dark-brown solid 0.39 g (82%)

Compound 4 (50 mg, 0.21 mmol) was dissolved in CH$_3$CN (4 ml). K$_2$CO$_3$ (86 mg, 0.62 mmol) was added thereto, followed by stirring for 10 minutes. Iodomethane (18 ul, 0.29 mmol) was added thereto and heated to 80° C., followed by stirring for one hour. The reaction solution was poured onto ice and extraction was performed using saturated aqueous NaHCO$_3$ and EA several times. The separated organic layer was dried over MgSO$_4$ and then filtered. The filtered solution was vacuum evaporated and then purified through recrystallization.

$^1$H NMR (300 MHz, DMSO) δ 7.82 (d, J=7.5 Hz, 1H), 7.72 (d, J=7.5 Hz, 1H), 7.62 (t, J=7.5 Hz, 1H), 7.42 (t, J=7.5 Hz, 1H), 4.57 (q, J=7.2 Hz, 6.9 Hz, 2H), 3.58 (s, 3H), 1.41 (t, J=6.9 Hz, 7.2 Hz, 3H)

EXAMPLE 73

Synthesis of Compound 73

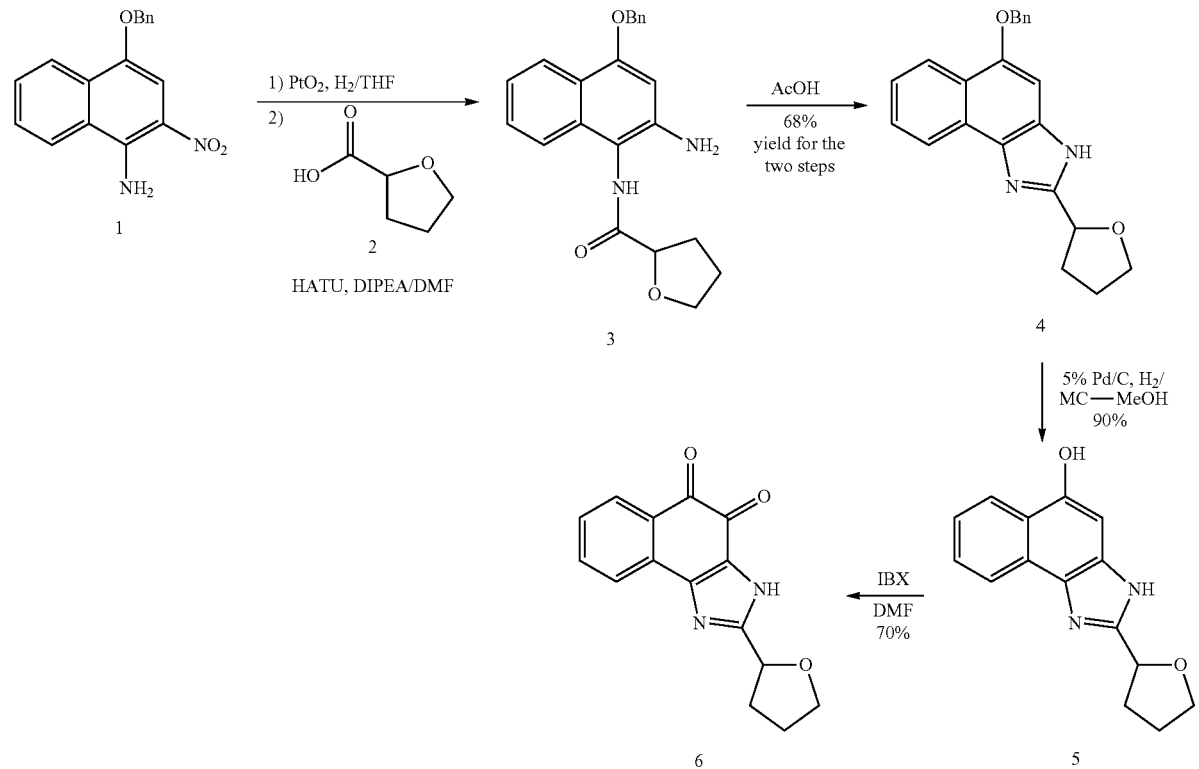

In an ice bath, Compound 3 (0.38 g, 1.67 mmol) was dissolved in DMF (11 ml) and then IBX (1.2 g, 2.01 mmol) was added thereto. Reaction was performed for 16 hours at room temperature and then extraction was performed using saturated aqueous NaHCO$_3$ and EA several times. The separated organic layer was dried over MgSO$_4$ and then filtered. The filtered solution was vacuum evaporated and then separation was performed through silica gel column chromatography. Subsequently, purification was performed through recrystallization.

Brown solid 0.15 g (38%)

$^1$H NMR (300 MHz, DMSO) δ 12.98 (br, s, 1H), 7.82 (d, J=7.8 Hz, 1H), 7.71-7.61 (m, 2H), 7.41 (t, J=7.8 Hz, 7.2 Hz, 1H), 4.51 (q, J=6.9 Hz, 7.2 Hz, 2H), 1.37 (t, J=6.9 Hz, 7.2 Hz, 3H)

Compound 1 (2 g, 6.8 mmol) and PtO$_2$ (0.15 g, 10 mol %) were dissolved THF (68 ml) and then stirred for 2 hours under a hydrogen atmosphere. Compound 2 (0.59 ml, 6.12 mmol) and HATU (2.3 g, 6.12 mmol) were dissolved in DMF (34 ml) and stirred for 5 minutes, and then a solution of Compound 1 was filtered through Celite in the reaction solution (MC 50 ml). DIPEA (3.5 ml, 20.39 mmol) was added thereto, followed by stirring for 30 minutes under a nitrogen atmosphere. The reaction solution was poured onto ice and extraction was performed using a saturated aqueous NaCl solution and EA several times. The separated organic layer was dried over MgSO$_4$, and then filtered and vacuum evaporated. The reaction product was dissolved in AcOH (68 ml) again and then stirred for one hour at 70° C. The reaction solution was poured onto ice and neutralization was performed using saturated aqueous NaHCO$_3$ and then extraction was performed using EA several times. The separated organic layer was dried over MgSO$_4$ and then filtered. The filtered solution was vacuum evaporated and then separation was performed through silica gel column chromatography. Subsequently, purification was performed through recrystallization.

Ivory solid 1.6 g (68%)

Compound 4 (1.6 g, 4.65 mmol) was dissolved in MeOH (25 ml) and DCM (25 ml) and then 5% Pd/C (0.99 g, 10 mol %) was added thereto. A reaction solution was stirred for 2 hours under a hydrogen atmosphere and then filtered through Celite. The filtered solution was vacuum evaporated and then purified through recrystallization.

Ivory solid 1.06 g (90%)

In an ice bath, Compound 5 (0.157 g, 0.62 mmol) was dissolved in DMF (6 ml) and then IBX (0.44 g, 0.74 mmol) was added thereto. Reaction was performed for 24 hours at room temperature, and then saturated aqueous NaHCO$_3$ and EA were added thereto and extraction was performed several times. The separated organic layer was dried over MgSO$_4$ and then filtered. The filtered solution was vacuum evaporated and then purified through recrystallization.

Red-brown solid 0.116 g (70%)

$^1$H NMR (300 MHz, DMSO) δ 13.57 (br, s, 1H), 7.88-7.85 (m, 2H), 7.67 (t, J=7.2 Hz, 7.8 Hz, 1H), 7.43 (t, J=7.8 Hz, 7.5 Hz, 1H), 4.97 (t, J=7.2 Hz, 6.3 Hz, 1H), 4.00-3.93 (m, 1H), 3.85-3.78 (m, 1H), 2.31-2.10 (m, 2H), 2.05-1.89 (m, 2H)

EXAMPLE 75

Synthesis of Compound 75

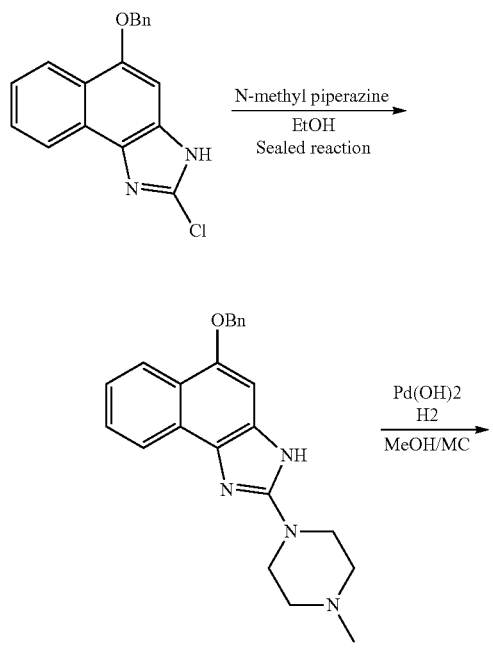

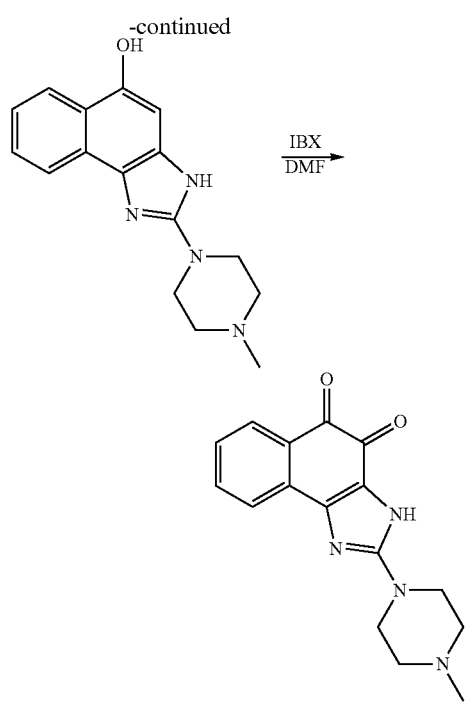

5-(benzyloxy)-2-(4-methylpiperazin-1-yl)-3H-naphtho[2,1-d]imidazole 5-(benzyloxy)-2-chloro-3H-naphtho[2,1-d]imidazole (100 mg, 0.324 mmol), pyrrolidine (1 ml), and EtOH (1 ml) were added to a sealed tube and then reacted for 48 hours at 130° C. Distilled water and EA were added thereto for extraction, and then an EA layer was vacuum distilled and separated through short-column chromatography, thereby obtaining a target compound. 150 mg (90%)

2-(4-methylpiperazin-1-yl)-3H-naphtho[2,1-d]imidazole-4,5-dione

MeOH (4 ml) was poured into 5-(benzyloxy)-2-(4-methylpiperazin-1-yl)-3H-naphtho[2,1-d]imidazole (150 mg, 0.403 mmol) and Pd (OH)$_2$ (20 mg) were added thereto. After degassing, substitution was performed using H$_2$ and then stirred for 4 hours at room temperature. After filtering using filter paper, vacuum distillation was performed and DMF (2 ml, 0.2 M) was added thereto, and then IBX (120 mg, 0.2 mmol) was added thereto, followed by stirring for 1 hour at room temperature. Aq. NaHCO$_3$ was added thereto and extraction was performed by adding EA thereto. An EA layer was dried over MgSO$_4$, filtered, vacuum distilled, and separated through a column, thereby obtaining a target compound. 20 mg (17%)

Compound 75: $^1$H NMR (300 MHz, CDCl$_3$) δ 8.09 (d, J=7.2 Hz, 1H), 8.04 (d, J=7.5 Hz, 1H), 7.61-7.54 (m, 2H), 4.25-4.20 (m, 2H), 4.0-3.89 (m, 2H), 2.68-2.50 (m, 4H), 2.39 (s, 3H)

EXAMPLE 76

Synthesis of Compound 76

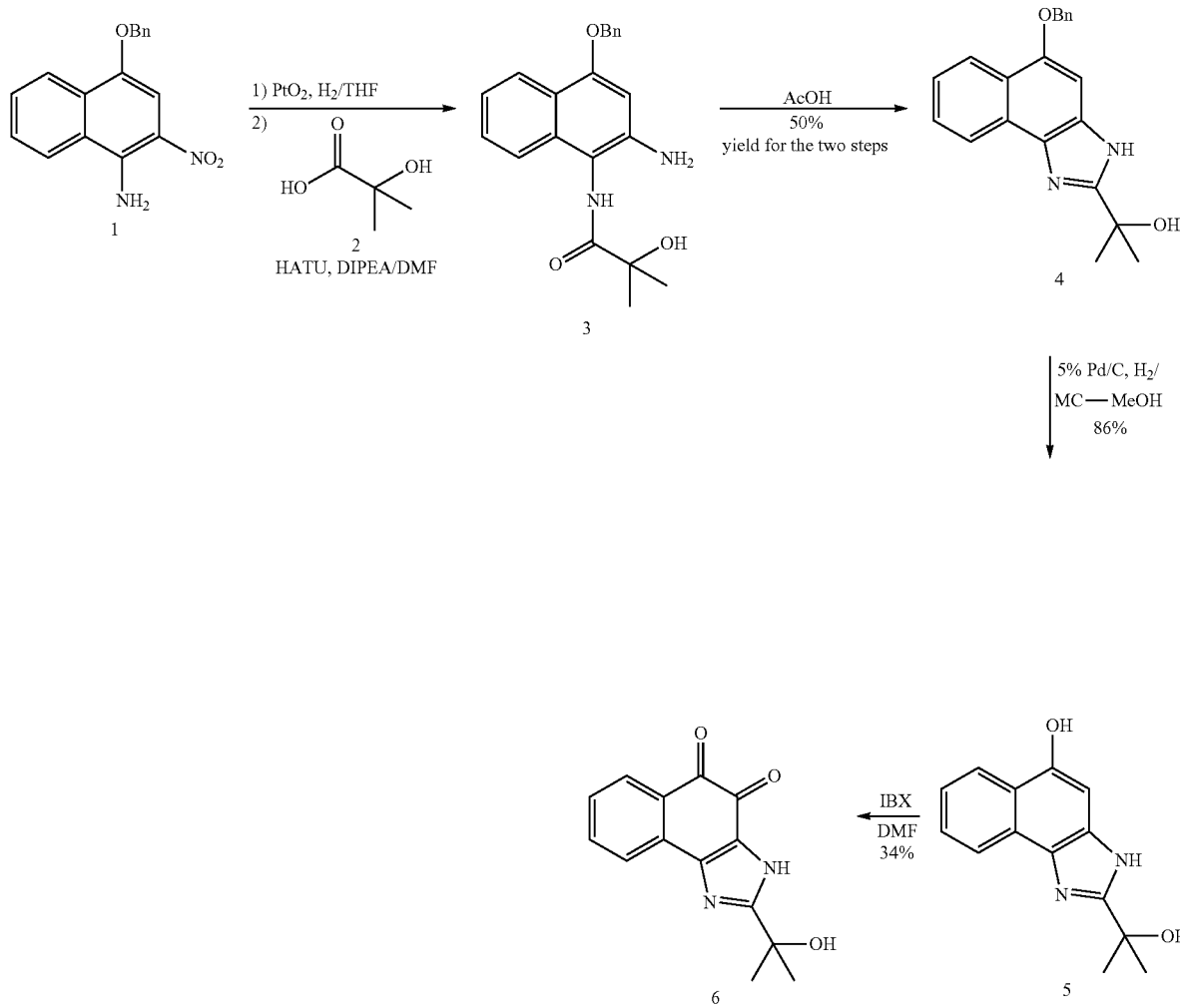

Compound 1 (0.5 g, 1.7 mmol) and PtO₂ (48 mg, 10 mol %) were dissolved in THF (17 ml) and then stirred for 2 hours under a hydrogen atmosphere. Compound 2 (0.14 g, 1.36 mmol) and HATU (0.52 g, 1.36 mmol) were dissolved in DMF (8.5 ml) and stirred for 10 minutes, and then a solution of Compound 1 was filtered through Celite in the reaction solution (MC 20 ml). DIPEA (0.9 ml, 5.1 mmol) was added thereto, followed by stirring for 30 minutes under a nitrogen atmosphere. The reaction solution was poured onto ice and extraction was performed using a saturated aqueous NaCl solution and EA several times. The separated organic layer was dried over MgSO₄, and then filtered and vacuum evaporated. The reaction product was dissolved in AcOH (34 ml) again and then stirred for 2.5 hours at 70° C. The reaction solution was poured onto ice and neutralization was performed using saturated aqueous NaHCO₃, and then extraction was performed using EA several times. The separated organic layer was dried over MgSO₄ and then filtered. The filtered solution was vacuum evaporated and then purified through recrystallization.

Ivory solid 0.28 g (50%)

Compound 4 (0.27 g, 0.82 mmol) was dissolved in a mixture of MeOH (5.5 ml), DCM (5.5 ml), and THF (2 ml), and then 5% Pd/C (0.17 g, 10 mol %) was added thereto. A reaction solution was stirred for 24 hours under a hydrogen atmosphere and then filtered through Celite. The filtered solution was vacuum evaporated and then purified through recrystallization.

Ivory solid 0.17 g (86%)

In an ice bath, Compound 5 (0.1 g, 0.413 mmol) was dissolved in DMF (8 ml) and then IBX (0.3 g, 0.495 mmol) was added thereto. Reaction was performed for 4.5 hours at room temperature and then extraction was performed using saturated aqueous NaHCO₃ and EA several times. A separated aqueous layer was reextracted using EA. An organic layer was dried over MgSO₄ and then filtered. The filtered solution was vacuum evaporated and then purified through recrystallization.

Bright-brown solid 36.1 m g (34%)

¹H NMR (300 MHz, CDCl₃) δ 11.52 (br, s, 1H), 7.97 (d, J=7.5 Hz, 1H), 7.85 (d, J=6.9 Hz, 1H), 7.56 (t, J=7.5 Hz, 1H), 7.38 (t, J=7.2 Hz, 7.5 Hz, 1H), 4.48 (br, s, 1H), 1.80 (s, 6H)

EXAMPLE 77

Synthesis of Compound 77

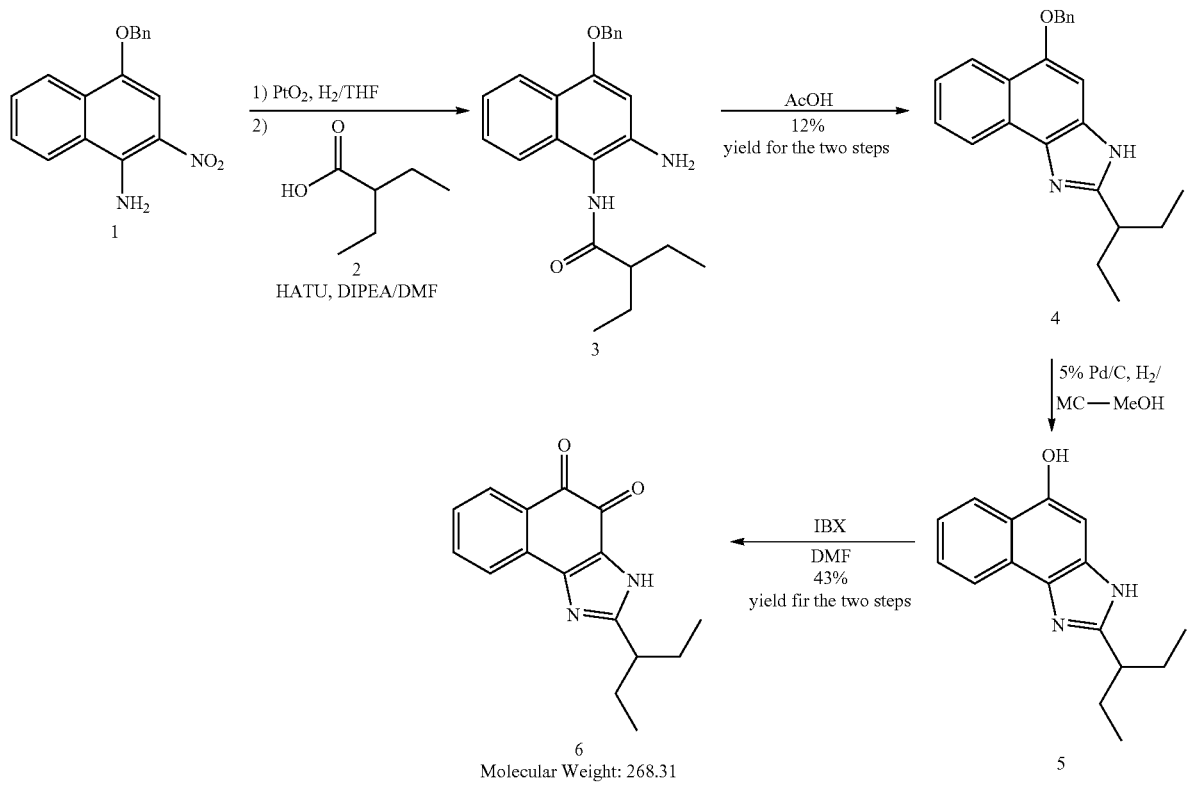

Compound 1 (0.5 g, 1.7 mmol) and PtO$_2$ (48 mg, 10 mol %) were dissolved in THF (17 ml) and then stirred for 2.5 hours under a hydrogen atmosphere. Compound 2 (0.17 ml, 1.36 mmol) and HATU (0.52 g, 1.36 mmol) were dissolved in DMF (8.5 ml) and stirred for 30 minutes, and then a solution of Compound 1 was filtered through Celite in the reaction solution (MC 20 ml). DIPEA (0.9 ml, 5.1 mmol) was added thereto, followed by stirring for 30 minutes under a nitrogen atmosphere. The reaction solution was poured onto ice and extraction was performed using a saturated aqueous NaCl solution and EA several times. The separated organic layer was dried over MgSO$_4$, and then filtered and vacuum evaporated. The reaction product was redissolved in AcOH (34 ml) and then stirred for 5 hours at 70° C. The reaction solution was poured onto ice and neutralization was performed using saturated aqueous NaHCO$_3$, and then extraction was performed using EA several times. The separated organic layer was dried over MgSO$_4$ and then filtered. The filtered solution was vacuum evaporated and then separation was performed through silica gel column chromatography. Subsequently, purification was performed through recrystallization.

Ivory solid 70.6 mg (12%)

Compound 4 (66.7 mg, 0.194 mmol) was dissolved in a mixture of MeOH (2 ml) and DCM (2 ml) and then 5% Pd/C (41 mg, 10 mol %) was added thereto. A reaction solution was stirred for 15 hours under a hydrogen atmosphere and then filtered through Celite. The filtered solution was vacuum evaporated. In an ice bath, a concentrated solution was dissolved in DMF (4 ml) and then IBX (0.14 g, 0.232 mmol) was added thereto. Reaction was performed for 2 hours at room temperature and then extraction was performed using saturated aqueous NaHCO$_3$ and EA several times. An organic layer was dried over MgSO$_4$ and then filtered. The filtered solution was vacuum evaporated and then purification was performed using PLC.

Red solid 22.5 mg (43%)

$^1$H NMR (300 MHz, CDCl$_3$) δ 11.20 (br, s, 1H), 8.03 (d, J=7.8 Hz, 1H), 8.01 (d, J=7.8 Hz, 1H), 7.62 (t, J=7.8 Hz, 1H), 7.41 (t, J=7.8 Hz, 1H), 2.90-2.81 (m, 1H), 1.87 (q, J=7.2 Hz, 4H), 0.93 (t, J=7.2 Hz, 6H)

EXAMPLE 78

Synthesis of Compound 78

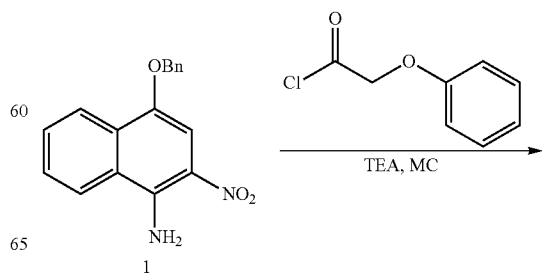

-continued

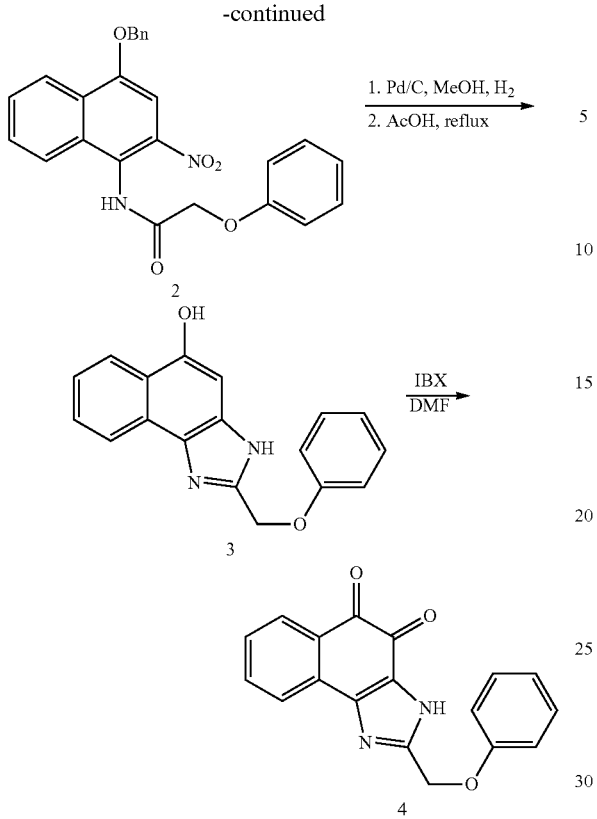

1->2

In a round bottom flask, Compound 1 (0.15 g, 0.5 mmol) was dissolved in MC (2.5 mL) and triethylamine (0.03 mL, 2.0 mmol) was added thereto. Stirring was performed for 10 minutes and then 2-phenoxyacetyl chloride (1.5 mmol) was slowly added thereto. After stirring for 3 hours, the reaction product was quenched with an aqueous NaHCO₃ solution. Extraction was performed using MC several times, and then treatment with Na₂SO₄, filtration, and vacuum evaporation were performed. Recrystallization was performed using EA/HX, thereby obtaining Compound 2 (0.15 g, 71%).

2->3

In a round bottom flask, Compound 2 (0.5 mmol) was dissolved in MeOH (0.2 M) and then 5% Pd/C (0.05 mol %) was added thereto. An inner space of the flask was fitted with a H₂ balloon and then reacted for 2 hours at room temperature. After reaction, filtration was performed through Celite, followed by concentration. AcOH (5 mL) was added to a concentrated reaction product and refluxed for 5 hours. The reaction product was vacuum evaporated, and then EA (20 mL) was added thereto and washing was performed using an aqueous NaHCO₃ solution three times. An EA layer was separated, treated with Na₂SO₄, filtered, and vacuum evaporated, and then purification was performed through silica column chromatography, thereby obtaining crude-Compound 3.

3->4

Compound 3 (0.3 mmol) was dissolved in DMF (0.1 M) and then temperature was lowered to 0° C. 47% IBX (0.36 mmol) was added thereto, followed by stirring for 1 hour. The reaction product was quenched using an aqueous NaHCO₃ solution and then extracted using EA. An EA layer was washed with an aqueous NaHCO₃ solution several times. An EA layer was treated with Na₂SO₄, filtered, and vacuum evaporated. Purification was performed through silica gel column chromatography, thereby obtaining Compound 4 (1.1 mg, Step 2 yield 1%).

1H NMR (300 MHz, DMSO) δ 12.98 (br, s, 1H), 7.47 (d, J=8.2 Hz, 1H), 7.40-7.35 (m, 2H), 7.18-7.11 (m, 3H), 6.97 (br, s, 1H), 6.75 (d, J=8.4 Hz, 1H), 4.33 (d, J=6.0 Hz, 2H), 2.66 (q, J=7.5 Hz, 2H), 1.23 (t, J=7.5 Hz, 3H)

EXAMPLE 79

Synthesis of Compound 79

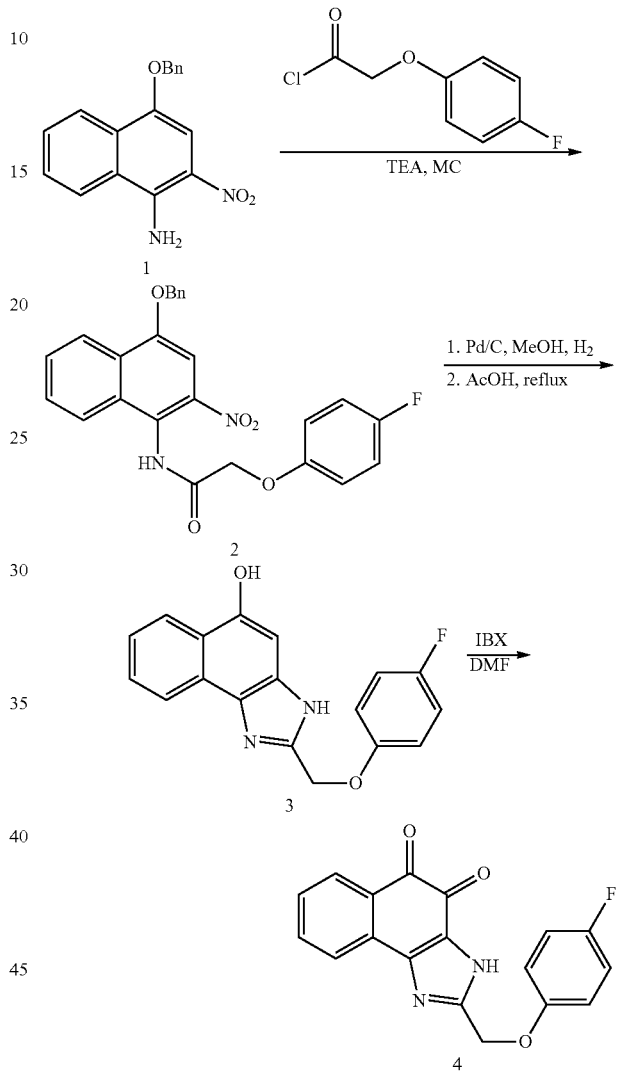

1->2

In a round bottom flask, Compound 1 (1.47 g, 5.0 mmol) was dissolved in MC (25 mL) and triethylamine (2.81 mL, 20 mmol) was added thereto. Stirring was performed for 10 minutes and then 2-(4-fluorophenoxy)acetyl chloride (15 mmol) was slowly added thereto. After stirring for 3 hours, the reaction product was quenched using an aqueous NaHCO₃ solution. Extraction was performed using MC several times, and then treatment with Na₂SO₄, filtration, and vacuum evaporation were performed. Purification was performed through silica gel column chromatography, thereby obtaining Compound 2 (2.0 g, 90%).

2->3

In a round bottom flask, Compound 2 (2.0 g, 4.48 mmol) was dissolved in MeOH (0.2 M) and then 5% Pd/C (0.05 mol %) was added thereto. An inner space of the flask was fitted with a H₂ balloon and then reacted for 2 hours at room temperature. After reaction, filtration was performed through Celite and then concentration was performed. AcOH (20 mL) was added to a concentrated reaction product and refluxed for 5 hours.

The reaction product was vacuum evaporated, and then EA (20 mL) was added thereto and the reaction product was washed with an aqueous NaHCO₃ solution three times. An EA layer was separated, treated with Na₂SO₄, filtered, and vacuum evaporated, and then recrystallized using EA/HX, thereby obtaining Compound 3 (0.57 g, 41%).

3->4

Compound 3 (0.57 g, 1.85 mmol) was dissolved in DMF (0.05M) and then temperature was lowered to 0° C. 47% IBX (1.32 g, 2.22 mmol) was added thereto, followed by stirring for 1 hour. The reaction product was quenched using an aqueous NaHCO₃ solution and then extracted using EA. An EA layer was washed with an aqueous NaHCO₃ solution several times. An EA layer was treated with Na₂SO₄, filtered, and vacuum evaporated. Purification was performed through silica gel column chromatography, thereby obtaining Compound 4 (25 mg, 5%).

1H NMR (300 MHz, CDCl₃) δ 10.54 (br, 1H), 8.11-8.06 (m, 1H), 7.97-7.94 (m, 1H), 7.52-7.42 (m, 1H), 7.07-6.93 (m, 4H), 5.27 (s, 2H)

EXAMPLE 80

Synthesis of Compound 80

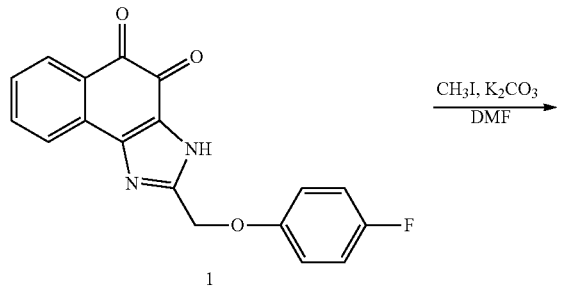

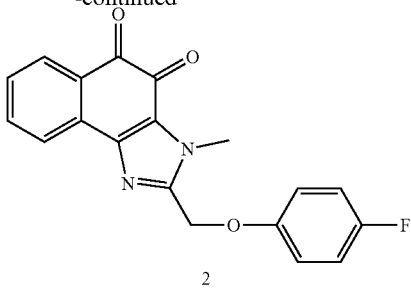

Compound 1 (19 mg, 0.059 mmol) was dissolved in DMF (0.1 M). K₂CO₃ (24 mg, 0.177 mmol) was added to the reaction product and then stirred for 20 minutes. CH₃I (12 mg, 0.083 mmol) was added to the reaction product and heated to 60° C. Progression of reaction was confirmed through TLC and then the reaction product was quenched by adding water (20 mL). Extraction was performed using EA (20 mL) three times and then a separated EA layer was washed with water (20 mL) three times. A separated EA layer was treated with Na₂SO₄, filtered, and vacuum evaporated. Recrystallization was performed using EA/HX, thereby obtaining Compound 2 (7.9 mg, 40%).

1H NMR (300 MHz, CDCl₃) δ 8.06-8.03 (dd, J=4.8, 1.2 Hz, 1H), 7.97-7.94 (dd, J=4.8, 1.2 Hz, 1H), 7.66-7.60 (td, J=7.5, 1.2 Hz, 1H), 7.44-7.38 (td, J=7.5, 1.2 Hz, 1H), 7.05-6.97 (m, 4H), 5.22 (s, 2H), 4.06 (s, 3H)

EXAMPLE 82

Compound 82 Synthesis of

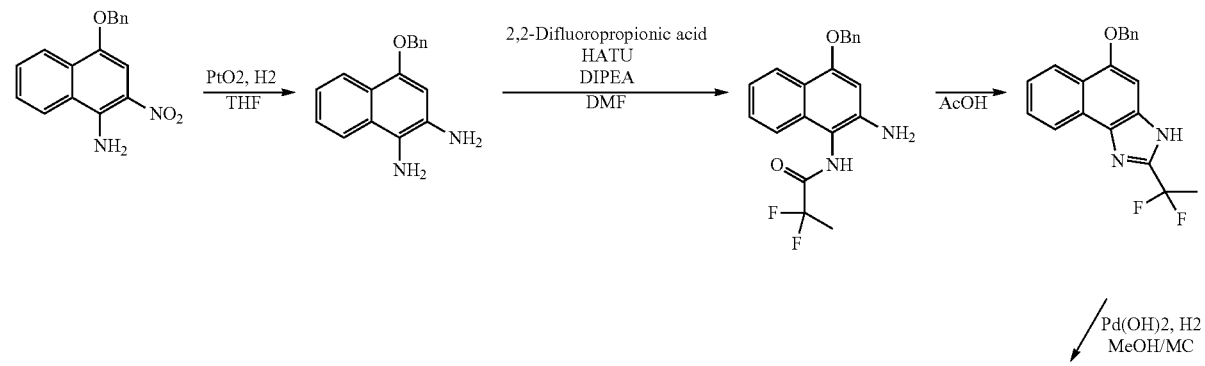

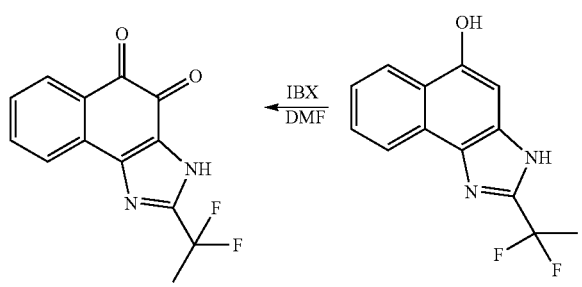

Compound 4: 5-(benzyloxy)-2-(1,1-difluoroethyl)-3H-naphtho[2,1-d]imidazole

THF (2 ml, 0.5M) was added to 4-(benzyloxy)-2-nitronaphthalen-1-amine (300 mg, 1.019 mmol), and then PtO2 (20 mg) was added thereto and degassing was performed. Subsequently, substitution was performed using H₂. Stirring was performed for 3 hours at room temperature and then filtration was performed. 2,2-Difluoropropionic acid (146 mg, 1.325 mmol), DMF (6 ml), and HATU (504 mg, 1.325 mmol) was added to the filtrate in one direction, followed by stirring for 10 minutes at room temperature. Stirred acid moiety was added to a filtrate and DIPEA (0.36 ml, 2.038 mmol) was added thereto, and then stirring was performed for 0.5 hours at room temperature. When SM disappeared, AcOH (11 ml, 0.1 M) was poured thereinto and reacted for one hour at 90° C. Aq. NaHCO₃ was added to the reaction product and then EA was added thereto for extraction. An EA layer was dried over MgSO₄, and filtration and vacuum distillation were performed. Subsequently, purification was performed using a column, thereby obtaining a target compound. 182 mg (53%)

Compound 5: 2-(1,1-difluoroethyl)-3H-naphtho[2,1-d]imidazol-5-ol

MeOH (2 ml) and MC (1 ml) were poured into 5-(benzyloxy)-2-(1,1-difluoroethyl)-3H-naphtho[2,1-d]imidazole (100 mg, 0.3 mmol) and Pd (OH)₂ was added thereto. After degassing, substitution was performed using H₂ and then stirred for 2.5 hours at room temperature. Filtration was performed through Celite and then recrystallization was performed using EA/Hex, thereby obtaining a target compound. 59 mg (80%)

Compound 82

DMF (1.2 ml, 0.1 M) was added to 2-(1,1-difluoroethyl)-3H-naphtho[2,1-d]imidazol-5-ol (30 mg, 0.12 mmol), and then IBX (78 mg, 0.132 mmol) was added thereto, followed by stirring for 24 hours at room temperature. 1 N HCl was added thereto and extraction was performed by adding EA thereto. An EA layer was dried over MgSO₄, filtered, vacuum distilled, and separated using prep TLC, thereby obtaining a target compound. 21 mg (67%)

Compound 82: ¹H NMR (300 MHz, CDCl₃) δ 8.07 (d, J=6.9 Hz, 1H), 7.98 (brs, 1H), 7.66 (t, J=7.2 Hz, 1H), 7.45 (t, J=7.2 Hz, 1H), 2.18 (t, J=18.9 Hz, 2H)

EXAMPLES 81, 83, 84, 85, 86 88, AND 89

Synthesis of Compounds 81, 83, 84, 85, 86 88, 89, and 90

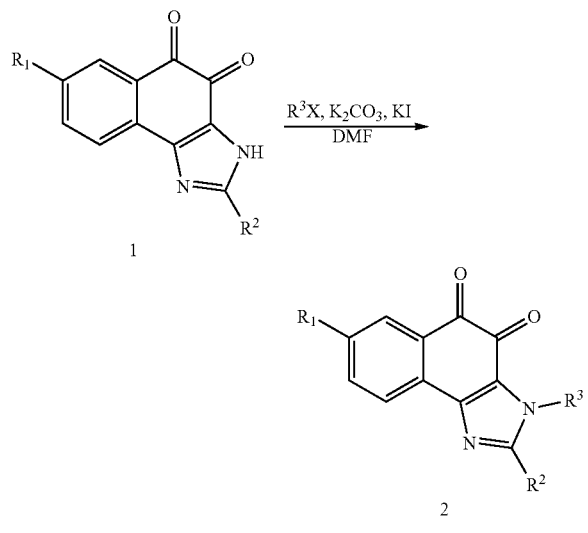

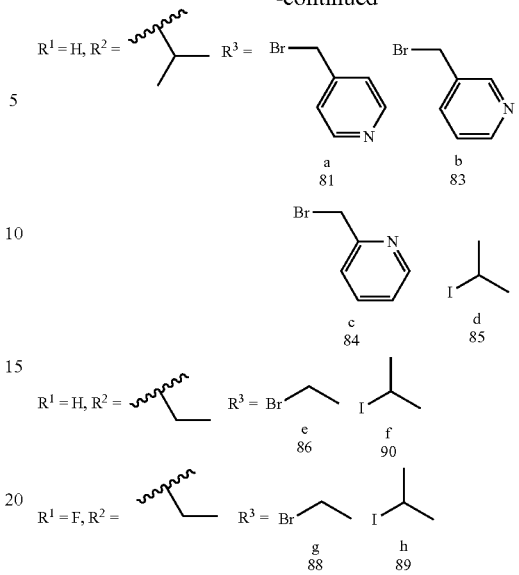

Experimental Method

Compound 1 (1.0 mmol) was dissolved in DMF (0.2M). K₂CO₃ (1.5 mmol) and KI (0.01 mmol) were added to the reaction product and then stirred for 20 minutes. R³X (1.2 mmol) was added to the reaction product and heated to 60° C. After confirming progression of reaction through TLC, the reaction product was quenched with water (20 mL). Extraction was performed using EA (20 mL) three times and then a separated EA layer was washed with water (20 mL) three times. A separated EA layer was treated with Na₂SO₄, filtered, and vacuum evaporated. Recrystallization was performed using EA/HX or purification was performed through silica column chromatography, thereby obtaining Compound 2.

[2a, Compound 81] yield: 10%, 1H NMR (300 MHz, DMSO) δ 8.53-8.50 (m, 2H), 7.92-7.87 (m, 2H), 7.72-7.67 (m, 1H), 7.49-7.43 (m, 1H), 7.19-7.18 (m, 2H), 5.64 (s, 2H), 3.12-3.08 (m, 1H), 1.18-1.16 (d, J=5.4 Hz, 6H)

[2b, Compound 83] yield: 29%, 1H NMR (300 MHz, CDCl₃) δ 8.57-8.55 (m, 1H), 8.52-8.51 (m, 1H), 8.04-8.02 (m, 2H), 7.65-7.60 (m, 1H), 7.56-7.53 (m, 1H), 7.43-7.37 (m, 1H), 7.29-7.25 (m, 1H), 5.60 (s, 2H), 3.10-3.05 (m, 1H), 1.34-1.36 (d, J=6.9 Hz, 6H)

[2c, Compound 84] yield: 10%, 1H NMR (300 MHz, CDCl₃) δ 8.53-8.52 (m, 1H), 7.67-7.57 (m, 2H), 7.39-7.27 (m, 2H), 7.24-7.19 (m, 1H), 5.71-5.54 (m, 2H), 3.36-3.32 (m, 1H), 1.37-1.35 (d, J=6.9 Hz, 6H)

[2d, Compound 85] yield: 49%, Compound 58: 1H NMR (300 MHz, DMSO-d6) δ 7.87 (d, J=8.1 Hz, 2H), 7.69 (t, J=7.8 Hz, 1H), 7.45 (t, J=7.8 Hz, 1H), 4.28 (t, J=6.6 Hz, 1H), 3.34-3.26 (m, 5H), 2.47-2.45 (m, 2H), 1.92-1.87 (m, 2H), 1.80-1.69 (m, 4H), 1.31 (d, J=6.9 Hz, 6H)

[2e, Compound 86] yield: 44%, 1H NMR (300 MHz, CDCl₃) δ 8.03-7.94 (m, 2H), 7.62-7.57 (m, 1H), 7.40-7.35 (m, 1H), 4.35-4.28 (q, J=6.9 Hz, 2H), 2.85-2.77 (q, J=6.9 Hz, 2H), 1.46-1.40 (m, 6H)

[2f, Compound 90] yield: 10%, 1H NMR (300 MHz, CDCl₃) δ 8.04-7.99 (m, 2H), 7.64-7.58 (m, 1H), 7.41-7.35 (m, 1H), 4.73 (m, 1H), 2.93-2.85 (q, J=7.5 Hz, 2H), 1.63-1.61 (d, J=6.9 Hz, 6H), 1.44-1.41 (t, J=7.5 Hz, 3H)

[2 g, Compound 88] yield: 10%, 1H NMR (300 MHz, CDCl₃) δ 7.98-7.94 (dd, J=8.4, 5.1 Hz, 1H), 7.71-7.68 (dd, J=8.4, 2.7 Hz, 1H), 7.33-7.27 (td, J=8.4, 2.7 Hz, 1H), 4.34-4.27 (q, J=7.2 Hz, 2H), 2.84-2.76 (q, J=7.5 Hz, 2H), 1.49-1.40 (m, 6H)

[2h, Compound 89] yield: 10%, 1H NMR (300 MHz, CDCl₃) δ 8.01-7.96 (m, 1H), 7.71-7.67 (m, 1H), 7.34-7.28 (m, 1H), 4.79 (m, 1H), 2.89-2.84 (q, J=7.5 Hz, 2H), 1.68-1.66 (d, J=6.6 Hz, 6H), 1.43-1.38 (t, J=7.5 Hz, 3H)

EXAMPLE 87

Synthesis of Compound 87

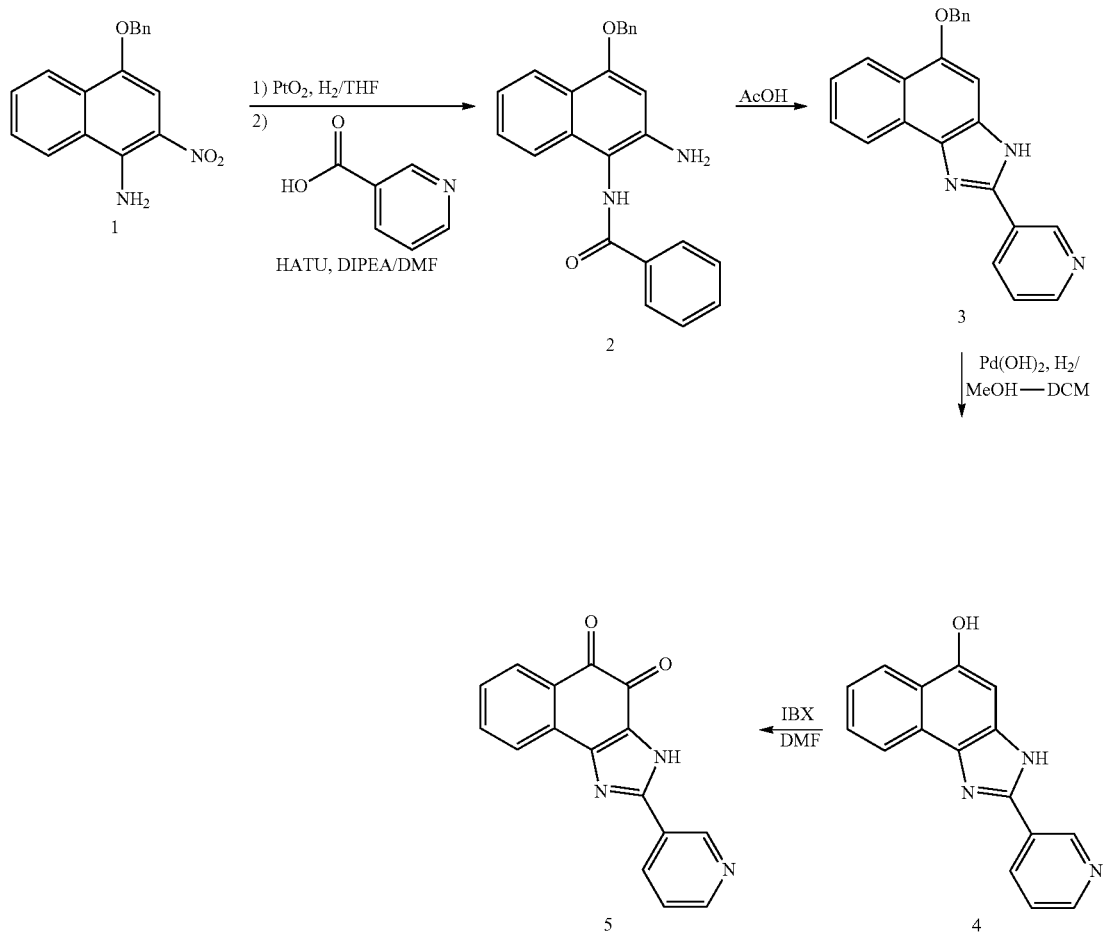

Compound 1 (300 mg, 6.8 mmol) and PtO₂ (20 mg, 10 mol %) were dissolved in THF (10 ml) and then stirred for 2 hours under a hydrogen atmosphere. Nicotinic acid (100 mg, 0.815 mmol) and HATU (310 mg, 0.815 mmol) were dissolved in DMF (34 ml) and stirred for 5 minutes, and then a solution of Compound 1 was filtered through Celite in the reaction solution (MC 10 ml). DIPEA (0.53 ml, 3.057 mmol) was added thereto, followed by stirring for 30 minutes under a nitrogen atmosphere. The reaction solution was poured onto ice and extraction was performed using a saturated aqueous NaCl solution and EA several times. The separated organic layer was dried over MgSO₄, and then filtered and vacuum evaporated. The reaction product was dissolved in AcOH (68 ml) again and then stirred for one hour at 70° C. The reaction solution was poured onto ice and neutralization was performed using saturated aqueous NaHCO₃. Next, extraction was performed using EA several times. The separated organic layer was dried over MgSO₄ and then filtered. The filtered solution was vacuum evaporated and then separation was performed through silica gel column chromatography. Subsequently, purification was performed through recrystallization.

Ivory solid 126 mg

Compound 6 (120 mg, 4.65 mmol) was dissolved in a mixture of MeOH (2 ml) and DCM (2 ml) and then 5% Pd/C (24 mg, 10 mol %) was added thereto. A reaction solution was stirred for 2 hours under a hydrogen atmosphere and then filtered through Celite. The filtered solution was vacuum evaporated and then purified through recrystallization.

Ivory solid 42 mg

In an ice bath, Compound 4 (40 mg, 0.153 mmol) was dissolved in DMF (1.5 ml) and then IBX (100 mg, 0.168 mmol) was added thereto. Reaction was performed for 24 hours at room temperature and then extraction was performed using saturated aqueous NaHCO₃ and EA several times. The separated organic layer was dried over MgSO₄ and then filtered. The filtered solution was vacuum evaporated and then purified through recrystallization.

Orange solid 20 mg

¹H NMR (300 MHz, small amount of CDCl₃+DMSO) δ 9.48 (s, 1H), 8.69 (d, J=5.1 Hz, 1H), 8.58 (d, J=8.1 Hz, 1H), 8.09 (d, J=7.5 Hz, 1H), 8.03 (d, J=6.9 hz, 1H), 7.71-7.67 (m, 1H), 7.50-7.43 (m, 2H)

145

EXAMPLE 91

Synthesis of Compound 91

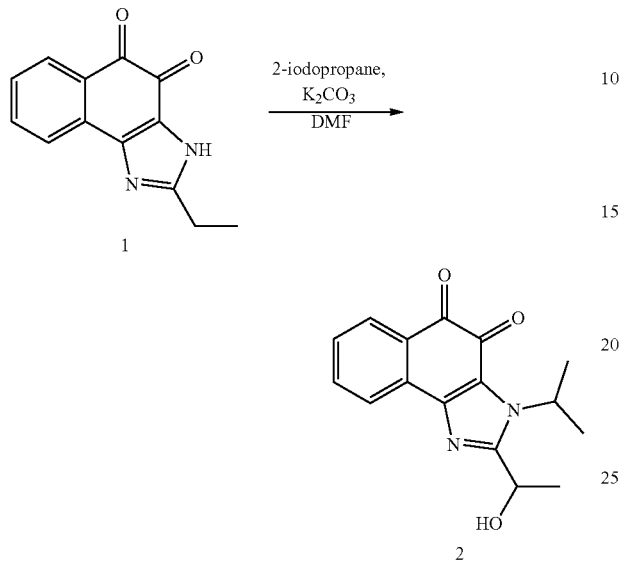

Experimental Method

Compound 1 (0.10 g, 0.442 mmol) was dissolved in DMF (2.2 mL). K$_2$CO$_3$ (0.09 g, 0.663 mmol) was added to the reaction product and then stirred for 20 minutes. 2-iodopropane (0.053 mL, 0.530 mmol) was added to the reaction product and heated to 60° C. Progression of reaction was confirmed through TLC and then the reaction product was quenched by adding water (20 mL). Extraction was performed using EA (20 mL) three times and then a separated EA layer was washed three times with 2N—NaOH (20 mL). A separated EA layer was treated with Na$_2$SO$_4$, filtered, and vacuum evaporated. A concentrated reaction product was purified through silica column chromatography, thereby obtaining Compound 2 (13.1 mg, 11%).

1H NMR (300 MHz, CDCl$_3$) δ 7.99-7.97 (m, 1H), 7.93-7.90 (m, 1H), 7.60-7.56 (m, 1H), 7.40-7.35 (m, 1H), 5.07 (m, 1H), 4.84 (m, 1H), 3.47 (br, 1H), 1.68-1.66 (d, J=6.6 Hz, 3H), 1.63-1.61 (d, J=6.9 Hz, 6H)

EXAMPLE 92

Synthesis of Compound 92

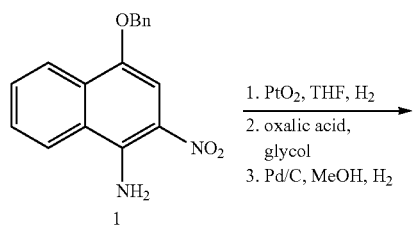

146

-continued

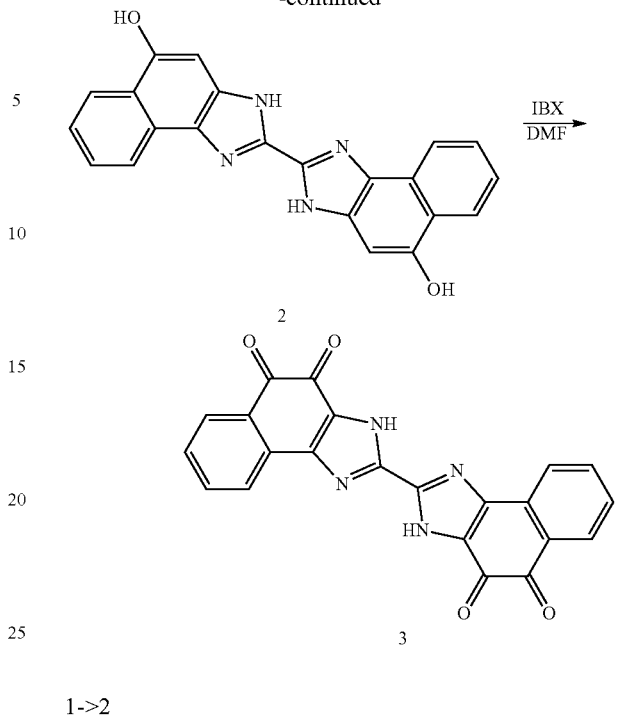

1->2

In a round bottom flask, Compound 1 (0.1 g, 0.34 mmol) was dissolved in THF (3.4 mL) and PtO$_2$ (0.007 g, 0.07 wt. %) was added thereto. An inner space of the flask was sufficiently filled using a H$_2$ balloon and then was vigorously stirred for 3 hours at room temperature. In another round bottom flask, oxalic acid dehydrate (0.017 g, 0.136 mmol) was dissolved in glycol (2.7 mL) and stirred for 10 minutes. A first reaction product was filtered using filter paper and washed with glycol (1 mL), and then a filtrate was directly added to a second reaction product. The reaction product reaction product was refluxed and stirred for 12 hours, and then was quench using an aqueous NaHCO$_3$ solution. The reaction product was extracted using EA. An EA layer was separated, treated with Na$_2$SO$_4$, filtered, and vacuum evaporated, and then AcOH (10 mL) was added thereto and refluxed for 2 hours. EA (20 mL) was added to the reaction product and washed with an aqueous NaHCO$_3$ solution three times. An EA layer was separated, treated with Na$_2$SO$_4$, filtered, and vacuum evaporated. A concentrated reaction product was dissolved in MeOH (0.2M) and then 5% Pd/C (0.05 mol %) was added thereto. An inner space of the flask was filled using a H$_2$ balloon and then reaction was performed for 2 hours at room temperature. After reaction, filtration was performed through Celite and then recrystallization was performed using EA/HX, thereby obtaining Compound 2.

2->3

Compound 2 was dissolved in DMF (0.1 M) and then temperature was lowered to 0° C. 47% IBX (1.2 eq) was added thereto, followed by stirring for 1 hour. The reaction product was quenched using an aqueous NaHCO$_3$ solution and then extracted using EA. An EA layer was washed with an aqueous NaHCO$_3$ solution several times. An EA layer was treated with Na$_2$SO$_4$, filtered, and vacuum evaporated, thereby obtaining Compound 3 (2.1 mg, Step 2 yield 2%).

1H NMR (300 MHz, DMSO) δ 8.92-8.90 (d, J=7.5 Hz, 2H), 8.20-8.17 (d, J=7.5 Hz, 2H), 7.99-7.94 (t, J=7.5 Hz, 2H), 7.83-7.78 (t, J=7.5 Hz, 2H)

EXAMPLE 93

Synthesis of Compound 93

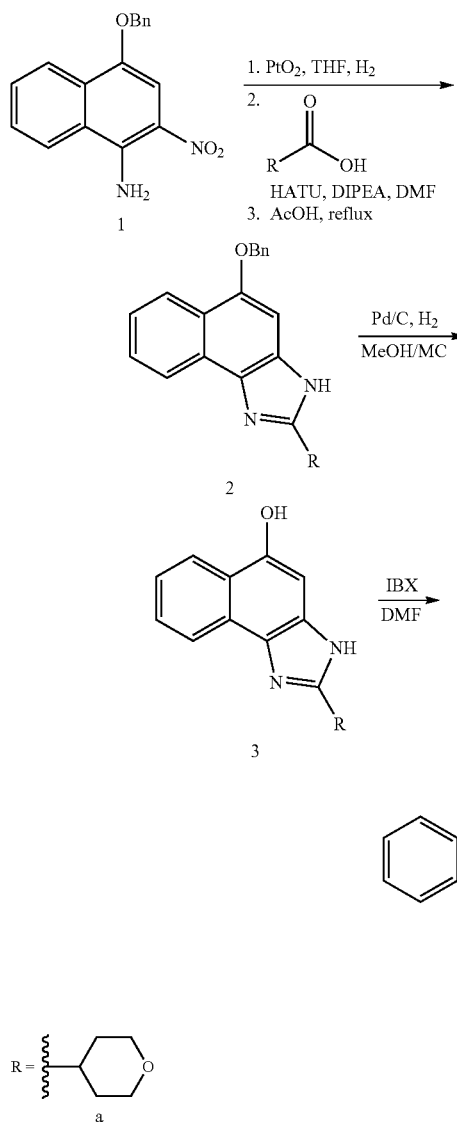

1->2

In a round bottom flask, Compound 1 (0.5 g, 1.7 mmol) was dissolved in THF (17 mL) and PtO₂ (0.04 g, 0.08 wt. %) was added thereto. An inner space of the flask was sufficiently filled using a H₂ balloon and then was vigorously stirred for 3 hours at room temperature. In another round bottom flask, acid (1.7 mmol) and HATU (1-[Bis (dimethylamino)methylene]-1H-1,2,3-triazolo[4,5-b]pyridinium 3-oxid hexafluorophosphate, 0.65 g, 1.7 mmol) were dissolved in DMF (3.5 mL) and stirred for 10 minutes. A first reaction product was filtered using filter paper and a reaction product filtrate was washed with DMF (5 mL). Subsequently, the filtrate was directly added to a second reaction product. Diisopropylethylamine (0.59 mL, 3.4 mmol) was slowly added to the reaction product. Stirring was performed for 2 hours at room temperature and then the reaction product was quenched using an aqueous NaHCO₃ solution. The reaction product reaction product was extracted using EA. An EA layer was separated, treated with Na₂SO₄, filtered, and vacuum evaporated, and then AcOH (10 mL) was added thereto and refluxed for 2 hours. The reaction product was vacuum evaporated, and then EA (20 mL) was added to an aqueous NaHCO₃ solution and washed three times. An EA layer was separated, treated with Na₂SO₄, filtered, and vacuum evaporated, and then purification was performed through silica column chromatography, thereby obtaining Compound 2.

2->3

In a round bottom flask, Compound 2 (1.00 mmol) was dissolved in MeOH/MC (each is 0.2 M) and then 5% Pd/C (0.05 mol %) was added thereto. An inner space of the flask was filled using a H₂ balloon and then reacted for 2 hours at room temperature. After reaction, filtration was performed through Celite. Subsequently, recrystallization was performed using EA/HX or purification was performed through silica gel column chromatography, thereby obtaining Compound 3.

3->4

Compound 3 (1.0 mmol) was dissolved in DMF (0.1 M) and then temperature was lowered to 0° C. 47% IBX (1.2 mmol) was added thereto, followed by stirring for 1 hour. The reaction product was quenched using an aqueous NaHCO₃ solution and then extracted using EA. An EA layer was washed with an aqueous NaHCO₃ solution several times. The EA layer was treated with Na₂SO₄, filtered, and vacuum evaporated. Recrystallization was performed using EA/HX or purification was performed through silica gel column chromatography, thereby obtaining Compound 4.

[4a, Compound 93] 1H NMR (300 MHz, DMSO) δ 13.37 (br, 1H), 7.87-7.81 (m, 2H), 7.69-7.64 (m, 1H), 7.45-7.40 (m, 1H), 3.94-3.91 (m, 2H), 3.47-3.39 (m, 2H), 3.08-3.01 (m, 1H), 1.90-1.78 (m, 4H)

EXAMPLES 94 AND 95

Synthesis of Compounds 94 and 95

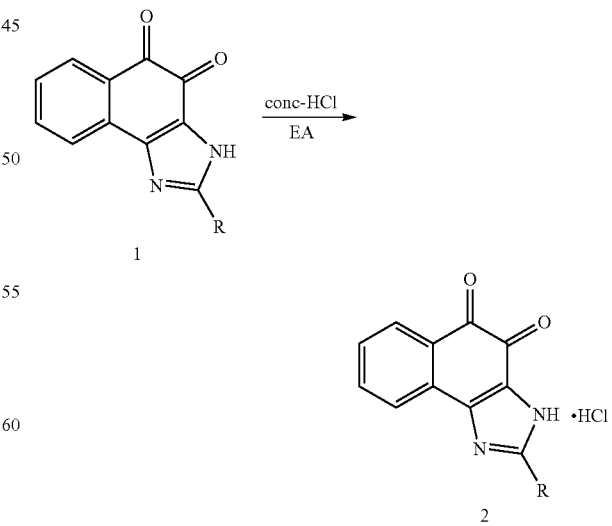

R = ethyl(a), isopropyl(b)

1->2

Compound 1 (2.0 mmol) was dissolved in EA (0.1 M) and then temperature was lowered to 0° C. 36% conc-HCl (4.0 mmol) was slowly added thereto, followed by stirring for 30 minutes. Extracted solids were filtered, washed with hexane (10 mL), and dried, thereby obtaining Compound 4.

[2a, Example 94] yield: 97%, 1H NMR (300 MHz, DMSO) δ 8.16-8.14 (m, 1H), 7.94-7.91 (m, 1H), 7.75-7.69 (m, 1H), 7.53-7.48 (m, 1H), 4.05-3.99 (m, 1H), 1.40-1.37 (d, J=6.9 Hz, 6H)

[2b, Example 95] yield: 95%, 1H NMR (300 MHz, DMSO) δ 8.06-8.04 (m, 1H), 7.94-7.91 (m, 1H), 7.75-7.69 (m, 1H), 7.53-7.47 (m, 1H), 2.92-2.84 (q, J=7.5 Hz, 2H), 1.36-1.31 (t, J=7.5 Hz, 3H)

EXAMPLE 96

Synthesis of Compound 96

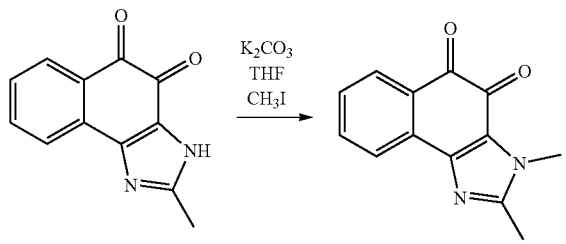 [SMILES: Cc1nc2c([nH]1)C(=O)C(=O)c1ccccc1-2 ; Cc1nc2c(n1C)C(=O)C(=O)c1ccccc1-2]

SM (90 mg, 0.42 mmol) was added to THF and then K$_2$CO$_3$ (112 mg, 0.84 mmol) and CH$_3$I (119 mg, 0.84 mmol) were added thereto. Subsequently, reaction was performed for 16 hours at 70° C. The reaction product was frozen, and then water was added thereto and extracted using EA. An organic layer was dried over Na$_2$SO$_4$, vacuum distilled, and subjected to column chromatography, thereby obtaining a target compound.

77 mg (82%)

1H NMR (300 MHz, CDCl$_3$) 8.04 (d, J=7.7 Hz, 1H), 7.93 (d, J=7.7 Hz, 1H), 7.60 (t, J=7.7 Hz, 1H), 7.40 (t, J=7.7 Hz, 1H), 3.90 (s, 3H), 2.49 (s, 3H);

EXAMPLE 97

Synthesis of Compound 97

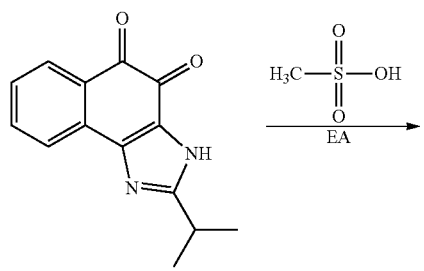

1->2

Compound 1 (1.0 g, 4.16 mmol) was dissolved in EA (0.1 M) and then temperature was lowered to 0° C. Methanesulfonic acid (0.54 mL, 8.32 mmol) was slowly added thereto, followed by stirring for 30 minutes. Extracted solids were filtered and washed with EA (10 mL), and then washed with hexane (10 mL) and dried, thereby obtaining Compound 2 (1.4 g, 99%).

1H NMR (300 MHz, DMSO) δ 8.16-8.14 (m, 1H), 7.94-7.91 (m, 1H), 7.75-7.69 (m, 1H), 7.53-7.48 (m, 1H), 4.05-3.99 (m, 1H), 1.40-1.37 (d, J=6.9 Hz, 6H)

EXPERIMENTAL EXAMPLE 1

NQO1 Activity Measurement

An enzyme reaction solution included 25 mM Tris/HCl (pH 7.4), 0.14% bovine serum albumin, 200 μM NADH, 77 μM cytochrome C, and 5 ng of NQO1 protein. Enzymatic reaction was initiated by adding NADH and performed at 37° C. In this regard, a reaction rate was measured by observing absorbance, which was increased due to reduction of cytochrome C, at 550 nm for 10 minutes and NQO1 activity was represented as an amount of reduced cytochrome C [nmol cytochrome C reduced/min/μg protein].

Extinction coefficient for cytochrome C:21.1 mmol/L/cm=21.1 μmol/ml/cm

Results are summarized in Table 1 below.

TABLE 1

| Compounds | NQO1 activity (5 μM, [nmol cytochrome C reduced/min/μg protein]) |
| --- | --- |
| Example 1 (Compound 1) | 177 |
| Example 2 (Compound 2) | 143 |
| Example 3 (Compound 3) | 139 |
| Example 4 (Compound 4) | 122 |
| Example 5 (Compound 5) | 153 |
| Example 6 (Compound 6) | 253 |
| Example 7 (Compound 7) | 55 |
| Example 8 (Compound 8) | 213 |
| Example 9 (Compound 9) | 172 |
| Example 10 (Compound 10) | 103 |
| Example 11 (Compound 11) | 178 |
| Example 12 (Compound 12) | 184 |
| Example 13 (Compound 13) | 291 |
| Example 14 (Compound 14) | 179 |
| Example 15 (Compound 15) | 183.3 |
| Example 16 (Compound 16) | 94.0 |
| Example 17 (Compound 17) | 206.9 |
| Example 18 (Compound 18) | 177.5 |
| Example 19 (Compound 19) | 24.6 |
| Example 20 (Compound 20) | 6.4 |
| Example 21 (Compound 21) | 9.1 |
| Example 22 (Compound 22) | 206.1 |

TABLE 1-continued

| Compounds | NQO1 activity (5 μM, [nmol cytochrome C reduced/min/μg protein]) |
|---|---|
| Example 23 (Compound 23) | 78.4 |
| Example 24 (Compound 24) | 208.2 |
| Example 25 (Compound 25) | 173.1 |
| Example 26 (Compound 26) | 223.5 |
| Example 27 (Compound 27) | 207.4 |
| Example 28 (Compound 28) | 177.2 |
| Example 29 (Compound 29) | 215.6 |
| Example 30 (Compound 30) | 165.1 |
| Example 31 (Compound 31) | 127.1 |
| Example 32 (Compound 32) | 124.2 |
| Example 33 (Compound 33) | 152.5 |
| Example 34 (Compound 34) | 153.5 |
| Example 35 (Compound 35) | 190.3 |
| Example 36 (Compound 36) | 164.6 |
| Example 37 (Compound 37) | 215.7 |
| Example 38 (Compound 38) | 142.1 |
| Example 39 (Compound 39) | 104.7 |
| Example 40 (Compound 40) | 192.9 |
| Example 41 (Compound 41) | 148.4 |
| Example 42 (Compound 42) | 57.0 |
| Example 43 (Compound 43) | 111.6 |
| Example 44 (Compound 44) | 43.4 |
| Example 45 (Compound 45) | 188.6 |
| Example 46 (Compound 46) | 160.1 |
| Example 47 (Compound 47) | 41.0 |
| Example 48 (Compound 48) | 59.8 |
| Example 49 (Compound 49) | 128.4 |
| Example 50 (Compound 50) | 100.6 |
| Example 51 (Compound 51) | 140.8 |
| Example 52 (Compound 52) | 60.3 |
| Example 53 (Compound 53) | 112.6 |
| Example 54 (Compound 54) | 126.9 |
| Example 55 (Compound 55) | 139.8 |
| Example 56 (Compound 56) | 24.6 |
| Example 57 (Compound 57) | 75.7 |
| Example 58 (Compound 58) | 53.4 |
| Example 59 (Compound 59) | 149.3 |
| Example 60 (Compound 60) | 140.1 |
| Example 61 (Compound 61) | 204.1 |
| Example 62 (Compound 62) | 113.3 |
| Example 63 (Compound 63) | 40.3 |
| Example 64 (Compound 64) | 189.5 |
| Example 65 (Compound 65) | 93.5 |
| Example 66 (Compound 66) | 56.0 |
| Example 67 (Compound 67) | 143.1 |
| Example 68 (Compound 68) | 143.0 |
| Example 69 (Compound 69) | 160.5 |
| Example 70 (Compound 70) | 83.9 |
| Example 71 (Compound 71) | 124.7 |
| Example 72 (Compound 72) | 51.0 |
| Example 73 (Compound 73) | 180.8 |
| Example 74 (Compound 74) | 193.5 |
| Example 75 (Compound 75) | 26.9 |
| Example 76 (Compound 76) | 183.5 |
| Example 77 (Compound 77) | 223.3 |
| Example 78 (Compound 78) | 81.7 |
| Example 79 (Compound 79) | 96.9 |
| Example 80 (Compound 80) | 162.6 |
| Example 81 (Compound 81) | 169.4 |
| Example 82 (Compound 82) | 70.2 |
| Example 83 (Compound 83) | 162.5 |
| Example 84 (Compound 84) | 172.0 |
| Example 85 (Compound 85) | 135.4 |
| Example 86 (Compound 86) | 220.0 |
| Example 87 (Compound 87) | 94.7 |
| Example 88 (Compound 88) | 187.4 |
| Example 89 (Compound 89) | 145.0 |
| Example 90 (Compound 90) | 241.3 |
| Example 91 (Compound 91) | 206.9 |
| Example 92 (Compound 92) | 186.8 |
| Example 93 (Compound 93) | 207.3 |
| Example 94 (Compound 94) | 135.6 |
| Example 95 (Compound 95) | 228.1 |
| Example 96 (Compound 96) | 21.4 |
| Example 97 (Compound 97) | — |

As shown in Table 1, it can be confirmed that the compounds according to the present invention exhibit NQO1 activity.

EXPERIMENTAL EXAMPLE 2

Measurement of Lactate Change Amount within Cells

Cells were treated with 400 μl of 6% PCA, and then collected and extracted. Centrifugation (13,000 rpm, 10 min) was performed. A precipitate was dried using a Speed-Vac and then a weight of dried precipitate was measured. A supernatant was neutralized using 400 μl of 1 M KOH and a final volume thereof was adjusted to 1 ml using 0.33 M $KH_2PO_4/K_2HPO_4$, pH 7.5. Centrifugation (13,000 rpm, 10 min) was performed and the amount of lactate was measured from a supernatant (Megazyme, K-LATE).

Results are summarized in Table 2 below.

TABLE 2

| Compounds | Lactate change amount within cells (nmol/mg cell) |
|---|---|
| Example 1 (Compound 1) | 6.1 |
| Example 2 (Compound 2) | 7.3 |
| Example 3 (Compound 3) | 11.3 |
| Example 4 (Compound 4) | 9.1 |
| Example 5 (Compound 5) | 8.5 |
| Example 6 (Compound 6) | 4.6 |
| Example 7 (Compound 7) | 11.4 |
| Example 8 (Compound 8) | 10.0 |
| Example 9 (Compound 9) | 8.0 |
| Example 10 (Compound 10) | 9.9 |
| Example 11 (Compound 11) | 7.2 |
| Example 12 (Compound 12) | 7.0 |
| Example 14 (Compound 14) | 12.4 |
| Example 15 (Compound 15) | 7.2 |
| Example 16 (Compound 16) | 5.8 |
| Example 17 (Compound 17) | 6.0 |
| Example 18 (Compound 18) | 6.6 |
| Example 19 (Compound 19) | 6.5 |
| Example 21 (Compound 21) | — |
| Example 22 (Compound 22) | — |
| Example 22 (Compound 22) | 7.3 |
| Example 23 (Compound 23) | 5.6 |
| Example 24 (Compound 24) | 4.3 |
| Example 25 (Compound 25) | 6.1 |
| Example 26 (Compound 26) | 5.7 |
| Example 27 (Compound 27) | 9.6 |
| Example 28 (Compound 28) | 6.8 |
| Example 29 (Compound 29) | 8.1 |
| Example 30 (Compound 30) | 6.3 |
| Example 31 (Compound 31) | 5.1 |
| Example 32 (Compound 32) | 5.8 |
| Example 33 (Compound 33) | 4.7 |
| Example 34 (Compound 34) | 4.9 |
| Example 35 (Compound 35) | 8.1 |
| Example 36 (Compound 36) | 7.8 |
| Example 37 (Compound 37) | 10.3 |
| Example 38 (Compound 38) | 5.2 |
| Example 39 (Compound 39) | 8.4 |
| Example 40 (Compound 40) | 9.7 |
| Example 41 (Compound 41) | 7.2 |
| Example 42 (Compound 42) | 8.9 |
| Example 43 (Compound 43) | 6.0 |
| Example 44 (Compound 44) | 9.5 |
| Example 45 (Compound 45) | 5.7 |
| Example 46 (Compound 46) | 8.9 |
| Example 47 (Compound 47) | 5.9 |
| Example 48 (Compound 48) | 5.1 |
| Example 49 (Compound 49) | 5.2 |
| Example 50 (Compound 50) | — |
| Example 51 (Compound 51) | — |
| Example 52 (Compound 52) | — |

TABLE 2-continued

| Compounds | Lactate change amount within cells (nmol/mg cell) |
|---|---|
| Example 53 (Compound 53) | — |
| Example 54 (Compound 54) | — |
| Example 55 (Compound 55) | — |
| Example 56 (Compound 56) | — |
| Example 57 (Compound 57) | — |
| Example 58 (Compound 58) | — |
| Example 59 (Compound 59) | — |
| Example 60 (Compound 60) | — |
| Example 61 (Compound 61) | — |
| Example 62 (Compound 62) | — |
| Example 63 (Compound 63) | — |
| Example 64 (Compound 64) | — |
| Example 65 (Compound 65) | — |
| Example 66 (Compound 66) | — |
| Example 67 (Compound 67) | — |
| Example 68 (Compound 68) | — |
| Example 69 (Compound 69) | — |
| Example 70 (Compound 70) | — |
| Example 71 (Compound 71) | — |
| Example 72 (Compound 72) | — |
| Example 73 (Compound 73) | — |
| Example 74 (Compound 74) | — |
| Example 75 (Compound 75) | — |
| Example 76 (Compound 76) | — |
| Example 77 (Compound 77) | — |
| Example 78 (Compound 78) | 8.0 |
| Example 79 (Compound 79) | — |
| Example 80 (Compound 80) | — |
| Example 81 (Compound 81) | — |
| Example 82 (Compound 82) | — |
| Example 83 (Compound 83) | — |
| Example 84 (Compound 84) | — |
| Example 85 (Compound 85) | — |
| Example 86 (Compound 86) | — |
| Example 87 (Compound 87) | — |
| Example 88 (Compound 88) | — |
| Example 89 (Compound 89) | — |
| Example 90 (Compound 90) | — |
| Example 91 (Compound 91) | — |
| Example 92 (Compound 92) | — |
| Example 93 (Compound 93) | — |
| Example 94 (Compound 94) | — |
| Example 95 (Compound 95) | — |
| Example 96 (Compound 96) | 5.7 |
| Example 97 (Compound 97) | — |

From Table 2, lactate activity within cells according to examples of the present invention can be confirmed. Since a ratio of NAD/NADH corresponds to a ratio of pyruvate/lactate, ratios of NAD/NADH within cytosols may be measured from the pyruvate/lactate ratio. Therefore, when the amount of lactate decreases, a ratio of NAD/NADH within a cell increases.

EXPERIMENTAL EXAMPLE 3-1

Weight Loss Effects in Obese Mice (ob/ob) Administered Compound According to Example 1

10 week-old C57BL/6J Lep ob/ob mice having genetic obesity characteristics available from ORIENTBIO were prepared. Two mice were raised in each polycarbonate breeding cage (200 W×260 L×130H (mm), Three-shine) in which temperature was 20 to 24° C., relative humidity was 35 to 65%, illuminance was 150 to 300 lux, night and day were 12 hours, and exhaust was performed at 10 to 15 air changes per hour. As a feed, low fat diet (11.9 kcal % fat, 5053, Labdiet) manufactured by ORIENTBIO was used. The feed was contained in a feeder and free intake was allowed. As drinking water, water, which was contained in a 250 mL polycarbonate based bottle, purified through a filter and a sterilizer was used and free intake was allowed.

The compound according to Example 1 synthesized in the present invention was orally administered to three C57BL/6J Lep ob/ob mice in amounts of 40 mg/kg, 80 mg/kg, and 120 mg/kg, respectively, once every day for two weeks. For administration, a disposable syringe fitted with a sonde for oral administration was used and 10 ml/kg of the compound was orally administered into the stomach. As controls, three C57BL/6J Lep ob/ob mice were administered 0.1% sodium lauryl sulfate (SLS) in an amount of 120 mg/kg in the same manner as described above. After administration, a time-dependent weight increase ratio, weight change, and intake amount were measured and results are illustrated in FIG. 1 below.

Weights of the experimental animals were measured immediately before administration of a test material and seven times a week from an administration initiation day to a test termination day. Increased total weights were calculated by subtracting weights measured on an experiment initiation day from weights measured one day before an experiment termination day. Food intake amounts were calculated by measuring feed supply amounts and remaining amounts twice a week from an initiation day of test material administration to a test termination day for each individual.

As shown in graphs of FIG. 1 below, it can be confirmed that weight increase ratios, weight change, and intake amounts of C57BL/6J Lep ob/ob mice administered the compound according to Example 1 are significantly decreased, when compared with controls.

EXPERIMENTAL EXAMPLE 3-2

Weight Loss Effects in Obese Mice (ob/ob) Administered Compound According to Example 1

Figure 2:
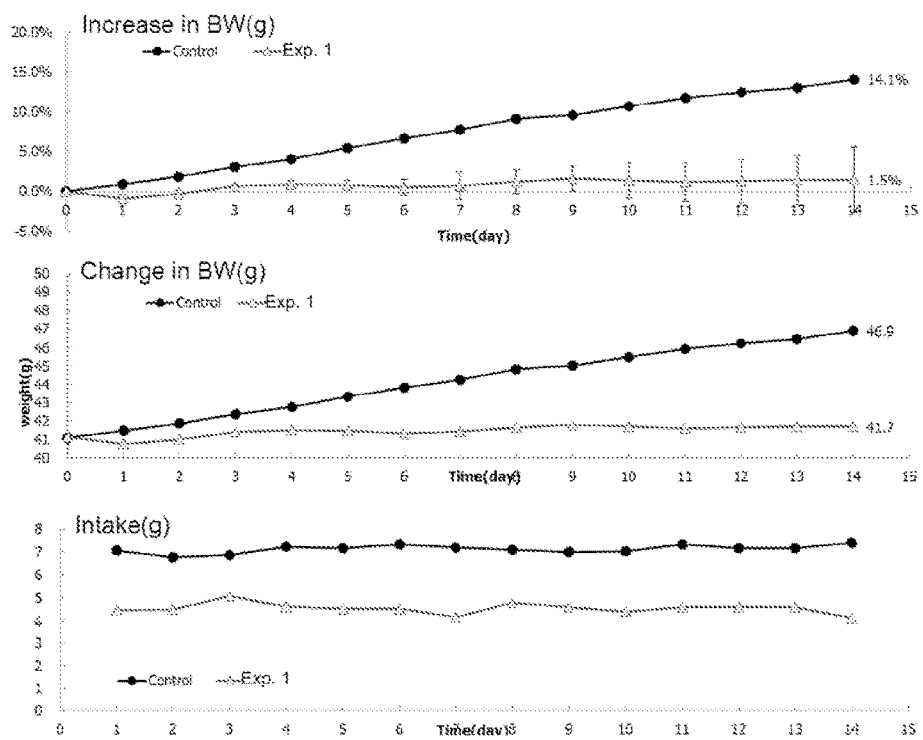
FIG. 2 illustrates graphs representing weight increase ratios, weight changes, and intake amounts in obese mice (ob/ob) administered a compound according to Example 1 and a control in Experimental Example 3-2.

Experiments were performed under the same conditions as in Experimental Example 3-1 except that 6 week-old C57BL/6J Lep ob/ob mice having genetic obesity characteristics available from ORIENTBIO were prepared, the compound according to Example 1 was administered to three C57BL/6J Lep ob/ob mice in an amount of 100 mg/kg, and 100 mg/kg of 0.1% SLS was administered to each of three C57BL/6J Lep ob/ob mice as controls. Weight increase ratios, weight change, and intake amounts depending on administration time were measured and results are illustrated in FIG. 2 below.

As illustrated in graphs of FIG. 2 below, it can be confirmed that weight increase ratios, weight change, and intake amounts of C57BL/6J Lep ob/ob mice administered the compound of Example 1 according to the method above are significantly decreased, when compared with controls.

EXPERIMENTAL EXAMPLE 3-3

Weight Loss Effects in Obese Mice (ob/ob) Administered Compounds According to Examples 3 and 13

Figure 3:
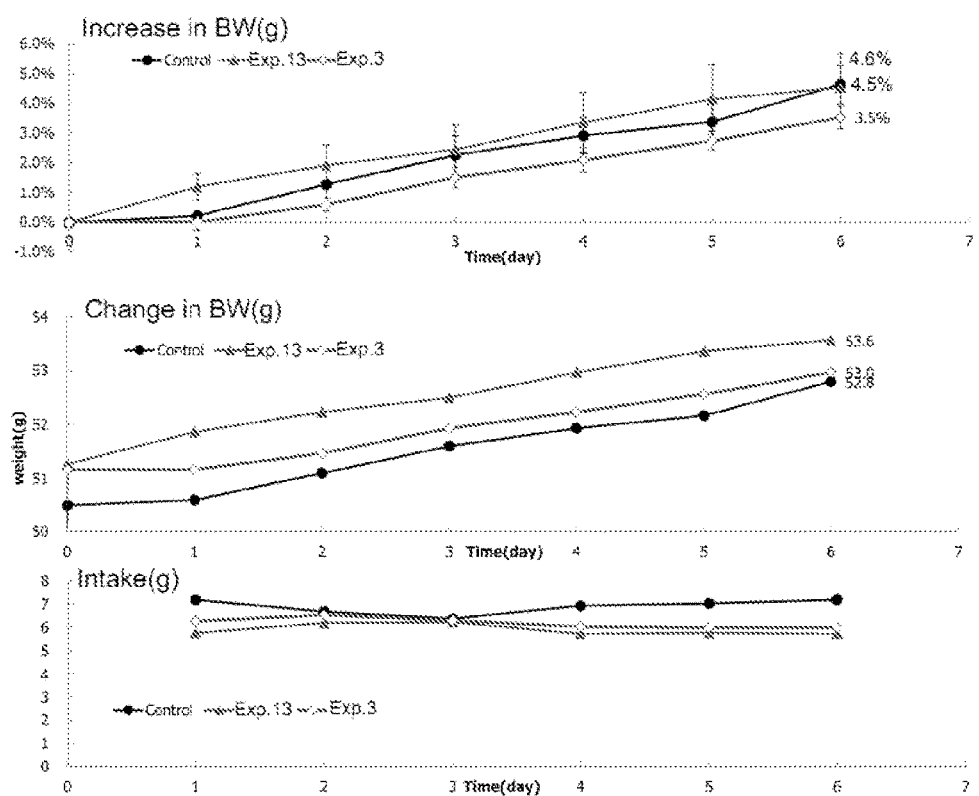
FIG. 3 illustrates graphs representing weight increase ratios, weight changes, and intake amounts in obese mice (ob/ob) administered a compound according to Example 3, a compound according to Example 13, and a control in Experimental Example 3-3.

Experiments were performed under the same conditions as in Experimental Example 3-1 except that 11 week-old C57BL/6J Lep ob/ob mice having genetic obesity characteristics available from ORIENTBIO were prepared, each of the compounds according to Examples 3 and 13 was administered to three C57BL/6J Lep ob/ob mice in an amount of 100 mg/kg, 100 mg/kg of 0.1% SLS was administered to each of three C57BL/6J Lep ob/ob mice as controls, and experiments were performed for a total of 6 days. Weight increase ratios, weight change, and intake amounts depending on administration time were measured and results are illustrated in FIG. 3 below.

As illustrated in graphs of FIG. 3 below, it can be confirmed that weight increase ratios and intake amounts of C57BL/6J Lep ob/ob mice 6 weeks after administration of the compounds of Examples 3 and 13 according to the method above are significantly decreased, when compared with controls.

EXPERIMENTAL EXAMPLE 3-4

Weight Loss Effects in Obese Mice (ob/ob) Administered Compound According to Examples 4 and 5

Figure 4:
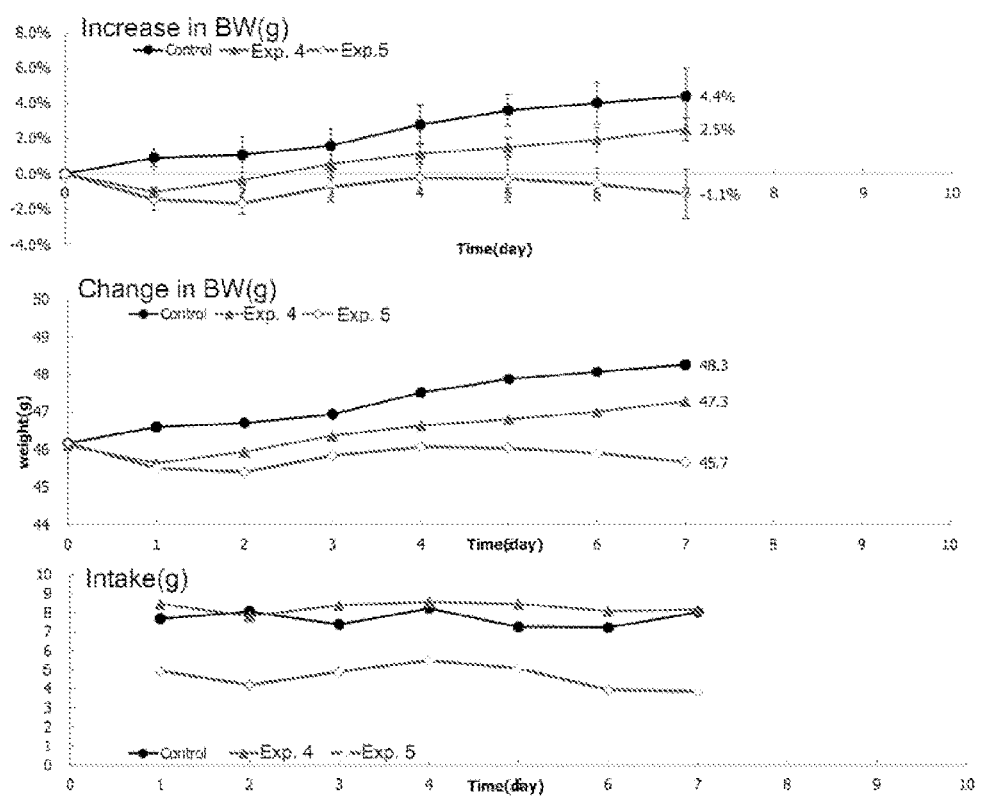
FIG. 4 illustrates graphs representing weight increase ratios, weight changes, and intake amounts in obese mice (ob/ob) administered a compound according to Example 4, a compound according to Example 5, and a control in Experimental Example 3-4.

Experiments were performed under the same conditions as in Experimental Example 3-1 except that 12 week-old C57BL/6J Lep ob/ob mice having genetic obesity characteristics available from ORIENTBIO were prepared, each of the compounds according to Examples 4 and 5 was administered to three C57BL/6J Lep ob/ob mice in an amount of 150 mg/kg, 150 mg/kg of 0.1% SLS was administered to each of three C57BL/6J Lep ob/ob mice as controls, and experiments were performed for a total of one week. Weight increase ratios, weight change, and intake amounts depending on administration time were measured and results are illustrated in FIG. 4 below.

As illustrated in graphs of FIG. 4 below, it can be confirmed that weight increase ratios and weight change of C57BL/6J Lep ob/ob mice administered the compounds of Examples 4 and 5 according to the method above are significantly decreased and intake amounts of C57BL/6J Lep ob/ob mice administered the compound according to Example 5 are significantly decreased, when compared with controls.

EXPERIMENTAL EXAMPLE 3-5

Weight Loss Effects in Obese Mice (ob/ob) Administered Compounds According to Examples 5 and 6

Figure 5:
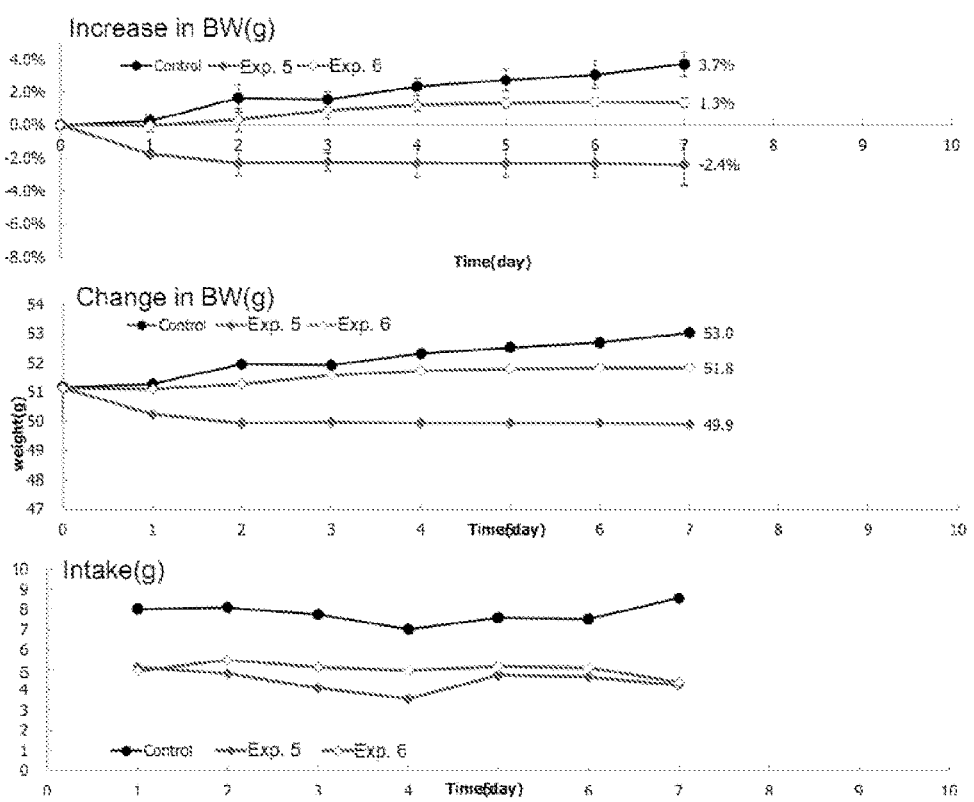
FIG. 5 illustrates graphs representing weight increase ratios, weight changes, and intake amounts in obese mice (ob/ob) administered a compound according to Example 5, a compound according to Example 6, and a control in Experimental Example 3-5.

Experiments were performed under the same conditions as in Experimental Example 3-1 except that 15 week-old C57BL/6J Lep ob/ob mice having genetic obesity characteristics available from ORIENTBIO were prepared, the compounds according to Examples 5 and 6 were administered to three C57BL/6J Lep ob/ob mice in an amount of 150 mg/kg, 150 mg/kg of 0.1% SLS was administered to each of three C57BL/6J Lep ob/ob mice as controls, and experiments were performed for a total of one week. Weight increase ratios, weight change, and intake amounts depending on administration time were measured and results are illustrated in FIG. 5 below.

As illustrated in graphs of FIG. 5 below, it can be confirmed that weight increase ratios, weight change, and intake amounts of C57BL/6J Lep ob/ob mice administered the compounds of Examples 5 and 6 according to the method above are significantly decreased, when compared with controls.

EXPERIMENTAL EXAMPLE 3-6

Weight Loss Effects in Obese Mice (ob/ob) Administered Compounds According to Examples 8, 9, And 12

Figure 6:
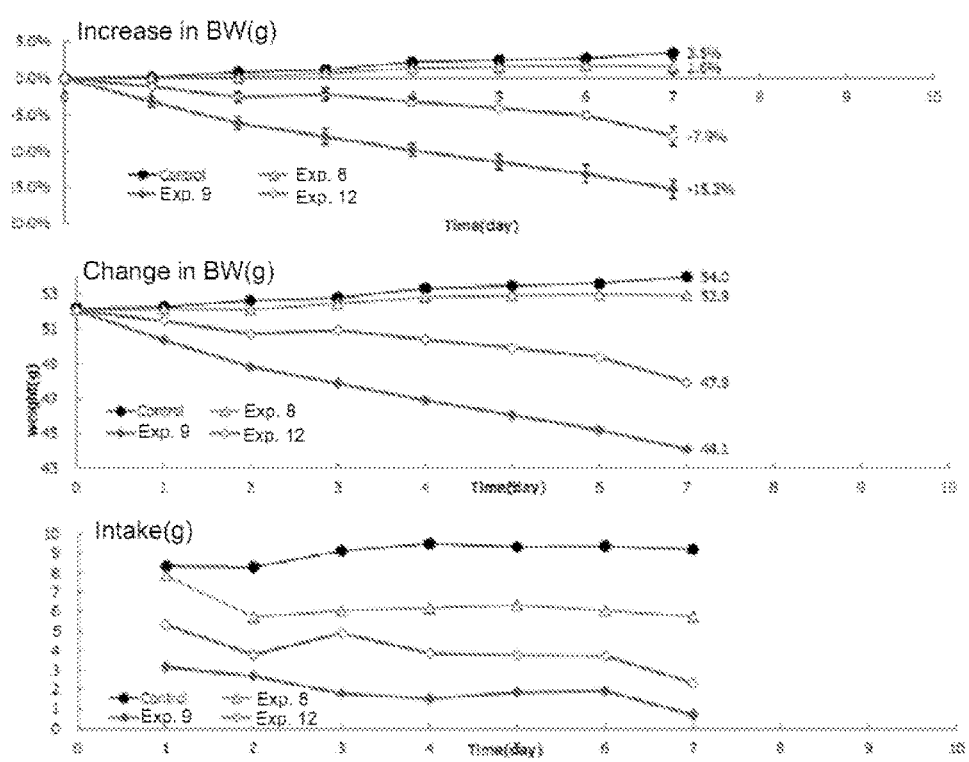
FIG. 6 illustrates graphs representing weight increase ratios, weight changes, and intake amounts in obese mice (ob/ob) administered a compound according to Example 8, a compound according to Example 9, a compound according to Example 12, and a control in Experimental Example 3-6.

Experiments were performed under the same conditions as in Experimental Example 3-1 except that 10 week-old C57BL/6J Lep ob/ob mice having genetic obesity characteristics available from ORIENTBIO were prepared, the compounds according to Examples 8, 9, and 12 were administered to three C57BL/6J Lep ob/ob mice in an amount of 150 mg/kg, 150 mg/kg of 0.1% SLS was administered to each of three C57BL/6J Lep ob/ob mice as controls, and experiments were performed for a total of one week. Weight increase ratios, weight change, and intake amounts depending on administration time were measured and results are illustrated in FIG. 6 below.

As illustrated in graphs of FIG. 6 below, it can be confirmed that weight increase ratios, weight change, and intake amounts of C57BL/6J Lep ob/ob mice administered the compounds of Examples 8, 9, and 12 according to the method above are significantly decreased, when compared with controls.

EXPERIMENTAL EXAMPLE 3-7

Weight Loss Effects in Obese Mice (ob/ob) Administered Compounds According to Examples 17, 18, 22, and 23

Figure 10:
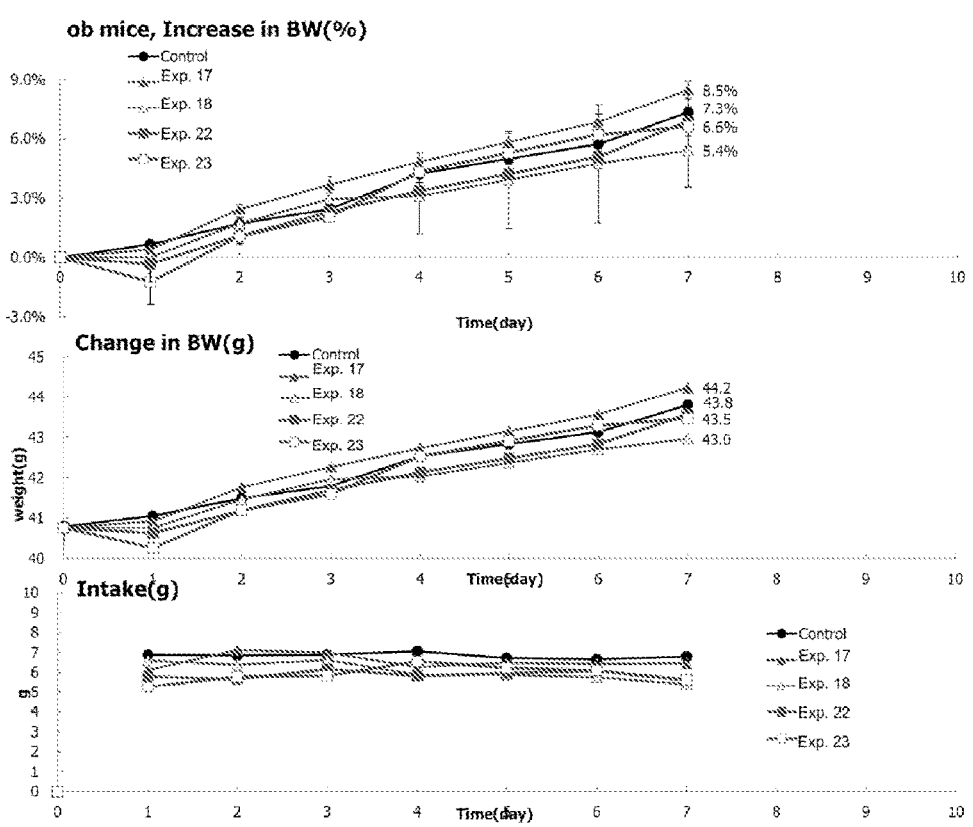
FIG. 10 illustrates graphs representing weight increase ratios (%), weight changes (g), and intake amounts (g) in obese mice (ob/ob) administered compounds according to Examples 17, 18, 22 and 23 and a control in Experimental Example 3-7.

Experiments were performed under the same conditions as in Experimental Example 3-1 except that 6 week-old C57BL/6J Lep ob/ob mice having genetic obesity characteristics available from ORIENTBIO were prepared, the compounds according to Examples 17, 18, 22, and 23 were administered to three C57BL/6J Lep ob/ob mice in an amount of 100 mg/kg, 100 mg/kg of 0.1% SLS was administered to each of three C57BL/6J Lep ob/ob mice as controls, and experiments were performed for a total of one week. Weight increase ratios, weight change, and intake amounts depending on administration time were measured and results are illustrated in FIG. 10 below.

As illustrated in graphs of FIG. 10 below, it can be confirmed that weight increase ratios, weight change, and intake amounts of C57BL/6J Lep ob/ob mice administered the compounds of Examples 17, 18, 22, and 23 according to the method above are significantly decreased in some sections, when compared with controls.

EXPERIMENTAL EXAMPLE 3-8

Weight Loss Effects in Obese Mice (ob/ob) Administered Compound According to Example 26

Figure 11:
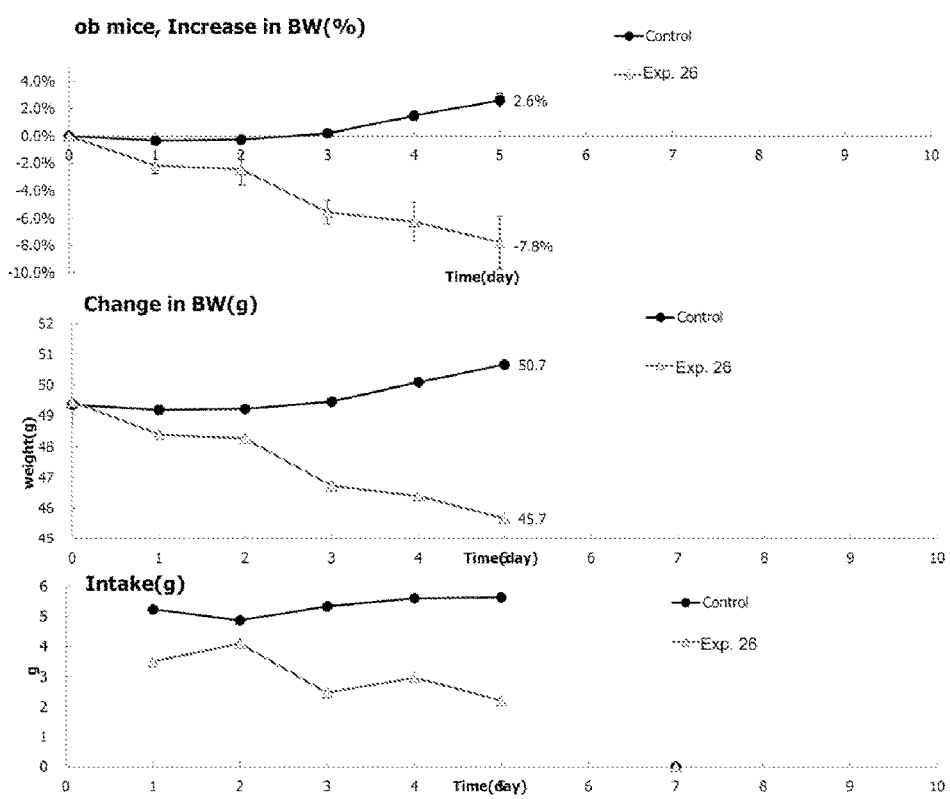
FIG. 11 illustrates graphs representing weight increase ratios (%), weight changes (g), and intake amounts (g) in obese mice (ob/ob) administered a compound according to Example 26, a compound according to Example 5, and a control in Experimental Example 3-8.

Experiments were performed under the same conditions as in Experimental Example 3-1 except that 10 week-old C57BL/6J Lep ob/ob mice having genetic obesity characteristics available from ORIENTBIO were prepared, the compound according to Example 26 was administered to three C57BL/6J Lep ob/ob mice in an amount of 150 mg/kg, 150 mg/kg of 0.1% SLS was administered to each of three C57BL/6J Lep ob/ob mice as controls, and experiments were performed for a total of five days. Weight increase ratios, weight change, and intake amounts depending on administration time were measured and results are illustrated in FIG. 11 below.

As illustrated in graphs of FIG. 11 below, it can be confirmed that weight increase ratios, weight change, and intake amounts of C57BL/6J Lep ob/ob mice administered the compound of Example 26 according to the method above are significantly decreased in some sections, when compared with controls.

EXPERIMENTAL EXAMPLE 3-9

Weight Loss Effects in Obese Mice (ob/ob) Administered Compound According to Example 30

Figure 12:
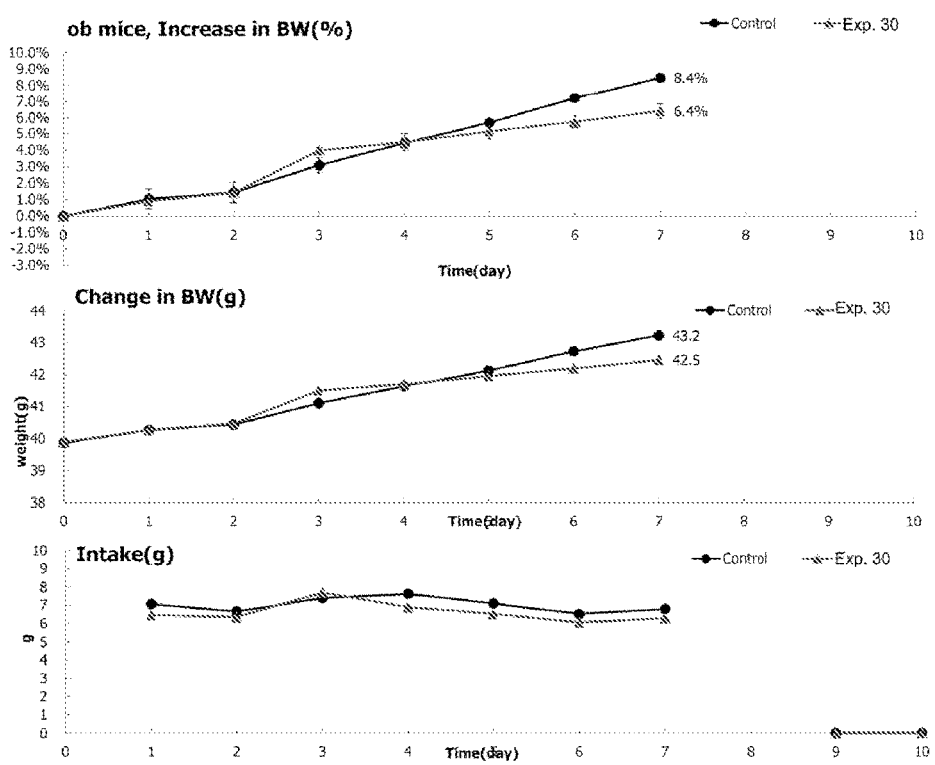
FIG. 12 illustrates graphs representing weight increase ratios (%), weight changes (g), and intake amounts (g) in obese mice (ob/ob) administered a compound according to Example 30 and a control in Experimental Example 3-9.

Experiments were performed under the same conditions as in Experimental Example 3-1 except that 6.5 week-old C57BL/6J Lep ob/ob mice having genetic obesity characteristics available from ORIENTBIO were prepared, the compound according to Example 30 was administered to three C57BL/6J Lep ob/ob mice in an amount of 100 mg/kg, 100 mg/kg of 0.1% SLS was administered to each of three C57BL/6J Lep ob/ob mice as controls, and experiments performed for a total of one week. Weight increase ratios, weight change, and intake amounts depending on administration time were measured and results are illustrated in FIG. 12 below.

As illustrated in graphs of FIG. 12 below, it can be confirmed that weight increase ratios, weight change, and intake amounts of C57BL/6J Lep ob/ob mice administered the compound of Example 30 according to the method above are significantly decreased in some sections, when compared with controls.

EXPERIMENTAL EXAMPLE 3-10

Weight Loss Effects in Obese Mice (ob/ob) Administered Administered Compounds According to Examples 1 and 35

Figure 13:
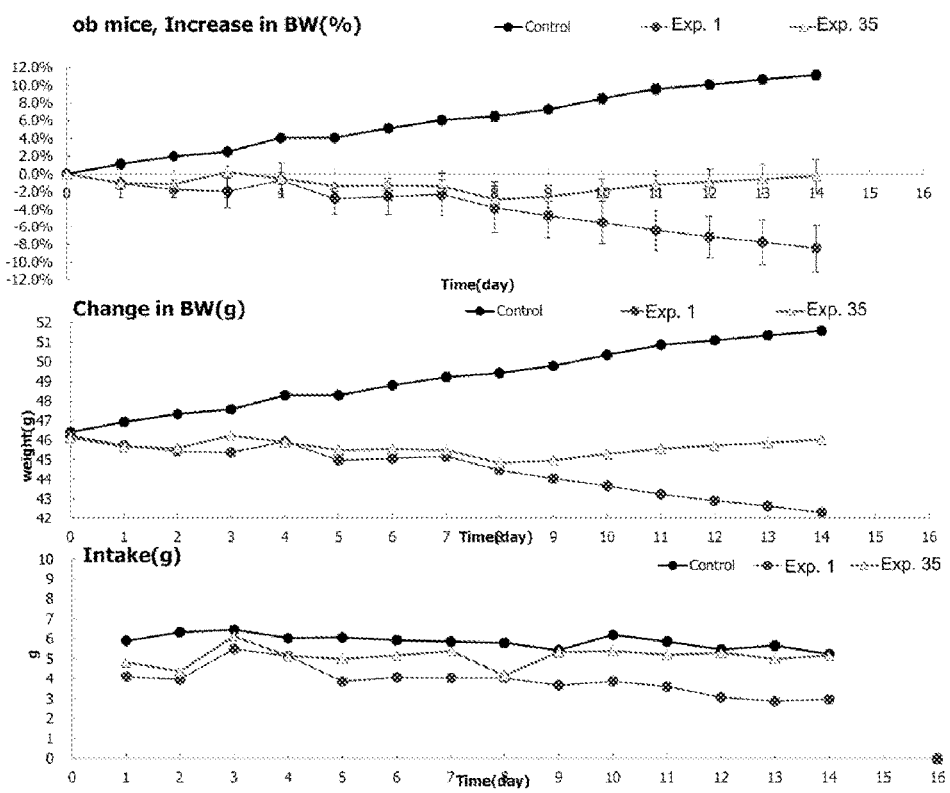
FIG. 13 illustrates graphs representing weight increase ratios (%), weight changes (g), and intake amounts (g) in obese mice (ob/ob) administered compounds according to Examples 1 and 35 and a control in Experimental Example 3-10.

Experiments were performed under the same conditions as in Experimental Example 3-1 except that 6 week-old C57BL/6J Lep ob/ob mice having genetic obesity characteristics available from ORIENTBIO were prepared, the compounds according to Examples 1 and 35 were administered to three C57BL/6J Lep ob/ob mice in an amount of 100 mg/kg, 100 mg/kg of 0.1% SLS was administered to each of three C57BL/6J Lep ob/ob mice as controls, and experiments were performed for a total of two weeks. Weight increase ratios, weight change, and intake amounts depending on administration time were measured and results are illustrated in FIG. 13 below.

As illustrated in graphs of FIG. 13 below, it can be confirmed that weight increase ratios, weight change, and intake amounts of C57BL/6J Lep ob/ob mice administered the compounds according to Examples 1 and 35 according to the method above are significantly decreased in some sections, when compared with controls.

EXPERIMENTAL EXAMPLE 3-11

Weight Loss Effects in Obese Mice (ob/ob) Administered Compounds According to Examples 1, 38, and 96

Figure 14:
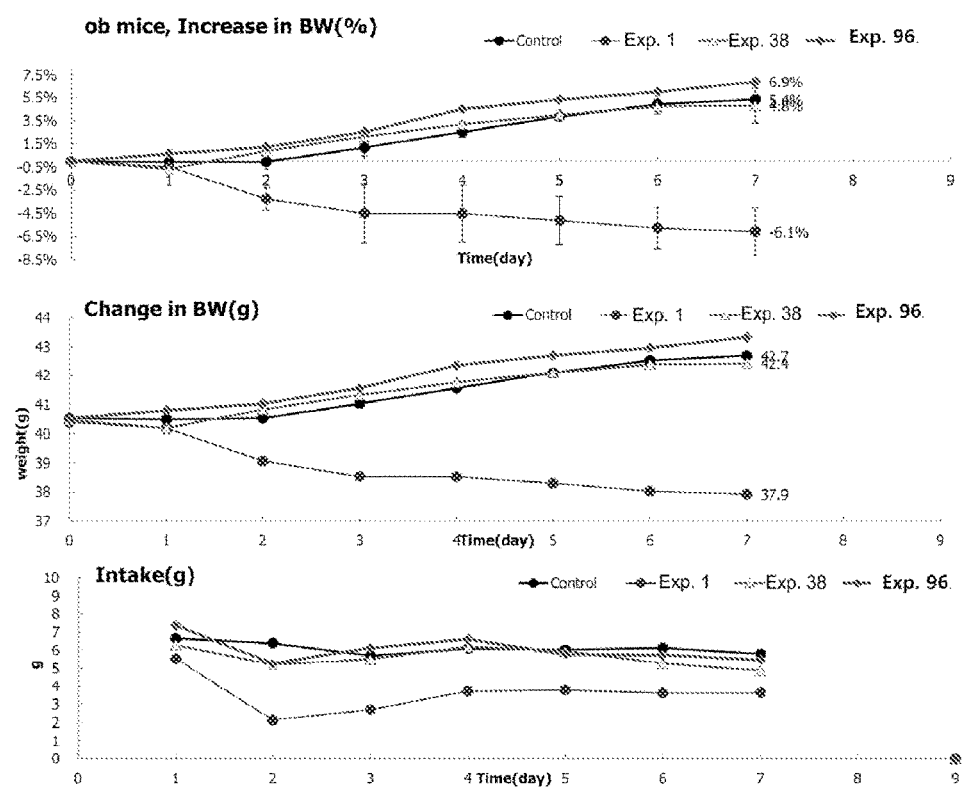
FIG. 14 illustrates graphs representing weight increase ratios (%), weight changes (g), and intake amounts (g) in obese mice (ob/ob) administered compounds according to Examples 1, 38, and 96 and a control in Experimental Example 3-11.

Experiments were performed under the same conditions as in Experimental Example 3-1 except that 6.5 week-old C57BL/6J Lep ob/ob mice having genetic obesity characteristics available from ORIENTBIO were prepared, the compounds according to Examples 1, 38, and 96 were administered to three C57BL/6J Lep ob/ob mice in an amount of 100 mg/kg, 100 mg/kg of 0.1% SLS was administered to each of three C57BL/6J Lep ob/ob mice as controls, and experiments were performed for a total of one week. Weight increase ratios, weight change, and intake amounts depending on administration time were measured and results are illustrated in FIG. 14 below.

As illustrated in graphs of FIG. 14 below, it can be confirmed that weight increase ratios, weight change, and intake amounts of C57BL/6J Lep ob/ob mice administered the compounds of Examples 1, 38, and 96 according to the method above are significantly decreased in some sections, when compared with controls.

EXPERIMENTAL EXAMPLE 3-12

Weight Loss Effects in Obese Mice (ob/ob) Administered Compounds According to Examples 1, 33, and 35

Figure 15:
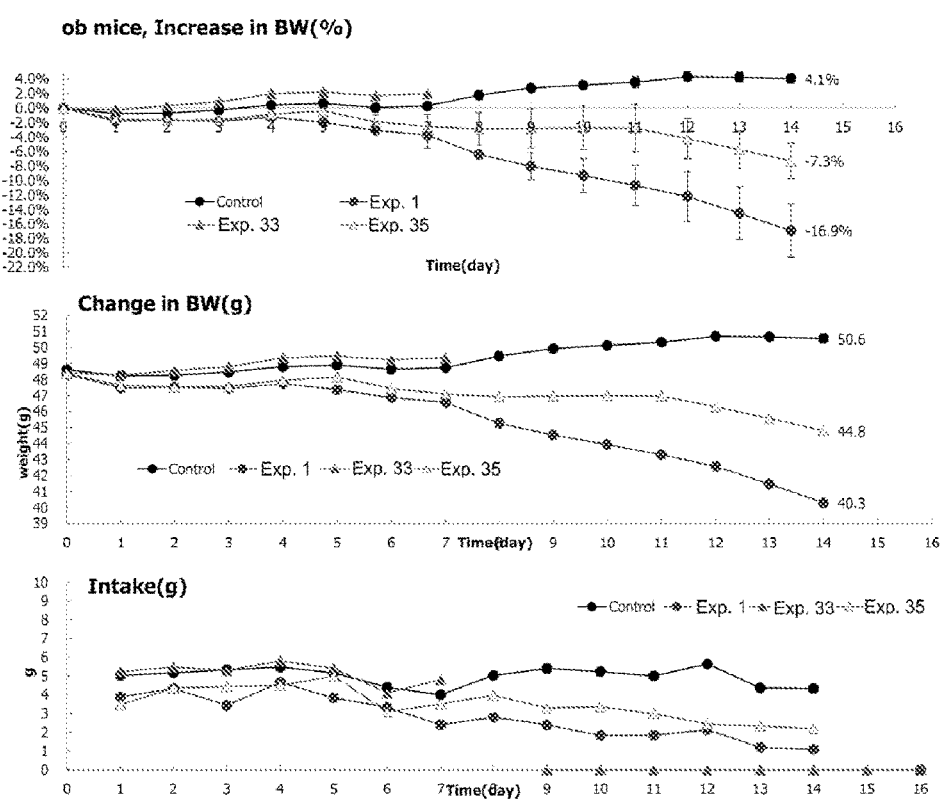
FIG. 15 illustrates graphs representing weight increase ratios (%), weight changes (g), and intake amounts (g) in obese mice (ob/ob) administered compounds according to Examples 1, 33, and 35 and a control in Experimental Example 3-12.

Experiments were performed under the same conditions as in Experimental Example 3-1 except that 6 week-old C57BL/6J Lep ob/ob mice having genetic obesity characteristics available from ORIENTBIO were prepared, the compounds according to Examples 1, 33, and 35 were administered to three C57BL/6J Lep ob/ob mice in an amount of 100 mg/kg, 100 mg/kg of 0.1% SLS was administered to each of three C57BL/6J Lep ob/ob mice as controls, and experiments were performed for a total of two weeks. Weight increase ratios, weight change, and intake amounts depending on administration time were measured and results are illustrated in FIG. 15 below.

As illustrated in graphs of FIG. 2 below, it can be confirmed that weight increase ratios, weight change, and intake amounts of C57BL/6J Lep ob/ob mice administered the compounds of Examples 1, 33, and 35 according to the method above are significantly decreased in some sections, when compared with controls.

EXPERIMENTAL EXAMPLE 3-13

Weight Loss Effects in Obese Mice (ob/ob) Administered Compounds According to Examples 1, 41, and 45

Figure 16:
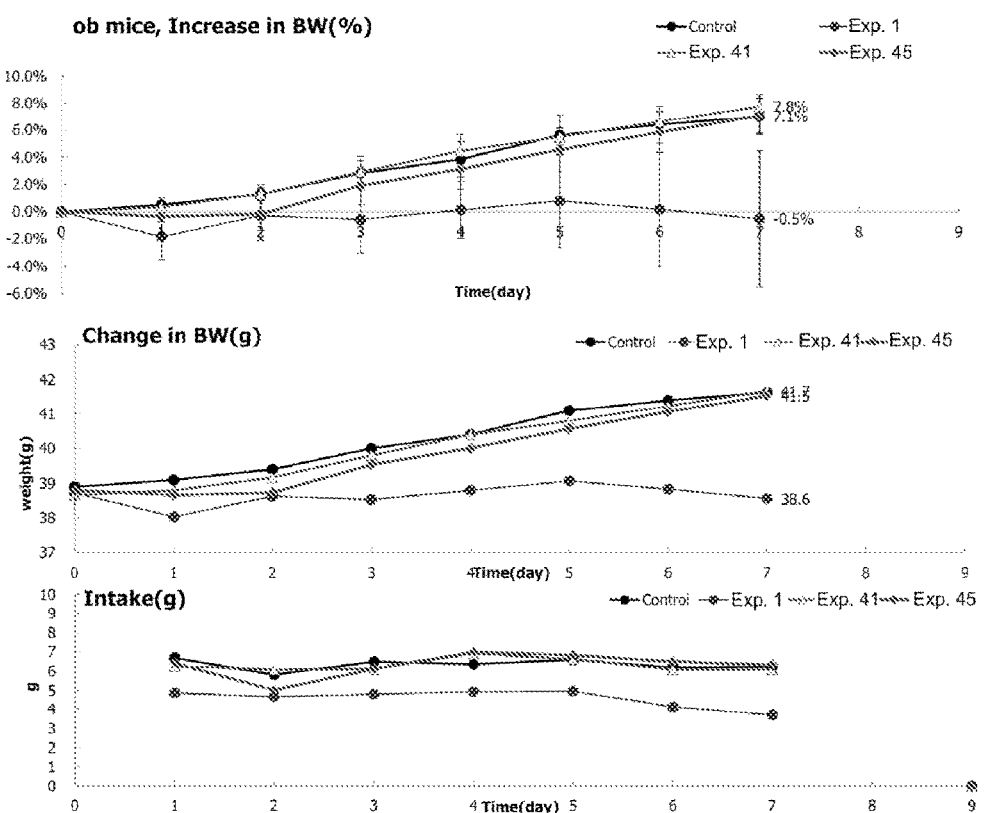
FIG. 16 illustrates graphs representing weight increase ratios (%), weight changes (g), and intake amounts (g) in obese mice (ob/ob) administered compounds according to Examples 1, 41 and 45 and a control in Experimental Example 3-13.

Experiments were performed under the same conditions as in Experimental Example 3-1 except that 6 week-old C57BL/6J Lep ob/ob mice having genetic obesity characteristics available from ORIENTBIO were prepared, the compounds according to Examples 1, 41, and 45 were administered to three C57BL/6J Lep ob/ob mice in an amount of 100 mg/kg, 100 mg/kg of 0.1% SLS was administered to each of three C57BL/6J Lep ob/ob mice as controls, and experiments were performed for a total of one week. Weight increase ratios, weight change, and intake amounts depending on administration time were measured and results are illustrated in FIG. 16 below.

As illustrated in graphs of FIG. 16 below, it can be confirmed that weight increase ratios, weight change, and intake amounts of C57BL/6J Lep ob/ob mice administered the compounds of Examples 1, 41, and 45 according to the method above are significantly decreased in some sections, when compared with controls.

EXPERIMENTAL EXAMPLE 4

Weight Loss Effects in Diabetic Mice (db/db) Administered with Compound According to Example 1

7 week-old C57BLKS/J db/db mice (chales river laboratories Japan, Inc) having genetic diabetic characteristics available from ORIENTBIO were prepared. Two mice were raised in each polycarbonate breeding cage (200 W×260

L×130H (mm), Three-shine) in which temperature was 22 to 24° C., relative humidity was 30 to 50%, illuminance was 150 to 300 lux, night and day were 12 hours, and exhaust was performed at 10 to 15 air changes per hour. As a feed, low fat diet (11.9 kcal % fat, 5053, Labdiet) manufactured by ORIENTBIO was used. The feed was contained in a feeder and free intake was allowed. As drinking water, water, which was contained in a 250 mL polycarbonate based bottle, purified through a filter and a sterilizer was used and free intake was allowed.

Figure 7:
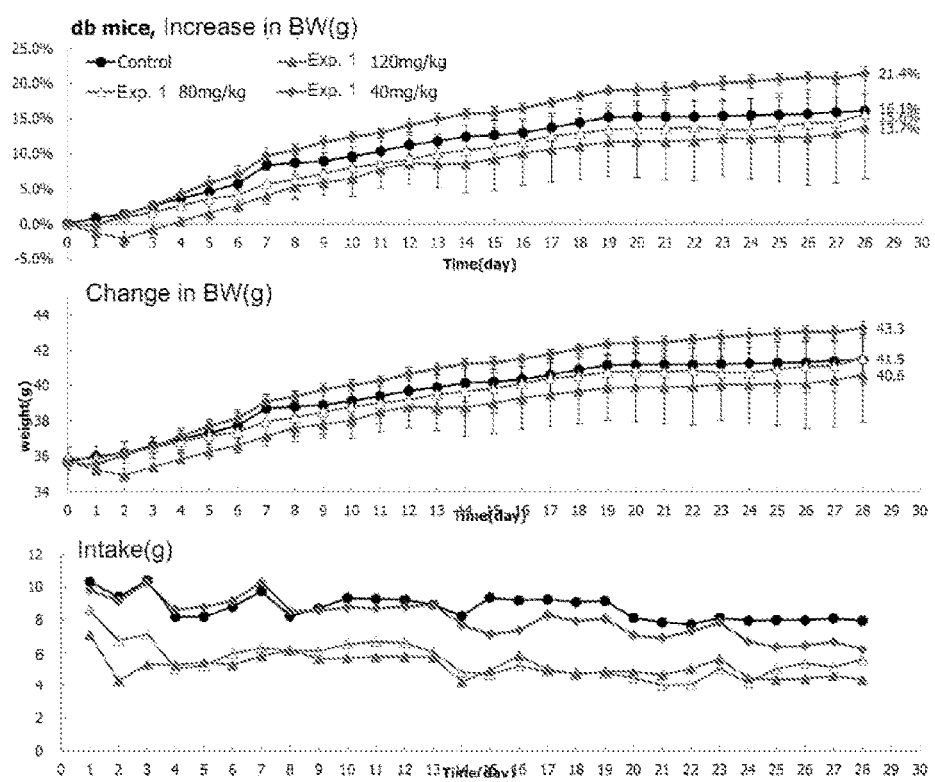
FIG. 7 illustrates graphs representing weight increase ratios, weight changes, and intake amounts in diabetic mice (db/db) administered a compound according to Example 1 and a control in Experimental Example 4.
Figure 8:
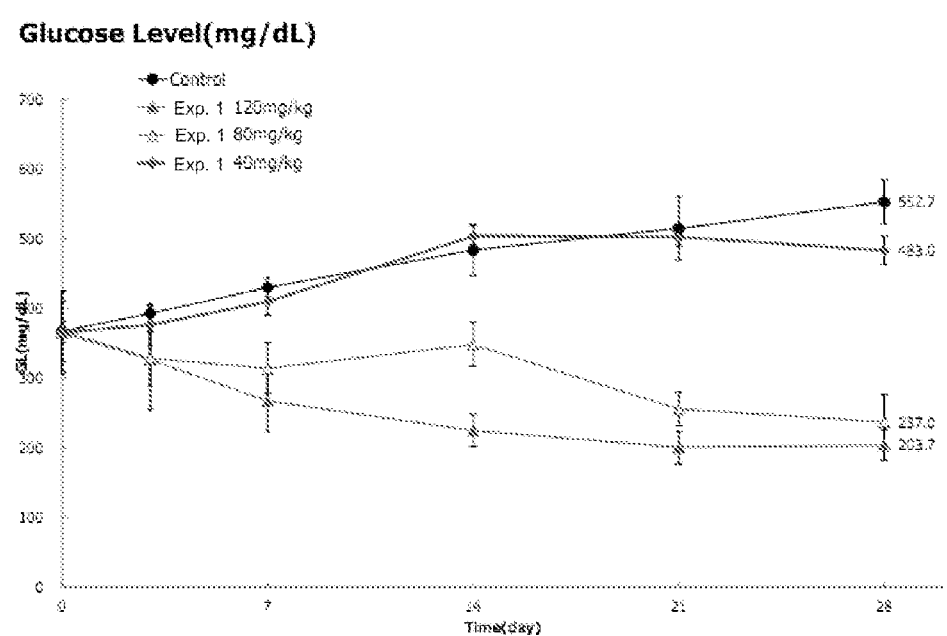
FIG. 8 illustrates graphs representing blood sugar levels in diabetic mice (db/db) administered a compound according to Example 1 and a control in Experimental Example 4.

The compound according to Example 1 synthesized in the present invention was orally administered to three C57BLKS/J db/db mice in amounts of 40 mg/kg, 80 mg/kg, and 120 mg/kg, respectively, once every day for four weeks. For administration, a disposable syringe fitted with a sonde for oral administration was used and 10 ml/kg of the compound was orally administered into the stomach. As controls, three C57BLKS/J db/db mice were administered 0.1% SLS in an amount of 120 mg/kg in the same manner as described above. After administration, a time-dependent weight increase ratio, weight change, and intake amount were measured and results are illustrated in FIG. 7 below. In addition, blood sugar was measured and results are illustrated in FIG. 8 below.

Weights of the experimental animals were measured immediately before administration of a test material and six times a week from an administration initiation day to a test termination day. Increased total weights were calculated by subtracting weights measured on an experiment initiation day from weights measured one day before an experiment termination day. Food intake amounts were calculated by measuring feed supply amounts and remaining amounts twice a week from an initiation day of test material administration to a test termination day for each individual. Blood sugar was measured before an administration initiation day of the test material and once a week between an administration initiation day and a test termination day.

As shown in graphs of FIGS. 7 and 8 below, it can be confirmed that weight increase ratios, weight change, intake amounts, and blood sugar amounts of C57BLKS/J db/db mice administered the compound according to Example 1 are significantly decreased, when compared with controls.

EXPERIMENTAL EXAMPLE 5

Glucose Level and Glycosylated Hemoglobin (Hb1Ac) Measurement Results in Diabetic Mice (db/db) Administered Compound According to Example 1

10 week-old C57BLKS/J db/db mice having genetic obesity characteristics available from ORIENTBIO were prepared. Two mice were raised in each polycarbonate breeding cage (200W×260L×130H (mm), Three-shine) in which temperature was 22 to 24° C., relative humidity was 30 to 50%, illuminance was 150 to 300 lux, night and day were 12 hours, and exhaust was performed at 10 to 15 air changes per hour. As a feed, low fat diet (11.9 kcal % fat, 5053, Labdiet) manufactured by ORIENTBIO was used. The feed was contained in a feeder and free intake was allowed. As drinking water, water, which was contained in a 250 mL polycarbonate based bottle, purified through a filter and a sterilizer was used and free intake was allowed.

Figure 9:
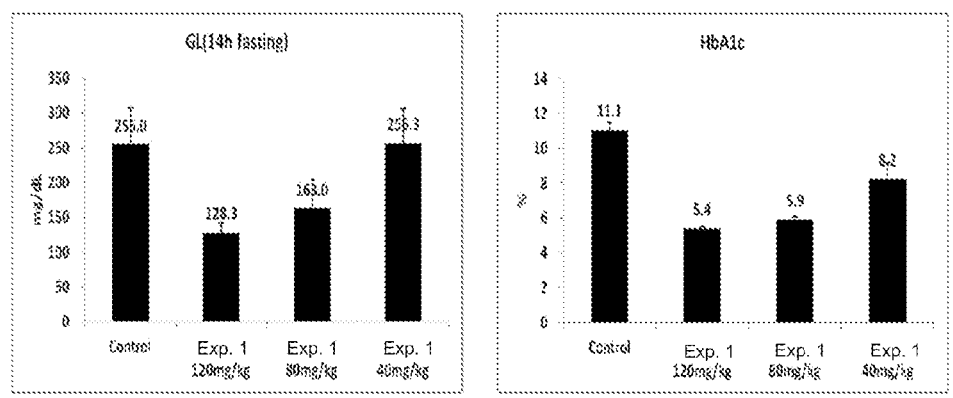
FIG. 9 illustrates graphs representing glucose levels and glycosylated hemoglobin (Hb1Ac) levels in fasting mice administered a compound according to Example 1 and a control in Experimental Example 5.

The compound according to Example 1 synthesized in the present invention was orally administered to three C57BLKS/J db/db mice in amounts of 40 mg/kg, 80 mg/kg, and 120 mg/kg, respectively. For administration, a disposable syringe fitted with a sonde for oral administration was used and 10 ml/kg of the compound was orally administered into the stomach. As controls, three C57BLKS/J db/db mice were administered 0.1% SLS in an amount of 120 mg/kg in the same manner as described above. After administration, the mice were fasted for 14 hours and glucose levels and glycosylated hemoglobin thereof were measured. Results are illustrated in FIG. 9 below.

As shown in graphs of FIG. 9 below, it can be confirmed that glucose levels and glycosylated hemoglobin of C57BLKS/J db/db mice administered the compound according to Example 1 are significantly decreased, when compared with controls.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A compound represented by Formula (1) below or a pharmaceutically acceptable salt, hydrate, solvate, prodrug, tautomer, enantiomer, or pharmaceutically acceptable diastereomer thereof:

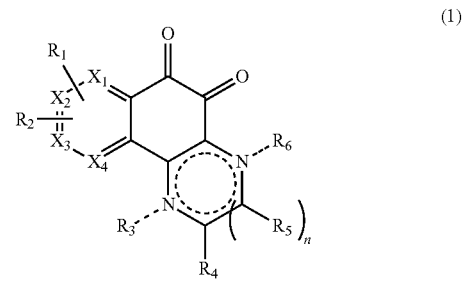

(1)

wherein $R_1$ and $R_2$ are each independently hydrogen, a halogen, substituted or unsubstituted C1-C20 alkoxy, substituted or unsubstituted C1-C6 alkyl, substituted or unsubstituted C4-C10 aryl, substituted or unsubstituted C4-C10 aryloxy, substituted or unsubstituted C2-C10 heteroaryl, —$NO_2$, —$NR'_1R'_2$, —$NR'_1$ (CO (O)$R'_2$), —$NR'_1$ (C (O)$NR'_1R'_2$), —CO (O)$R'_1$, —C(O)$NR'_1R'_2$, —CN, —SO (O)$R'_1$, —SO (O)$NR'_1R'_2$, —$NR'_1$ (SO (O)$R'_2$), or —$CSNR'_1R'_2$, or $R_1$ and $R_2$ form a ring structure of substituted or unsubstituted C4-C10 aryl through coupling or a ring structure of substituted or unsubstituted C2-C10 heteroaryl, where $R'_1$ and $R'_2$ are each independently hydrogen, substituted or unsubstituted C1-C6 alkyl, substituted or unsubstituted C3-C8 cycloalkyl, substituted or unsubstituted C4-C10 aryl, substituted or unsubstituted C4-C10 aryloxy, substituted or unsubstituted C1-C8 heteroaryl, substituted or unsubstituted —$(CR''_1R''_2)$m'-C4-C10 aryl, or substituted or unsubstituted $NR''_1R''_2$; where $R''_1$ and $R''_2$ are each independently hydrogen, or C1-C3 alkyl, or $R''_1$ and $R''_2$ form a ring structure of substituted or unsubstituted C4-C10 aryl through coupling;

$R_3$ is hydrogen, a halogen, substituted or unsubstituted C2-C20 alkene, substituted or unsubstituted C1-C20 alkoxy, substituted or unsubstituted C2-C8 heterocyloalkyl, substituted or unsubstituted C4-C10 aryloxy, substituted or unsubstituted C1-C10 heteroaryl, substituted or unsubstituted —$(CR'_5R'_6)_m$—C4-C10 aryloxy, substituted or unsustituted —(CR'₅R'₆)ₘ—C4-C10 heteroaryl, substituted or unsubstituted —(CR'₅R'₆)ₘ—C4-C10 heterocycloalkyl, substituted or unsubstituted —(CR'₅R'₆)ₘ—OR'₃, —CO (O)R'₃, —CONR'₃R'₄, —NR'₃R'₄, —NR'₃(C (O)R'₄), —SO (O)R'₃, —SO (O)NR'₃R'₄, —NR'₃(SO (O)R)'₄), —CSNR'₃R'₄, —CH₂A when the compound of Formula (1) is "A", or -A when the compound of Formula (1) is "A";

R₄, R₅, and R₆ are each independently hydrogen, a halogen, substituted or unsubstituted C1-C9 alkyl, substituted or unsubstituted C2-C20 alkene, substituted or unsubstituted C1-C20 alkoxy, substituted or unsubstituted C3-C8 cycloalkyl, substituted or unsubstituted C2-C8 heterocycloalkyl, substituted or unsubstituted C4-C10 aryl, substituted or unsubstituted C4-C10 aryloxy, substituted or unsubstituted C1-C10 heteroaryl, substituted or unsubstituted —(CR'₅R'₆)ₘ—C4-C10 aryl, substituted or unsubstituted —(CR'₅R'₆)ₘ—C4-C10 aryloxy, substituted or unsubstituted —(CR'₅R'₆)ₘ—C4-C10 heteroaryl, substituted or unsubstituted —(CR'₅R'₆)ₘ—C4-C10 heterocycloalkyl, substituted or unsubstituted —(CR'₅R'₆)ₘ—NR'₃R'₄, substituted or unsubstituted —(CR'₅R'₆)ₘ—OR'₃, —CO (O)R'₃, —CONR'₃R'₄, —NR'₃R'₄, —NR'₃ (C (O)R'₄), —SO (O)R'₃, —SO (O)NR'₃R'₄, —NR'₃ (SO (O)R'₄), —CSNR'₃R'₄, —CH₂A when the compound of Formula (1) is "A", or –A when the compound of Formula (1) is "A";

where R'₃ and R'₄ are each independently hydrogen, substituted or unsubstituted C1-C6 alkyl, substituted or unsubstituted C3-C8 cycloalkyl, substituted or unsubstituted C4-C10 aryl, substituted or unsubstituted —(CH₂)ₘ—C4-C10 aryl, substituted or unsubstituted —(CH₂)ₘ—C4-C10 aryloxy, or —CO (O)R"₃, or R'₃ and R'₄ form a ring structure of substituted or unsubstituted C4-C10 heterocycloalkyl through coupling or substituted or unsubstituted C4-C10 heteroaryl;

R'₅ and R'₆ are each independently hydrogen or C1-C3 alkyl; R"₃ is C1-C6 alkyl;

the substituted group is at least one selected from the group consisting of hydroxy, a halogen, C1-C10 alkyl, C2-C10 alkenyl, C2-C10 alkynyl, C1-C10 alkoxy, C1-C10 alkoxycarbonyl, C3-C8 cycloalkyl, C2-C8 heterocycloalkyl, C4-C10 aryl, and C2-C10 heteroaryl; and R3 and R4 are each independently not C4-C10 aryl, R₄ and R6 are each independently not C4-C10 aryl, R₄ is not hydrogen, methyl, or

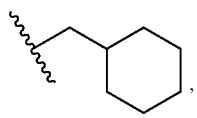 [SMILES: *CC1CCCCC1]

when R3 is defined as above, and R5 is not phenyl;
m and m' are each independently a natural number of 1 to 4; the heteroatom is at least one selected from N, O, and S;

X₁, X₂, X₃ and X₄ are each independently CR₁ or CR₂; and n is 0.

2. The compound or the pharmaceutically acceptable salt, hydrate, solvate, prodrug, tautomer, enantiomer, or pharmaceutically acceptable diastereomer thereof according to claim 1, wherein the compound of Formula (1) is a compound of Formula (3) and/or a compound of Formula (4):

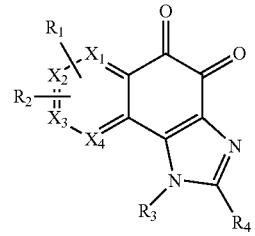

(3)

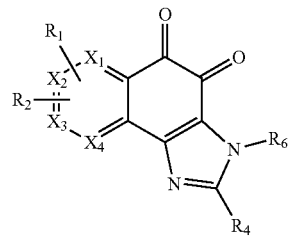

(4)

wherein R₁ to R₄, R₆, X₁, X₂, X₃, and X₄ are the same as defined in Formula (1).

3. The compound or the pharmaceutically acceptable salt, hydrate, solvate, prodrug, tautomer, enantiomer, or pharmaceutically acceptable diastereomer thereof according to claim 2, wherein R₁ and R₂ are each independently H, F, Cl, —NO₂, NH₂, —N (CH₃)₂, —NHCOCH₃, —NHCOC₃H₅ or —NHCH₂C₆H₅F; and
each of X₂ and X₃ is CR₁ or CR₂.

4. The compound or the pharmaceutically acceptable salt, hydrate, solvate, prodrug, tautomer, enantiomer, or pharmaceutically acceptable diastereomer thereof according to claim 2, wherein R₁ and R₂ are each independently H, F, Cl, —NO₂, NH₂, —N (CH₃)₂, —NHCOCH₃, —NHCOC₃H₅ or —NHCH₂C₆H₅F;
each of X₂ and X₃ is CR₁ or CR₂;
R₃ is hydrogen, a halogen, substituted or unsubstituted —(CR'₅R'₆)ₘ—C4-C10 aryloxy, substituted or unsubstituted —(CR'₅R'₆)ₘ—C4-C10 heteroaryl, substituted or unsubstituted —(CR'₅R'₆)ₘ—C4-C10 heterocycloalkyl, substituted or unsubstituted —(CHR'₅)ₘ—NR'₃R'₄, —CO (O)R'₃, —CONR'₃R'₄, —NR'₃R'₄, —NR'₃ (C (O)R'₄), or —CH₂ A when the compound of Formula (1) is "A";
R₆ is hydrogen, a halogen, substituted or unsubstituted C1-C9 alkyl, substituted or unsubstituted C3-C8 cycloalkyl, substituted or unsubstituted —(CR'₅R'₆))ₘ—C4-C10 aryl, substituted or unsubstituted —(CR'₅R'₆)ₘ—C4-C10 aryloxy, substituted or unsubstituted —(CR'₅R'₆)ₘ—C4-C10 heteroaryl, substituted or unsubstituted —(CR'₅R'₆)ₘ—C4-C10 heterocycloalkyl, substituted or unsubstituted —(CHR'₅)ₘ—NR'₃R'₄, —CO (O)R'₃, CONR'₃R'₄, —NR'₃R'₄, —NR'₃ (C (O)R'₄), or —CH₂A when the compound of Formula (1) is "A";
R₄ is a halogen, substituted or unsubstituted C2-C9 alkyl, substituted or unsubstituted C1-C10 alkoxy, substituted or unsubstituted C3-C8 cycloalkyl, substituted or unsubstituted C2-C8 heterocycloalkyl, substituted or unsubstituted C4-C10 aryl, substituted or unsubstituted C4-C10 aryloxy, substituted or unsubstituted C1-C10 heteroaryl, substituted or unsubstituted —(CR'₅R'₆)ₘ—

C4-C10 aryl, substituted or unsubstituted —(CR'₅R'₆)ₘ—C4-C10 aryloxy, substituted or unsubstituted —(CR'₅R'₆)ₘ—C4-C10 heteroaryl, substituted or unsubstituted —(CHR'₅))ₘ—NR'₃—C4-C10 aryl, substituted or unsubstituted —(CR'₅R'₆)ₘ—C4-C10 heterocycloalkyl, substituted or unsubstituted —(CR'₅R'₆)ₘ—NR'₃R'₄, substituted or unsubstituted —(CR'₅R'₆)ₘ—OR'₃, —NR'₃R'₄, or -A when the compound of Formula (1) is "A";

where R'₃ and R'₄ are each independently hydrogen, substituted or unsubstituted C1-C6 alkyl, substituted or unsubstituted C3-C8 cycloalkyl, substituted or unsubstituted —(CH₂)ₘ—C4-C10 aryl, substituted or unsubstituted —(CH₂)ₘ—C4-C10 aryloxy, or —CO(O)R"₃, or R'₃ and R'₄ form a ring structure of substituted or unsubstituted C4-C10 heterocycloalkyl through coupling, or a ring structure of substituted or unsubstituted C4-C10 heteroaryl;

R'₅, and R'₆ are each independently hydrogen or C1-C3 alkyl;

R"₃ is C1-C6 alkyl;

wherein the substituted group is at least one selected from the group consisting of hydroxy, a halogen, C1-C10 alkyl, C2-C10 alkenyl, C2-C10 alkynyl, C1-C10 alkoxy, C1-C10 alkoxycarbonyl, C3-C8 cycloalkyl, C2-C8 heterocycloalkyl, C4-C10 aryl, and C2-C10 heteroaryl;

m is a natural number of 1 to 4; and the heteroatom is at least one selected from N, O, and S.

5. The compound or the pharmaceutically acceptable salt, hydrate, solvate, prodrug, tautomer, enantiomer, or pharmaceutically acceptable diastereomer thereof according to claim 2, wherein the compound of Formula (3) or the compound of Formula (4) is one of compounds below:

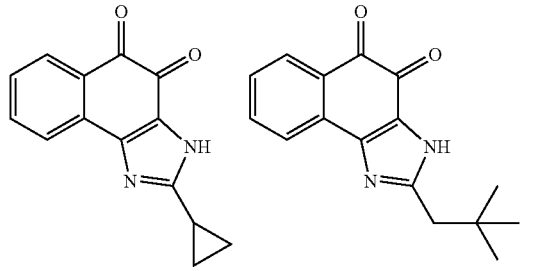

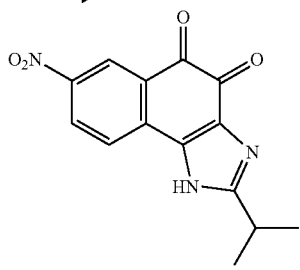

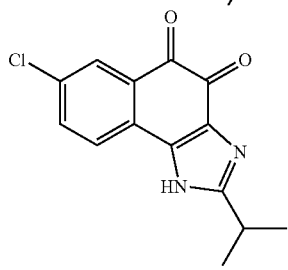

-continued

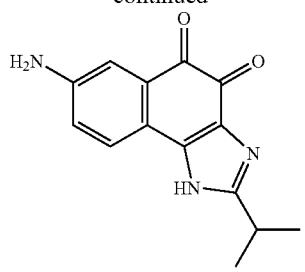

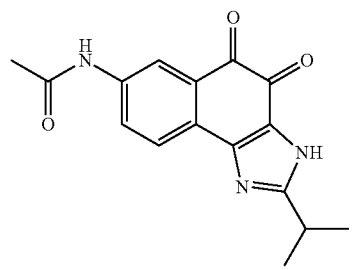

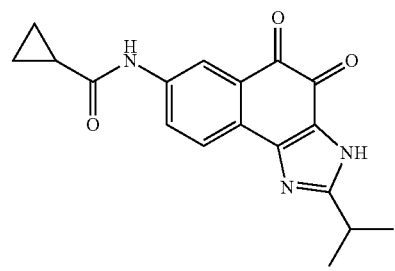

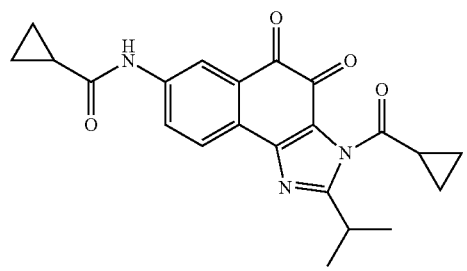

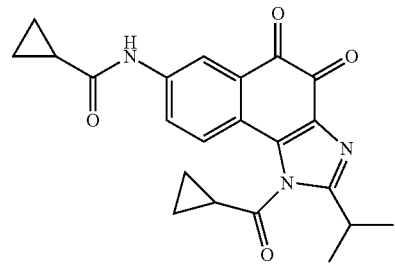

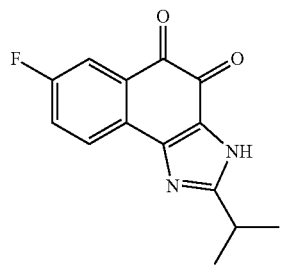

165
-continued
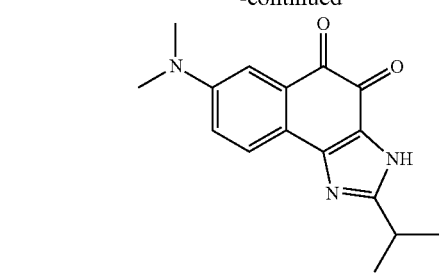
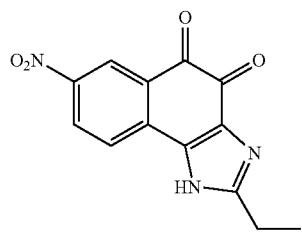
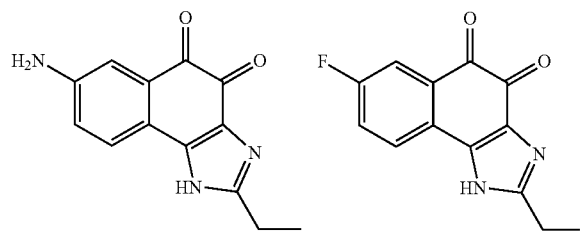
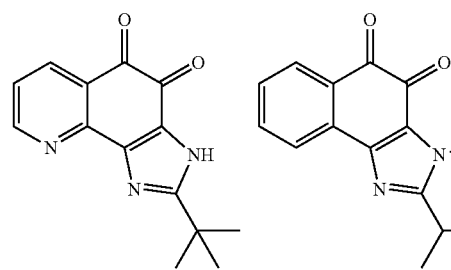
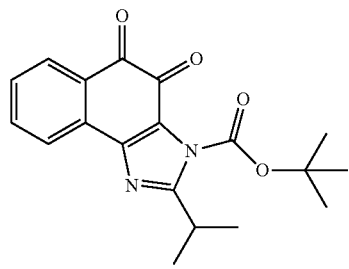
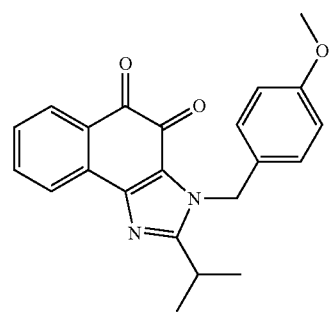
166
-continued
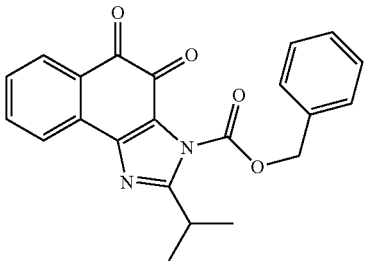
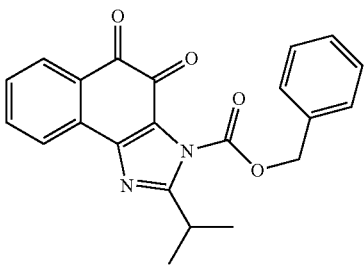
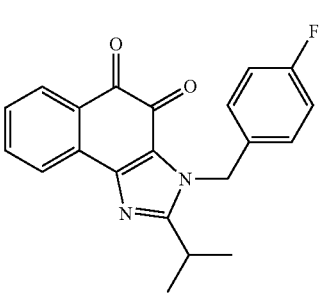
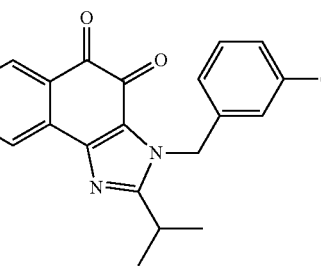
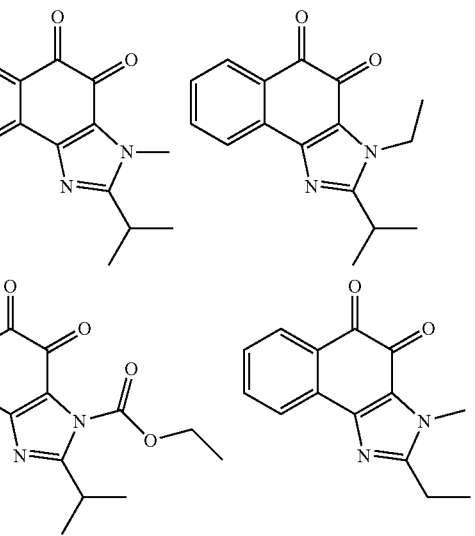
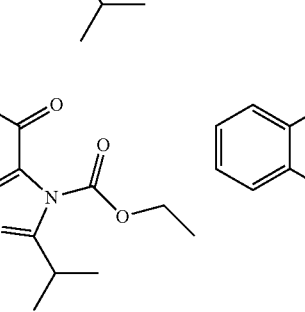

167
-continued
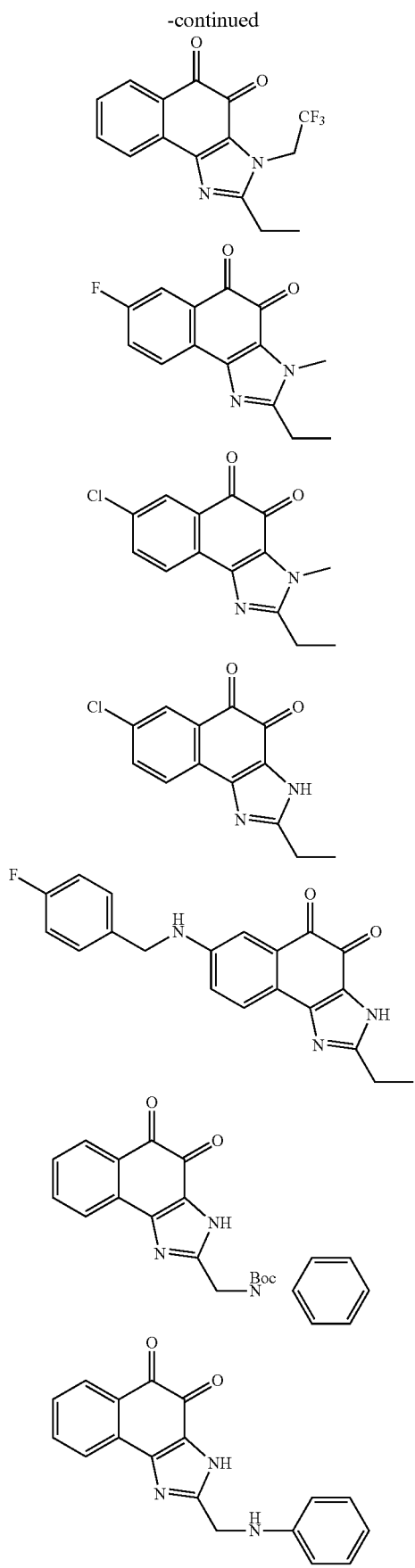
168
-continued
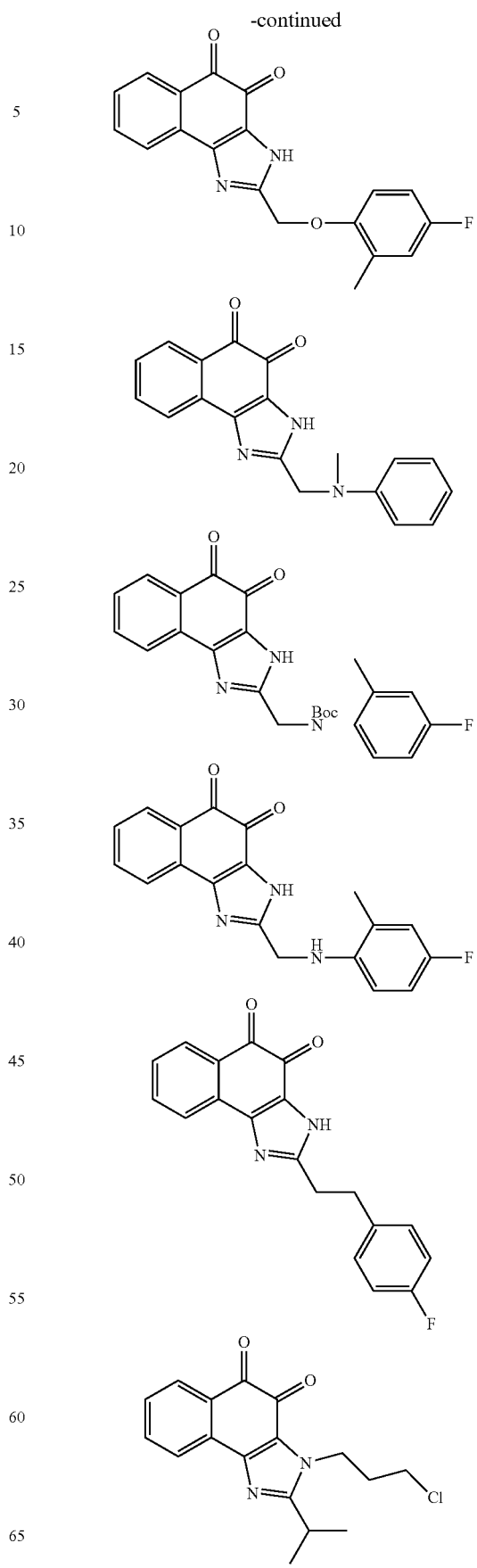

169
-continued
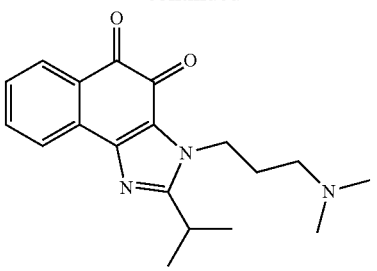
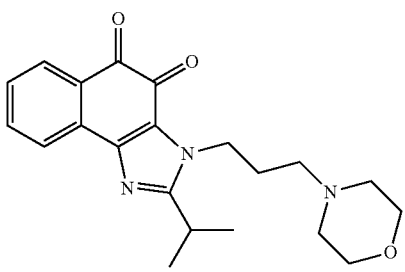
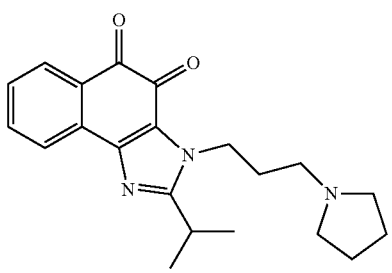
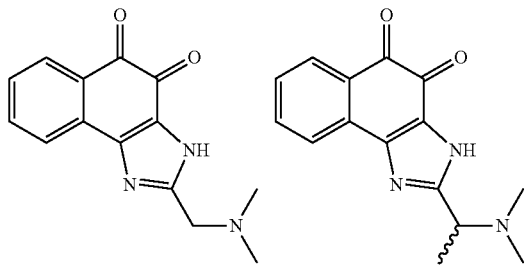
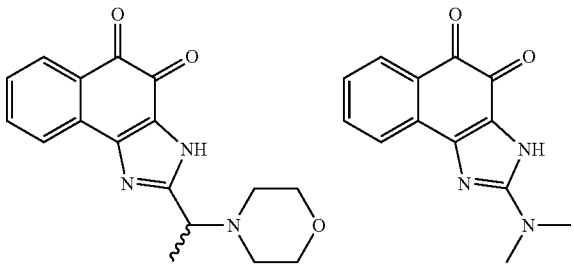
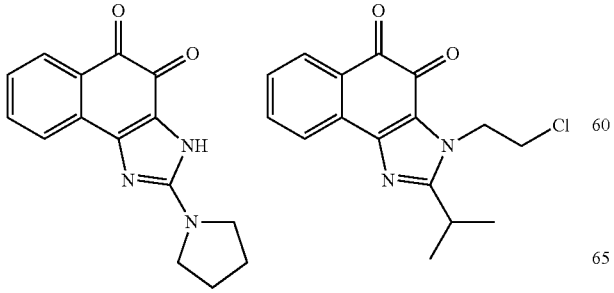
170
-continued
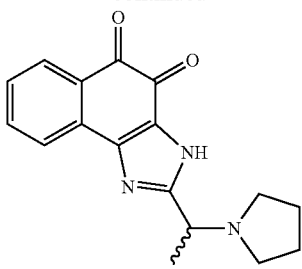
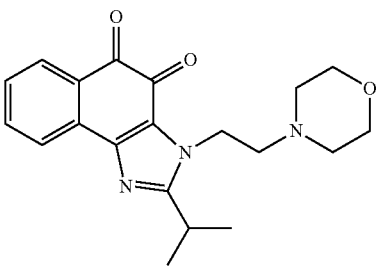
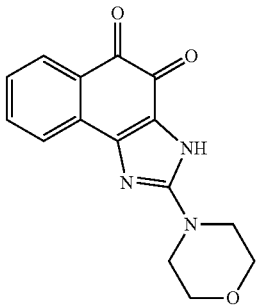
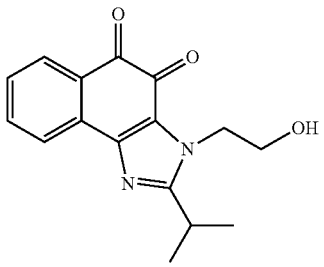
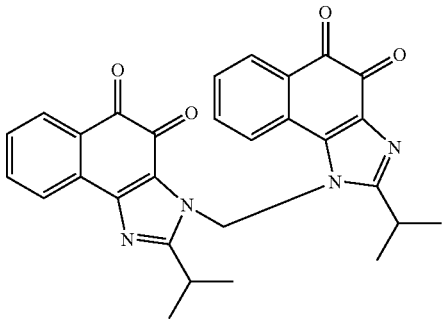
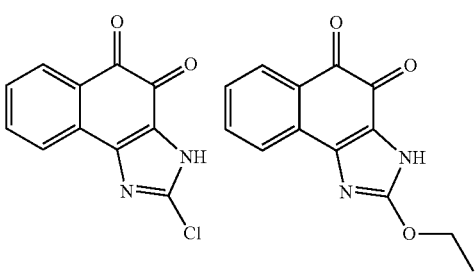

171
-continued
172
-continued
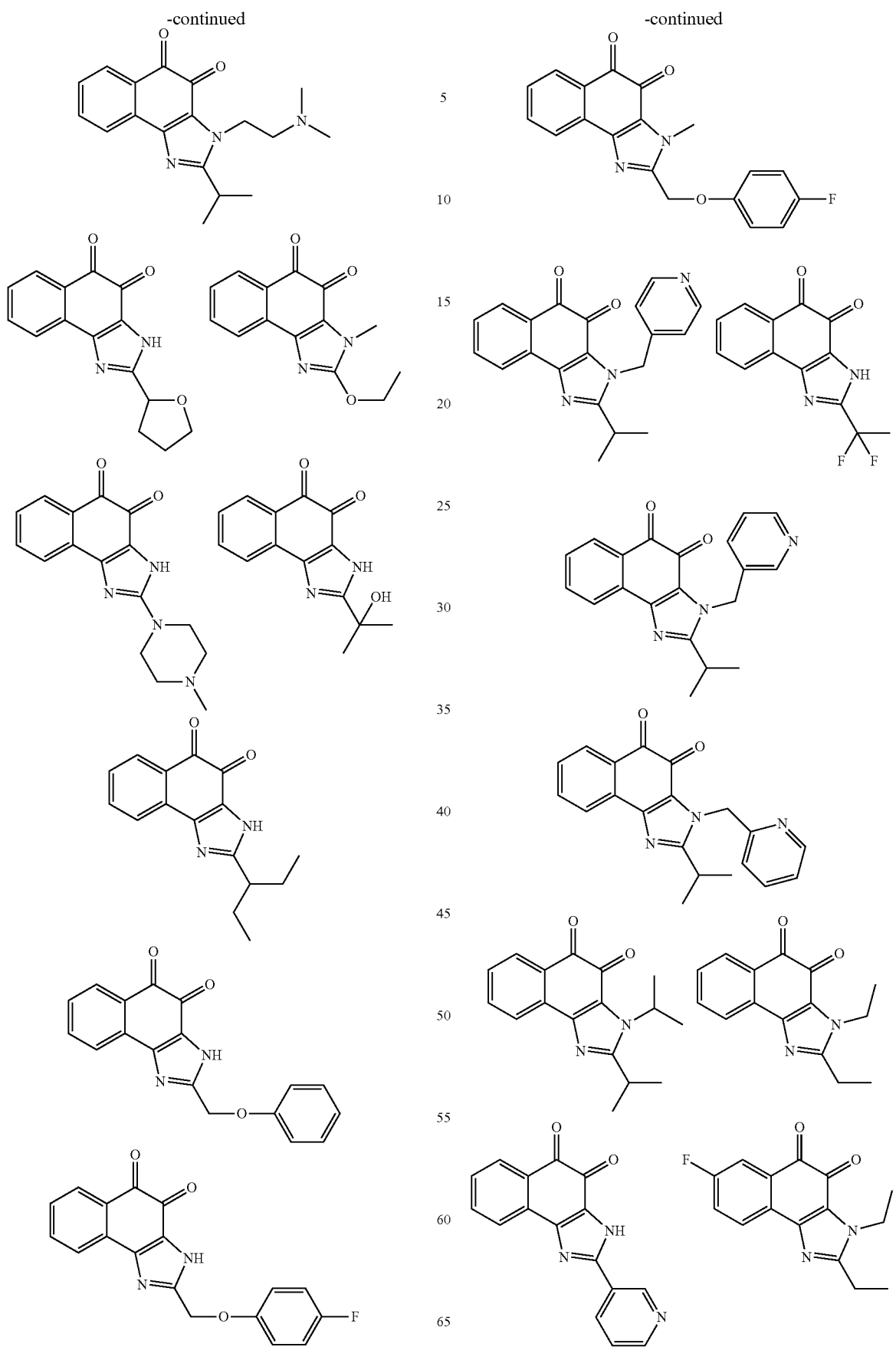

-continued
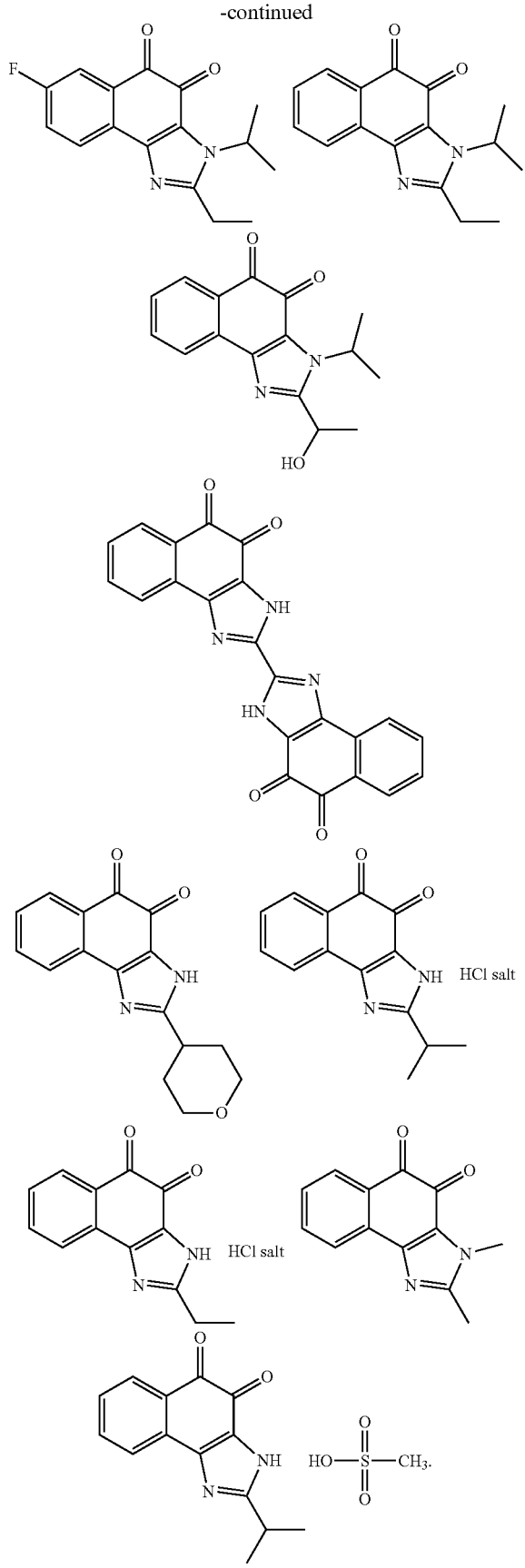
6. The compound or the pharmaceutically acceptable salt, hydrate, solvate, prodrug, tautomer, enantiomer, or pharmaceutically acceptable diastereomer thereof according to claim 2, wherein the compound of Formula (3) or the compound of Formula (4) is one of compounds below:
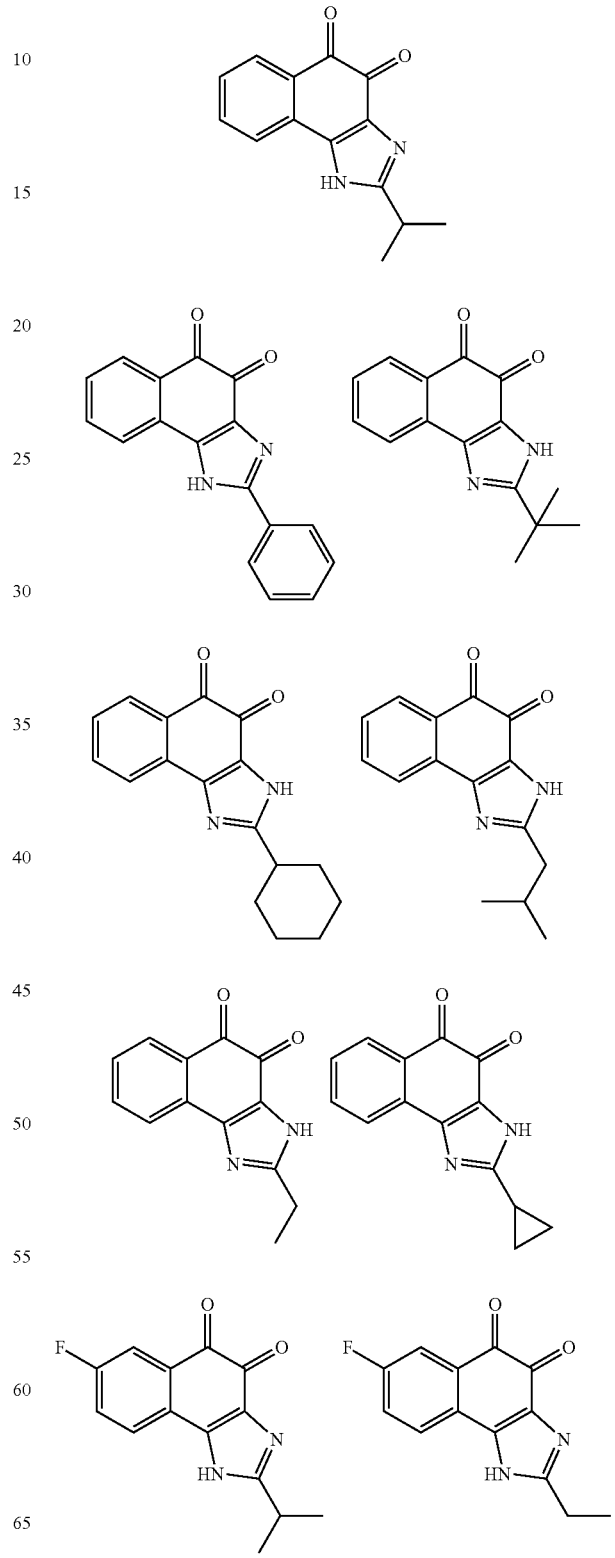

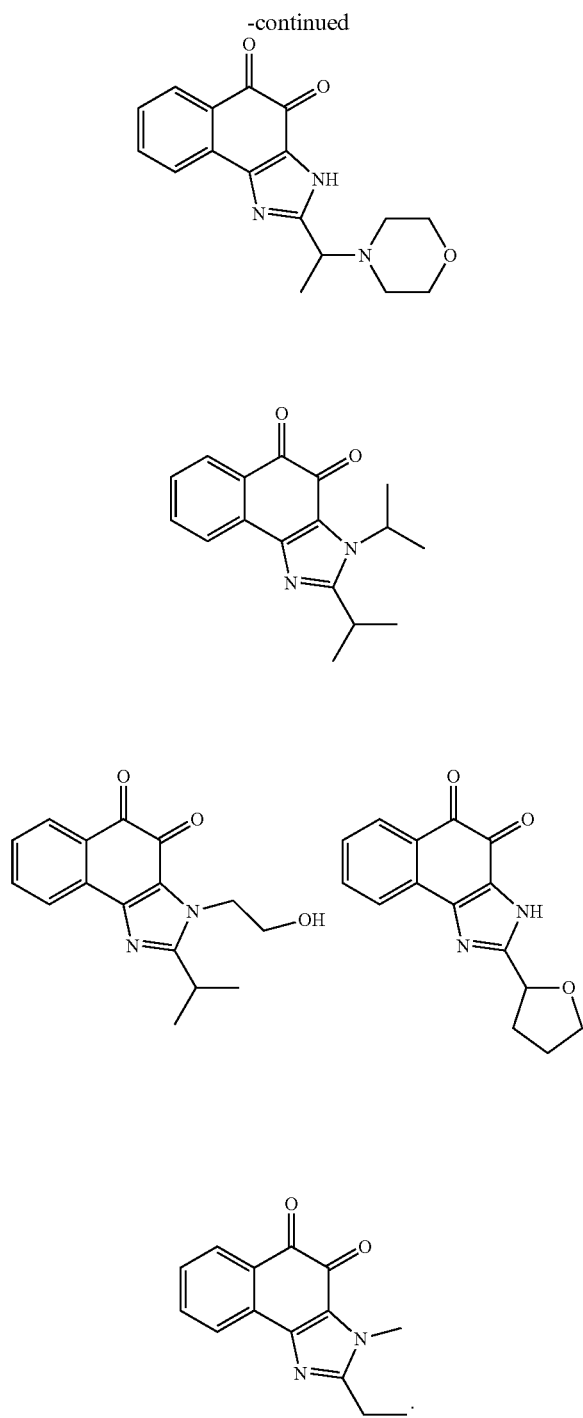

7. The compound or the pharmaceutically acceptable salt, hydrate, solvate, prodrug, tautomer, enantiomer, or pharmaceutically acceptable diastereomer thereof according to claim 2, wherein the compound of Formula (3) or the compound of Formula (4) is one of compounds below:

8. A pharmaceutical composition for treatment of metabolic syndromes comprising (a) a therapeutically effective amount of the compound of Formula (1) according to claim 1 and/or a pharmaceutically acceptable salt, hydrate, solvate, tautomer, enantiomer, and/or pharmaceutically acceptable diastereomer thereof; and (b) a pharmaceutically acceptable carrier, diluent, or vehicle, or a combination thereof, wherein said metabolic syndrome is selected from the group consisting of obesity and diabetes.

9. The compound or the pharmaceutically acceptable salt, hydrate, solvate, prodrug, tautomer, enantiomer, or pharmaceutically accepted diastereomer enantiomer thereof according to claim 1, wherein the compound is

* * * * *